US012577576B2

(12) United States Patent
Qi et al.

(10) Patent No.: US 12,577,576 B2
(45) Date of Patent: Mar. 17, 2026

(54) SYSTEMS AND METHODS FOR PLANT GENOME EDITING USING Cas 12a ORTHOLOGS

(71) Applicant: University of Maryland, College Park, College Park, MD (US)

(72) Inventors: Yiping Qi, Potomac, MD (US); Yingxiao Zhang, Greenbelt, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 307 days.

(21) Appl. No.: 17/090,766

(22) Filed: Nov. 5, 2020

(65) Prior Publication Data

US 2021/0130838 A1    May 6, 2021

Related U.S. Application Data

(60) Provisional application No. 62/930,940, filed on Nov. 5, 2019.

(51) Int. Cl.
| | |
|---|---|
| *C12N 15/82* | (2006.01) |
| *C12N 9/22* | (2006.01) |
| *C12N 15/11* | (2006.01) |

(52) U.S. Cl.
CPC ........... *C12N 15/8241* (2013.01); *C12N 9/22* (2013.01); *C12N 15/111* (2013.01); *C12N 2310/20* (2017.05)

(58) Field of Classification Search
CPC .... C12N 15/8241; C12N 9/22; C12N 15/111; C12N 2310/20
See application file for complete search history.

(56) References Cited

U.S. PATENT DOCUMENTS

| | | | |
|---|---|---|---|
| 2019/0071717 A1 * | 3/2019 | Zhang .................... | C12N 15/11 |
| 2021/0180076 A1 | 6/2021 | Qi | |

FOREIGN PATENT DOCUMENTS

| | | | | |
|---|---|---|---|---|
| WO | WO-2019138052 A1 * | 7/2019 | ............. | A01H 6/024 |
| WO | 2022040169 A1 | 2/2022 | | |
| WO | 2022236071 | 11/2022 | | |
| WO | 2022236071 A1 | 11/2022 | | |

OTHER PUBLICATIONS

Zetsche B et al. Keio J Med. Sep. 25, 2020;69(3):59-65 (Year: 2020).*
Lin et al. J Genet Genomics. Jun. 20, 2021;48(6):444-451 (Year: 2021).*
Safari F et al. Cell Biosci. May 9, 2019;9:36 (Year: 2019).*
Zetsche B et al. BioRxiv Preprint, May 2017 (Year: 2017).*
Murugan K et al. J Biol Chem. Apr. 24, 2020;295(17):5538-5553 (Year: 2020).*
Gleditzsch D et al. RNA Biol. Apr. 2019;16(4):504-517 (Year: 2019).*
Tang X et al. Nat Plants. Feb. 17, 2017;3:17018 (Year: 2017).*
Webster GR et al. Biotechnol Bioeng. Mar. 2017;114(3):492-502 (Year: 2017).*
Pyzocha NK et al. ACS Chem Biol. Feb. 16, 2018;13(2):347-356 (Year: 2018).*
Nishimasu et al. Mol Cell. Jul. 6, 2017;67(1):139-147.e2 (Year: 2017).*
Xu R et al. Plant Biotechnol J. Jun. 2017;15(6):713-717 (Year: 2017).*
NCBI WP_046697655 (NCBI Blast Database, accession No. WP_046697655, MbCas12a gene, published Oct. 13, 2019) (Year: 2019).*
Jun et al. Rice Science vol. 26, Issue 2, pp. 69-76, published Mar. 2019 (Year: 2019).*
Ren, Q., et al., "Improved plant cystosine base editors with high editing activity, purity, and specificity", Plant Biotechnolgy Journal, 2021, pp. 2052-2068, vol. 19, Publisher: John Wiley & Sons Ltd.
Gao, L., et al., "Engineered Cpf1 variants with altered PAM specificities", Nature Biotechnology, 2017, doi:10.1038/nbt.3900, Publisher: Nature America, Inc.
Hu, X., et al., "Targeted mutagenesis in rice using CRISPR-Cpf1 system", Journal of Genetics and Genomics, 2017, DOI: 10.1016/j.jgg.2016.12.001.
Lee, K., et al., "Activities and specificities of CRISPR/Cas9 and Cas12a nucleases for targeted mutagenesis in maize", Plant Biotechnology Journal, 2018, doi:10.1111/pbi.12982, Publisher: Society for Experimental Biology.
Liu, Z., et al., "ErCas12a CRISPR-MAD7 for Model Generation in Human Cells, Mice, and Rats", The CRISPR Journal, 2020, DOI:10.1089/crispr.2019.0068, vol. 3, No. 2, Publisher: Mary Ann Liebert, Inc.
Malzahn, A.A., et al., "Application of CRISPR-Cas12a temperature sensitivity fo improved genome editing in rice, maize, and *Arabidopsis*", BMC Biology, 2019, https://doi.org/10.1186/s12915-019-0629-5, vol. 17, No. 9, Publisher: Open Access.
Tang, X., et al., "A CRISPR-Cpf1 system for effcient genome editing and transcriptional repression in plants", Nature Plants, 2017, DOI: 10.1038/nplants.2017.18, vol. 3, No. 17018, Publisher: Macmillan Publishers Limited.

(Continued)

*Primary Examiner* — Kimberly Chong
*Assistant Examiner* — Douglas Charles Ryan
(74) *Attorney, Agent, or Firm* — HULTQUIST, PLLC; Steven J. Hultquist

(57) ABSTRACT

A non-naturally occurring heterologous CRISPR-Cas12a genomic editing system is described, including or encoding at least one Cas12a ortholog endonuclease selected from among Lb5Cas12a, CMaCas12a, BsCas12a, BoCas12a, MlCas12a, Mb2Cas12a, MbCas12a TsCas12a, and MAD7® ErCas12a endonucleases. The ortholog endonucleases enable genomic editing of plants at low temperatures, e.g., below 25° C. The CRISPR-Cas12a system can be employed for targeting PAM sites such as TTN, TTV, TTTV, NTTV, TATV, TATG, TATA, YTTN, GTTA, and GTTC, utilizing corresponding gRNAs, and is readily adapted to multiplexed editing operations of plants such as rice and other food crops.

23 Claims, 28 Drawing Sheets

Specification includes a Sequence Listing.

(56) References Cited

OTHER PUBLICATIONS

Wang, M., et al., "Simplified single transcriptional unit CRISPR systems", Shanghai Center for Plant Stress Biology and Center for Excellence in Molecular Plant Sciences, 2018, doi: 10.1111/jipb. 12667, Publisher: Chinese Academy of Sciences.

Zetsche, B., et al., "Cpf1 Is a Single RNA-Guided Endonuclease of a Class 2 CRISPR-Cas System", Cell, 2015, Page(s) http://dx.doi. org/10.1016/j.cell.2015.09.038, vol. 163, Publisher: Elsevier Inc.

Zetsche, B., et al., "A Survey of Genome Editing Activity for 16 Cas12a Orthologs", The Keio Journal of Medicine, 2020, pp. 59-65; DOI:10.2302/kjm.2019-0009-OA, vol. 69, No. 3.

Zhong, Z., et al., "Plant Genome Editing Using FnCpf1 and LbCpf1 Nucleases at Redefined and Altered PAM Sites", Molecular Plant, 2018, https://doi.org/10.1016/j.molp.2018.03.008.

U.S. Appl. No. 63/186,054, filed May 7, 2021, Yiping Qi, et al., Genome Editing in Plants Using Cas12a Nucleases.

Tang, X., et al., "A Single Transcript CRISPR-Cas9 System for Efficient Genome Editing in Plants", Molecular Plant 9, 2016, pp. 1088-1091.

Tang, X., et al., "Single transcript unit CRISPR 2.0 systems for robust Cas9 and Cas12a mediated plant growth", Plant Biotechnology Journal, 2019, pp. 1431-1445; doi: 10. 7150/ifbs. 24581, vol. 17.

You, Q., et al., "CRISPRMatch: An Automatic Calculation and Visualization Tool for High-throughput CRISPR Genome-editing Data Analysis", Int. J. Biol. Sci, 2018, pp. 858-862; doi: 10. 7150/ifbs. 24581, vol. 14, No. 8.

Zhang, Y., et al., "The emerging and uncultivated potential of CRISPR technology in plant science", Nature Plants, 2019, pp. 778-794; https://doi.org/10.1038/s41477-019-0461-5, vol. 5.

Zhang, Y., et al., "Expanding the scope of plant genome engineering with Cas12a orthologs and highly multiplexable editing systems", Nature Communications, 2021, 12:1944; https://doi.org/10.1038/s41467-021-22330-w.

Hu, H., Et A., "Improving the efficiency of the CRISPR-Cas12a system with tRNA-crRNA arrays", The Crop Journal, 2020, pp. 403-407, vol. 8, Publisher: Crop Science Society of China.

Lowder, L.G., et al., "A CRISPR/Cas9 Toolbox for Multiplexed Plant Genome Editing and Transcriptional Regulation", Plant Physiology, 2015, pp. 971-985, vol. 169, Publisher: American Society of Plant Biologists.

Wang, M., et al., "Multiplex Gene Editing in Rice Uing the CRISPR-Cpf1 System", Molecular Plant, 2017, pp. 1011-1013, vol. 10.

Wang, M., et al., "Multiplex gene editing in rice with simplified CRISPR-Cpf1 and CRISPR-Cas9 systems", Journal of Integrative Plant Biology, 2018, pp. 626-631, vol. 60, Publisher: Institute of Botany, Chinese Academy of Sciences.

* cited by examiner

| Cas12a | Tested T0 line | Edit (number, ratio) | Biallelic edit (number, ratio) |
|--------|----------------|----------------------|--------------------------------|
| Lb | 30 | 27, 90.0% | 23, 76.7% |
| Lb5 | 11 | 6, 54.5% | 5, 45.5% |
| Bs | 16 | 6, 37.5% | 3, 18.8% |
| Bo | 24 | 7, 29.2% | 2, 8.3% |
| MAD7 | 18 | 8, 44.4% | 5, 27.8% |
| Ml | 14 | 0, 0.0% | 0, 0.0% |
| Mb2 | 19 | 13, 68.4% | 10, 52.6% |
| Mb | 17 | 12, 70.6% | 5, 29.4% |
| Ts | 20 | 20, 100% | 15, 75% |

FIG. 4B
| Cas12a | Tested T0 line | Edit (number, ratio) | Biallelic edit (number, ratio) |
|:---:|:---:|:---:|:---:|
| Lb | 12 | 11, 91.7% | 11, 91.7% |
| Lb5 | 19 | 13, 68.4% | 9, 47.4% |
| Bs | 17 | 15, 88.2% | 12, 70.6% |
| Bo | 14 | 2, 14.3% | 1, 7.1% |
| MAD7 | 28 | 25, 89.3% | 17, 60.78% |
| Ml | 22 | 9, 40.9% | 1, 4.5% |
| Mb2 | 18 | 15, 83.3% | 13, 72.2% |
| Mb | 29 | 18, 62.1% | 9, 31.0% |
| Ts | 20 | 17, 85.0% | 10, 50% |
FIG. 5A
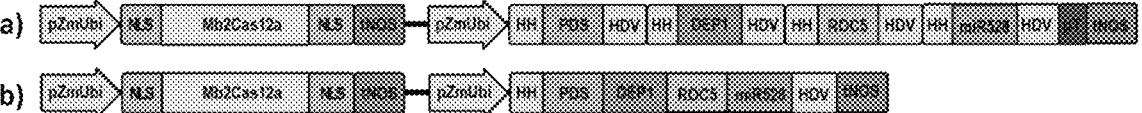
FIG. 5B
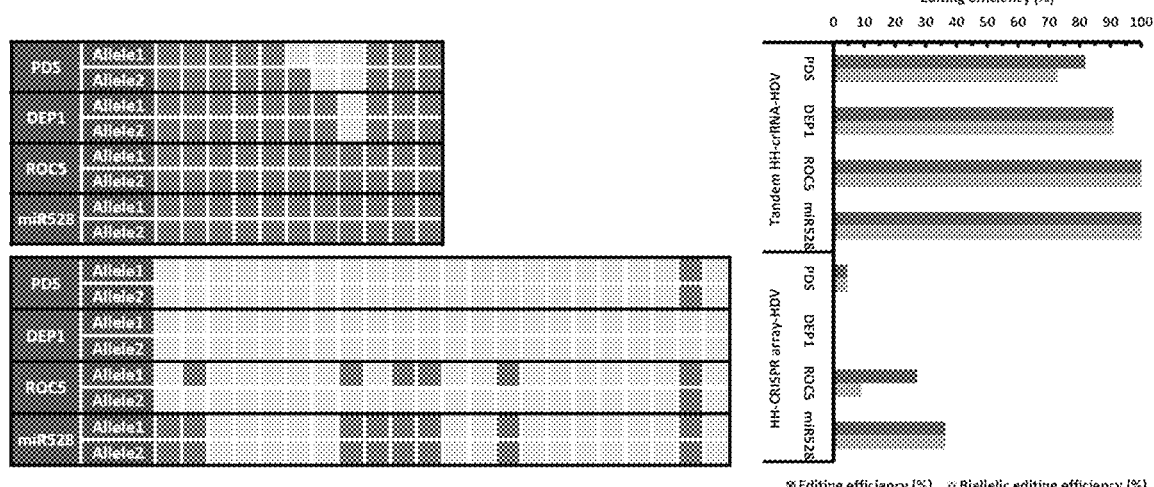

FIG. 5C

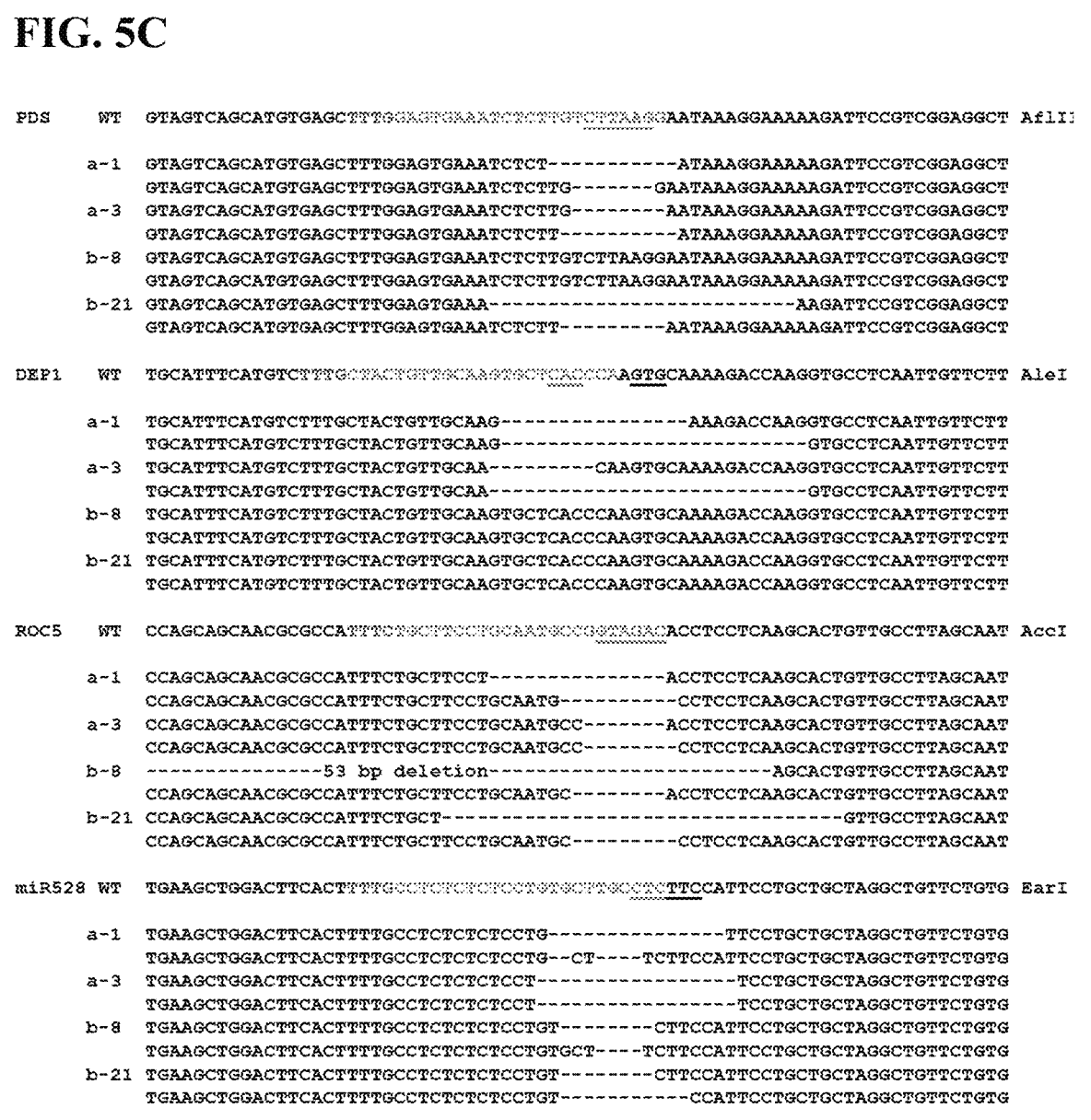

```
PDS    WT    GTAGTCAGCATGTGAGCTTTGGAGTGAAATCTCTTGTCTTAAGGAATAAAGGAAAAAGATTCCGTCGGAGGCT AflII a-1   GTAGTCAGCATGTGAGCTTTGGAGTGAAATCTCT-----------ATAAAGGAAAAAGATTCCGTCGGAGGCT
             GTAGTCAGCATGTGAGCTTTGGAGTGAAATCTCTTG-------GAATAAAGGAAAAAGATTCCGTCGGAGGCT
       a-3   GTAGTCAGCATGTGAGCTTTGGAGTGAAATCTCTTG--------AATAAAGGAAAAAGATTCCGTCGGAGGCT
             GTAGTCAGCATGTGAGCTTTGGAGTGAAATCTCTT---------ATAAAGGAAAAAGATTCCGTCGGAGGCT
       b-8   GTAGTCAGCATGTGAGCTTTGGAGTGAAATCTCTTGTCTTAAGGAATAAAGGAAAAAGATTCCGTCGGAGGCT
             GTAGTCAGCATGTGAGCTTTGGAGTGAAATCTCTTGTCTTAAGGAATAAAGGAAAAAGATTCCGTCGGAGGCT
       b-21  GTAGTCAGCATGTGAGCTTTGGAGTGAAA---------------------------AAGATTCCGTCGGAGGCT
             GTAGTCAGCATGTGAGCTTTGGAGTGAAATCTCTT--------AATAAAGGAAAAAGATTCCGTCGGAGGCT

DEP1   WT    TGCATTTCATGTCTTTGCTACTGTTGCAAGTGCTCACCCAAGTGCAAAAGACCAAGGTGCCTCAATTGTTCTT AleI a-1   TGCATTTCATGTCTTTGCTACTGTTGCAAG------------------AAAGACCAAGGTGCCTCAATTGTTCTT
             TGCATTTCATGTCTTTGCTACTGTTGCAAG-------------------------GTGCCTCAATTGTTCTT
       a-3   TGCATTTCATGTCTTTGCTACTGTTGCAA---------CAAGTGCAAAAGACCAAGGTGCCTCAATTGTTCTT
             TGCATTTCATGTCTTTGCTACTGTTGCAA--------------------------GTGCCTCAATTGTTCTT
       b-8   TGCATTTCATGTCTTTGCTACTGTTGCAAGTGCTCACCCAAGTGCAAAAGACCAAGGTGCCTCAATTGTTCTT
             TGCATTTCATGTCTTTGCTACTGTTGCAAGTGCTCACCCAAGTGCAAAAGACCAAGGTGCCTCAATTGTTCTT
       b-21  TGCATTTCATGTCTTTGCTACTGTTGCAAGTGCTCACCCAAGTGCAAAAGACCAAGGTGCCTCAATTGTTCTT
             TGCATTTCATGTCTTTGCTACTGTTGCAAGTGCTCACCCAAGTGCAAAAGACCAAGGTGCCTCAATTGTTCTT

ROC5   WT    CCAGCAGCAACGCGCCATTTCTGCTTCCTGCAATGCCGGAAAGCCGGAGAGACCTCCTCAAGCACTGTTGCCTTAGCAAT AccI a-1   CCAGCAGCAACGCGCCATTTCTGCTTCCT----------------ACCTCCTCAAGCACTGTTGCCTTAGCAAT
             CCAGCAGCAACGCGCCATTTCTGCTTCCTGCAATG----------CCTCCTCAAGCACTGTTGCCTTAGCAAT
       a-3   CCAGCAGCAACGCGCCATTTCTGCTTCCTGCAATGCC-------ACCTCCTCAAGCACTGTTGCCTTAGCAAT
             CCAGCAGCAACGCGCCATTTCTGCTTCCTGCAATGCC--------CCTCCTCAAGCACTGTTGCCTTAGCAAT
       b-8   ----------------53 bp deletion------------------------AGCACTGTTGCCTTAGCAAT
             CCAGCAGCAACGCGCCATTTCTGCTTCCTGCAATGC--------ACCTCCTCAAGCACTGTTGCCTTAGCAAT
       b-21  CCAGCAGCAACGCGCCATTTCTGCT----------------------------------GTTGCCTTAGCAAT
             CCAGCAGCAACGCGCCATTTCTGCTTCCTGCAATGC---------CCTCCTCAAGCACTGTTGCCTTAGCAAT miR528 WT    TGAAGCTGGACTTCACTTTTGCCTCTCTCTCCTGTGCTTTCCATTCCTGCTGCTAGGCTGTTCTGTG EarI a-1   TGAAGCTGGACTTCACTTTTGCCTCTCTCTCCTG----------------TTCCTGCTGCTAGGCTGTTCTGTG
             TGAAGCTGGACTTCACTTTTGCCTCTCTCTCCTG--CT----TCTTCCATTCCTGCTGCTAGGCTGTTCTGTG
       a-3   TGAAGCTGGACTTCACTTTTGCCTCTCTCTCCT-----------------TCCTGCTGCTAGGCTGTTCTGTG
             TGAAGCTGGACTTCACTTTTGCCTCTCTCTCCT-----------------TCCTGCTGCTAGGCTGTTCTGTG
       b-8   TGAAGCTGGACTTCACTTTTGCCTCTCTCTCCTGT--------CTTCCATTCCTGCTGCTAGGCTGTTCTGTG
             TGAAGCTGGACTTCACTTTTGCCTCTCTCTCCTGTGCT----TCTTCCATTCCTGCTGCTAGGCTGTTCTGTG
       b-21  TGAAGCTGGACTTCACTTTTGCCTCTCTCTCCTGT--------CTTCCATTCCTGCTGCTAGGCTGTTCTGTG
             TGAAGCTGGACTTCACTTTTGCCTCTCTCTCCTGT-----------CCATTCCTGCTGCTAGGCTGTTCTGTG
```

OsPDS-TATC

OsDEP1-TATC

OsPDS-TATG

OsROC5-TATG

Figure 8B:
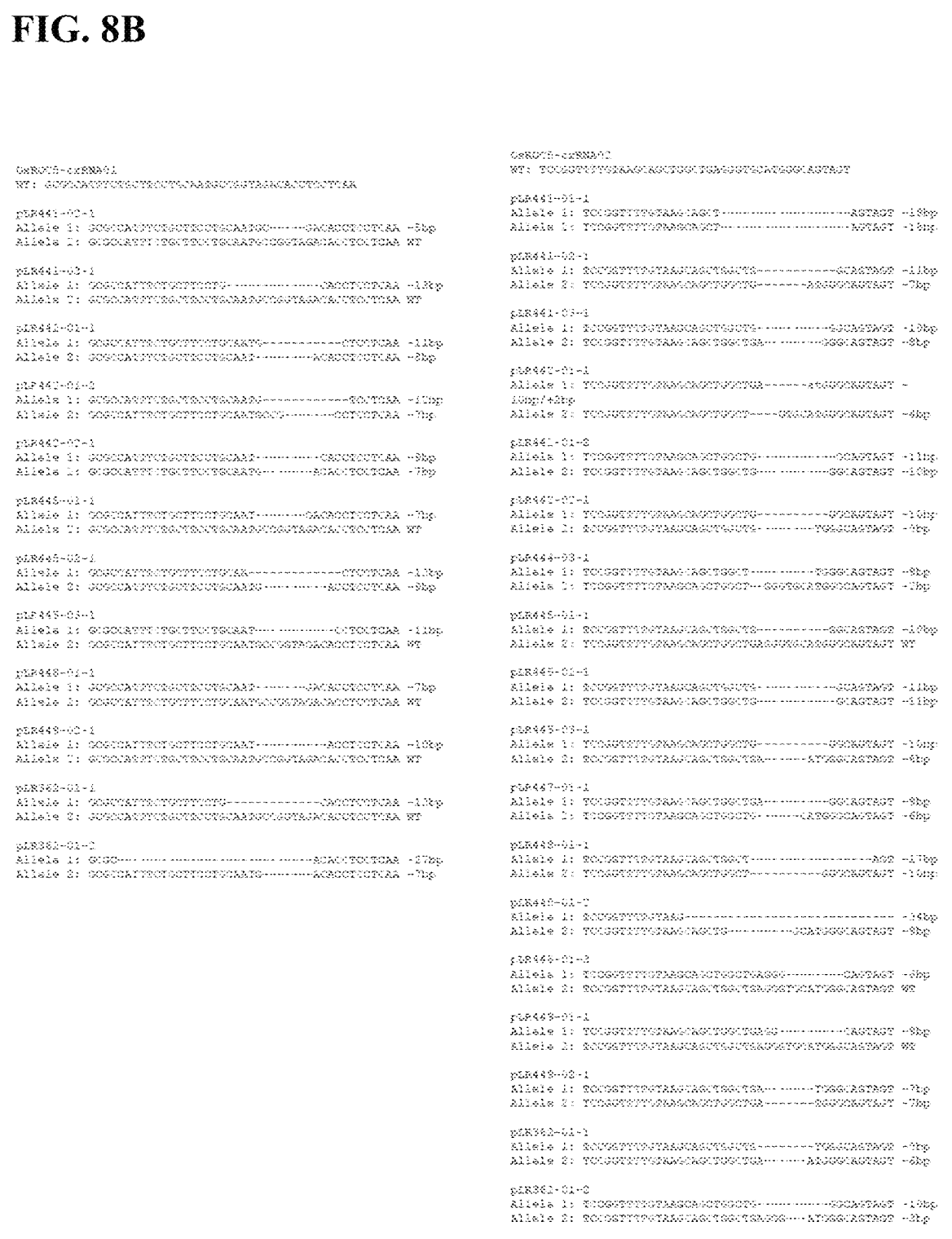

```
OsROT5-crRNA01
WT: GCGTCATTCTGCTTCTTCTAAGCTGCTAGCACTCCTCAA pLR441-02-1
Allele 1: GCGTCATTCTGCTTCCTGCAAGGC------------GACACCTCCTCAA -8bp
Allele 2: GCGTCATTCTGCTTCTTGCAAGCTCGGTAGCACTCCTCAA WT pLR441-03-1
Allele 1: GCGTCATTCTGCTTCCTG------------CACCTCCTCAA -13bp
Allele 2: GCGTCATTCTGCTTCCTGCAAGCTCGGTAGCACTCCTCAA WT pLR441-01-1
Allele 1: GCGTCATTCTGCTTTCTGTAATC------------CTCCTCAA -11bp
Allele 2: GCGTCATTCTGCTTCCTGCAAG------------ACGCCTCCTCAA -8bp pLR441-04-2
Allele 1: GCGTCAGTTCTGCTTCTGCAAG------------GCCTCAA -10bp
Allele 2: GCGTCATTCTGCTTCTGCATGCG------------CCTCAA -7bp pLR442-02-1
Allele 1: GCGTCATTCTGCTTCCTGCAAT------------CACCTCCTCAA -9bp
Allele 2: GCGTCATTCTGCTTCCTGCAATC------------ACACTCCTCAA -7bp pLR443-01-1
Allele 1: GCGTCATTCTGCTTCCTGCAAT------------GACACCTCCTCAA -7bp
Allele 2: GCGTCATTCTGCTTCCTGCAAGCTCGGTAGCACTCCTCAA WT pLR446-02-1
Allele 1: GCGTCATTCTGCTTTCTGTAA------------CTCCTCAA -13bp
Allele 2: GCGTCATTCTGCTTCCTGCAAG------------ACCTCCTCAA -9bp pLR443-03-1
Allele 1: GCGTCATTCTGCTTCCTGCAAT------------CCTCCTCAA -11bp
Allele 2: GCGTCATTCTGCTTCCTGCAATGCCGTAGCACCTCCTCAA WT pLR448-01-1
Allele 1: GCGTCATTCTGCTTCCTGCAAD------------GATACCTCCTCAA -7bp
Allele 2: GCGTCATTCTGCTTTCTGTAATGCCGTAGCACGCCTCCTCAA WT pLR448-02-1
Allele 1: GCGTCATTCTGCTTCCTGCAAT------------ACCTCCTCAA -10bp
Allele 2: GCGTCATTCTGCTTCCTGCAAGCTCGGTAGCACTCCTCAA WT pLR362-01-1
Allele 1: GCGTCATTCTGCTTTCTG------------CACCTCCTCAA -13bp
Allele 2: GCGTCATTCTGCTTCCTGCAAGCCGGTAGCACCTCCTCAA WT pLR362-01-2
Allele 1: GCGC------------ACACCTCCTCAA -27bp
Allele 2: GCGTCATTCTGCTTCCTGCATG------------ACGCCTCCTCAA -7bp
```

```
OsROT5-crRNA02
WT: TCCGGTTTTGTAAGCAGCTGGCTGAGGTCACTGGCAGTAGT pLR441-01-1
Allele 1: TCCGGTTTTGTAAGCAGCT------------AGTAGT -18bp
Allele 2: TCCGGTTTTGTAAGCAGCT------------AGTAGT -18bp pLR441-02-1
Allele 1: GCCGGTTTTGTAAGCAGCTGGCTG------------GCAGTAGT -11bp
Allele 2: TCCGGTTTTGTAAGCAGCTGGCTG------------AGGGCAGTAGT -7bp pLR441-03-1
Allele 1: TCCGGTTTTGTAAGCAGCTGGCTG------------GGCAGTAGT -10bp
Allele 2: TCCGGTTTTGTAAGCAGCTGGCTGA------------GGGCAGTAGT -8bp pLR441-01-1
Allele 1: TCCGGTTTTGTAAGCAGCTGGCTGA------------ctGGGCAGTAGT -10bp/+2bp
Allele 2: TCCGGTTTTGTAAGCAGCTGGCT------------CGCACAGGGCAGTAGT -4bp pLR441-01-2
Allele 1: TCCGGTTTTGTAAGCAGCTGGCTG------------CCAGTAGT -11bp
Allele 2: TCCGGTTTTGTAAGCAGCTGGCTG------------GGCAGTAGT -10bp pLR442-02-1
Allele 1: TCCGGTTTTGTAAGCAGCTGGCTG------------GGCAGTAGT -10bp
Allele 2: GCCGGTTTTGTAAGCAGCTGGCTG------------TGGCAGTAGT -7bp pLR444-03-1
Allele 1: TCCGGTTTTGTAAGCAGCTGGCT------------TGGGCAGTAGT -9bp
Allele 2: TCCGGTTTTGTAAGCAGCTGGCT------------GGGTGCAGGGCAGTAGT -7bp pLR445-01-1
Allele 1: GCCGGTTTTGTAAGCAGCTGGCTG------------GGCAGTAGT -10bp
Allele 2: TCCGGTTTTGTAAGCAGCTGGCTGAGGTCACTGGCAGTAGT WT pLR445-01-1
Allele 1: GCCGGTTTTGTAAGCAGCTGGCTG------------GCAGTAGG -11bp
Allele 2: TCCGGTTTTGTAAGCAGCTGGCTG------------GTAGTAGT -11bp pLR443-03-1
Allele 1: TCCGGTTTTGTAAGCAGCTGGCTG------------GGCAGTAGT -10bp
Allele 2: GCCGGTTTTGTAAGCAGCTGGCTGA------------ATGGCAGTAGT -8bp pLR447-01-1
Allele 1: TCCGGTTTTGTAAGCAGCTGGCTGA------------GGCAGTAGT -9bp
Allele 2: TCCGGTTTTGTAAGCAGCTGGCTG------------CATGGGCAGTAGT -6bp pLR448-01-1
Allele 1: GCCGGTTTTGTAAGCAGCTGGCT------------AGT -17bp
Allele 2: TCCGGTTTTGTAAGCAGCTGGCT------------GGCAGTAGT -10bp pLR446-01-1
Allele 1: GCCGGTTTTGTAAG------------ -16bp
Allele 2: TCCGGTTTTGTAAGCAGCTG------------GCATGGGCAGTAGT -8bp pLR446-01-2
Allele 1: TCCGGTTTTGTAAGCAGCTGGCTGAGGC------------CAGTAGT -6bp
Allele 2: GCCGGTTTTGTAAGCAGCTGGCTGAGGTCATGGCAGTAGT WT pLR443-01-1
Allele 1: TCCGGTTTTGTAAGCAGCTGGCTGAGG------------CAGTAGT -9bp
Allele 2: GCCGGTTTTGTAAGCAGCTGGCTGAGGTGTGATGGCAGTAGT WT pLR443-02-1
Allele 1: GCCGGTTTTGTAAGCAGCTGGCTGA------------TGGGCAGTAGT -7bp
Allele 2: TCCGGTTTTGTAAGCAGCTGGCTGA------------GGGCAGTAGT -7bp pLR362-01-1
Allele 1: GCCGGTTTTGTAAGCAGCTGGCTG------------TGGGCAGTAGT -9bp
Allele 2: TCCGGTTTTGTAAGCAGCTGGCTGA------------ATGGGCAGTAGT -8bp pLR362-01-2
Allele 1: TCCGGTTTTGTAAGCAGCTGGCTG------------GGCAGTAGT -10bp
Allele 2: GCCGGTTTTGTAAGCAGCTGGCTGAGG------------ATGGCAGTAGT -8bp
```

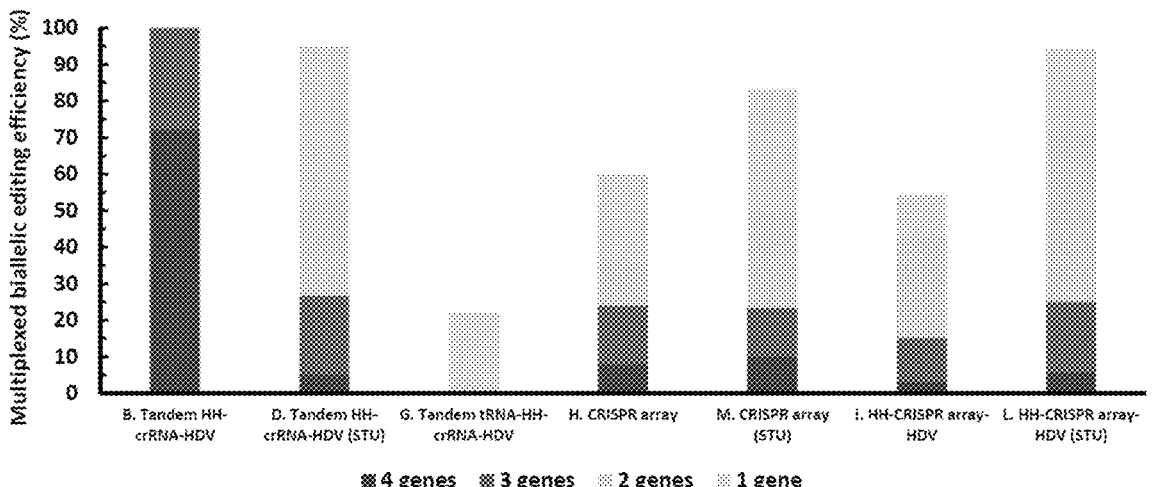
FIG. 17C
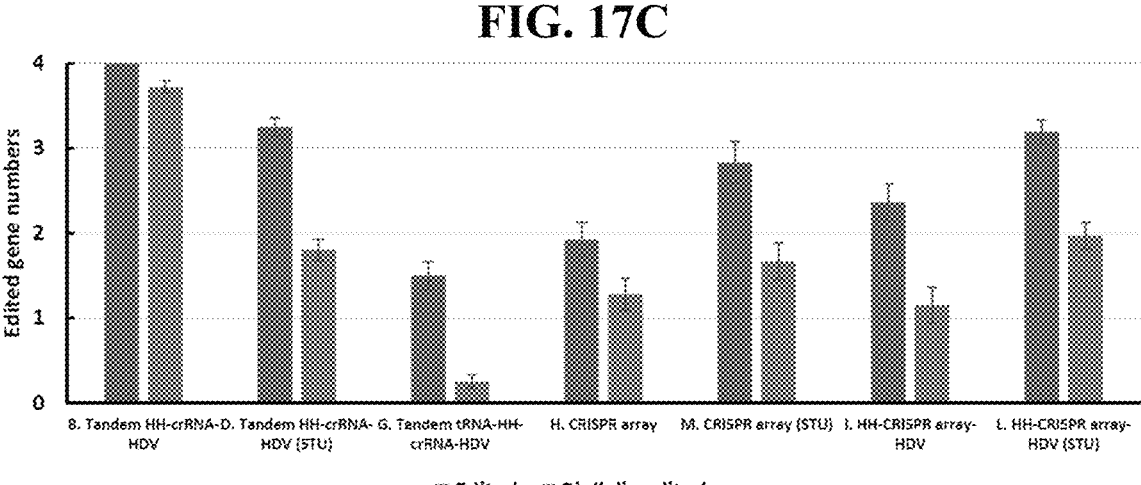
FIG. 18A
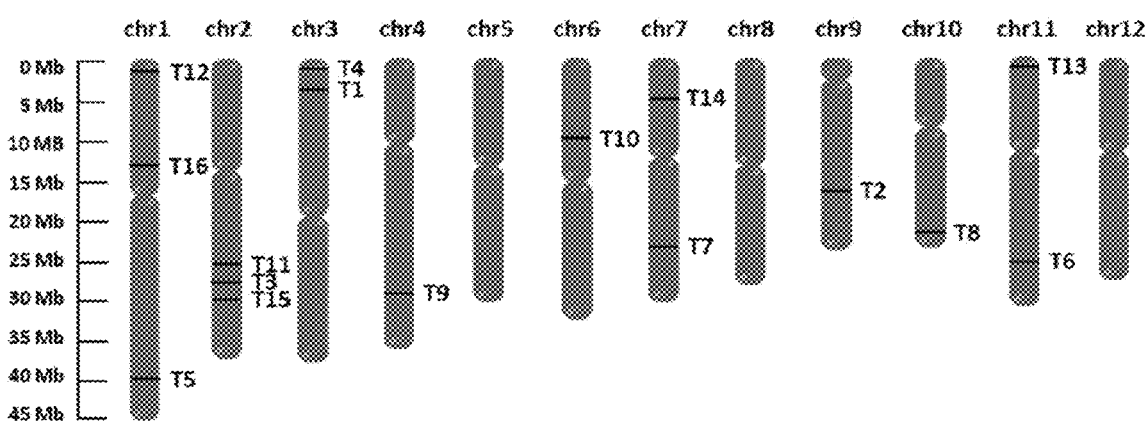

FIG. 18B

```
T1     WT    ACCTTT...AATAAACGAAAAACA                    T9     WT    CACTTT...GTCGTGGTGGGA
LINE 14      ACCTTTGGAGT----------------------GAAAAAGA    LINE 14      CACTTTCT-------------------GTAGGAGGA
             AGCTTTGGAGTGAAATCTCTTG---------AATAAAGGAAAAGA              CACTTTCTGTATCTCCGACA------TCACGTCGTGGTAGGAGGA
LINE 21      AGCTTTGGAGTGAAATCTCTT-----------AATAAAGGAAAAGA   LINE 21      CACTTTCTGTAT--------(34 bp deletion)---------
             AGCTTTGGAGTGAAATCTCTT----------AATAAAGGAAAAGA              CACTTTCTGTATCTCCGACAC----------------TAGGAGGA T2     WT    GTCTTT...AGTGCAAAAGACCAA                     T10    WT    GACTTTGGAT...AGCCCTCGGGCACACC
LINE 14      GTCTTTGCTACTGTTGCAAGTGCTCACCCAAGTGCAAAAGACCAA    LINE 14      GACTTTGGATGATGCATCA-------------CCTCGGGCACACC
             GTCTTTGCTACTGTTGCAAGTGC-----------------AAAAGACCAA             GACTTTGGATGATGCATCAG------GAACGCCCTCGGGCACACC
LINE 21      GTCTTTGCTACTGTTGCAA----------AAGTGCAAAAGACCAA    LINE 21      GACTTTGGATGATGCATC----------CGCCCTCGGGCACACC
             GTCTTTGCTACTGTTGCAAG---------------------AGACCAA              GACTTTGGATGATGCATCAGGTA----------CTCGGGCACACC T3     WT    CCATTT...ACCTCCTCAAGCACT                     T11    WT    GCATTTA...TCTGTGCTCATGAG
LINE 14      CCATTTCTGCTTCTGCAATG-----------ACACCTCCTCAAGCACT   LINE 14      GCATTTA-GGGTGGA----------------------G
             CCATTTCTGCTTCCTGCAATG---------CACCTCCTCAAGCACT              GCATTTA-GGGTGAAAG-GGAC-------------TCTGTGCTCATGAG
LINE 21      CCATTTCTGCTTCCTGCAA---------------ACCTCCTCAAGCACT   LINE 21      GCATTTA-GGGTGAAAG-GGAC-----------ATCTGTGCTCATGAG
             CCATTTCTGCTTCCTGCAAT------------CTCCTCAAGCACT              GCATTTA-GGGTGAAAG-GGAC-----C--------GTGCTCATGAG T4     WT    ACTTT...TTGCATTCCTGCTGC                      T12    WT    CCATTT...ATAGATTACAAGGAG
LINE 14      ACTTTTGCCTCTCTCTCCTGTGCTTGCCTCTTTCATTCCTGCTGC    LINE 14      CCATTTCTGGGGCCTTGCGA-----------TAGATTACAAGGAG
             AGTTTTGCCTCTCTCCTGTGCTTGCCTCTTCATTCCTGCTGC              CCATTTCTGGGGCCTTGC---------------GATTACAAGGAG
LINE 21      ACTTTTGCCTCTCTCCTGTGCTTGCCTTTTCATTCCTGCTGC    LINE 21      CCATTTCTGGGGCCTTGCAAG--------CATAGATTACAAGGAG
             AGTTTTGCCTCTCTCCTGTGCTTGCCTCTTCATTCCTGCTGC              CCATTTCTGGGGCCTTGCAAGG----CCTGCATAGATTACAAGGAG T5     WT    TTGTTTGAA...GCCCCACATCTACCA                  T13    WT    AAATTTG...AAACACACTAGTCATATC
LINE 14      TTGTTTGAAGAAGGGTTATGGC-------GCTTGCCCCACATCTACCA   LINE 14      AAATTTGCCGGCAGCTAATAGG--------ACACACTAGTCATATC
             TTGTTTGAAGAAGGGTTATGGC-------TTGCCCCACATCTACCA              AAATTTGCCGGCAGCTAA--------TAAACACACTAGTCATATC
LINE 21      TTGTTTGAAGAAGGGTTATGGC-------TGCCCCACATCTACCA    LINE 21      AAATTTGCCGGCAGCTAATAGG---------ACACTAGTCATATC
             TTGTTTGAAGAAGGGTTATGGT-------TGCCCCACATCTACCA              AAATTTGCCGGCAGCTAATA-----------CACACTAGTCATATC T6     WT    GGATTT...ATGGCCCGGCCATGT                     T14    WT    TGCTTTATA...ACACAGGAGGAGGTTG
LINE 14      GGATTTGGGCCATGGAGACAG-----------ATGGCCCGGCCATGT   LINE 14      TGCTTTATAGGTGGAAACAAT---------------GAGGAGGAGGTTG
             GGATTTGGGCCATGGAGACAG-----------------GCCCGGCCATGT            TGCTTTATAGGTGGAAACAAT---------------TG
LINE 21      GGATTTGGGCATGGAGACAG--------GATGGCCCGGCCATGT    LINE 21      TGCTTTATAGGTGGAAACAA-----------------GGAGGAGGTTG
             GGATTTGGGCCATGGAGACAG-------------------ATGT              TGCTTTATAGGTGGAAACAAT------------GAGGAGGAGGTTG T7     WT    ACCTTT...AATACTTTATTTAAGTC                   T15    WT    CTCTTT...AGGTAAGAAAGAACT
LINE 14      ACCTTTGGGCACCATATGCCTT-------------ACTTTATTTAAGTC  LINE 14      CTCTTTCTCCTGAGGAGCAAGA-----------------AAGAACT
             ACCTTTGGGCACCATATGCTT---------------TTATTTAAGTC              CTCTTTCTCCTGAGGAGCAAG-G----T---CAGGTAAGAAAGAACT
LINE 21      ACCTTTGGGCACCATATGCTTGCT----------TACTTTATTTAAGTC  LINE 21      CTCTTTCTCCTGAGGAGCAAG------------TAAGAAAGAACT
             ACCTTTGGGCACCATATGCTTGCT------------TTATTTAAGTC              CTCTTTCTCCTGAGGAGCAAG-------------------AACT T8     WT    ACCTTT...GCCCACCTACATTGAT                    T16    WT    ATGTTTGAGCATATG...AAAAAACTGAATCCCAA
LINE 14      ACCTTTAACCCTGTGTGA--------------------T       LINE 14      ATGTTTGAGCATATGGTTGTAA---------ACTGAATCCCAA
             ACCTTTAACCCTGTGTGAAT-----------CCACCTACATTGAT              ATGTTTGAGCATATGGTTGTAA---------ACTGAATCCCAA
LINE 21      ACCTTTAACCCTGTGTGAATG--------CCCACCTACATTGAT    LINE 21      ATGTTTGAGCA--------------------------A
             ACCTTTAACCCTGTGTGAATGGTCAGTAAGCCCACCTACATTGAT              ATGTTTGAGCATATG------(41 bp deletion)-----------
```

FIG. 19A

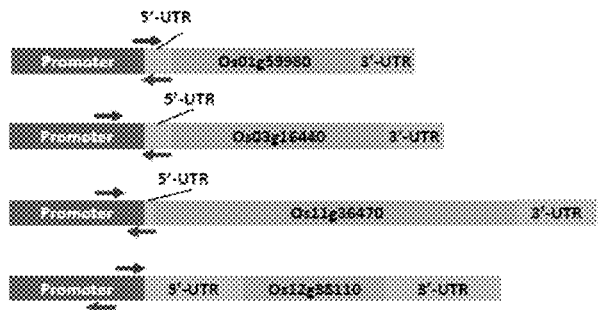

FIG. 19B
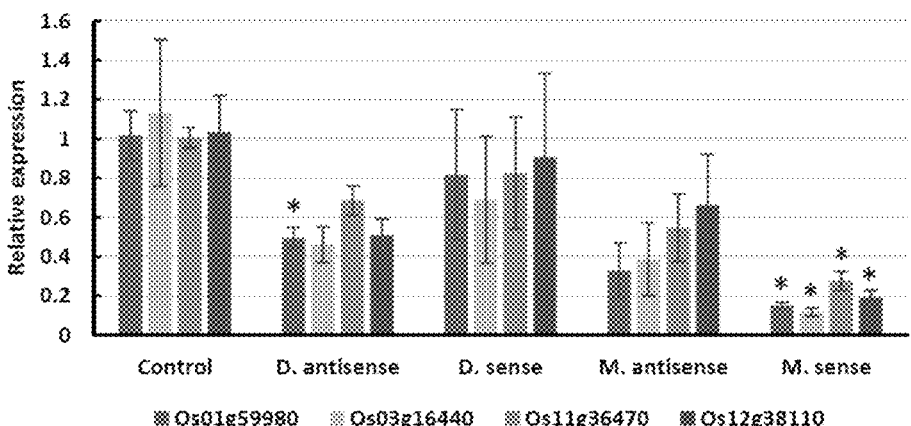
FIG. 19C
FIG. 19D

SYSTEMS AND METHODS FOR PLANT GENOME EDITING USING Cas 12a ORTHOLOGS

CROSS-REFERENCE TO RELATED APPLICATION

The benefit under 35 USC § 119 of U.S. Provisional Patent Application 62/930,940 filed Nov. 5, 2019 in the names of Yiping QI and Yingxiao ZHANG for "SYSTEM AND METHODS FOR PLANT GENOME EDITING USING CAS12a ORTHOLOGS" is hereby claimed. The disclosure of U.S. Provisional Patent Application 62/930, 940 is hereby incorporated herein by reference, in its entirety, for all purposes.

REFERENCE TO SEQUENCE LISTING

This application includes an electronically submitted sequence listing in .txt format. The .txt file contains a sequence listing entitled 264_UpdatedSequence-Listing_ST25.txt" created on Sep. 26, 2024 and is 433,536 bytes in size. The sequence listing contained in this .txt file is part of the specification and is hereby incorporated by reference herein in its entirety.

FIELD

The present disclosure relates generally to systems and methods for genome editing of plants. In more specific aspects, the present disclosure relates to orthologs of Clustered Regularly Interspaced Short Palindromic Repeats (CRISPR)-associated protein 12 (CRISPR-Cas12a) endonuclease having utility for gene editing at moderate temperatures, e.g., 25° C. and lower temperature, to nuclease complexes of such protein orthologs and guide RNA, to CRISPR plant gene editing systems, to methods of using such gene editing systems for transforming plants, and to plants transformed by such gene editing.

DESCRIPTION OF THE RELATED ART

CRISPR (clustered regularly interspaced short palindromic repeats) is a family of DNA sequences found in genomes of bacteria and Archaea, deriving from previously infecting bacteriophages from which pathogenic DNA segments have been cut by CRISPR-associated (Cas) proteins and assimilated into the immune systems of such prokaryotic organisms. In the CRISPR-Cas process, the target DNA region is cut by the Cas nuclease after the Cas protein has been guided to the cut site by a guide RNA (gRNA) template complementary to the target DNA strand, in the presence of a necessary protospacer adjacent motif (PAM) downstream of and in close proximity to the cut site on the DNA. Various CRISPR-associated (Cas) nucleases have been identified. These include for example CRISPR-associated protein 9, which is present in the CRISPR-Cas system of *Streptococcus pyogenes*, and contains the nuclease domains HNH and RuvC, for cleaving target DNA and nontarget DNA, respectively.

The implications of the CRISPR-Cas system as a genome editing tool were recognized almost immediately after the CRISPR-Cas system was first discovered, and major efforts have been made globally to develop techniques and applications for its scientific and commercial use.

Among Cas proteins, Cas12a has been utilized in corresponding CRISPR-Cas12a systems to target AT-rich regions, and has demonstrated high editing efficiencies in some plants, but nonetheless has deficiencies that have limited its utility. Cas12a has a major limitation of requiring relatively long PAM sequences, which are less frequent than NGG PAMs required for Cas9. For example, LbCas12a, a commonly used Cas12a nuclease, requires a relatively long PAM sequence (TTTV) and does not achieve high efficiencies for NTTV PAMs or TATV PAMs. In addition, existing Cas12a nucleases typically require high temperatures (e.g., 28° C. and above) in the editing process. Such Cas12a nucleases therefore are not suitable for use in genomic editing of plants that live at and require lower temperatures, and which are susceptible to heat shock and degradation at the conditions required for the use of these existing nucleases.

It therefore would be a substantial advance in the art to provide CRISPR-Cas systems that overcome such PAM sequence deficiencies and high temperature constraints, and that achieve high target specificity and enable high-efficiency genomic editing of plants, including plant species requiring low temperatures. It would likewise be a substantial advance in the art to provide CRISPR-Cas systems of such character that additionally exhibit high multiplexed editing activity when simultaneously targeting multiple plant genes.

SUMMARY

The present disclosure generally relates to genomic editing of plants, and more specifically to Cas12a endonucleases, to CRISPR-Cas12a systems, to methods of genomically editing plants, and to transformed plants produced by such editing.

In one aspect, the disclosure relates to a non-naturally occurring heterologous CRISPR-Cas 12a genomic editing system, comprising or encoding at least one Cas 12a ortholog endonuclease selected from the group consisting of Lb5Cas12a, CMaCas12a, BsCas12a, BoCas12a, MlCas12a, Mb2Cas12a, MbCas12a TsCas12a, and MAD7® ErCas12a endonucleases.

In another aspect, the disclosure relates to a method of genomically editing a plant, comprising introducing into such plant a non-naturally occurring heterologous CRISPR-Cas12a genomic editing system of the present disclosure, to cause the Cas12a ortholog nuclease to cleave DNA in the plant to alter the plant's gene expression.

Other aspects, features and embodiments of the disclosure will be more fully apparent from the ensuing description and appended claims.

BRIEF DESCRIPTION OF THE DRAWINGS

FIG. 1A shows the editing efficiencies of LbCas12a and nine Cas12a orthologs at OsDEP1 and OsEPFL9 sites with TTTV PAMs, and FIG. 1B shows corresponding results for OsROC5 and OsDEP1 sites with TTV PAMs. FIGS. 1C and 1D show the distribution of deletion sizes and deletion positions of Mb2Cas12a at two TTTV and two TTV PAM sites (OsDEP1-TTTV=SEQ ID NO: 51; OsEPFL9-TTTV=SEQ ID NO: 52; OsDEP1-TTV=SEQ ID NO: 53; and OsROC5-TTV=SEQ ID NO: 54). FIG. 1E shows the editing efficiencies of Mb2Cas12a at 18 VTTV PAM sites. WT editing efficiencies were subtracted for each PAM site in FIG. 1E. Error bars represent standard errors of three biological replicates.

FIGS. 3A-3D show the specificity and protospacer length requirement of Cas12a orthologs. FIGS. 3A-3B show the editing efficiencies of four Cas12a orthologs at OsEPFL9 with mismatched crRNAs. Sequences are the same for each of Mb2, Lb5, Bs, and MAD7® ErCas12a (MM6=SEQ ID NO: 55; MM5=SEQ ID NO: 56; MM4=SEQ ID NO: 57; MM3=SEQ ID NO: 58; MM2=SEQ ID NO: 59; MM1=SEQ ID NO: 60; no MM=SEQ ID NO: 61). FIGS. 3C-3D show the editing efficiencies of four Cas12a orthologs at OsEPFL9 with shortened crRNAs. Sequences are the same for each of Mb2, Lb5, Bs, and MAD7® ErCas12a (23 nt=SEQ ID NO: 62; 21 nt=SEQ ID NO: 63; 19 nt=SEQ ID NO: 64; 17 nt=SEQ ID NO: 65; 15 nt=SEQ ID NO: 66). WT editing efficiencies were subtracted. Error bars represent standard errors of three biological replicates.

FIGS. 4A and 4B show the results of gene editing using Cas12a orthologs in stable transgenic plants, in the editing efficiencies of eight Cas12a orthologs at OsDEP1 and OsEPFL9 sites with TTTV PAMs.

FIGS. 5A-5C illustrate multiplexed gene editing using Cas12a orthologs in stable transgenic plants. FIG. 5A is a schematic illustration of two constructs that were used for multiplexed genome editing targeting four genes using Mb2Cas12a. FIG. 5B shows editing efficiencies and biallelic editing efficiencies for each target gene. Dark grey indicates edited allele while light grey indicates non-edited allele. FIG. 5C shows genotyping results of four independent transgenic lines. Two lines are shown for each construct (PDS (WT=SEQ ID NO: 67; a-1, line 1=SEQ ID NO: 68; a-1, line 2=SEQ ID NO: 69; a-3, line 1=SEQ ID NO: 70; a-3, line 2=SEQ ID NO: 71; b-8, line 1=SEQ ID NO: 72; b-8, line 2=SEQ ID NO: 73; b-21, line 1=SEQ ID NO: 74, b-21, line 2=SEQ ID NO: 75); DEP1 (WT=SEQ ID NO: 76; a-1, line 1=SEQ ID NO: 77; a-1, line 2=SEQ ID NO: 78; a-3, line 1=SEQ ID NO: 79; a-3, line 2=SEQ ID NO: 80; b-8, line 1=SEQ ID NO: 81; b-8, line 2=SEQ ID NO: 82; b-21, line 1=SEQ ID NO: 83, b-21, line 2=SEQ ID NO: 84); ROCS (WT=SEQ ID NO: 85; a-1, line 1=SEQ ID NO: 86; a-1, line 2=SEQ ID NO: 87; a-3, line 1=SEQ ID NO: 88; a-3, line 2=SEQ ID NO: 89; b-8, line 1=SEQ ID NO: 90; b8, line 2=SEQ ID NO: 91; b-21, line 1=SEQ ID NO: 92, b-21, line 2=SEQ ID NO: 93); miR528 (WT=SEQ ID NO: 94; a-1, line 1=SEQ ID NO: 95; a-1, line 2=SEQ ID NO: 96; a-3, line 1=SEQ ID NO: 97; a-3, line 2=SEQ ID NO: 98; b-8, line 1=SEQ ID NO: 99; b8, line 2=SEQ ID NO: 100; b-21, line 1=SEQ ID NO: 101, b-21, line 2=SEQ ID NO: 102)).

FIG. 7A shows six multiplexing strategies consisting of 10 multiplexing systems ('A' through T). FIG. 7B shows genotyping results of individual T0 lines for 10 multiplexing systems. Biallelic or homozygous editing was indicated by dark green color. Unedited (e.g. WT allele) was indicated by light green color. Three independent T0 lines were analyzed for each system except for 'D' where only two lines were used.

FIGS. 8A-8B show genotypes of T0 plants for eleven multiplexing strategies (OsDEP1-crRNA01 (WT=SEQ ID NO: 103); pLR442-01-1 (Allele 1=SEQ ID NO: 104; Allele 2=SEQ ID NO: 105); pLR442-01-2 (Allele 1=SEQ ID NO:

Figure 1A:
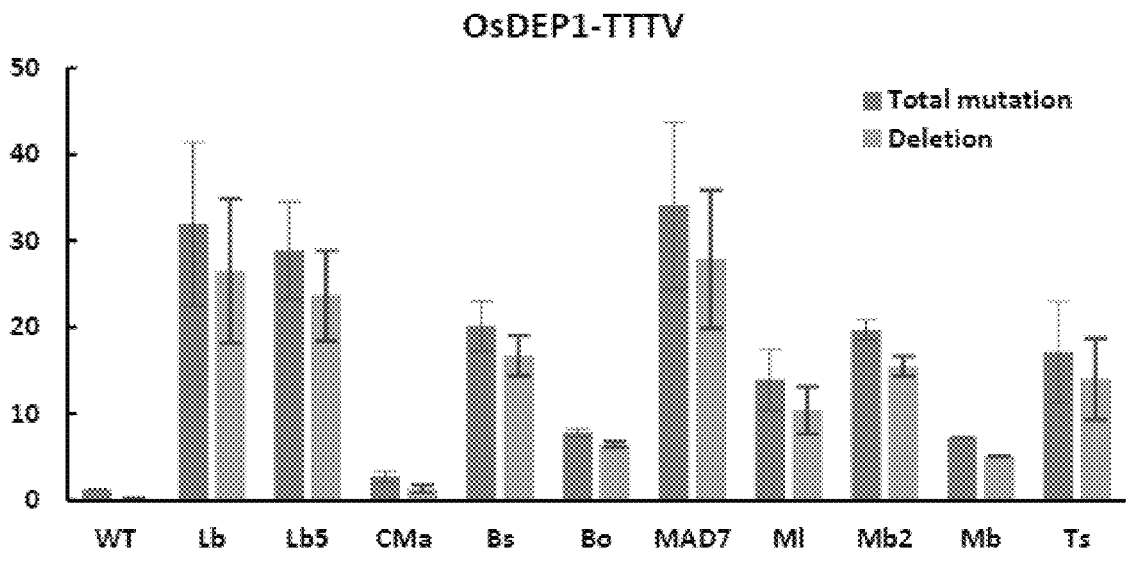
FIGS. 1A-1E show the results of genome editing using Cas12a orthologs in plant cells.
Figure 1A:
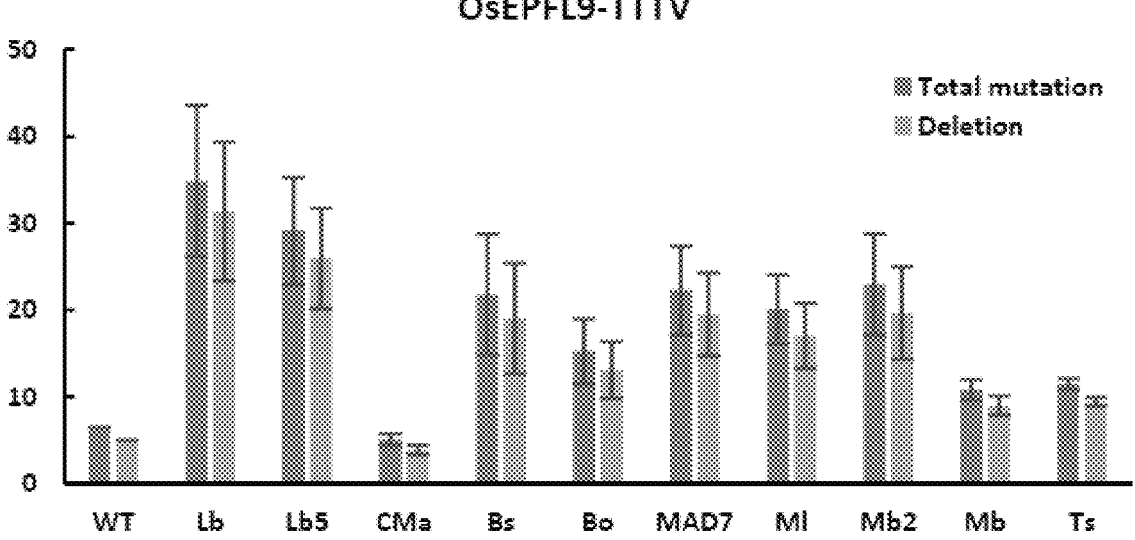

106; Allele 2=SEQ ID NO: 107); pLR442-02-1 (Allele 1=SEQ ID NO: 108; Allele 2=SEQ ID NO: 109); pLR445-01-1 (Allele 1=SEQ ID NO: 110; Allele 2=SEQ ID NO: 111); pLR445-02-1 (Allele 1=SEQ ID NO: 112; Allele 2=SEQ ID NO: 113); pLR446-02-1 (Allele 1=SEQ ID NO: 114; Allele 2=SEQ ID NO: 115); pLR447-02-1 (Allele 1=SEQ ID NO: 116; Allele 2=SEQ ID NO: 117); pLR448-01-1 (Allele 1=SEQ ID NO: 118; Allele 2=SEQ ID NO: 119); pLR448-01-2 (Allele 1=SEQ ID NO: 120; Allele 2=SEQ ID NO: 121); pLR448-01-3 (Allele 1 and Allele 2 each <10 bp in length); pLR362-01-1 (Allele 1=SEQ ID NO: 122; Allele 2=SEQ ID NO: 123); pLR362-01-2 (Allele 1=SEQ ID NO: 124; Allele 2=SEQ ID NO: 125); OsDEP1-crRNA02 (WT (=SEQ ID NO: 126); pLR441-01-1 (Allele 1=SEQ ID NO: 127; Allele 2=SEQ ID NO: 128); pLR441-03-1 (Allele 1=SEQ ID NO: 129; Allele 2=SEQ ID NO: 130); pLR442-01-1 (Allele 1=SEQ ID NO: 131; Allele 2=SEQ ID NO: 132); pLR442-01-2 (Allele 1=SEQ ID NO: 133; Allele 2=SEQ ID NO: 134); pLR442-02-1 (Allele 1=SEQ ID NO: 135; Allele 2=SEQ ID NO: 136); pLR445-01-1 (Allele 1=SEQ ID NO: 137; Allele 2=SEQ ID NO: 138); pLR445-02-1 (Allele 1=SEQ ID NO: 139; Allele 2=SEQ ID NO: 140); pLR445-03-1 (Allele 1=SEQ ID NO: 1412; Allele 2=SEQ ID NO: 142); pLR448-01-1 (Allele 1=SEQ ID NO: 143; Allele 2=SEQ ID NO: 144); pLR448-01-2 (Allele 1=SEQ ID NO: 145; Allele 2=SEQ ID NO: 146); pLR448-01-3 (Allele 1=SEQ ID NO: 147; Allele 2=SEQ ID NO: 148); pLR449-01-1 (Allele 1=SEQ ID NO: 149; Allele 2=SEQ ID NO: 150); pLR449-02-1 (Allele 1=SEQ ID NO: too short; Allele 2=SEQ ID NO: 151); pLR362-01-1 (Allele 1=SEQ ID NO: 152; Allele 2=SEQ ID NO: 153); and pLR362-01-2 (Allele 1=SEQ ID NO: 154; Allele 2=SEQ ID NO: 155); OsROC5-crRNA01 (WT (=SEQ ID NO: 156); pLR441-02-1 (Allele 1=SEQ ID NO: 157; Allele 2=SEQ ID NO: 158); pLR441-03-1 (Allele 1=SEQ ID NO: 159; Allele 2=SEQ ID NO: 160); pLR442-01-1 (Allele 1=SEQ ID NO: 161; Allele 2=SEQ ID NO: 162); pLR442-01-2 (Allele 1=SEQ ID NO: 163; Allele 2=SEQ ID NO: 164); pLR442-02-1 (Allele 1=SEQ ID NO: 165; Allele 2=SEQ ID NO: 166); pLR445-01-1 (Allele 1=SEQ ID NO: 167; Allele 2=SEQ ID NO: 168); pLR445-02-1 (Allele 1=SEQ ID NO: 169; Allele 2=SEQ ID NO: 170); pLR445-03-1 (Allele 1=SEQ ID NO: 171; Allele 2=SEQ ID NO: 172); pLR448-01-1 (Allele 1=SEQ ID NO: 173; Allele 2=SEQ ID NO: 174); pLR449-02-1 (Allele 1=SEQ ID NO: 175; Allele 2=SEQ ID NO: 176); pLR362-01-1 (Allele 1=SEQ ID NO: 177; Allele 2=SEQ ID NO: 178); pLR362-01-2 (Allele 1=SEQ ID NO: 179; Allele 2=SEQ ID NO: 180); OsROC5-crRNA02 (WT (=SEQ ID NO: 181); pLR441-01-1 (Allele 1=SEQ ID NO: 182; Allele 2=SEQ ID NO: 183); pLR441-02-1 (Allele 1=SEQ ID NO: 184; Allele 2=SEQ ID NO: 185); pLR441-03-1 (Allele 1=SEQ ID NO: 186; Allele 2=SEQ ID NO: 187); pLR442-01-1 (Allele 1=SEQ ID NO: 188; Allele 2=SEQ ID NO: 189); pLR442-01-2 (Allele 1=SEQ ID NO: 190; Allele 2=SEQ ID NO: 191); pLR442-02-1 (Allele 1=SEQ ID NO: 192; Allele 2=SEQ ID NO: 193); pLR442-03-1 (Allele 1=SEQ ID NO: 194; Allele 2=SEQ ID NO: 195); pLR445-01-1 (Allele 1=SEQ ID NO: 196; Allele 2=SEQ ID NO: 197); pLR445-02-1 (Allele 1=SEQ ID NO: 198; Allele 2=SEQ ID NO: 199); pLR445-03-1 (Allele 1=SEQ ID NO: 200; Allele 2=SEQ ID NO: 201); pLR447-01-1 (Allele 1=SEQ ID NO: 202; Allele 2=SEQ ID NO: 203); pLR448-01-1 (Allele 1=SEQ ID NO: 204; Allele 2=SEQ ID NO: 205); pLR448-01-2 (Allele 1=SEQ ID NO: 206; Allele 2=SEQ ID NO: 207); pLR448-01-3 (Allele 1=SEQ ID NO: 208; Allele 2=SEQ ID NO: 209); pLR449-01-1 (Allele 1=SEQ ID NO: 210; Allele 2=SEQ ID NO: 211); pLR449-02-1 (Allele 1=SEQ ID NO: 212; Allele 2=SEQ ID NO: 213); pLR362-01-1 (Allele 1=SEQ ID NO: 214; Allele 2=SEQ ID NO: 215); and pLR362-01-2 (Allele 1=SEQ ID NO: 216; Allele 2=SEQ ID NO: 217)).

Figure 9A:
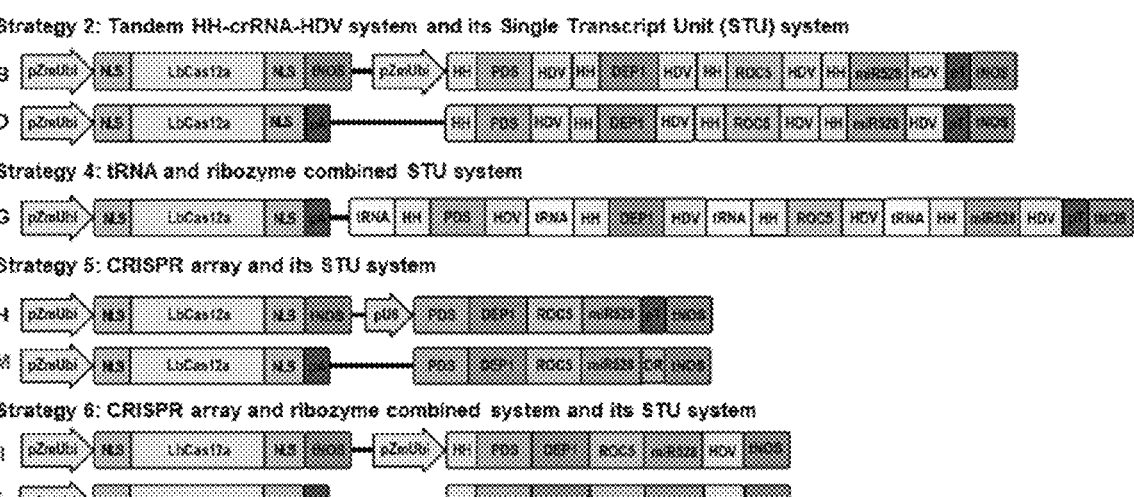
Figure 9B:
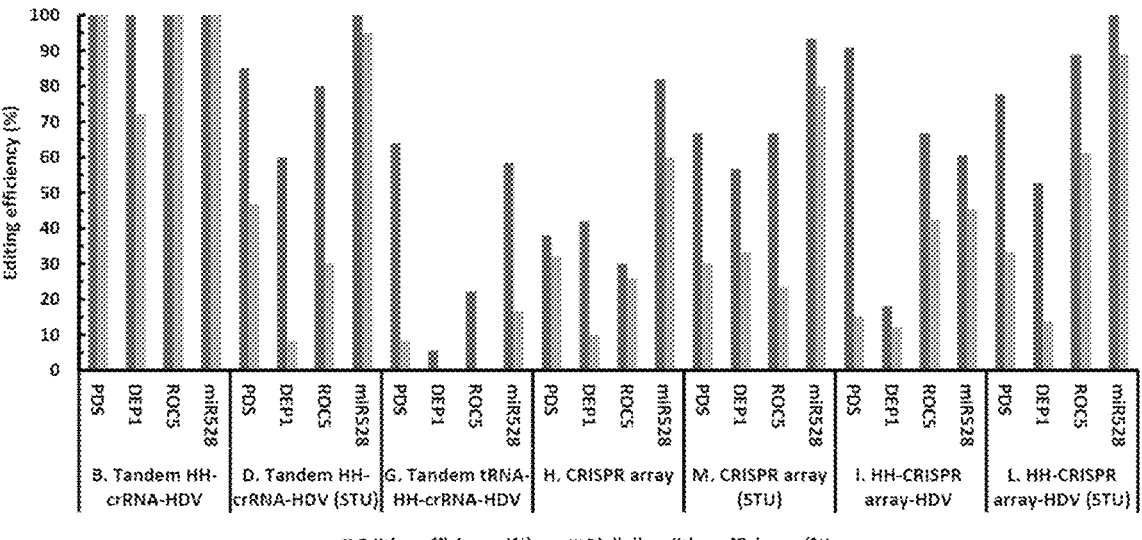

FIGS. 9A-9B illustrate the testing of seven refined multiplexing strategies for targeting four genes in rice T0 lines. FIG. 9A shows seven multiplexing systems based on four strategies. FIG. 9B is a graph of editing efficiency at four target genes by each of the seven multiplexing strategies. A total of 30 to 60 T0 lines were assayed for each construct. Both editing efficiency (in blue) and biallelic editing efficiency (in gray) are shown.

Figure 10:
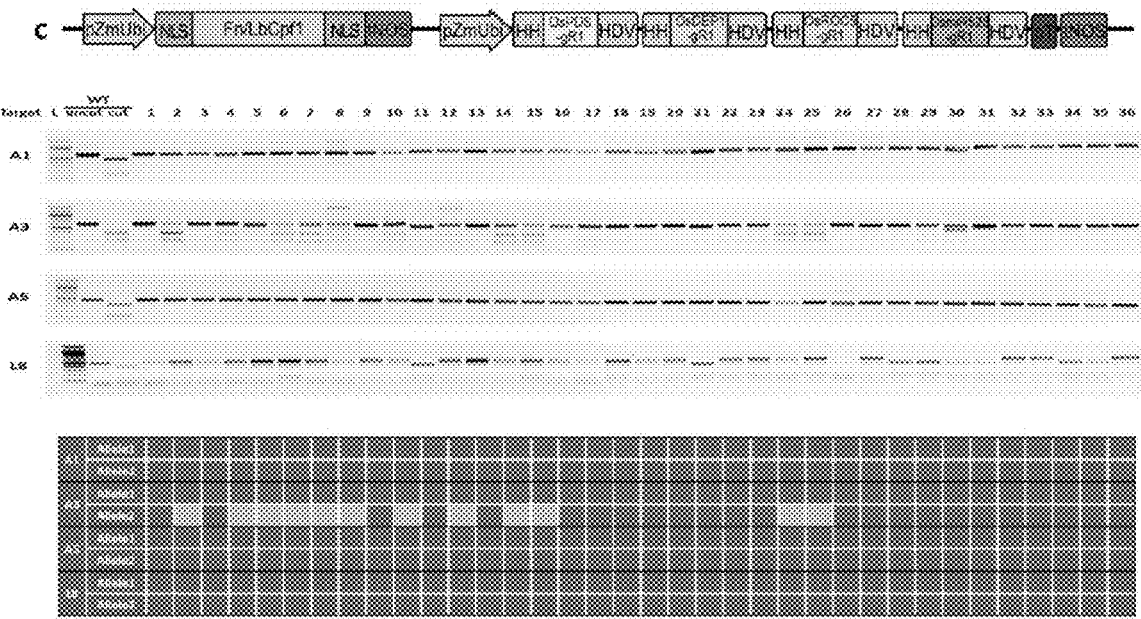

FIG. 10 illustrates an analysis of multiplexing strategy 'C' at four target genes with 36 T0 lines. An illustration of the multiplexing strategy is shown in the upper panel. The middle panel shows RFLP base genotyping data at four target sites along independent lines. The lower panel shows editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 11:
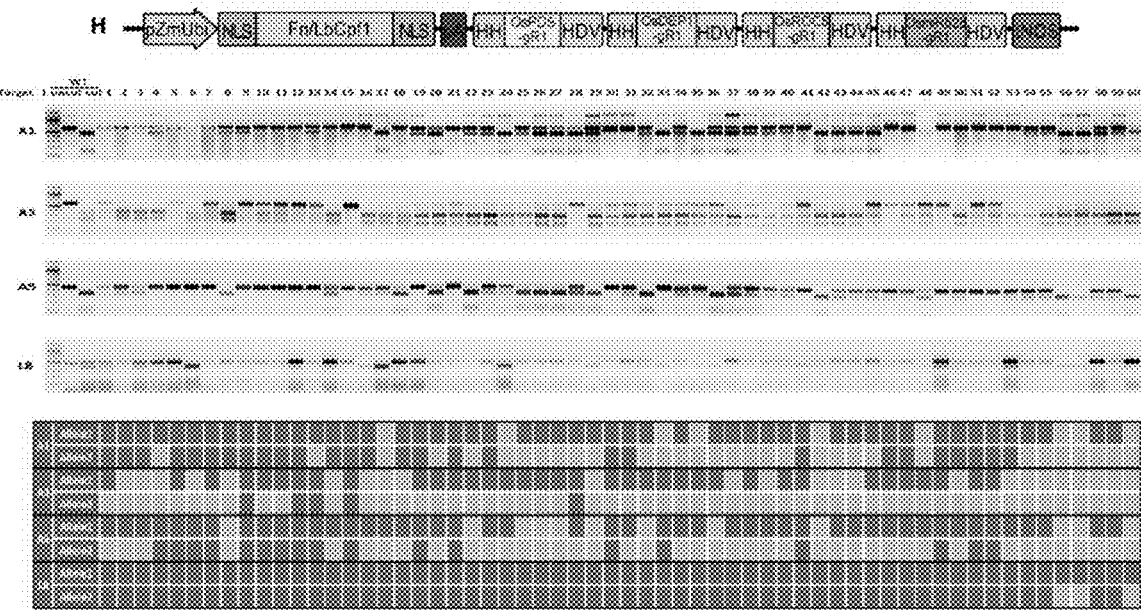

FIG. 11 illustrates an analysis of multiplexing strategy 'H' at four target genes with 60 T0 lines. An illustration of the multiplexing strategy is shown in the upper panel. The middle panel shows RFLP base genotyping data at four target sites along independent lines. The lower panel is a summary table showing editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 12:
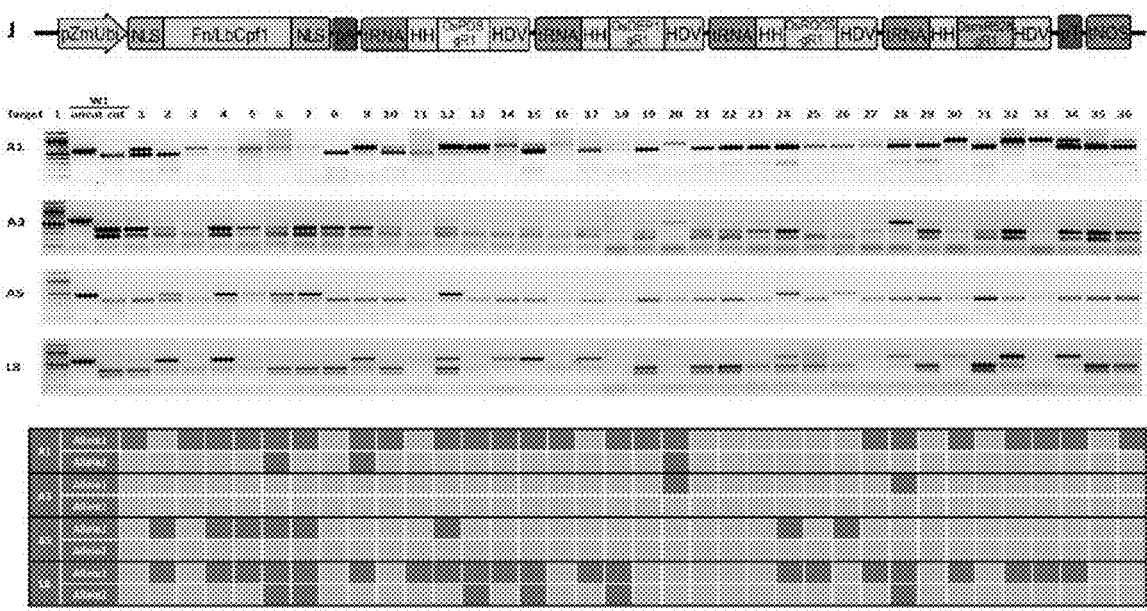

FIG. 12 shows an analysis of multiplexing strategy T at four target genes with 36 T0 lines. An illustration of the multiplexing strategy is shown in the upper panel. The middle panel shows RFLP base genotyping data at four target sites along independent lines. The lower panel is a summary table showing editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 13:
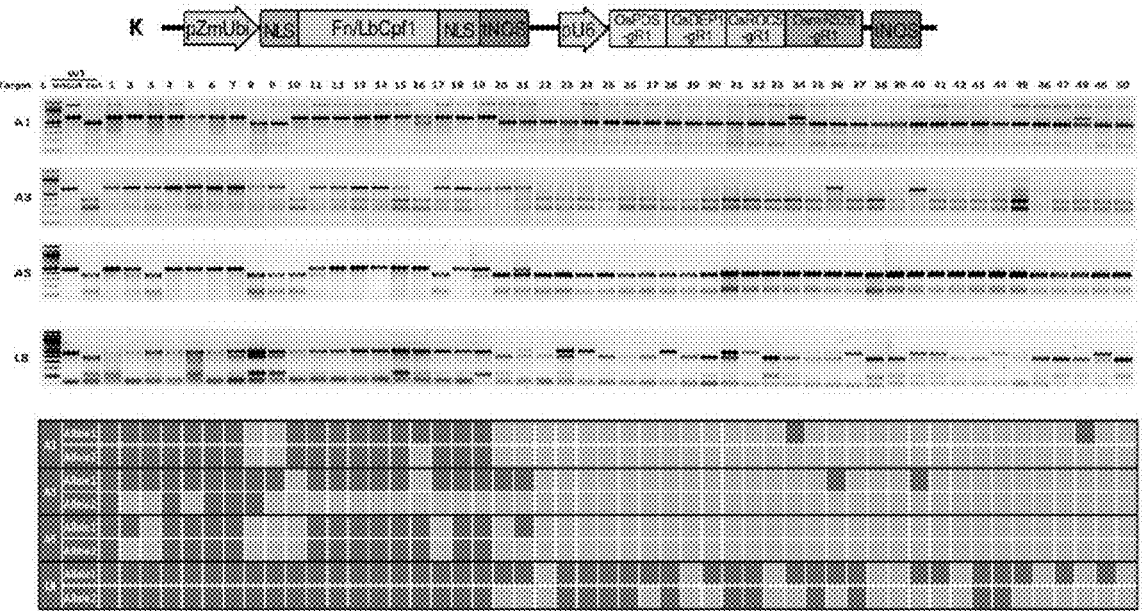

FIG. 13 shows an analysis of multiplexing strategy 'K' at four target genes with 50 T0 lines. An illustration of the multiplexing strategy is shown in the upper panel. The middle panel shows RFLP base genotyping data at four target sites along independent lines. The lower panel is a summary table showing editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 14:
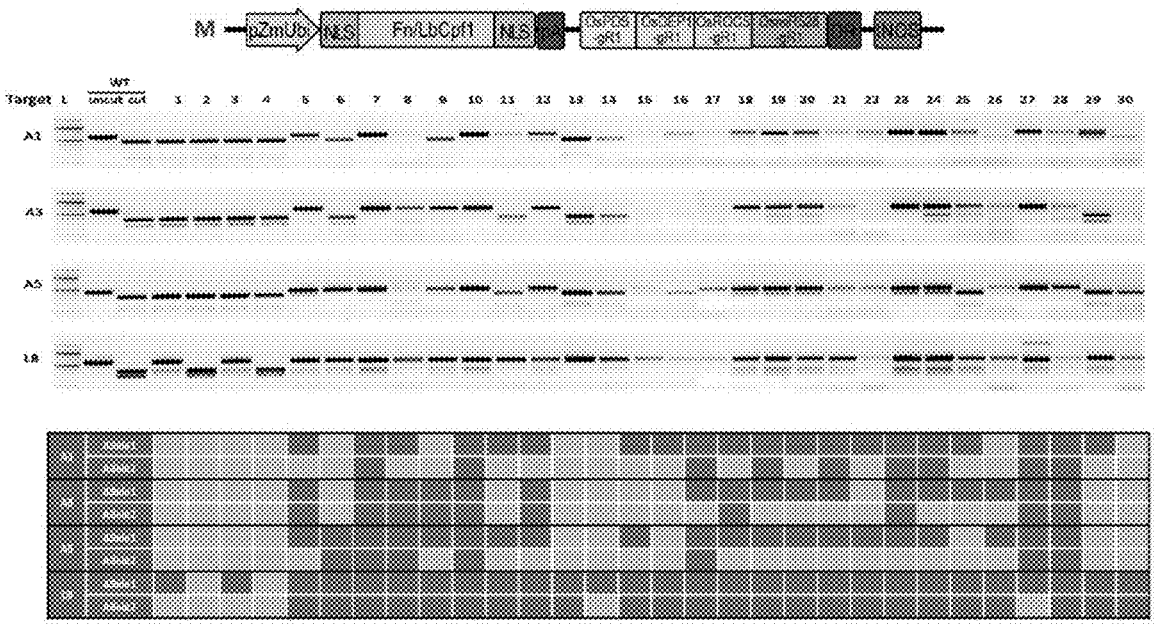

FIG. 14 shows an analysis of multiplexing strategy 'M' at four target genes with 30 T0 lines. An illustration of the multiplexing strategy is shown in the upper panel. The middle panel shows RFLP base genotyping data at four target sites along independent lines. The lower panel is a summary table showing editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 15:
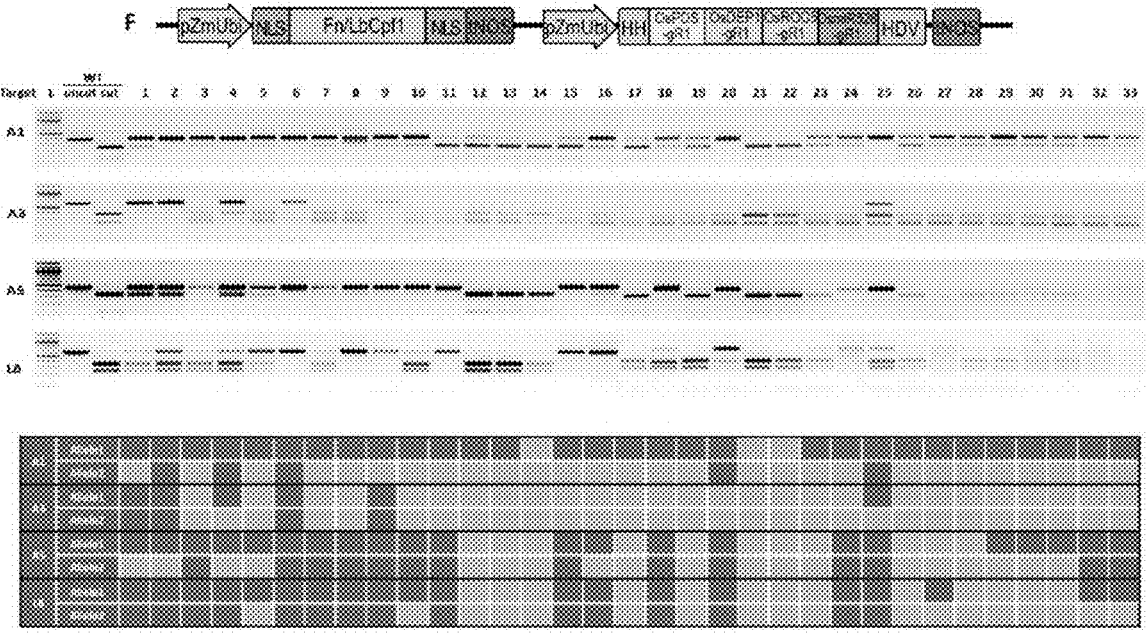

FIG. 15 shows an analysis of multiplexing strategy 'F' at four target genes with 33 T0 lines. An illustration of the multiplexing strategy is shown in the upper panel. The middle panel shows RFLP base genotyping data at four target sites along independent lines. The lower panel is a summary table showing editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 16:
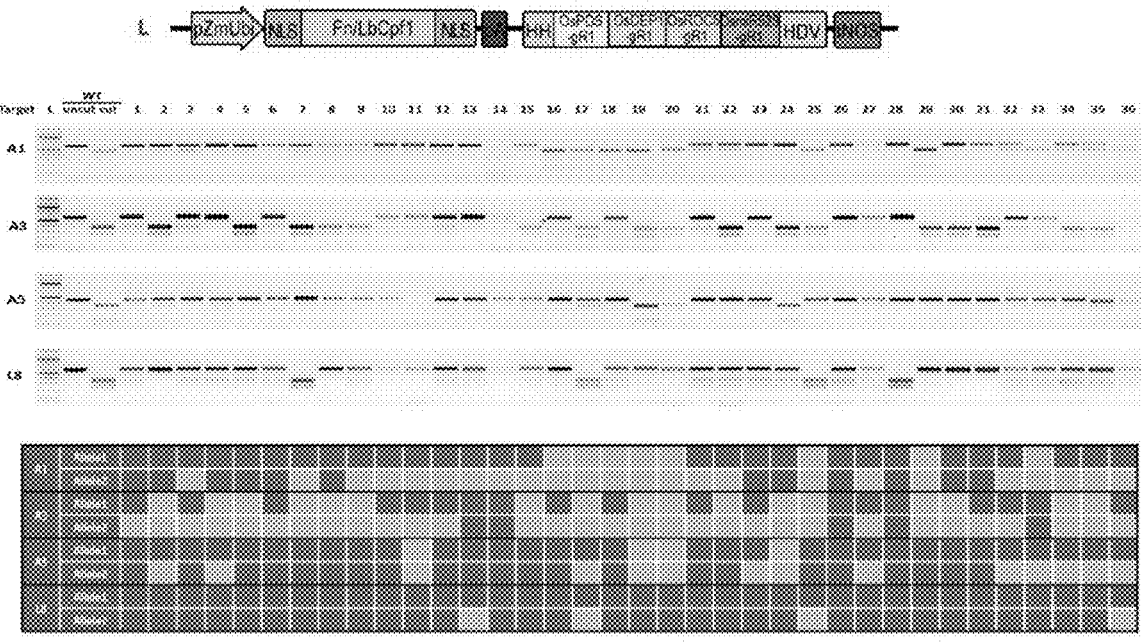

FIG. 16 shows an analysis of multiplexing strategy 'L' at four target genes with 36 T0 lines. An illustration of the multiplexing strategy is shown in the upper panel. The middle panel shows RFLP base genotyping data at four target sites along independent lines. The lower panel is a summary table showing editing (green) or non-editing (light green) of both alleles based on RFLP and Sanger sequencing. A1: OsPDS-gR1. A3: OsDEP1-gR1. A5, OsROC5-gR1. L8, OsmiR528-gR1.

Figure 17A:
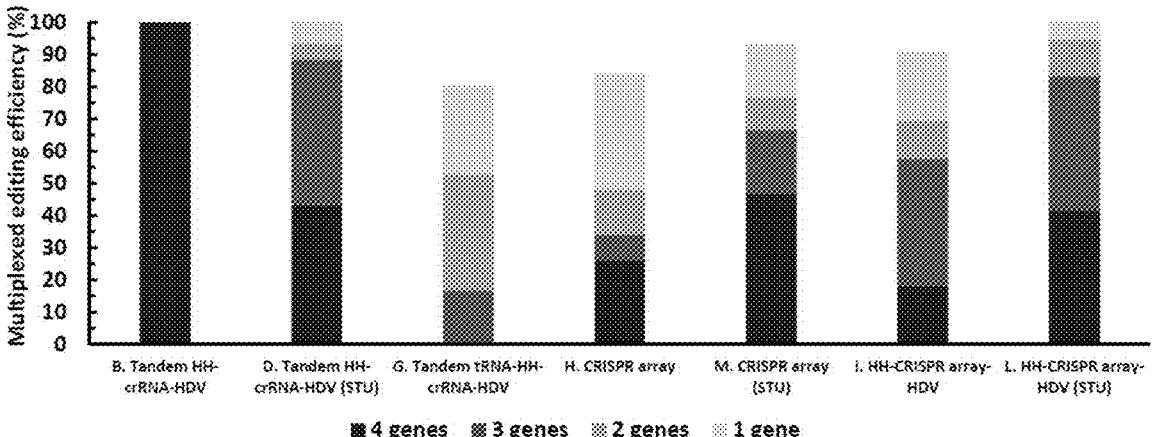

FIGS. 17A-17C illustrate a detailed analysis of multiplexed editing efficiencies in rice T0 lines. FIG. 17A shows a comparison of multiplexed editing efficiency for seven systems. FIG. 17B shows a comparison of multiplexed biallelic editing efficiency for seven systems. FIG. 17C shows a comparison of editing and biallelic editing efficiencies based on gene numbers.

FIGS. 18A-18B illustrate simultaneous editing of 16 target sites in rice by the most efficient multiplexing system. FIG. 18A is an illustration of the 16 target sites in the rice genome.

FIG. 18B sets forth genotyping results showing that 15 out 16 target sites carried biallelic or homozygous mutations in rice T0 lines #14 and #21 (T1 (WT=SEQ ID NO: 218; LINE 14/first line=SEQ ID NO: 219; LINE 14/second line=SEQ ID NO: 220; LINE 21/first line=SEQ ID NO: 221; LINE 21/second line=SEQ ID NO: 222); T2 (WT=SEQ ID NO: 223; LINE 14/first line=SEQ ID NO: 224; LINE 14/second line=SEQ ID NO: 225; LINE 21/first line=SEQ ID NO: 226; LINE 21/second line=SEQ ID NO: 227); T3 (WT=SEQ ID NO: 228; LINE 14/first line=SEQ ID NO: 229; LINE 14/second line=SEQ ID NO: 230; LINE 21/first line=SEQ ID NO: 231; LINE 21/second line=SEQ ID NO: 232); T4 (WT=SEQ ID NO: 233; LINE 14/first line=SEQ ID NO: 234; LINE 14/second line=SEQ ID NO: 235; LINE 21/first line=SEQ ID NO: 236; LINE 21/second line=SEQ ID NO: 237); T5 (WT=SEQ ID NO: 238; LINE 14/first line=SEQ ID NO: 239; LINE 14/second line=SEQ ID NO: 240; LINE 21/first line=SEQ ID NO: 241; LINE 21/second line=SEQ ID NO: 242); T6 (WT=SEQ ID NO: 243; LINE 14/first line=SEQ ID NO: 244; LINE 14/second line=SEQ ID NO: 245; LINE 21/first line=SEQ ID NO: 246; LINE 21/second line=SEQ ID NO: 247); T7 (WT=SEQ ID NO: 248; LINE 14/first line=SEQ ID NO: 249; LINE 14/second line=SEQ ID NO: 250; LINE 21/first line=SEQ ID NO: 251; LINE 21/second line=SEQ ID NO: 252); T8 (WT=SEQ ID NO: 253; LINE 14/first line=SEQ ID NO: 254; LINE 14/second line=SEQ ID NO: 255; LINE 21/first line=SEQ ID NO: 256; LINE 21/second line=SEQ ID NO: 257); T9 (WT=SEQ ID NO: 258; LINE 14/first line=SEQ ID NO: 259; LINE 14/second line=SEQ ID NO: 260; LINE 21/first line=SEQ ID NO: 261; LINE 21/second line=SEQ ID NO: 262); T10 (WT=SEQ ID NO: 263; LINE 14/first line=SEQ ID NO: 264; LINE 14/second line=SEQ ID NO: 265; LINE 21/first line=SEQ ID NO: 266; LINE 21/second line=SEQ ID NO: 267); T11 (WT=SEQ ID NO: 268; LINE 14/first line=SEQ ID NO: 269; LINE 14/second line=SEQ ID NO: 270; LINE 21/first line=SEQ ID NO: 271; LINE 21/second line=SEQ ID NO: 272); T12 (WT=SEQ ID NO: 273; LINE 14/first line=SEQ ID NO: 274; LINE 14/second line=SEQ ID NO: 275; LINE 21/first line=SEQ ID NO: 276; LINE 21/second line=SEQ ID NO: 277); T13 (WT=SEQ ID NO: 278; LINE 14/first line=SEQ ID NO: 279; LINE 14/second line=SEQ ID NO: 280; LINE 21/first line=SEQ ID NO: 281; LINE 21/second line=SEQ ID NO: 282); T14 (WT=SEQ ID NO: 283; LINE 14/first line=SEQ ID NO: 284; LINE 14/second line=SEQ ID NO: 285; LINE 21/first line=SEQ ID NO: 286; LINE 21/second line=SEQ ID NO: 287); T15

(WT=SEQ ID NO: 288; LINE 14/first line=SEQ ID NO: 289; LINE 14/second line=SEQ ID NO: 290; LINE 21/first line=SEQ ID NO: 291; LINE 21/second line=SEQ ID NO: 292); T16 (WT=SEQ ID NO: 293; LINE 14/first line=SEQ ID NO: 294; LINE 14/second line=SEQ ID NO: 295; LINE 21/first line=SEQ ID NO: 296; LINE 21/second line=SEQ ID NO: 297).

Figure 19E:
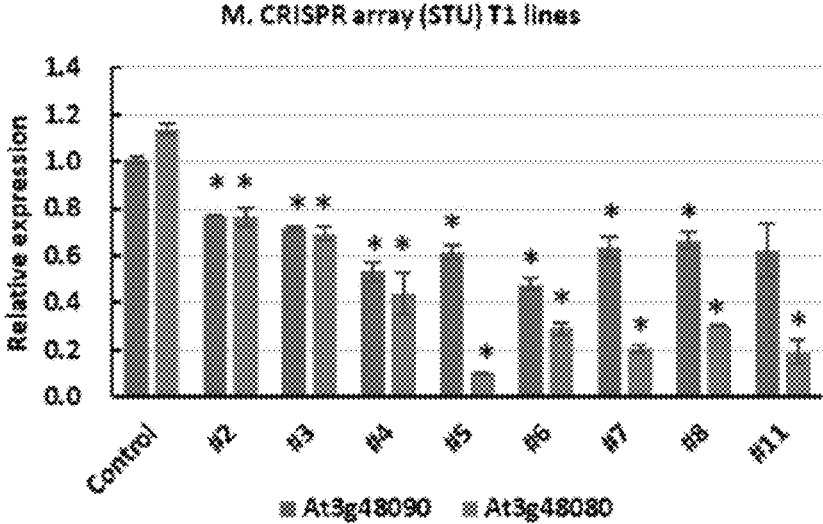
Figure 19F:
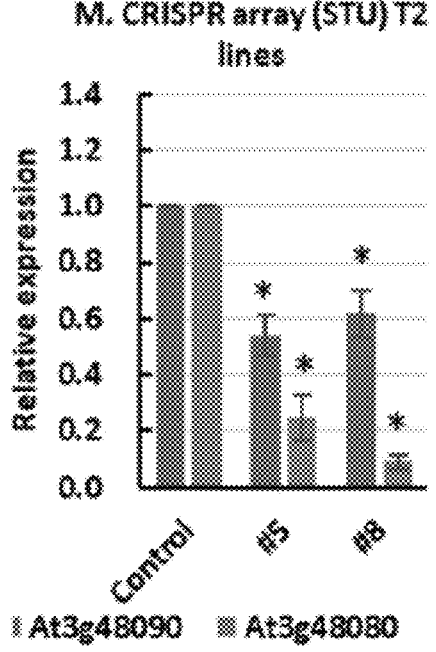

FIGS. 19A-19F illustrate multiplexed transcriptional repression with two compacted STU dCas12a-SRDX systems. FIG. 19A shows schematics of the rice target genes and crRNAs. FIG. 19B illustrates simultaneous transcriptional repression of four genes in rice protoplasts by two STU systems, 'D' and 'M'. FIG. 19C shows schematics of the *Arabidopsis* target genes and crRNAs. FIG. 19D illustrates simultaneous transcriptional repression of two tandemly arrayed genes in *Arabidopsis* T1 lines by the STU system 'D'. FIG. 19E illustrates simultaneous transcriptional repression in *Arabidopsis* T1 lines by the STU system 'M'. FIG. 19F shows that targeted transcriptional repression is inherited to the T2 generation. Transcription levels of target genes were quantified by qRT-PCR. Error bars represent standard deviations of biological replicates (n=3).

Figure 20:
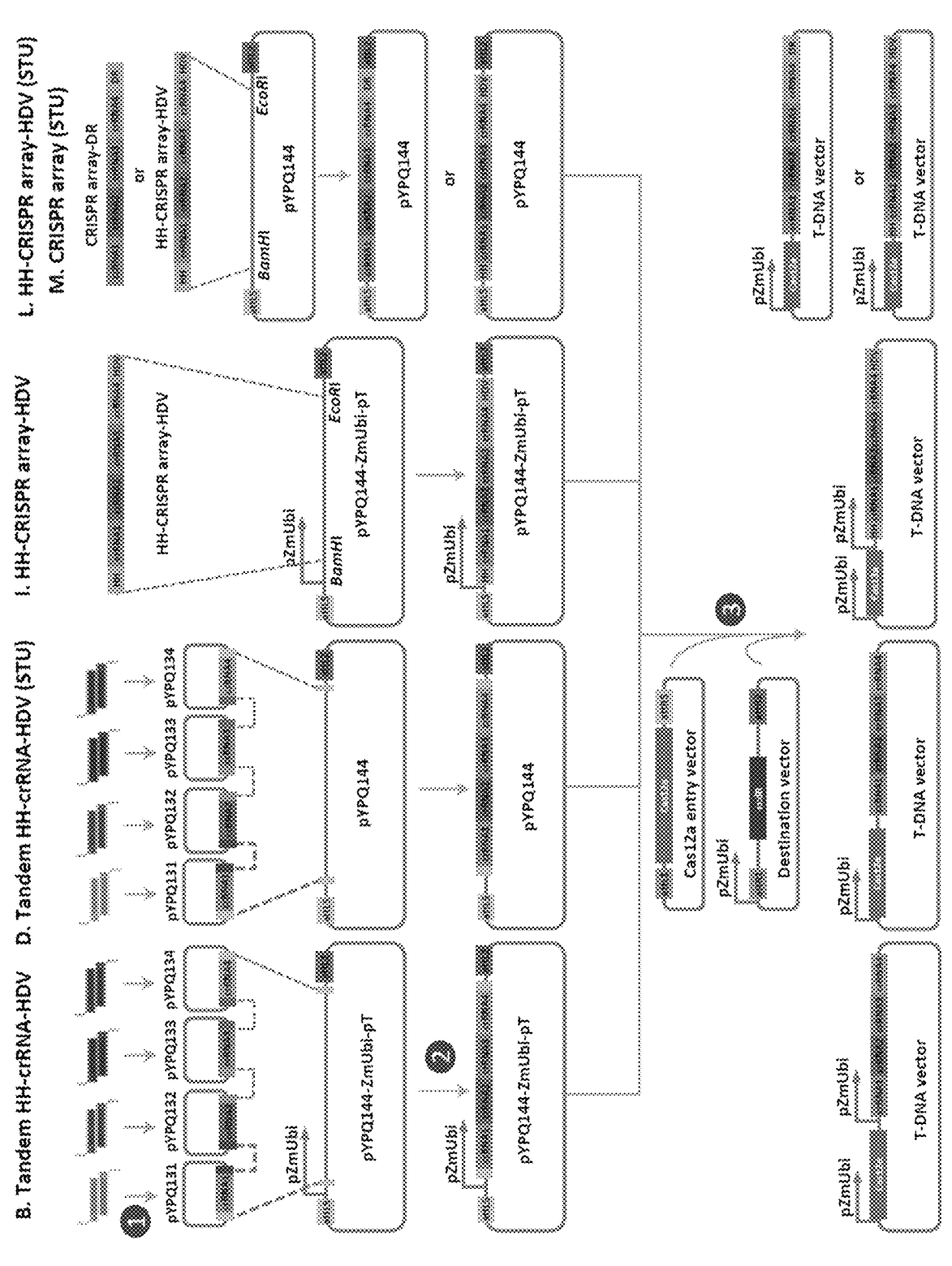

FIG. 20 illustrates modular assembly systems for multiplexed plant genome engineering, in which assembly of multiplexed Cas12a systems follows a streamlined modular approach. In step 1, the protospacers for crRNAs are cloned into crRNA entry clones for HH-crRNA-HDV based systems. CRISPR arrays can be directly synthesized for crRNA array-based systems. In step 2, assembly of multiple crRNA cassettes is achieved either through Golden Gate cloning (for HH-crRNA-HDV systems) or conventional cloning at BamHI and EcoRI sites (for crRNA array systems), resulting attR5-attL5 crRNA expression vectors. In step 3, final T-DNA expression vectors are assembled by three-way Gateway recombination reactions.

DETAILED DESCRIPTION

The present disclosure relates to genomic editing of plants.

In various aspects, the disclosure relates to a non-naturally occurring heterologous CRISPR-Cas 12a genomic editing system, comprising or encoding at least one Cas 12a ortholog endonuclease selected from the group consisting of Lb5Cas12a, CMaCas12a, BsCas12a, BoCas12a, MlCas12a, Mb2Cas12a, MbCas12a TsCas12a, and MAD7® ErCas12a endonucleases (SEQ ID NOs: 1-9, respectively), as described more fully hereinafter.

The CRISPR-Cas12a genomic editing system may comprise at least one guide RNA (gRNA) operatively arranged with the ortholog endonuclease for genomic editing of a target DNA binding the gRNA. In embodiments, the system may comprise a CRISPR-Cas12a expression system encoding the Cas12a ortholog nucleases and crRNAs for forming gRNAs that are coactive with the Cas12a nucleases.

Cas12a ortholog endonuclease-encoding nucleotide sequences of the present disclosure include the following endonuclease nucleotide sequences: Lb5Cas12a (ortholog endonuclease-encoding sequence SEQ ID NO: 1); CMaCas12a (ortholog endonuclease-encoding sequence SEQ ID NO: 2); BsCas12a (ortholog endonuclease-encoding sequence SEQ ID NO: 3); BoCas12a (ortholog endonuclease-encoding sequence SEQ ID NO: 4); MlCas12a (ortholog endonuclease-encoding sequence SEQ ID NO: 5); Mb2Cas12a (ortholog endonuclease-encoding sequence SEQ ID NO: 6); MbCas12a (ortholog endonuclease-encoding sequence SEQ ID NO: 7); TsCas12a (ortholog endonuclease-encoding sequence SEQ ID NO: 8); and MAD7® ErCas12a (ortholog endonuclease-encoding sequence SEQ ID NO: 9). In various embodiments, the Cas12a ortholog endonuclease-encoding nucleotides may comprise derivatives of the endonuclease-encoding nucleotides of SEQ ID NOs: 1-9, having at least 80%, 85%, 90%, 95%, 97%, 98%, 99%, 99.5%, or more sequence identity to the sequences of SEQ ID NOs: 1-9.

In a specific aspect, the CRISPR-Cas12a system may comprise one or vectors comprising at least one CRISPR RNA (crRNA) regulatory element operably linked to at least one nucleotide sequence encoding a CRISPR-Cas12a system crRNA for producing gRNA for targeting a target sequence, and at least one regulatory element, which may be the same as the crRNA regulatory element, or different therefrom, operably linked to a nucleotide sequence encoding the Cas12a ortholog endonuclease, for generation of a CRISPR-Cas12a editing structure by which the gRNA targets the target sequence and the Cas12a ortholog endonuclease cleaves a target DNA to alter gene expression in the cell, and wherein the CRISPR-associated nuclease, and the gRNA, do not naturally occur together. In such system, the at least one crRNA regulatory element may comprise one or more than one RNA polymerase II (Pol II) promoter, or alternatively, a single transcript unit (STU) regulatory element, or one or more promoter(s) selected from the group consisting of ZmUbi, OsU6, OsU3, and U6 promoters.

Vector sequences that may be utilized in forming or constructing genomic editing systems of the present disclosure include, without limitation: pYPQ230 (Addgene #86210) SEQ ID NO: 10; pYPQ281 (Mb; Addgene #138113) SEQ ID NO: 11; pYPQ282 (Ts; Addgene #138114) SEQ ID NO: 12; pYPQ283 (Ml; Addgene #138115) SEQ ID NO: 13; pYPQ284 (Mb2; Addgene #138116) SEQ ID NO: 14; pYPQ284-RVR (Addgene #138117) SEQ ID NO: 15; pYPQ285 (Lb5; Addgene #138120) SEQ ID NO: 16; pYPQ285-RVR (Addgene #138121) SEQ ID NO: 17; pYPQ286 (CMa; Addgene #138122) SEQ ID NO: 18; pYPQ287 (Bs; Addgene #138123) SEQ ID NO: 19; pYPQ287-RVR (Addgene #138124) SEQ ID NO: 20; pYPQ288 (Bo; Addgene #138125) SEQ ID NO: 21; pYPQ289 (MAD7® ErCas12a; Addgene #138126) SEQ ID NO: 22; pYPQ289-RVR (Addgene #138127) SEQ ID NO: 23; pYPQ131-STU-Lb (Addgene #138096) SEQ ID NO: 24; pYPQ132-STU-Lb (Addgene #138099) SEQ ID NO: 25; pYPQ133-STU-Lb (Addgene #138102) SEQ ID NO: 26; pYPQ134-STU-Lb (Addgene #138105) SEQ ID NO: 27; pYPQ131-STU-As (Addgene #138094) SEQ ID NO: 28; pYPQ132-STU-As (Addgene #138097) SEQ ID NO: 29; pYPQ133-STU-As (Addgene #138100) SEQ ID NO: 30; pYPQ134-STU-As (Addgene #138103) SEQ ID NO: 31; pYPQ131-STU-Fn (Addgene #138095) SEQ ID NO: 32; pYPQ132-STU-Fn (Addgene #138098) SEQ ID NO: 33; pYPQ133-STU-Fn (Addgene #138101) SEQ ID NO: 34; pYPQ134-STU-Fn (Addgene #138104) SEQ ID NO: 35; pYPQ142 (Addgene #69294) SEQ ID NO: 36; pYPQ143 (Addgene #69295) SEQ ID NO: 37; pYPQ144 (Addgene #69296) SEQ ID NO: 38; pYPQ142-ZmUbi (Addgene #138106) SEQ ID NO: 39; pYPQ143-ZmUbi (Addgene #138107) SEQ ID NO: 40; pYPQ144-ZmUbi-pT (Addgene #138108) SEQ ID NO: 41; pYPQ233 (Addgene #86211) SEQ ID NO: 42; pYPQ223 (Addgene #86209) SEQ ID NO: 43; pYPQ239 (Addgene #108859) SEQ ID NO: 44; pYPQ223-STU (Addgene #138109) SEQ ID NO: 45; pYPQ230-STU (Addgene #138110) SEQ ID NO: 46; pYPQ233-STU (Addgene #138111) SEQ ID NO: 47; pYPQ239-STU (Addgene

138112) SEQ ID NO: 48; pYPQ202 (Addgene #86198) SEQ ID NO: 49; and pYPQ203 (pMDC32-Ubi1, Addgene #86207) SEQ ID NO: 50. The Addgene identification number in the preceding listing is the depository identification number for the vector as deposited at the Addgene public vector/plasmid repository (Watertown, MA, USA).

The genomic editing system of the present disclosure may comprise a STU regulatory element that is operably linked to a nucleotide sequence encoding a CRISPR-Cas12a system crRNA and to a nucleotide sequence encoding the Cas12a ortholog endonuclease, e.g., wherein the STU regulatory element comprises a RNA polymerase II (Pol II) promoter.

The genomic editing system of the present disclosure in other implementations comprises one or more crRNA regulatory elements operably linked to respective multiple nucleotide sequences encoding respective ones of multiple CRISPR-Cas12a system crRNAs, for targeting multiple target sequences, for multiplexed genomic editing by the at least one Cas12a ortholog endonuclease.

In various embodiments, the system includes a nucleotide sequence encoding the Cas12a ortholog endonuclease, a nucleotide sequence encoding a crRNA for forming a gRNA for the Cas12a ortholog endonuclease, and multiple ones of a same promoter, wherein one of the multiple ones of the same promoter is operably linked with the nucleotide sequence encoding the Cas12a ortholog endonuclease, and another one of the multiple ones of the same promoter is operably linked with the nucleotide sequence encoding the crRNA for forming the gRNA for the Cas12a ortholog endonuclease, with the same promoter being effective to produce expression in both nucleotide sequences.

The editing system in other applications may be constituted as comprising one or more expression cassettes comprising crRNA expression-regulating regulatory elements operably linked to nucleotide sequences encoding crRNAs for forming gRNAs hybridizing to target sequences of DNA, and nuclease expression-regulating regulatory elements operably linked to nucleotide sequences encoding the Cas12a ortholog endonuclease that is editingly effective with the gRNAs, wherein the crRNA expression-regulating regulatory elements and nuclease expression-regulating regulatory elements comprise the same or different promoters.

In other embodiments, the system may comprise an expression cassette in which one or more crRNA nucleotide sequence is present, wherein hammerhead (HH) and hepatitis delta virus (HDV) ribozymes flank each crRNA nucleotide sequence in a HH-crRNA-HDV arrangement. In embodiments of such system, the cassette expresses the Cas12a ortholog endonuclease, e.g., Mb2Cas 12a endonuclease (SEQ ID NO: 298).

The system may be constituted as comprising one or more expression cassettes, comprising multiple crRNA nucleotide sequences, wherein hammerhead (HH) and hepatitis delta virus (HDV) ribozymes flank each crRNA nucleotide sequence in a HH-crRNA-HDV arrangement. In embodiments, such system may be constituted with such one or more expression cassettes expressing the Cas12a ortholog endonuclease, such as the Mb2Cas12a endonuclease. The expression of both the Mb2Cas12a endonuclease and multiple crRNAs from the multiple crRNA nucleotide sequences may for example be operatively effected by a ZmUbi promoter.

The system in specific implementations may comprise one or more expression cassettes, comprising one or CRISPR array, wherein hammerhead (HH) and hepatitis delta virus (HDV) ribozymes flank each CRISPR array in a HH-CRISPR array-HDV arrangement.

The Cas12a ortholog endonucleases of the present disclosure encompass RVR variants thereof. The system in various embodiments may comprise one or more crRNA nucleotide sequence operatively linked with a regulatory element, to express one or more crRNA including a protospacer sequence at least 19 bp in length.

Another aspect of the present disclosure relates to a method of genomically editing a plant, comprising introducing into such plant a non-naturally occurring heterologous CRISPR-Cas12a genomic editing system of a type as variously described hereinabove, to cause the Cas12a ortholog nuclease to edit DNA in the plant to alter the plant's gene expression. The method may be performed so that the CRISPR-Cas12a genomic editing system targets PAM sites such as TTN, TTV, TTTV, NTTV, TATV, TATG, TATA, YTTN, GTTA, and/or GTTC.

Such method may be carried out at moderate temperatures, e.g., below 25° C. and above temperature producing freezing or frost damage of the plant. The editing method of the disclosure may be performed on a wide variety of plants, including for example Arabadopsis, maize, and rice. In particular application to rice, the editing method may be carried out to edit the rice plant at one or more of OsPDS, OsDEP1, OsROC5, and OsmiR528 genes thereof.

In the method of the disclosure, the CRISPR-Cas12a genomic editing system advantageously comprises gRNAs that are targetingly effective for multiple genomic loci in the plant, to enable multiplexed genomic editing of the plant by the Cas12a ortholog endonuclease, as hereinafter more fully described.

Accordingly, the disclosure contemplates CRISPR-Cas12a plant genome editing systems comprising or encoding Cas12a ortholog endonucleases, Lb5Cas12a, CMaCas12a, BsCas12a, BoCas12a, MlCas12a, Mb2Cas12a, MbCas12a, TsCas12a, and MAD7® ErCas12a, having utility for targeting short PAMs in plants and enabling CRISPR-Cas12a editing of plants at lesser temperatures than have heretofore been required for CRISPR-Cas12a editing, thereby greatly expanding the scope of plants that are able to be genomically modified by CRISPR-Cas12a editing.

The CRISPR-Cas12a nuclease systems advantageously comprise the Cas12a ortholog endonucleases of the present disclosure (Lb5Cas12a, CMaCas12a, BsCas12a, BoCas12a, MlCas12a, Mb2Cas12a, MbCas12a, TsCas12a, and MAD7® ErCas12a) and guide RNA. Expression systems for such CRISPR-Cas12a nuclease systems may readily be prepared in accordance with the present disclosure, encoding the Cas12a nucleases and crRNAs for forming gRNAs that are coactive with the Cas12a nucleases. The CRISPR-Cas12a nuclease systems may comprise constructs, e.g., complexes or otherwise operatively coupled structures, comprising any of such Cas12a ortholog endonucleases with corresponding guide RNA targeting a target sequence in a plant, so that the guide RNA targets the target sequence and the Cas 12a ortholog endonuclease cleaves DNA in the plant to alter its gene expression. The plant may be of any suitable type, and as discussed above, may for example include rice (e.g., *Oryza sativa, Oryza glaberrima*), maize (e.g., *Zea mays*), *Arabidopsis* (e.g., *Arabidopsis thaliana*), etc.

The CRISPR-Cas12a constructs of the Cas12a ortholog endonucleases and guide RNA comprise constructs of heterologous character, as non-naturally occurring constructs useful for genomic editing of plants.

Recombinant non-naturally occurring gene editing systems of the disclosure may comprise one or vectors comprising at least one CRISPR RNA (crRNA) regulatory element operable in a plant cell and operably linked to at least one nucleotide sequence encoding a CRISPR-Cas12a system crRNA for producing gRNA for targeting a target sequence in a plant, and at least one regulatory element, which may be the same as the crRNA regulatory element, or different therefrom, operable in the plant cell and operably linked to a nucleotide sequence encoding the CRISPR-associated protein 12a ortholog nuclease, for generation of a CRISPR-Cas12a editing structure by which the gRNA targets the target sequence and the CRISPR-associated protein 12a ortholog nuclease cleaves a plant target DNA to alter gene expression in the plant, and wherein the CRISPR-associated nuclease, and the gRNA, do not naturally occur together.

The gene editing system may be constituted with one or more crRNA regulatory elements operable in a plant cell and operably linked to respective multiple nucleotide sequences encoding respective ones of multiple CRISPR-Cas12a system crRNAs, for targeting multiple target sequences in a plant, for multiplexed genomic editing of the plant by the CRISPR-associated protein 12a ortholog nuclease(s).

The crRNA regulatory element in the gene editing system may be of any of various types, and may for example comprise one or more than one RNA polymerase II (Pol II) promoter, or a single transcript unit (STU) regulatory element. In specific implementations, the regulatory element in the gene editing system may include one or more promoters such as ZmUbi promoter, OsU6 promoter, OsU3 promoter, U6 promoter, or other suitable promoter or promoters. STU regulatory elements may be employed to enable highly compact gene editing expression systems, allowing for coordinated expression of both the Cas12a endonuclease and the crRNAs using a single promoter. For example, a single Poll II promoter may be employed in various gene editing systems of the present disclosure as a regulatory element for driving both the Cas12a endonuclease and the crRNAs expression in the system. In other applications, multiple ones of a same promoter may be employed for expression of the Cas12a endonuclease and the crRNAs. For example, dual or other multiple Pol II promoter arrangements may be employed in the editing system. It will be recognized that numerous arrangements of regulatory elements may be employed in the gene editing systems of the present disclosure, in specific implementations thereof.

Gene editing constructs of the present disclosure thus may be embodied in one or more expression cassettes containing one or more regulatory elements operably linked to nucleotide sequences encoding crRNAs for forming gRNAs that will hybridize to the target sequence(s) of the plant DNA, and the same or different one or more regulatory elements operably linked to nucleotide sequences encoding the Cas12a ortholog nuclease(s) of the present disclosure. The expression cassette(s) may be constituted to express any of a wide variety of transactivating CRISPR RNAs (tracrRNAs) for producing the gRNAs.

The recombinant engineered, non-naturally occurring gene editing systems of the disclosure may include structures in expression cassettes in which one or more crRNA nucleotide sequence is present, wherein hammerhead (HH) and hepatitis delta virus (HDV) ribozymes flank each crRNA nucleotide sequence in a HH-crRNA-HDV arrangement. The cassette(s) may be constituted for expression of the Cas12a ortholog nuclease(s) of the present disclosure, e.g., Mb2Cas12a endonuclease. As an example, such cassette(s) may be constituted with multiple crRNAs nucleotide sequences, each in the HH-crRNA-HDV conformation, with expression of both the Mb2Cas12a endonuclease and the crRNAs being driven by a ZmUbi promoter. Other cassette structures that may be employed in the broad practice of the present disclosure include crRNA nucleotide sequences or CRISPR arrays flanked by HH and HDV ribozymes at respective ends thereof, together with other promoters and sequences for the Cas12a ortholog nucleases of the present disclosure.

The Cas12a ortholog nuclease(s) of the present disclosure may be provided as RVR variants.

As discussed hereinafter, the genomic editing system may include crRNAs including protospacer sequences at least 19 bp in length.

Accordingly, the present disclosure contemplates a method of genomic editing of a plant, comprising introducing into such plant an editing construct, cassette, or system of the present disclosure, including or encoding one or more of the Cas12a ortholog nuclease(s) variously described herein. The plants may be of any suitable types, and transfection may be effected by any appropriate techniques.

The editing method may be carried out with the CRISPR-Cas12a systems of the disclosure to target PAM sites including any one or more of TTN, TTV, TTTV, NTTV, TATV, TATG, TATA, YTTN, GTTA, and GTTC.

The method may be carried out at varying temperatures, including temperatures that in various embodiments are below 32° C., below 28° C., below 25° C., below 22° C., below 20° C., or lower, and above temperatures resulting in freezing or frost damage of plants being edited.

In various applications, the CRISPR-Cas12a ortholog genome editing systems of the disclosure may be utilized with appropriate multiple crRNAs to simultaneously target multiple different genes in the plant being edited, for multiplexed genomic editing. As illustrated in ensuing examples, the CRISPR-Cas12a ortholog genome editing system may be constituted to incorporate crRNAs enabling editing of OsPDS, OsDEP1, OsROC5, and OsmiR528 target genes in rice.

The genome editing systems of the present disclosure may be readily prepared in a modular assembly process that is described hereinafter, and more specifically illustrated in FIG. 20 hereof.

In the various examples set out hereinafter, Cas12a orthologs were screened, resulting in the discovery of Cas12a orthologs that were able to edit TTTV PAM sites with medium to high efficiencies in plants. Among them, Mb2Cas12a were demonstrated to efficiently target NTTV PAMs. Moreover, Mb2Cas12a was shown to exhibit low-temperature tolerance, high target specificity, and high multiplexed editing activity. The RVR variants of Mb2Cas12a were observed to efficiently target TATV PAMs. The characterization herein of Cas12a orthologs of the present disclosure, especially Mb2Cas12a, in plants, dramatically expands the CRISPR-Cas12a toolbox by broadening the PAM recognition range. Further, the demonstrated low temperature tolerance of Mb2Cas12a allows the application of the CRISPR-Cas12a system in many plant species that live at and require low temperatures.

In connection with developing efficient genome editing and transcriptional repression systems based on CRISPR-Cas12a and singular CRISPR RNAs (crRNAs), it is vital to develop efficient multiplexed Cas12a systems for boosting plant genome engineering scale and capability. In the ensuing Examples, 12 multiplexing systems were systematically compared, represented by six different strategies, for genome editing in rice as a model plant of global food supply significance. Side-by-side comparison in stable transgenic rice plants resulted in identification of the most efficient multiplexing system based on dual Pol II promoters and a tandem HH-crRNA-HDV array, which produced 100% biallelic mutations at all four target sites, and this potent system has been applied to efficiently and simultaneously generate biallelic and homozygous mutations at 15 target sites in a single plant within one generation. Such Cas12a system therefore represents the most efficient multiplexed CRISPR system developed to date in rice. Other efficient multiplexed Cas12a systems have been developed including three compact single transcript unit (STU) systems that are based on different crRNA processing strategies. The systems have demonstrated utility for simultaneous transcriptional repression of multiple target genes in both rice and *Arabidopsis*.

In a further aspect, the present disclosure provides a streamlined assembly process for the high-performance multiplexed Cas12a systems of the present disclosure, utilizing vectors that the present inventors have deposited at the Addgene public repository (Addgene Plasmid Repository, Watertown, Massachusetts, US).

The features and advantages of the present disclosure are more fully shown and appreciated by reference to the following examples, which are not intended to be considered or construed as limiting the present disclosure, and are presented as illustrative of features and aspects of the present disclosure, in specific embodiments thereof.

In the following Examples 1-8, the following materials and methods were employed.

Vector Construction

All vectors were constructed based on a three-way Gateway cloning system. The attL1-attR5 entry vectors were generated to express all Cas12a orthologs, which were rice codon optimized, synthesized and cloned into pYPQ230 (Addgene #86210) to replace LbCas12a, including pYPQ281 (Mb; Addgene #138113), pYPQ282 (Ts; Addgene #138114), pYPQ283 (Ml; Addgene #138115), pYPQ284 (Mb2; Addgene #138116), pYPQ285 (Lb5; Addgene #138120), pYPQ286 (CMa; Addgene #138122), pYPQ287 (Bs; Addgene #138123), pYPQ288 (Bo; Addgene #138125), pYPQ289 (MAD7® ErCas12a; Addgene #138126). The attL5-attL2 entry vectors used in this study for crRNA expression of Cas12a orthologs was pYPQ141-ZmUbi-RZ-Fn (Addgene #108864). The crRNAs were synthesized as duplexed oligonucleotides, and then phosphorylated, annealed and ligated into Esp3I (BsmBI) linearized pYPQ141-ZmUbi-RZ-Fn. These two entry vectors were further assembled with the destination vector pYPQ203 (pMDC32-Ubi1, Addgene #86207) through LR reactions.

Plant Material and Growth Condition

Rice plants were the *Japonica* cultivar Nipponbare and Kitaake. 14-16 days old seedlings grown on ½ MS medium in dark at 28° C. were used for protoplast isolation. Calli induced from mature rice embryos, which were cultured on the N6-D medium under light at 32° C., were used for rice stable transformation.

Rice Protoplast Transformation

Rice protoplast was isolated and transformed according to previously published protocols. Briefly, 14-16 days old rice leaves grown in dark were cut into 0.5-1.0 mm strips and incubated in the enzyme solution at 28° C. for 8 hours without light. The digested cells were filtered by 75 μm cell strainer and washed by the W5 buffer. 30 μg plasmid DNA was mixed with 2004, protoplast ($2 \times 10^6$/mL). Equal amount of PEG transformation buffer was then added, and the entire mixture was incubated for 30 minutes at room temperature. The reactions were stopped by adding 9004, W5 buffer. Protoplast was collected by centrifugation and transferred into 12-well culture plates. Plates were incubated at 32° C. or 22° C. in dark for 2 days. The protoplasts were collected for DNA extraction.

Rice Stable Transformation

Rice was transformed using *Agrobacterium*-mediated method as described in the published protocols with slight modifications. Briefly, *Agrobacterium tumefaciens* strain EHA105 harboring binary vectors was used to inoculate rice calli. Inoculated calli were co-cultured with the *Agrobacterium* for 3 days, washed and moved to selection medium containing 50 mg/L hygromycin. After 4 weeks, resistant calli were moved to regeneration medium I to induce shoot growth. Small shoots were further transferred to regeneration medium II to obtain full transgenic plants. DNA was extracted from young leaves of T0 plant using the CTAB method for genotyping.

Calculation of Mutation Frequencies by RFLP

The targeted genomic regions were amplified, and the PCR products were digested with restriction enzymes with cutting sites overlapping with the expected editing sites. Digested products were visualized with electrophoresis on 2% TAE agarose gels. Mutation frequencies were quantified based on band intensity using Image Lab™ Software (Bio-Rad Laboratories, Inc.).

Sanger Sequencing and Deep Sequencing to Characterize Editing Efficiencies and Profiles PCR amplicons from stable transgenic rice were subjected for Sanger sequencing. DNA sequences were decoded using DSDecodeM. PCR amplicons generated from protoplast assay were barcoded and sequenced using Illumina HiSeq 2500. The clean data were mapped using Burrows-Wheeler Aligner and analyzed using python and R.

Example 1

Genome Editing Using Nine Cas12a Orthologs in Plant Cells

Nine Cas12a orthologs were screened for targeting of relaxed or shortened PAMs. These orthologs had not been previously demonstrated for genome editing and plants. Eight Cas 12a have shown preference for TTN PAMs in in vitro PAM identification assay, including Lb5Cas12a, CMaCas12a, BsCas12a, BoCas12a, MlCas12a, Mb2Cas12a, MbCas12a and TsCas12a. MAD7® ErCas12a has been shown to recognize YTTN PAMs in *E. coli* and yeast (*Saccharomyces cerevisiae*) (Inscripta, Inc.).

Figure 1B:
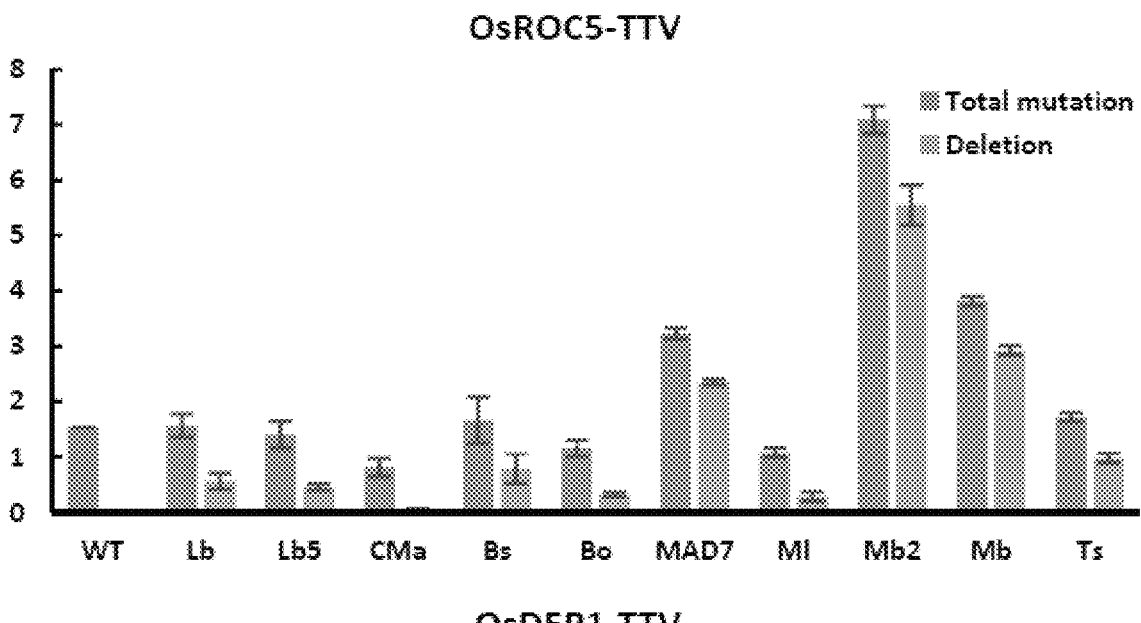
Figure 1B:
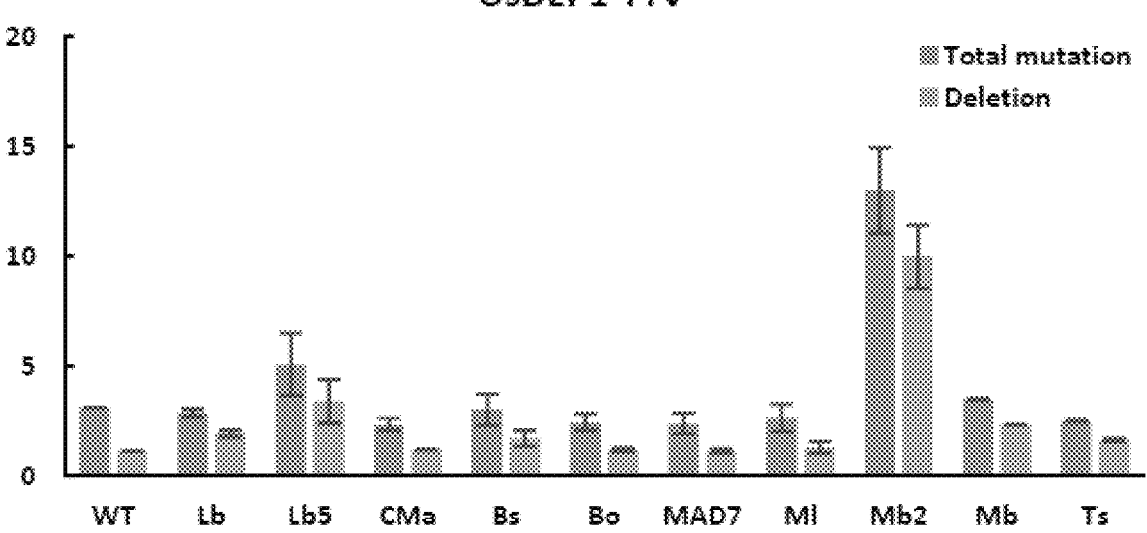

Four T-DNA constructs were generated for each Cas12a ortholog to edit four targets in rice genome, including OsDEP1 and OsEPFL9 with TTTV PAMs, as well as OsROC5 and OsDEP1 with TTV PAMs. Cas12a and its crRNA were expressed using the dual Pol II (RNA Polymerase II) promoter system, as well as the ribozyme crRNA processing system. Editing efficiencies of all Cas12a orthologs were first evaluated using rice protoplast assay, followed by high-throughput amplicon sequencing (FIG. 1A and FIG. 1B). At target site OsDEP1 with the TTTV PAM, Lb5Cas12a (28.8%), BsCas12a (20.1%), MAD7® ErCas12a (34.1%), and Mb2Cas12a (19.7%) showed efficient genome editing, which were comparable to LbCas12a (31.9%). BoCas12a (7.8%). MlCas12a (13.9%), and MbCas12a (7.2%) showed medium editing efficiencies, while CMaCas12a (2.7%) showed minimal editing activity. Similarly, at target site OsEPFL9 with the TTTV PAM, all Cas12a orthologs demonstrated medium to high editing activities (10.8-29.1%) except CMaCas12a (5.1%). How-ever, at target site OsROC5 and OsDEP1 with TTV PAMs, most Cas12a orthologs showed low editing activities (0.8-5.1%). Interestingly, Mb2Cas12a was able to efficiently edit both target sites with TTV PAMs (7.1% and 13.0%), indicating its potential ability to target short AT rich PAMs.

Figure 1C:
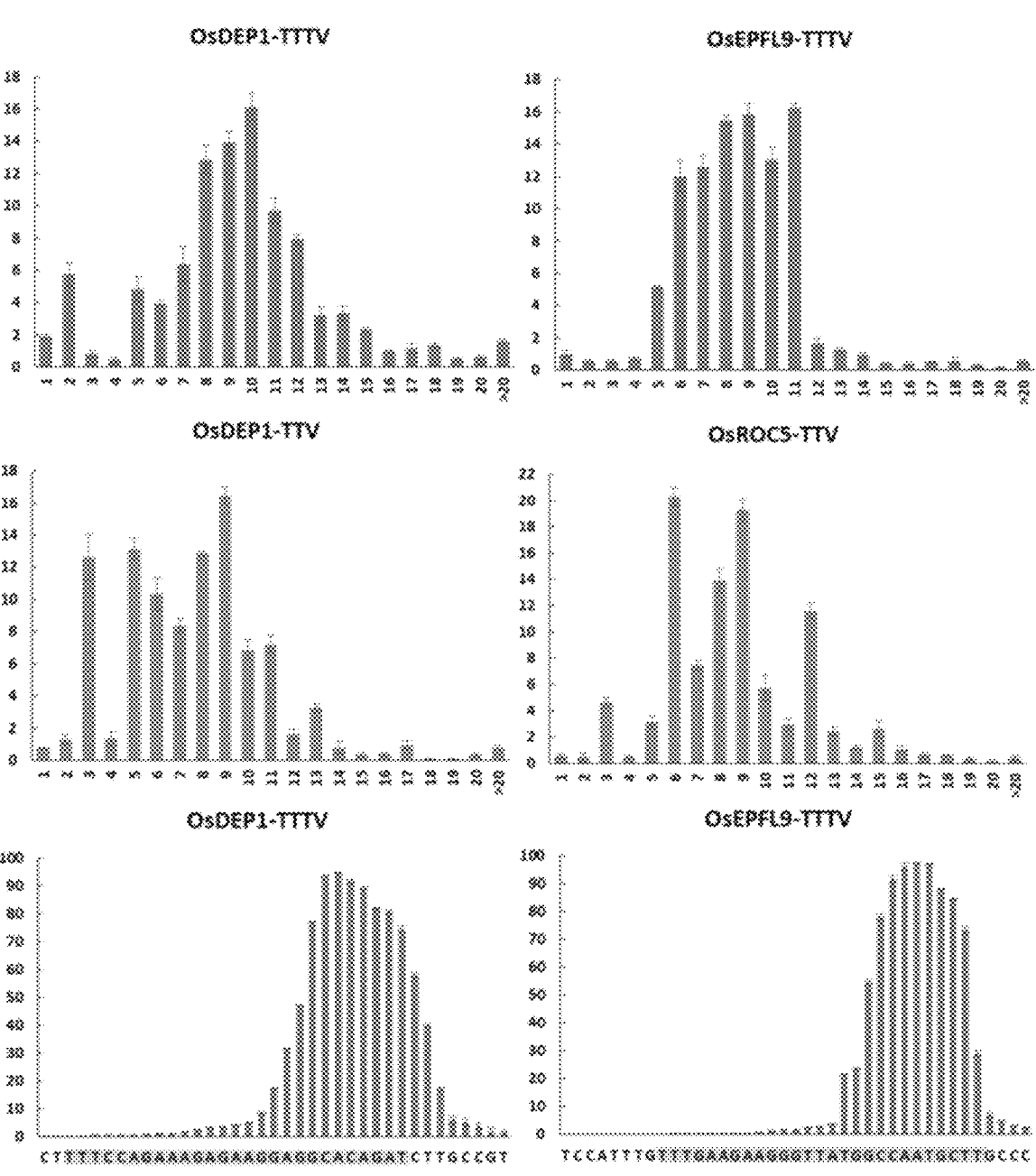
Figure 1D:
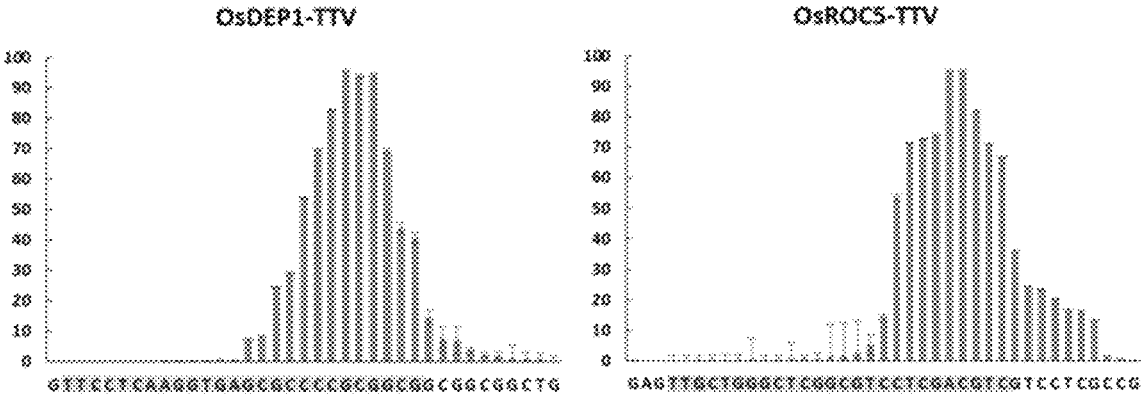

The high-throughput amplicon sequencing data also revealed the editing profiles of all Cas12a orthologs. The majority of the mutations (approximately 80%) was deletion (FIG. 1A and FIG. 1B). Large deletions were generated ranging from 5 to 15 bp, with slight shift among different target sites (FIG. 1C and FIG. 1D). There were no significant differences of the editing profiles between sites with TTTV and TTV PAMs. Except for Mb2Cas12a, all Cas12a orthologs predominantly created a 3 bp deletion at the OsDEP1-TTV site, probably due to micro-homology at the cleavage site and low editing activity. Deletion was generated at 13-27 bp away from the PAMs (TTV or TTTV), which was consistent with what we have observed for LbCas12a (FIG. 1C and FIG. 1D).

Example 2

Mb2Cas12a Efficient Targeting of NTTV PAMs

Figure 1E:
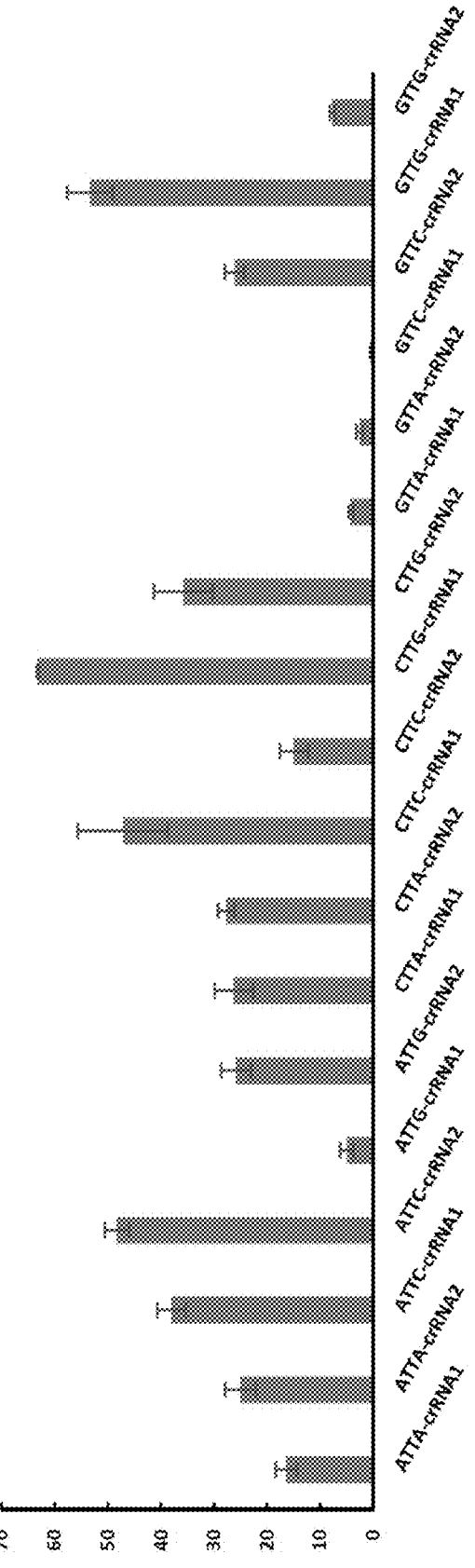

To investigate whether Mb2Cas 12a can target all VTTV PAMs, 18 target sites were chosen in the rice genome, with two target sites for each possible VTTV combination. Protoplast assay showed that Mb2Cas12a can efficiently edit 13 out of 18 target sites with mutation efficiencies about or more than 15% (FIG. 1E). Among these 13 sites, *ATTA*-crRNA1 and ATTC-crRNA2, which were not edited by FnCas12a in a previous study, were edited by Mb2Cas12a with efficiencies of 16.3% and 48.3%, respectively. Moreover, Mb2Cas 12a were able to edit target sites with GTTA and GTTC PAMs, which were rarely targetable by FnCas12a. A 26.1% editing efficiency was even obtained at site GTTC-crRNA2. Taken together, Mb2Cas12a demonstrated that it can target all NTTV PAMs, showing a broader PAM recognition range than FnCas12a.

Example 3

Mb2Cas12a Tolerance of Low Temperatures

Figure 2A:
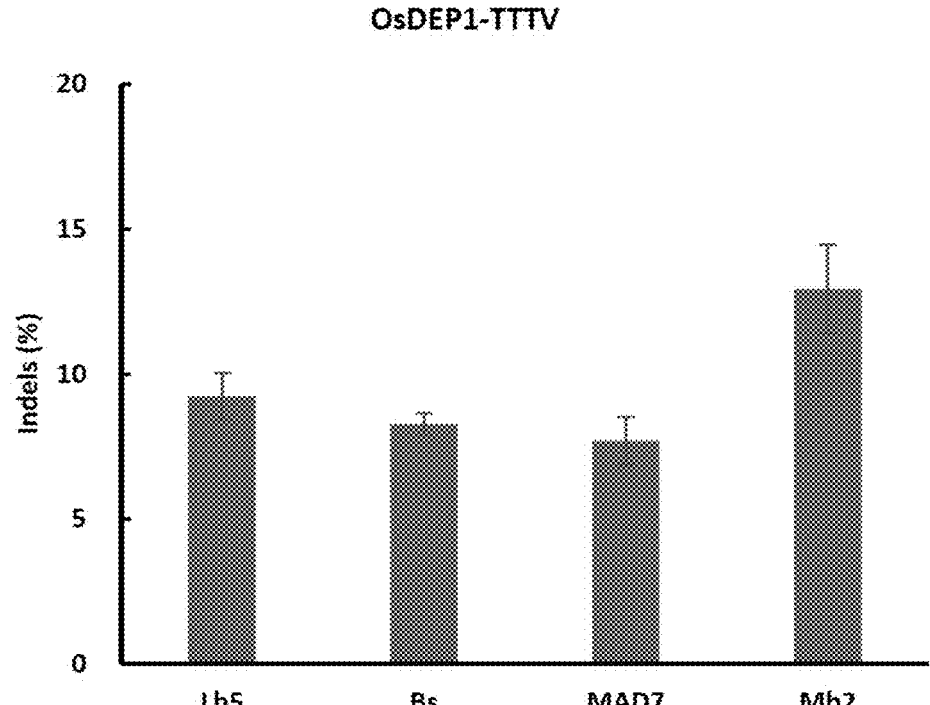
FIGS. 2A and 2B show the temperature sensitivity of Cas12a orthologs in plant cells, by the percentage of Indels induced by Cas12a orthologs at 22° C. and 32° C. Error bars represent standard errors of three biological replicates.
Figure 2A:
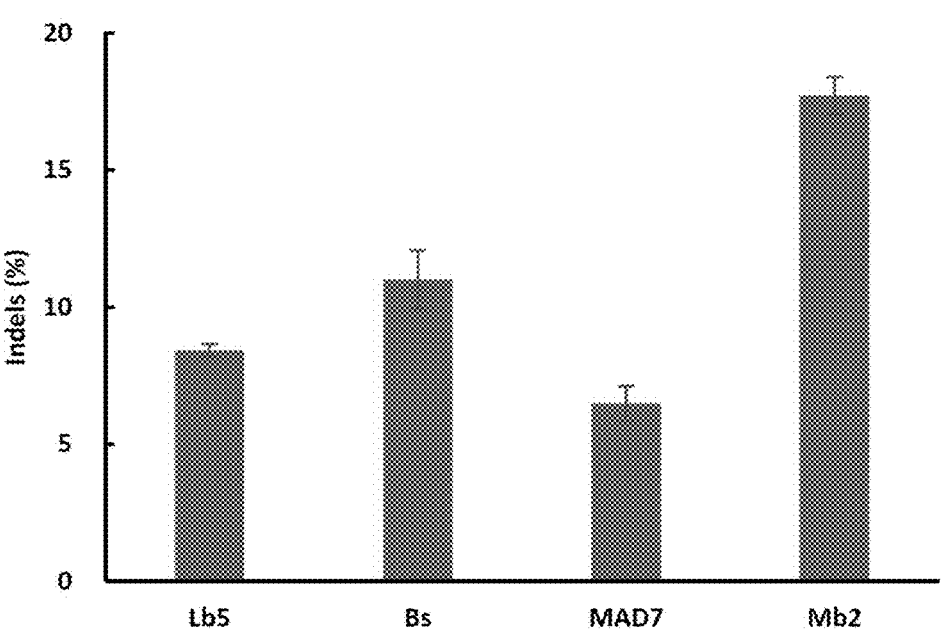
Figure 2B:
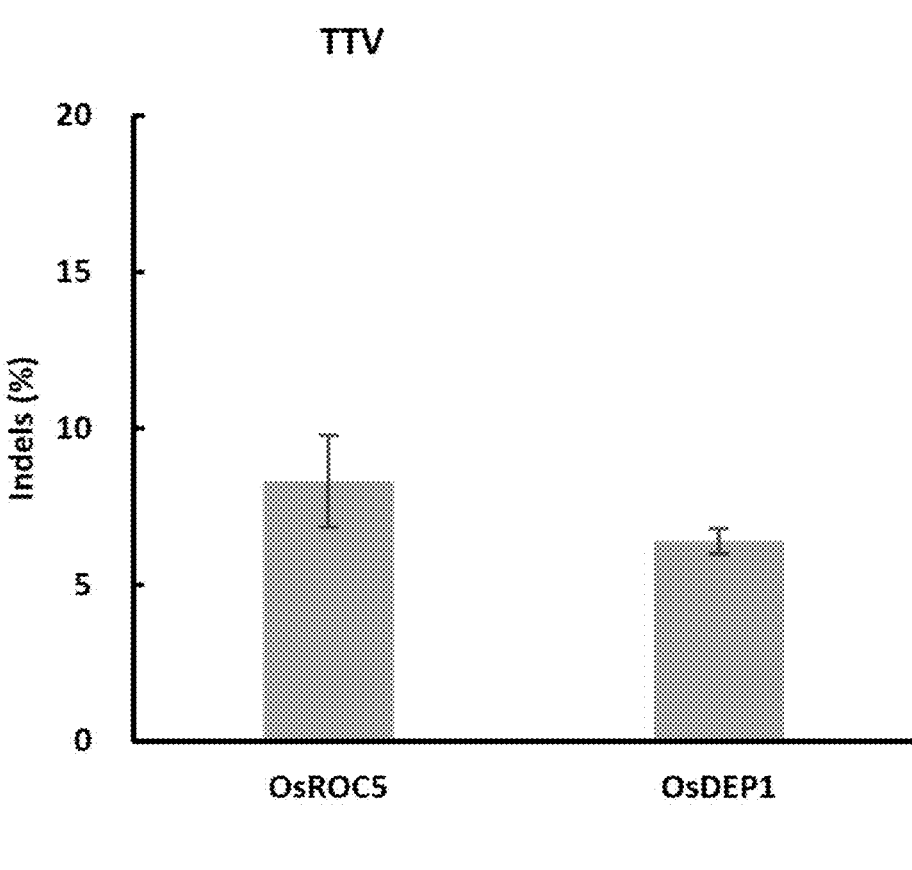

To determine whether the editing activity of Mb2Cas 12a decreases at lower temperature, as is observed for LbCas12a, four Cas12a orthologs that showed high editing efficiencies at 32° C. in previous experiments, were tested at 22° C. These included Mb2Cas12a, Lb5Cas12a, BsCas12a, and MAD7® ErCas12a (FIGS. 2A and 2B). At the two target sites with TTTV PAMs, the percentages of Indels (Insertions and deletions) induced by Mb2Cas12a was the highest among all Cas12a orthologs tested, indicating Mb2Cas12a can efficiently edit target sites with TTTV PAMs even at lower temperatures. Moreover, Mb2Cas12a induced 8.3% and 6.4% Indels at OsROC5 and OsDEP1 sites with TTV PAMs at 22° C. Together, the results showed that Mb2Cas12a is able to edit both TTTV and TTV sites at lower temperatures, and is less sensitive to temperatures than other orthologs.

Example 4

High Targeting Specificity of Cas12a Orthologs

Figure 3A:
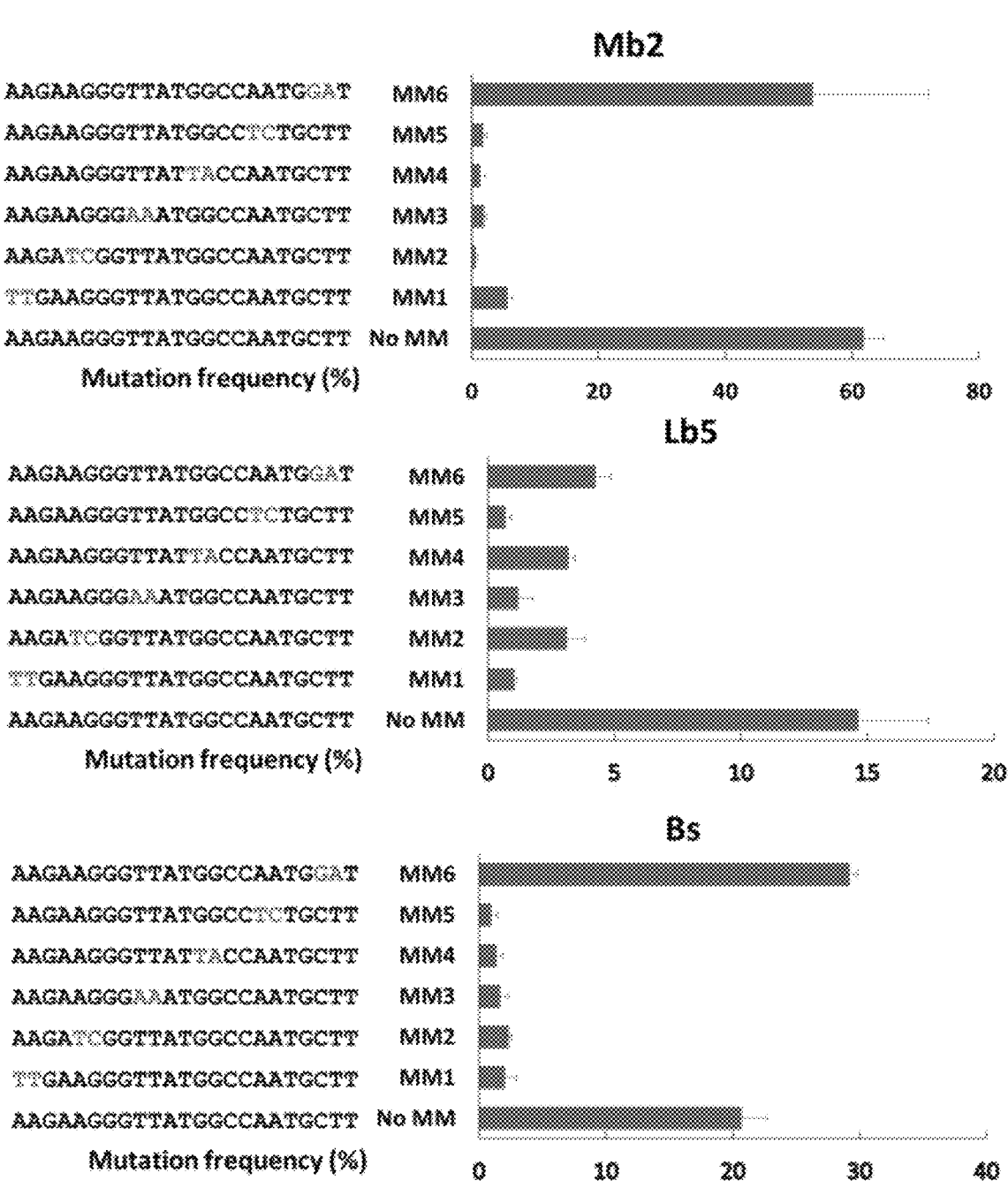
Figure 3B:
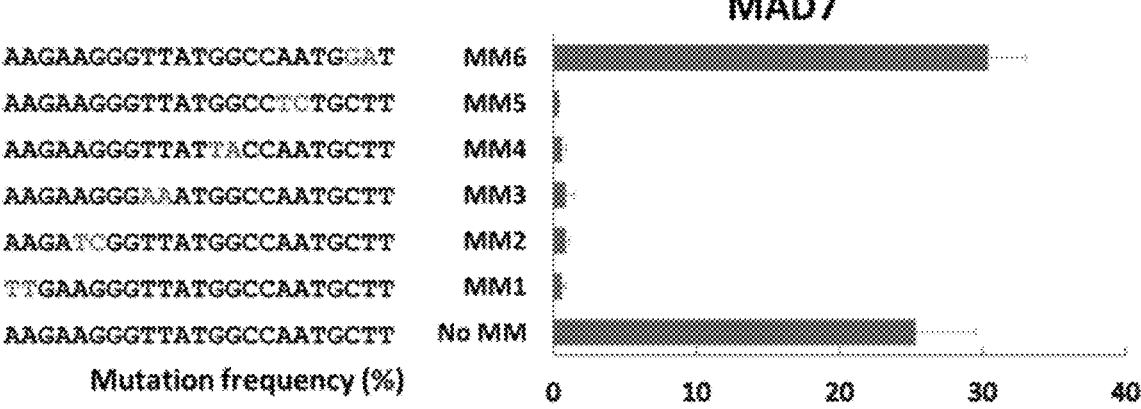

To test the specificity of the four Cas12a orthologs Mb2Cas12a, Lb5Cas12a, BsCas12a, and MAD7® ErCas12a, mismatches were introduced into the crRNA. Two mismatched base pairs were introduced at once, with MM1 the closest from the PAM while MM6 was the furthest. All four Cas12a were only able to tolerate mismatches at the last three base pairs distal from the PAM, indicating they all have high targeting specificity (FIG. 3A and FIG. 3B). These results are consistent with prior observations for LbCas12a and FnCas12a.

Example 5

Figure 3C:
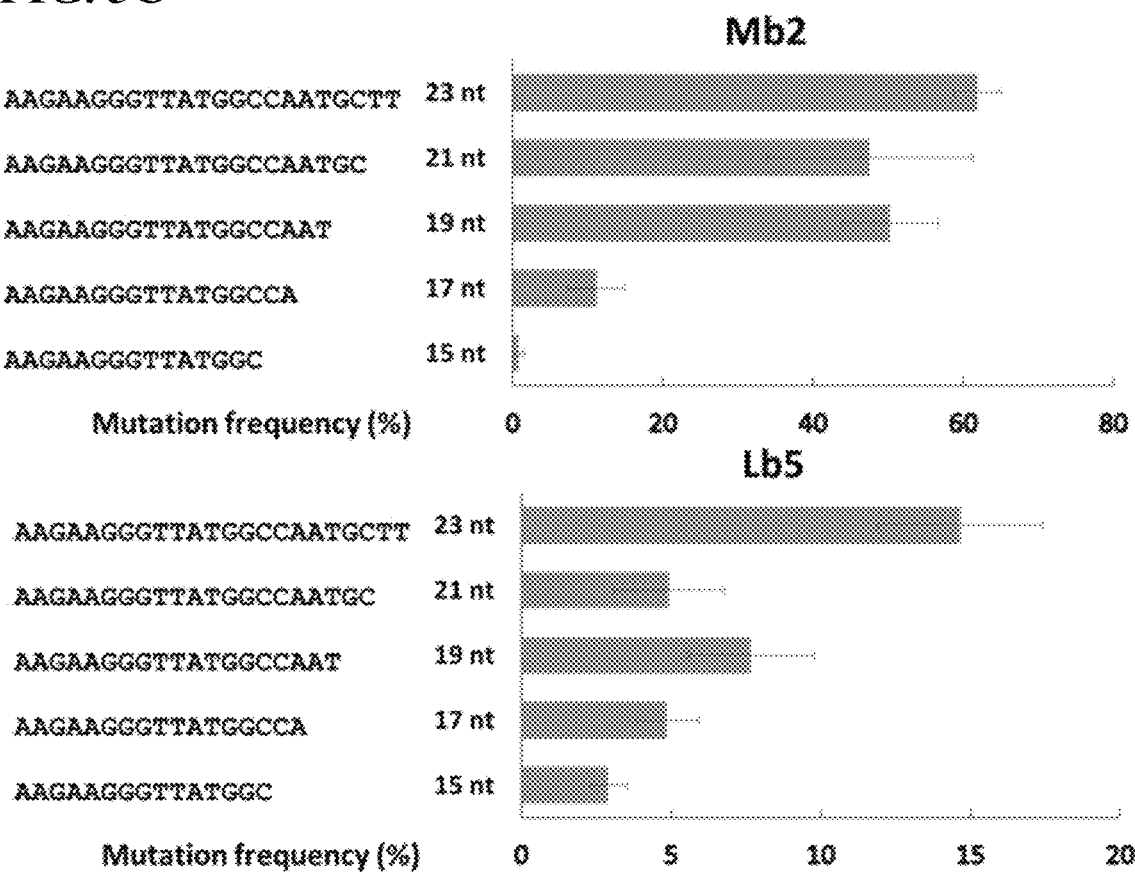
Figures 3D, 4A:
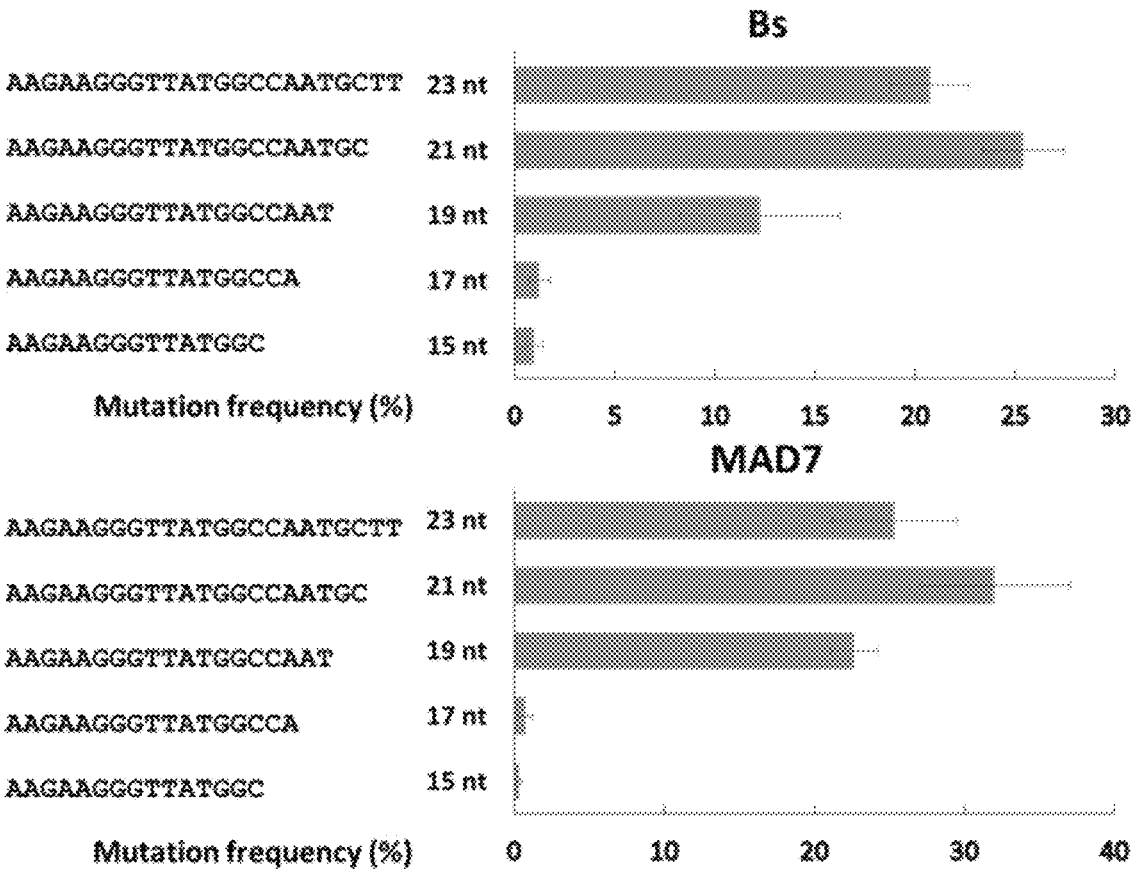

Protospacer 19 bp or Longer is Required for Efficient Genome Editing of Cas12a Orthologs Protospacer length is critical for editing efficiency and targeting specificity. Previous studies on Cas9 have shown that shortened protospacer can eliminate the editing activity of Cas9, while still maintaining the DNA-binding ability. In addition, shorter protospacer may reduce the off-target effects of Cas9 genome editing. To determine the minimum length requirement of protospacer sequence for Cas 12a orthologs, shortened crRNA were used for genome editing of four Cas12a orthologs, Mb2Cas12a, Lb5Cas12a, BsCas12a, and MAD7® ErCas12a (FIGS. 3C and 3D). Mb2Cas12a and Lb5Cas12a showed decreased editing efficiency when the crRNA was shortened. Their editing activities were almost eliminated when the crRNA was shortened to 15 bp. However, the maximum editing efficiencies were obtained for BsCas12a and MAD7® ErCas12a when the crRNA was 21 bp. Their activities were completely abolished when the crRNA was 17 bp or shorter. Based on these results, protospacer 19 bp or longer is required for efficient genome editing in rice by these four Cas12a orthologs.

Example 6

Genome Editing Using Nine Cas12a Orthologs in Stable Transgenic Plants

To further evaluate the editing abilities of all Cas12a orthologs (except CMaCas12a) used in the study, stable transgenic rice lines were generated. At TTTV sites, most of the Cas12a orthologs showed medium to high editing activities (FIGS. 4A and 4B). At site OsEPFL9, BsCas12a, MAD7® ErCas12a, and TsCas12a showed editing efficiencies over 80%, which were comparable to LbCas12a. Mb2Cas12a also showed efficient editing activity at both targeting sites (68.4% and 83.3%). These data evidence that the five Cas12a orthologs that were evaluated (Lb5Cas12a, BsCas12a, MAD7® ErCas12a, Mb2Cas12a, and TsCas12a) enable high frequency genome editing in stable transgenic rice lines.

Example 7

Efficient Multiplexed Gene Editing Using Mb2Cas12a in Stable Transgenic Plants

To edit multiple genes using Mb2Cas12a simultaneously, two multiplex strategies were used to express four crRNAs in one cassette. The first strategy was a tandem HH-crRNA-HDV strategy, with HH (hammerhead) and HDV (hepatitis delta virus) ribozymes flanking each crRNA to enable their precise processing to mature crRNA (FIG. 5A). The second strategy was the HH-CRISPR array-HDV strategy, allowing crRNA processed as a CRISPR array with the HH and HDV ribozymes facilitating the process of the first and the last crRNA (FIG. 5A). Both Mb2Cas12a and crRNAs were driven by the ZmUbi promoter, and used to generate stable transgenic lines.

Using the first strategy, the gene editing efficiencies ranged from 81.8% to 100%, with biallelic mutation rate from 72.7% to 100% (FIG. 5B). Among all transgenic plants tested, 81.8% were edited at all four genes, of which 72.7% were biallelically edited. However, the second strategy only resulted in both mutation rate and biallelic rate from 0 to 36.4%, which could be interpreted as showing that FnCas12's CRISPR array, not MbCas12a's own, was used for processing by Mb2Cas12a (FIG. 5B). Sequencing data revealed the editing profiles in multiplexed edited transgenic plants, which were consistent with the protoplast assay and singular gene editing in stable transgenic plants (FIG. 5C; FIGS. 1A-1E and FIGS. 4A-4B). These results show that Mb2Cas 12a can efficiently edit multiple genes simultaneously in stable transgenic plants using the tandem HH-crRNA-HDV strategy. The CRISPR array-based processing may be susceptible to improvement by using Mb2Cas12a's own crRNA scaffold.

Example 8

RVR Variants of Cas12a Orthologs can Efficiently Target TATV PAMs

To further broaden the target range of Cas12a orthologs, RVR variants were generated for the four Cas12a orthologs Mb2Cas12a (SEQ ID NO: 299), Lb5Cas12a, BsCas12a, and MAD7. Previous studies in plants indicated that the RVR variant of LbCas12a was only able to target the TATG PAM, while the RVR variant of FnCas12a barely showed any activities at TATV target sites.

Figure 6A:
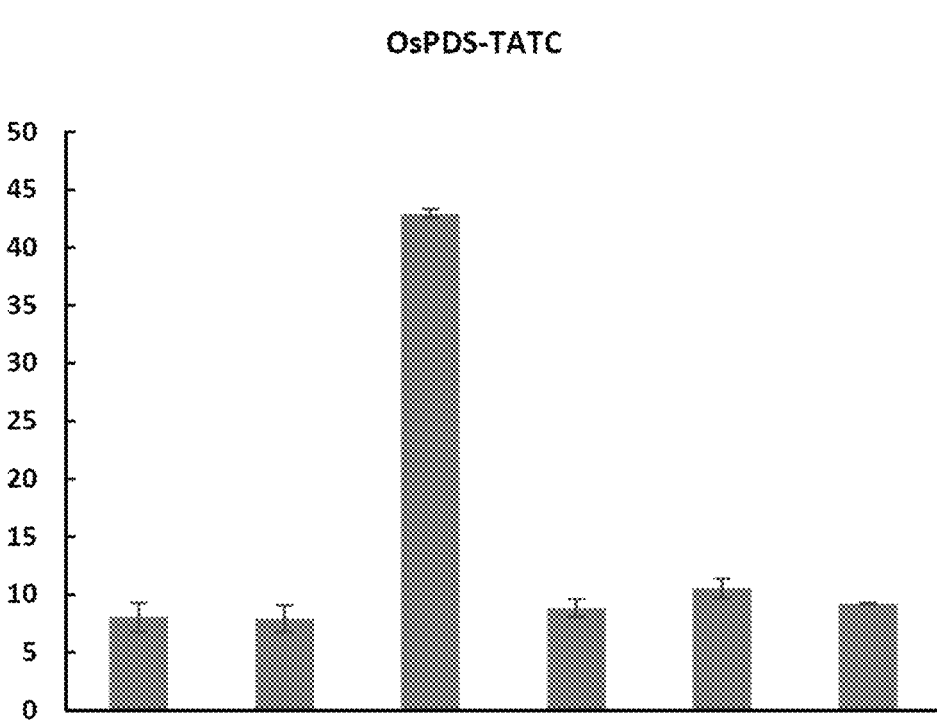
FIGS. 6A-6C the results of genome editing using variants of Cas 12a orthologs in stable transgenic plants, in editing efficiencies of RVR variants of LbCas12a and four Cas12a orthologs at six TATV sites. Error bars represent standard errors of three biological replicates.
Figure 6A:
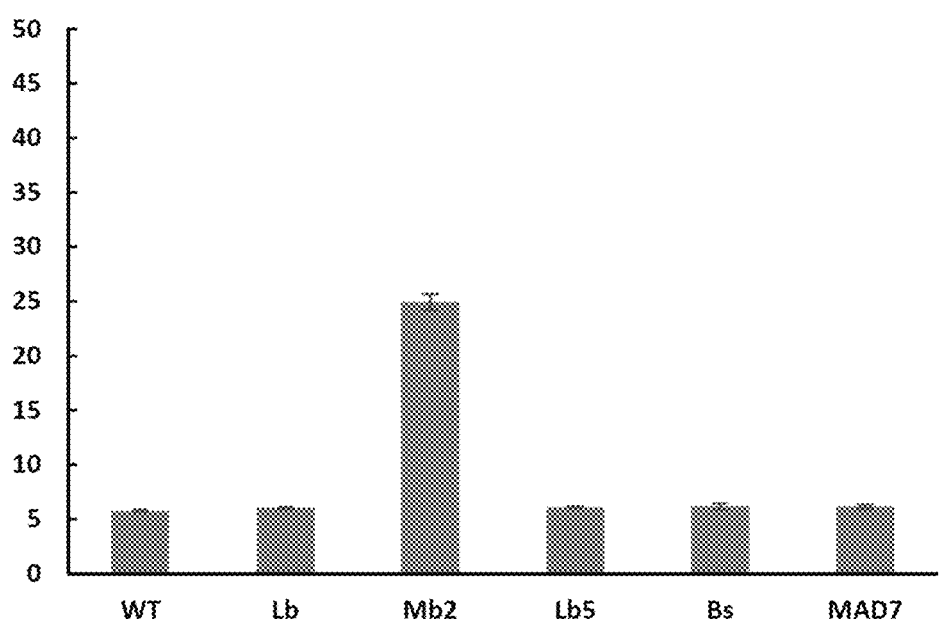
Figure 6B:
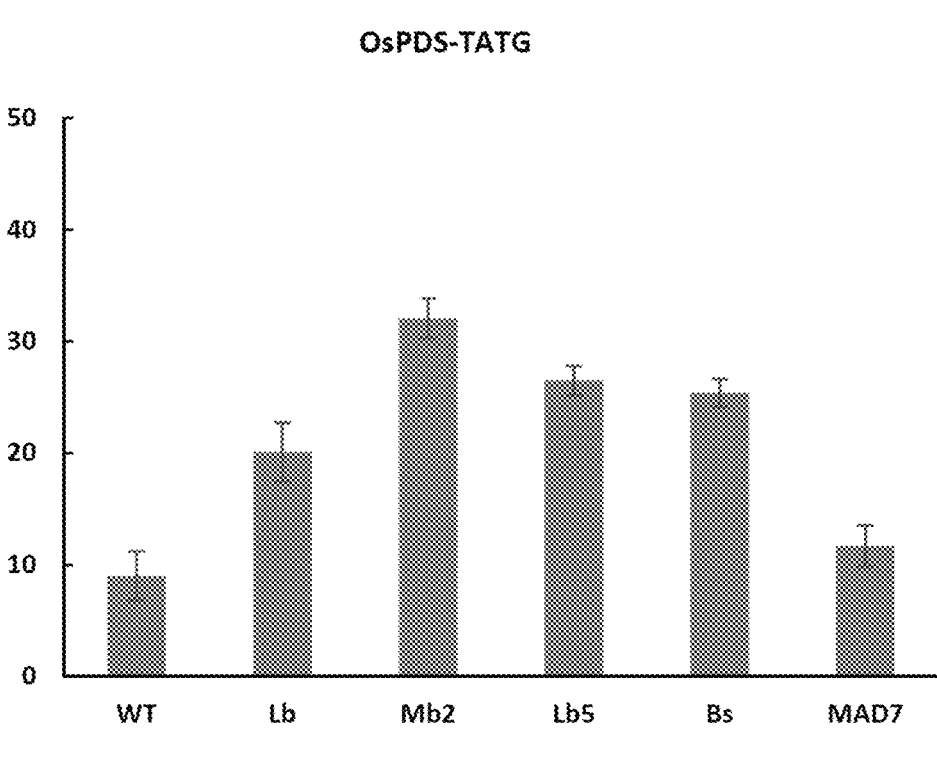
Figure 6B:
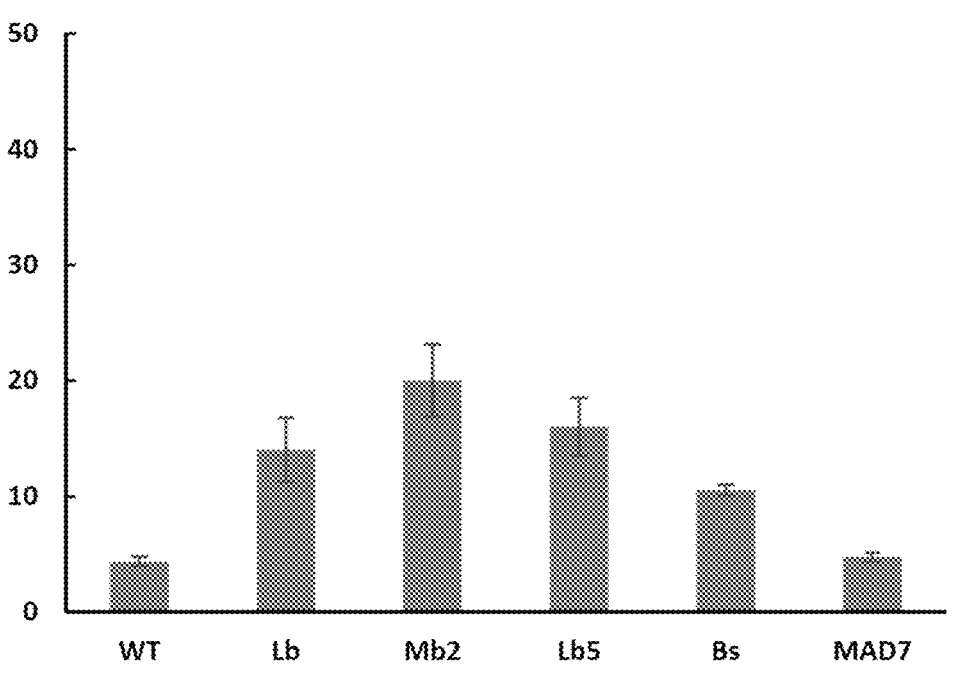
Figure 6C:
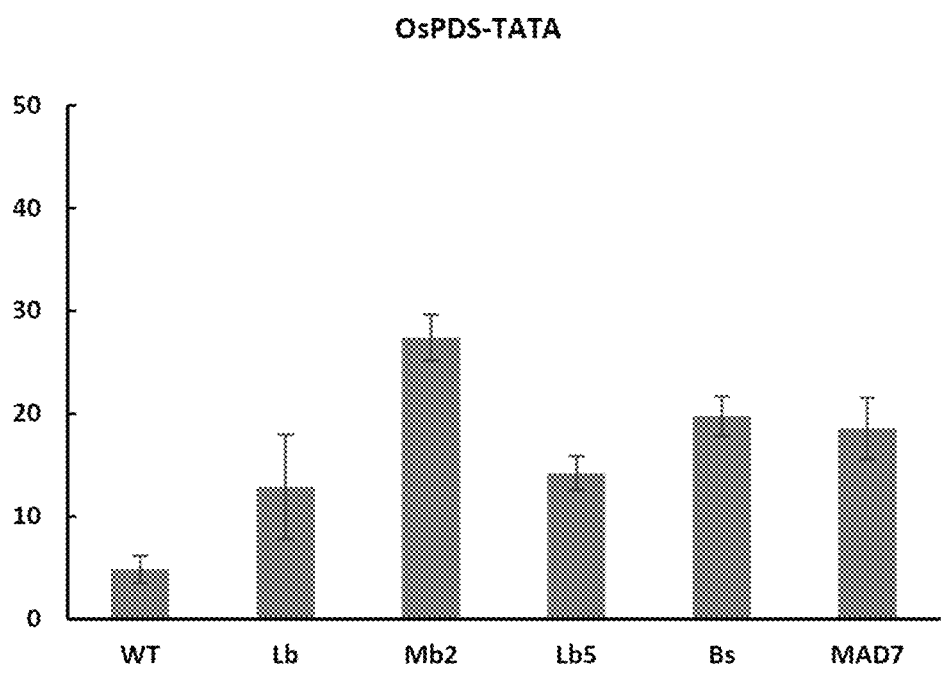
Figure 6C:
Figure 6C:
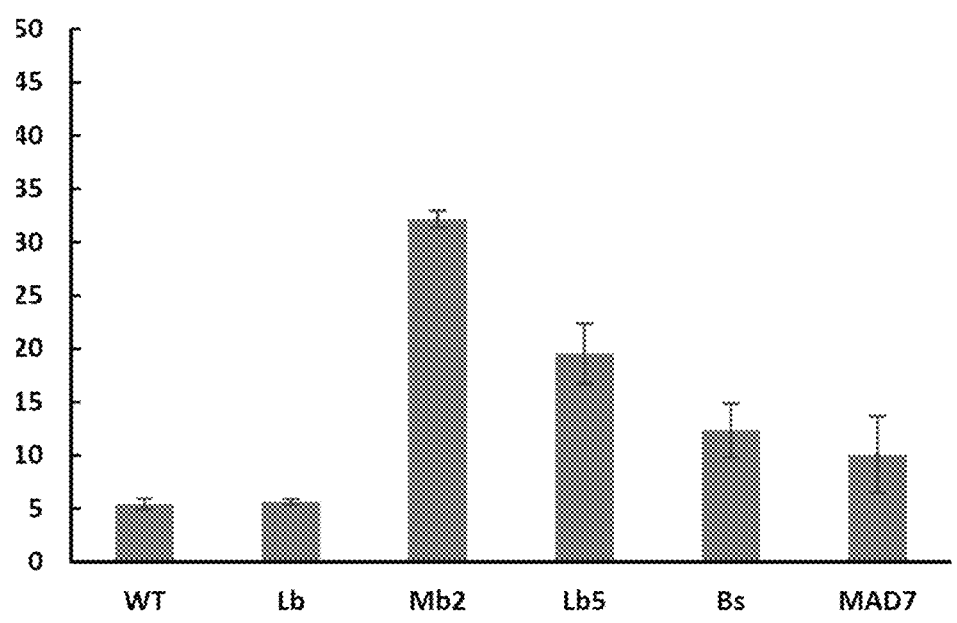

Six sites with TATV PAMs were used to test the editing activities of Cas12a ortholog variants. Mb2Cas12a was able to edit all the target sites with TATV PAMs, with efficiencies from 20% to 42.9% (FIGS. 6A-6C). Mb2Cas12a outperformed all other Cas12a nucleases that were tested, including LbCas12a. In addition, Lb5Cas12a, BsCas12a and MAD7® ErCas12a were found to edit sites with TATG and TATA PAMs, but not the TATC PAM. The foregoing results increased the target sites that are accessible to Cas12a orthologs, and show the beneficial application of this Mb2Cas12a-RVR variant for editing TATV PAMs in plants.

Example 9

Comparison of Ten Multiplexed Cas12a Systems in Rice

Figure 7A:
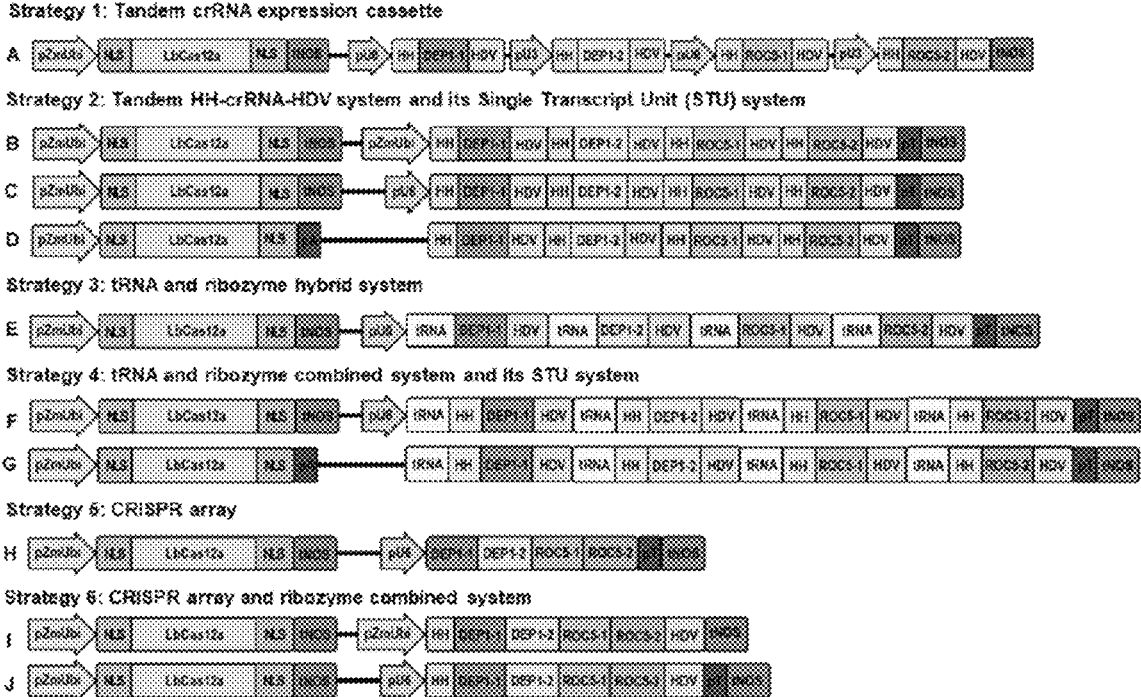
FIGS. 7A-7B illustrate the testing of ten multiplexing Cas12a strategies for targeting four sites in two genes in rice. Part

To develop multiplexed Cas12a systems of higher editing efficiency, 10 multiplexed Cas12a systems were first tested, which can be grouped into 6 strategies (FIG. 7A). In all systems, the same rice codon-optimized LbCas12a was driven by a maize ubiquitin promoter (pZmUbi1) with the same vector backbone. All the systems were tested for multiplexing four crRNAs, with two crRNAs targeting OsDEP1 and the other two targeting OsROC5. Strategy 1 utilized tandem crRNA expression cassettes where each crRNA has its own promoter, either OsU6 (pU6) or OsU3 (pU3). The crRNAs were processed by ribozymes hammer head (HH) and hepatitis delta virus (HDV). Separate Pol II promoters were not used for expressing each crRNA, based on consideration of the length of each Pol II promoter (e.g. ~2 kb for pZmUbi1). Strategy 2 was to compare the tandem HH-crRNA-HDV system under three expression conditions: by a Pol II promoter (pZmUbi1), by pU6, or by a STU system (also driven by pZmUbi1). Strategy 3 utilized a Pol III promoter (pU6) to drive a tRNA-crRNA-HDV array, taking advantage of tRNA processing and tRNA's possible promoter activity. Given that tRNA processing may leave a few extra nucleotides at the 5' end, Strategy 4 explored the use of pU6 to express a tRNA-HH-crRNA-HDV array with the objective of ensuring more precise processing of crR- NAs at both ends while still benefiting from tRNA's promoter activity. An STU version was also included in this strategy. Strategy 5 was the pU6-driven CRISPR array system that had been previously explored. Strategy 6 used HH and HDV ribozymes to flank the entire crRNA array in order to compensate potential suboptimal self-processing of crRNAs by the Cas12a protein itself. Both Pol II promoter (pZmUbi1) and Pol III promoter (pU6) were compared in this strategy.

Figure 7B:
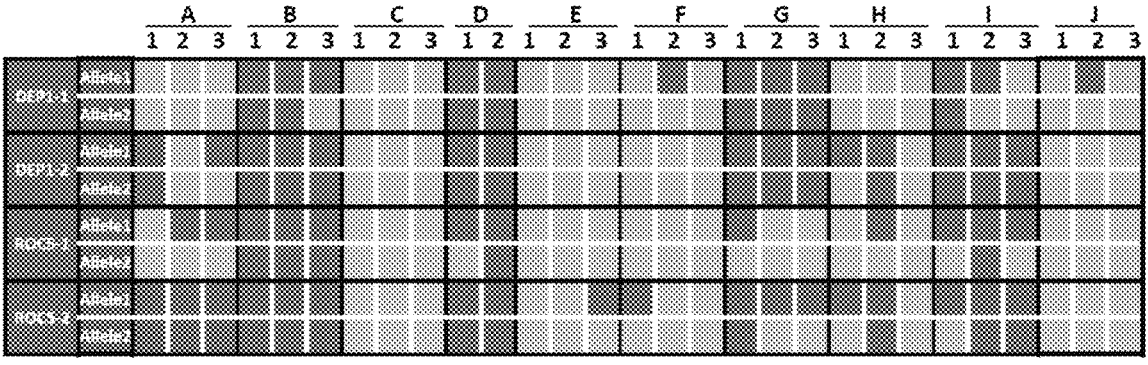

To compare these 10 multiplex systems, the resulting T-DNA vectors were used for generating stable transgenic rice lines with *Agrobacterium* mediated transformation. Three independent T0 lines were genotyped at all four target sites for each strategy except for system 'D' where only two independent T0 lines were examined. A large number of T0 lines were not pursued for each construct, since this screen was a first round. Based on the genotyping data from the limited T0 lines, these strategies were ranked in the following order of high activity to low activity: System 'B' or 'D'>System 'G' or 'I'>System 'A'>System 'H'>System 'C', 'E', 'F', or 'J' (FIG. 7B). The best performing multiplex systems ('B' and 'D') resulted in T0 lines each containing biallelic mutations for nearly all four target sites and these strategies relied on the Pol II promoter (either dual Pol II or STU) and the HH-crRNA-HDV array (FIGS. 7B and FIG. 8A and 8B). By contrast, the least performing multiplex systems ('C', 'E', 'F' and 'J') at most contained only one monoallelic mutation at one of the four target sites and these strategies all used the Pol III promoter (pU6) despite different crRNA processing mechanisms (FIG. 7B and FIGS. 8A and 8B). These results suggest that Pol III promoter-based systems are not suitable for expressing multiple crRNAs, even though they are the earliest proven multiplex Cas12a systems in humans and plants.

Example 10

Refined Comparison of Seven Multiplex Cas12a Systems in Rice

Based on the results of the first-round testing in Example 9, consideration was focused on dual Pol II promoter or STU systems since they use Pol II promoters for crRNA expression. In this second round, four crRNAs were chosen to target four different genes: OsPDS, OsDEP1, OsROC5, and OsmiR528. This design allowed further testing of the systems with a different set of crRNAs, but also made the subsequent genotyping work more straightforward because it was only necessary to focus on targeted mutagenesis at each target gene without concern about larger deletions generated by simultaneous targeting of the same gene with two crRNAs. The retained strategies were strategies 2, 4, 5 and 6 including systems 'B', 'D', 'G', 'H', and 'I' for further comparison (FIG. 9A). The system 'H' used pU6 to express a crRNA array and was included as a control. Two additional STU systems were included, 'M' and 'L' (FIG. 9A). The STU system 'M' used a crRNA array with the last crRNA ending with an extra direct repeat (DR). The STU system 'L' used HH and HDR to flank the crRNA array. In total, seven multiplex Cas12a systems were designed for simultaneous editing at four target genes.

In this second round testing, rice transformation was conducted on a larger scale. For the seven systems 'B', 'D', 'G', 'H', 'M', 'I' and 'L', 36, 60, 36, 50, 30, 33 and 36 T0 lines were generated, respectively. Each T0 plant was assessed by the restriction fragment length polymorphism (RFLP) assay and Sanger sequencing at all four target sites and scored allelic mutation outcomes (FIGS. 10-16). The system 'B' stood out as the most efficient multiplex system and resulted in 100% targeted mutagenesis at every single target site in every T0 line assessed (FIGS. 9B and 10). More impressively, all T0 lines carried biallelic mutations at three target genes: OsPDS, OsROC5 and OsmiR528. For OsDEP1, 24 out of 36 lines (66.7%) carried biallelic mutations and the remaining 12 carried monoallelic mutations. The second tier of high efficiency multiplex systems included 'D', 'M' and where editing efficiency was over 50% for every target site. For OsmiR528, system 'D' achieved 100% editing efficiency and 95% (57 out of 60 lines) biallelic editing efficiency; system 'M' achieved 93.3% (28 out of 30 lines) editing efficiency and 80% (24 out of 30 lines) biallelic editing efficiency; system 'L' achieved 100% editing efficiency and 88.9% (32 out of 36 lines) biallelic editing efficiency. In these three systems, editing efficiencies were lowest at OsDEP1 site (60% for system 'D', 59.4% for system 'M' and 52.8% for system 'L'), which suggests intrinsically low activity of this crRNA. The remaining three systems were ranked in the following order of high activity to low activity: system 'I', system 'H' and system 'G'.

To gain further insights, multiplexed editing efficiency was analyzed and all seven systems were ranked accordingly. System 'B' was the best performer, achieving 100% multiplexed editing (FIG. 17A). The second-tier systems, 'D', 'M' and were again clustered together with similar efficiencies: 40-50% were quadruple editing lines; 20-40% more triple editing lines; the remaining were double, single or non-editing lines (FIG. 17A). Interestingly, system 'H' had a higher proportion of quadruple editing lines than system 'I', although the latter contained a much higher proportion of triple editing lines (FIG. 17A). A further breakdown of multiplexed biallelic editing efficiency showed a very consistent trend with the overall editing activity (FIG. 17B). Finally, we ranked all seven strategies based on how many genes they can simultaneously edit (FIG. 17C). This analyses collectively resulted in four tiers based on editing activities (FIGS. 17A-17C). Tier 1 contained only system 'B' where all four genes were edited with high biallelic editing efficiency, further confirming this dual Pol II promoter and tandem HH-crRNA-HDV system is most efficient multiplexing system among all tested. Tier 2 contained systems 'D', 'M' and where on average three genes were edited and two genes were edited biallelically. All these three systems are compact STU systems rely on a single Pol II promoter. Tier 3 contains systems 'H' and 'I' where on average two genes were edited and only one gene was edited biallelically. Tier 4 contains system 'G', where on average only one and a half gene were edited and nearly none was edited biallelically. Hence, system 'G' is the most inefficient multiplex system among the seven. Comparison of 'H' and 'M' across two tiers suggests that the ZmUbi1 based STU system is more efficient than the OsU6 system for expressing a CRISPR array. Interestingly, when crRNAs were expressed in an HH-CRISPR array-HDV configuration, the STU system worked better than the dual Pol III promoter (e.g. comparing 'I' and These results suggest that the promoter system and crRNA processing system collectively dictate the functionality and activity of the multiplexed Cas12a systems.

Example 11

Simultaneous Targeting of Sixteen Rice Sites for Assessing Multiplex Cas12a System Since system 'B' showed the most efficient multiplexed editing at four target sites, the performance of this system at a significantly scaled up multiplexing level was evaluated. To this end, a single T-DNA vector based on this system was generated to simultaneously target 16 genomic sites across nine chromosomes in rice (FIG. 18A). A few T0 lines were initially tested for editing at 8 sites with the RFLP assay. This initial analysis suggested that these 8 sites were biallelically edited in nearly all T0 lines, evidencing a high editing efficiency at all targets. To fully assess the editing outcome, 2 lines were subjected to Sanger sequencing at all 16 target sites. It was found that every target site had been edited, except target 4 (FIG. 18B). More impressively, 14 sites were biallelically edited in both lines (FIG. 18B). These data suggest that the system 'B' is a very efficient and reliable multiplex Cas12a system, suitable for large-scale genome engineering.

Example 12

Multiplexed Transcriptional Repression in Rice with Two Compact STU dCas12a-SRDX Systems Previously, transcriptional repression of single genes in plants with dCas12a-SRDX had been generated. Accordingly, it was hypothesized that multiplexed Cas12a systems of the present disclosure should allow for simultaneous transcriptional repression of multiple genes. The STU systems represent the most compact expression systems while allowing for coordinated expression of both Cas12a and crRNAs under a single promoter. Two of the three best performing STU systems, 'D' and 'M', were tested for multiplexed transcriptional repression. First, the systems were tested in rice by simultaneous targeting four genes: Os11g36470, Os12g38110, Os03g16440, and Os01g59980. For each system, two sets of crRNAs were designed with one set of four targeting the upper stand of the promoters and the other set of four targeting the lower stand of the promoters (FIG. 19A). The resulting four T-DNA vectors, along with the no-crRNA control vector, were used for transfection of rice protoplasts. Target gene expression were quantified in samples two days after transfection by qRT-PCR. The two constructs for system 'D' (antisense and sense) resulted in transcription repression to 40-60% of the control level for every target gene (FIG. 19B). Similar level of transcriptional repression was observed for one construct of system 'M-antisense' where all four crRNAs target the lower stand of the promoters (FIG. 19B). Interestingly, more pronounced transcriptional repression was observed for the other construct of system 'M-sense' with crRNAs targeting the upper stand of the promoter, where transcription was reduced to ~20% of the control at each target gene (FIG. 19B).

To further compare the 'D' and 'M' systems for transcriptional repression, two tandemly arrayed genes, At3g48090 and At3g48080, which encode two Enhanced Disease Susceptibility 1 (EDS1) homologs, were targeted. Two crRNAs were designed to target each promoter of the two genes. The two resulting T-DNA vectors, with each multiplexing four crRNAs, were used to transform Arabidopsis by the floral dip methods. Seven independent T0 lines from the 'D' system were tested for target gene repression by qRT-PCR. Weak repression was observed for At3g48090 as the transcripts were only reduced to 60-80% of the WT level (FIG. 19D). However, pronounced transcription repression was obtained for At3g48080 as the transcripts were reduced to 20-40% of the WT level (FIG. 19D). Eight independent T1 lines for the 'M' system were tested, with similar results, namely, minor transcriptional repression for At3g48090 and significant repression for At3g48080 (FIG. 19E). To assess whether transcriptional repression was inheritable to the next generation, two T1 lines (#5 and #8) were followed to T2 generation. Bulked T2 plants were tested by qRT-PCR and the results showed weak repression of At3g48090 and strong repression of At3g48080, consistent with the data from their parental lines.

Example 13

A Multiplexed Cas12a Toolbox for Plant Genome Engineering

The comparison and characterization of many multiplexed Cas12a systems identified the best-performing system, 'B', for high-efficiency genome editing. Other Pol II promoter systems such as 'D', 'I', 'L' and 'M' resulted in reasonably high genome editing efficiencies and three of them ('D', 'L' and 'M') are STU systems. Two of these STU systems, 'D' and 'M', have been demonstrated for transcriptional repression in both rice and *Arabidopsis*. The assembly of these five best-performing systems is based on modular approaches, including Golden Gate cloning and Gateway cloning, and ready implementation of these systems can be made, using the modular vectors identified in Table 1 below for the assembly, in the assembly approach illustrated in FIG. 14.

final 'Step 3' assembly is based on three-way Gateway LR reactions, a single cloning step that combines an attL1-attR5 Cas12a entry clone, an attL5-attL2 crRNA expression cassette, and an attR1-attR5 destination vector (FIG. 20). This modular assembly approach follows a synthetic biology part design and is fully compatible with previous CRISPR-Cas9 and Cas12a tool systems.

Recent studies have reported multiplexed Cas12a genome editing systems in rice and in dicot plants. Two studies have used an OsU6 or OsU3 promoter to express a CRISPR array in stable transgenic rice plants. Researchers used an OsU6 promoter to express four crRNAs and obtained total editing efficiency and biallelic editing efficiency of 40%-60% and 10-20%, respectively, for LbCas12a, and 43.8%-75% and 6.3%-28.1%, respectively, for FnCas12a. Other researchers used an OsU3 promoter to express four crRNAs and obtained editing efficiency and biallelic editing efficiency of 34.2%-45% and 2.2-43.5%, respectively. In work conducted by the present inventors relating to the present disclosure, when an OsU6 promoter was used to express a CRISPR array of four crRNAs, editing efficiencies of similar ranges as in these prior reports were obtained: 30-82% for total mutations and 10-60% for biallelic mutations. However, as the results obtained by the present inventors have convincingly shown, the systems that use a strong Pol II promoter (e.g., ZmUbi1) outperform the systems based on a Pol III promoter for crRNA expression (FIGS. 7A-7B, 9A-9B, and 17A-C).

TABLE 1

Golden Gate and Gateway compatible vectors for assembly of top-performing multiplex Cas12a systems for plant genome editing and transcriptional repression

| Vector type | Vector name (Addgene #) | Reference |
|---|---|---|
| Golden gate assembly vector | pYPQ131-STU-Lb (#138096); pYPQ132-STU-Lb (#138099); pYPQ133-STU-Lb (#138102); pYPQ134-STU-Lb (#138105); pYPQ131-STU-As (#138094); pYPQ132-STU-As (#138097); pYPQ133-STU-As (#138100); pYPQ134-STU-As (#138103); pYPQ131-STU-Fn (#138095); pYPQ132-STU-Fn (#138098); pYPQ133-STU-Fn (#138101); pYPQ134-STU-Fn (#138104); | present disclosure |
| Recipient vector | pYPQ142 (#69294); pYPQ143 (#69295); pYPQ144 (#69296) | Lowder et al., 2015 |
| | pYPQ142-ZmUbi (#138106); pYPQ143-ZmUbi (#138107); pYPQ144-ZmUbi-pT (#138108) | present disclosure |
| Cas12a entry vector | pYPQ230 (Lb editing: #86210); | Tang et al., 2017 |
| | pYPQ233 (Lb repression; #86211); pYPQ223 (As repression; #86209) | |
| | pYPQ239 (Fn editing; #108859) | Zhong et al., 2018 |
| | pYPQ230-STU (Lb editing; #138110); pYPQ239-STU (Fn editing; #138112); | present disclosure |
| | pYPQ233-STU (Lb repression; #138111); pYPQ223-STU (As repression; #138109) | |
| Destination vector | pYPQ202 (#86198); pYPQ203 (#86207) | Tang et al., 2017 |

References:
Tang, X. et al. A CRISPR-Cpf1 system for efficient genome editing and transcriptional repression in plants. *Nature Plants* 3, 17103 (2017).
Zhong, Z. et al. Plant genome editing using FnCpf1 and LbCpf1 nucleases at redefined and altered PAM sites. *Molecular Plant* 11, 999-1002 (2018).
Lowder, L. G. et al. A CRISPR/Cas9 toolbox for multiplexed plant genome editing and transcriptional regulation. *Plant Physiol.* 169, 971-985 (2015).

To assemble the HH-crRNA-HDV based systems ('B' and 'D'), protospacer of each crRNA may be cloned into the Golden Gate entry vectors (pYPQ131, pYPQ132, pYPQ133, and pYPQ134) in 'Step 1' (FIG. 20). Then, these crRNA cassettes can be assembled into pYPQ144 vectors by Golden Gate cloning in 'Step 2'. If needed, multiplexing more than four HH-crRNA-HDV cassettes can be easily accommodated with a higher order assembly. To assemble CRISPR array-based systems ('I', 'L' and 'M'), DNA synthesis of such an array can be performed for direct cloning into the crRNA expression vectors (e.g. pYPQ144-ZmUbi1-pT and pYPQ144) so that 'Step 1' is omitted (FIG. 20). The There are two general approaches to express crRNAs with Pol II promoters. The first approach is to express crRNAs with a dedicated Pol II promoter as an independent transcription unit, which can enable highly efficient genome editing with singular crRNAs as the present inventors have previously shown in rice, maize and *Arabidopsis*. To develop a best dual Pol II promoter system for multiplexed genome editing with Cas12a, a tandem HH-crRNA-HDV system ('B') and an HH-CRISPR array-HDV system (T) under ZmUbi1 were expressed. The former system was found to be far more efficient than the latter, resulting in 100% editing efficiency at all four target sites (FIGS.

9A-9B). The less efficient system, HH-CRISPR array-HDV, showed a comparable editing efficiency to a similar system recently published.

To further demonstrate the dual Pol II promoter and tandem HH-crRNA-HDV system, 16 sites were targeted in the rice genome and could easily identify T0 plants with 14 target sites biallelically edited. This potent Cas12a system for high capacity multiplexed genome editing represents a major advance in the art and has multiple promising applications in plants. For example, this system can be used to target multiple members of a gene family to better address functional redundancy in reverse genetics. Given that Cas12a typically generates much larger deletions than Cas9, promoter bashing methods based on Cas12a may be more effective than those based on Cas9. Hence, the highly efficient multiplexed Cas12a system of the present disclosimilar systems reported earlier and the STU-2.0 system that the present inventors have recently developed. Better performance of the present inventors' new STU systems may be explained by the choices of promoter, terminator, Cas12a codon optimization, vector backbone, etc. For example, there are three differences between the new STU vectors and the previous one: poly A sequence context, terminator and length of direct repeat of CRISPR arrays. Strikingly, it was found that the STU system is more efficient than the dual Pol II promoter system if crRNAs are expressed in an HH-CRISPR array-HDV configuration (comparing 'I' and 'L') (FIGS. 17A-17C). This in turn suggests that developing a highly efficiency multiplexed Cas12a system requires an optimal combination of the expression system and the crRNA processing system.

TABLE 2

Comparison of Cas12a multiplexing studies in stable transgenic rice

| Study | Cas12a | Cas12a promoter | crRNA promoter | Targets | Multiplexing strategy | Editing efficiency | Biallelic editing efficiency |
|---|---|---|---|---|---|---|---|
| Wang et al., 2017 | FnCas12a | ZmUbi | U6 | 4 | CRISPR array | 43.8-75% | 6.3-28.1% |
| | LbCas12a | ZmUbi | U6 | 4 | CRISPR array | 40-60% | 10-20% |
| Wang et al., 2018 | FnCas12a | ZmUbi | ZmUbi | 8 | HH-CRISPR array-HDV | 0-70.8% | 0-66.7% |
| | FnCas12a | ZmUbi | — | 8 | CRISPR array-DR (STU) | 0-70.8% | 0-41.7% |
| | LbCas12a | ZmUbi | CmYLCV | 9 | tRNA- CRISPR array-DR-tRNA | 4.2-54.2% | 0-50% |
| | LbCas12a | ZmUbi | — | 9 | tRNA- CRISPR array-DR-tRNA (STU) | 4.2-70.8% | 0-41.7% |
| Tang et al., 2019 | LbCas12a | ZmUbi | — | 4 | CRISPR array-DR (STU) | 29.2-50% | 4.2-33.3% |
| Hu et al., 2019 | FnCas12a | OsACTIN1 | U3 | 4 | CRISPR array | 34.2-45% | 2.2-43.5% |
| | FnCas12a | OsACTIN1 | U3 | 4 | Truncated tRNA-crRNA array | 29.2-55.6% | 3.2-19.4% |
| Present disclosure | LbCas12a | ZmUbi | ZmUbi | 4 | Tandem HH-crRNA-HDV | 100% | 72.2-100% |
| | LbCas12a | ZmUbi | — | 4 | Tandem HH-crRNA-HDV (STU) | 60-100% | 8.3-95% |
| | LbCas12a | ZmUbi | — | 4 | HH-CRISPR array-HDV (STU) | 52.8-100% | 13.9-88.9% |
| | LbCas12a | ZmUbi | — | 4 | CRISPR array-DR (STU) | 56.7-93.3% | 23.3-80% |
| | LbCas12a | ZmUbi | ZmUbi | 4 | HH-CRISPR array-HDV | 18.2-90.9% | 12.1-45.5% |
| | LbCas12a | ZmUbi | U6 | 4 | CRISPR array | 30-82% | 10-60% |
| | LbCas12a | ZmUBi | ZmUbi | 4 | Tandem tRNA-HH-crRNA-HDV | 5.6-63.9% | 0-16.7% |

References:

Hu, X., Meng, X., Li, J., Wang, K., and Yu, H. (2020). Improving the efficiency of the CRISPR-Cas12a system with tRNA-crRNA arrays. Crop J. 8, 403-407.
Tang, X., Ren, Q., Yang, L., Bao, Y., Zhong, Z., He, Y., Liu, S., Qi, C., Liu, B., Wang, Y., et al. (2019). Single transcript unit CRISPR 2.0 systems for robust Cas9 and Cas12a mediated plant genome editing. Plant Biotechnol. J. 17, 1431-1445.
Wang, M., Mao, Y., Lu, Y., Tao, X., and Zhu, J. (2017). Multiplex gene editing in rice using the CRISPR-Cpf1 system. Mol. Plant 10, 1011-1013.
Wang, M., Mao, Y., Lu, Y., Wang, Z., Tao, X., and Zhu, J.-K. (2018). Multiplex gene editing in rice with simplified CRISPR-Cpf1 and CRISPR-Cas9 systems. J. Integr. Plant Biol. 60, 626-631.

sure enables engineering of quantitative traits by targeting cis elements with multiplexed guide RNAs as previously demonstrated with Cas9. Another appealing feature of the present Cas12a system ('B') is its nearly 100% biallelic editing efficiency for all target sites, making this system preeminent among all multiplexed CRISPR systems developed so far. With this highest biallelic editing efficiency that can be possibly achieved, it is very easy to obtain transgene-free multi-gene knockout plants in next generation, simply following Mendelian segregation. By contrast, all other previously established multiplexed Cas12a systems have low biallelic editing efficiencies, making it extremely hard to obtain edited lines with simultaneous biallelic edits, not to mention in a transgene-free fashion.

The second approach to express crRNAs with a Pol II promoter is single transcript unit (STU) systems. Four STU systems have been compared, and three of them ('D', 'M', and 'L') showed overall comparable editing efficiency in T0 lines (FIGS. 9A-9B and Table 2 below). They represent a second-tier of high-efficiency multiplexed Cas12a systems, and their editing efficiencies are significantly higher than The use of single promoter in STU systems allows for more synchronized expression of both Cas12a and crRNAs, making it highly suitable for transcriptional regulation. In the work by the present inventors related to the present disclosure, the use of two improved STU systems for simultaneous transcriptional repression of multiple genes in both rice and Arabidopsis has been demonstrated. In rice protoplasts, the transcripts of four target genes were reduced to as low as ~20% of the wild-type (WT) level by the most potent repression system (FIG. 19B). Notably, only a single crRNA was used for each target gene. Two EDS1 homologs in Arabidopsis were targeted and it was found that both genes were differentially repressed: more pronounced repression of At3g48080 than At3g48090 (FIGS. 19D-19F).

The multiplexed Cas12a transcriptional repression systems of the present disclosure provide researchers with an array of new tools for use in plant reverse genetics and genetic engineering, and enable the development of more robust transcriptional repression systems or strategies based on Cas12a, which may involve, for example, optimization of protospacer design, development of improved repressors, and multiplexing of more crRNAs for each of target genes.

It was previously shown that the tRNA base guide RNA processing system resulted in high-efficiency Cas9 based genome editing in rice. In the present effort, a tRNA-crRNA-HDV array has been compared with a tRNA-HH-crRNA-HDV array for processing multiple crRNAs, resulting in the finding that these systems were less efficient than the systems based on CRISPR arrays or HH-crRNA-HDV arrays (FIGS. 7A-7B, 9A-9B, and Table 2). These data suggest that inclusion of multiple tRNAs in the arrays resulted in an overall negative effect on maturation of crRNAs and hence their editing efficiencies. Indeed, when only one or two tRNAs were used to flank the CRISPR array, better results were observed by others, albeit with relatively low editing activities. CRISPR arrays with or without tRNAs were previously positioned into a 5' UTR of Cas12a with limited success toward achieving high editing efficiencies. Altogether, while the CRISPR array or HH-crRNA-HDV array systems can result in high efficiency genome editing, it is evident that additional effort is required to rigorously specify the use of tRNA for developing robust multiplexed Cas12a expression systems.

As shown by the foregoing, the present inventors have developed a highly efficient multiplexed Cas12a system for plant genome editing, based on dual Pol II promoters and an HH-crRNA-HDV array. When scaled from four target sites to 15 target sites, 100% biallelic editing was achieved at nearly all target sites. As also shown by the foregoing, the present inventors have additionally developed multiple improved STU systems for multiplexed Cas12a genome editing and transcriptional repression, which can be readily assembled by streamlined Golden Gate cloning and Gateway cloning (FIG. 20), with the vectors deposited at Addgene that have been identified hereinabove.

It will therefore be appreciated that the tool systems of the present disclosure make rice, as a globally important food crop, more amenable to multiplexed and large-scale genome engineering, and that such advantages extend to other plant species. Since conventionally used Cas12a proteins require higher temperatures to reach optimal editing activities, the Cas12a orthologs of the present disclosure, and engineered variants thereof, having high activities at lower temperatures, represent a substantial advance in the art, enabling multiplexing systems that are usefully employed across the plant kingdom, including for genomic editing of plants that heretofore were not amenable to CRISPR-Cas modification.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A non-naturally occurring CRISPR-Cas12a plant genomic editing system, comprising or encoding (i) an RVR variant Mb2Cas12a endonuclease comprising SEQ ID NO: 299, and (ii) at least one guide RNA (gRNA) coactive with the RVR variant Mb2Cas12a endonuclease for genomic editing of a target DNA binding the gRNA, wherein the RVR variant Mb2Cas12a endonuclease and the at least one guide RNA (gRNA) do not naturally occur together, and wherein the CRISPR-Cas12a plant genomic editing system is in a rice plant and the RVR variant Mb2Cas12a endonuclease edits the rice plant in OsPDS, OsDEP1, and OsROC5 genes thereof at sites with TATV PAMs at editing efficiencies from 20% to 42.9%.

2. The system of claim 1, comprising a vector comprising the sequence of SEQ ID NO: 15.

3. The system of claim 1, comprising a CRISPR-Cas 12a expression system encoding the RVR variant Mb2Cas12a endonuclease and crRNAs for forming gRNAs that are coactive with the RVR variant Mb2Cas12a endonuclease.

4. A non-naturally occurring multiplexing plant genomic editing system, comprising one or more vectors comprising at least one CRISPR RNA (crRNA) polymerase II (pol II)

regulatory element operably linked to nucleotide sequences encoding CRISPR-Cas12a system crRNAs for producing gRNAs for targeting multiple target sequences, and at least one regulatory element, which may be the same as the crRNA regulatory element, or different therefrom, operably linked to at least one nucleotide sequence encoding an RVR variant Mb2Cas12a endonuclease comprising SEQ ID NO: 299, for generation of a CRISPR-Cas12a editing structure by which the gRNAs target the multiple target sequences and the RVR variant Mb2Cas 12a endonuclease cleaves target DNA to alter gene expression in the cell, wherein the RVR variant Mb2Cas 12a endonuclease, and the gRNAs, do not naturally occur together, and wherein the CRISPR-Cas12a plant genomic editing system is in a rice plant in which the RVR variant Mb2Cas 12a endonuclease targets multiple genes including OsPDS, OsDEP1, and OsROC5 in the rice plant at PAM sites including TTV, TTTV, and TATV.

5. The system of claim 1, comprising a STU regulatory element that is operably linked to a nucleotide sequence encoding a CRISPR-Cas12a system crRNA and to a nucleotide sequence encoding the RVR variant Mb2Cas12a endonuclease.

6. The system of claim 5, wherein the STU regulatory element comprises a RNA polymerase II (Pol II) promoter.

7. The system of claim 1, comprising one or more crRNA regulatory elements operably linked to respective multiple nucleotide sequences encoding respective ones of multiple CRISPR-Cas12a system crRNAs, for targeting multiple target sequences, for multiplexed genomic editing by the RVR variant Mb2Cas12a endonuclease.

8. The system of claim 1, comprising a nucleotide sequence encoding the RVR variant Mb2Cas12a endonuclease, a nucleotide sequence encoding a crRNA for forming a gRNA for the RVR variant Mb2Cas12a endonuclease, and multiple ones of a same promoter, wherein one of the multiple ones of the same promoter is operably linked with the nucleotide sequence encoding the RVR variant Mb2Cas12a endonuclease, and another one of the multiple ones of the same promoter is operably linked with the nucleotide sequence encoding the crRNA for forming the gRNA for the RVR variant Mb2Cas12a endonuclease, with the same promoter being effective to produce expression in both nucleotide sequences.

9. The system of claim 1, comprising one or more expression cassettes comprising crRNA expression-regulating regulatory elements operably linked to nucleotide sequences encoding crRNAs for forming gRNAs hybridizing to target sequences of DNA, and nuclease expression-regulating regulatory elements operably linked to nucleotide sequences encoding the RVR variant Mb2Cas12a endonuclease that is effective with the gRNAs for said genomic editing, wherein the crRNA expression-regulating regulatory elements and nuclease expression-regulating regulatory elements comprise the same or different promoters.

10. The system of claim 1, comprising an expression cassette in which one or more crRNA nucleotide sequences are present, wherein hammerhead (HH) and hepatitis delta virus (HDV) ribozymes flank each crRNA nucleotide sequence in a HH-crRNA-HDV arrangement.

11. The system of claim 10, wherein the cassette expresses the RVR variant Mb2Cas 12a endonuclease.

12. The system of claim 1, comprising one or more expression cassettes, comprising multiple crRNA nucleotide sequences, wherein hammerhead (HH) and hepatitis delta virus (HDV) ribozymes flank each crRNA nucleotide sequence in a HH-crRNA-HDV arrangement.

13. The system of claim 12, wherein the one or more expression cassettes express the RVR variant Mb2Cas12a endonuclease.

14. The system of claim 13, wherein expression of both the RVR variant Mb2Cas 12a endonuclease and multiple crRNAs from the multiple crRNA nucleotide sequences is operatively effected by a ZmUbi promoter.

15. The system of claim 1, comprising one or more expression cassettes, comprising one or more CRISPR arrays, wherein hammerhead (HH) and hepatitis delta virus (HDV) ribozymes flank each CRISPR array in a HH-CRISPR array-HDV arrangement.

16. The system of claim 4, wherein the system targets the PAM sites of TATC, TATG, and TATA, with editing efficiency of 20% to 42.9%.

17. The system of claim 1, comprising one or more crRNA nucleotide sequences operatively linked with a regulatory element, to express one or more crRNA including a protospacer sequence at least 19 bp in length.

18. A method of genomically editing a rice plant, comprising introducing into such rice plant a non-naturally occurring heterologous CRISPR-Cas 12a genomic editing system according to claim 1, to cause the RVR variant Mb2Cas12a nuclease to cleave DNA in the rice plant to alter the rice plant's gene expression.

19. The method of claim 18, wherein the CRISPR-Cas 12a genomic editing system targets PAM sites including any one or more of TATG and TATA.

20. The method of claim 18, as carried out at a temperature below 25° C. and above temperature producing freezing or frost damage of the plant.

21. The method of claim 18, wherein the rice plant is edited at one or more of OsPDS, OsDEP1, and OsROC5.

22. The method of claim 18, wherein the CRISPR-Cas12a genomic editing system comprises gRNAs that are targetingly effective for multiple genomic loci in the plant, to enable multiplexed genomic editing of the plant by the RVR variant Mb2Cas12a endonuclease.

23. A non-naturally occurring CRISPR-Cas12a plant genomic editing system, comprising or encoding (i) an RVR variant Mb2Cas12a endonuclease comprising the sequence of SEQ ID NO: 299 including the mutations N563R, K569V, and N573R, and (ii) at least one guide RNA (gRNA) coactive with the RVR variant Mb2Cas12a endonuclease for genomic editing of a target DNA binding the gRNA, wherein the RVR variant Mb2Cas12a endonuclease and the at least one guide RNA (gRNA) do not naturally occur together, and wherein the CRISPR-Cas 12a plant genomic editing system is in a rice plant and edits genes therein at sites with TATV PAMs at editing efficiency of 20% to 42.9%.

* * * * *

SEQUENCE LISTING

```
<160> NUMBER OF SEQ ID NOS: 299

<210> SEQ ID NO 1
<211> LENGTH: 3618
<212> TYPE: DNA
<213> ORGANISM: Artificial Sequence
<220> FEATURE:
<223> OTHER INFORMATION: Synthetic construct

<400> SEQUENCE: 1
atgtactatg aatccctgac caaacaatac cctgtttcca aaacaatccg caatgagctg      60
attcctatag gtaaaaccct ggataacatc cgccaaaata acatcttgga atcagacgtt     120
aaaagaaagc agaattacga acatgtcaaa ggtatacttg atgaatacca caaacagctc     180
ataaacgaag cgttggataa ctgtacgctt ccctcactga aaatagcggc tgagatctac     240
ctcaaaaacc agaaggaggt gtcagacaga gaagatttca acaaaaccca ggatctgttg     300
cgcaaggagg ttgtggagaa actcaaggcg catgaaaatt ttactaagat aggaaaaaaa     360
gatattcttg atttgttgga gaagcttcct agcatatccg aggacgacta caatgccctg     420
gaaagtttca gaactttta cacatacttc acatcgtata ataaggtccg ggaaaatctg     480
tatagcgata aagagaaaag ttctactgtt gcgtacaggc ttatcaatga gaattttcca     540
aagtttctcg acaacgtcaa atcatatcgg ttcgtcaaaa ctgcgggcat tttggctgac     600
ggattgggag aggaggagca ggacagcctg ttcatagtgg agactttcaa caagacattg     660
acccaggatg gcattgatac atataactcc caggtcggca agataaactc ctcgataaac     720
ctctacaacc agaaaaacca gaaggcaaac ggcttccgga aaatcccaaa gatgaaaatg     780
ctttataagc agatcttgag tgatcgggag gagtctttca tcgatgaatt tcagtcagac     840
gaagttctta tcgacaacgt tgagagttac ggctctgtgc ttattgagag cctcaagtcg     900
tcaaaggttt ctgcattttt tgatgcactt cgggagagta aaggtaaaaa cgtttacgtt     960
```

-continued

```
aagaatgacc tggcgaaaac agcaatgtca aacatagttt ttgagaactg gaggaccttc    1020
gatgaccttc tgaatcaaga gtacgatttg gcgaacgaaa ataaaaagaa ggacgacaag    1080
tactttgaga agaggcaaaa ggagctgaaa aagaataaat cgtattcgtt ggaacatctt    1140
tgcaacctct ctgaggattc ctgcaacctg atagaaaact acatccacca gatcagtgac    1200
gatattgaaa acattattat taacaatgaa accttttttgc ggatagtgat taatgagcac    1260
gatcgcagta gaaaacttgc taaaaataga aaagctgtta aagcaataaa ggatttcctt    1320
gacagtatta aggtgctcga gcgggagttg aaactgatca attcttcagg acaagagttg    1380
gaaaaagacc ttatcgtcta tagcgctcac gaggaacttc tggtggaact gaaacaagtt    1440
gattcgcttt ataacatgac gaggaactac ctgaccaaaa agccctttc tactgagaaa    1500 gtcaaactca attttaatcg gtcgacgctt ctgaatggct gggaccgcaa caaagagact    1560
gataacctcg gggttctctt gctgaaagat ggcaagtatt atctgggtat aatgaataca    1620
tcagcaaata aggcattcgt taacccgcct gtggctaaaa ccgagaaggt tttttaaaaaa    1680 gtggactaca agctgttgcc agtgccgaac cagatgttgc ccaaggtttt ttttgcgaaa    1740
agcaatattg atttctataa tccatcgagc gagatatatt ccaactacaa aaaaggtacc    1800
cataaaaagg gtaacatgtt ttcacttgag gactgccaca acctgattga tttctttaaa    1860
gagagtatta gtaagcacga agattggagt aagtttggat tcaaattttc tgatactgcg    1920
agttacaatg atataagtga attctatcgg gaagtcgaaa aacagggtta caagcttacg    1980
tacactgaca tagatgaaac atacattaat gacctgattg agcgcaatga gttgtacctg    2040
tttcagatct ataacaaaga tttttccatg tatagcaaag gcaagctcaa cttgcatacc    2100
ctgtatttta tgatgctctt cgatcaaagg aatatcgatg acgttgttta taagctgaat    2160
ggtgaagcag aagttttta ccgcccagcc tcgatcagtg aagatgagct gatcattcac    2220 aaaagcgggtg aagagattaa gaataagaac cctaatcggg ccaggacgaa agaaacttca    2280 acgtttttcct atgatattgt caaagacaaa aggtactcga aggataagtt taccccttcac    2340 attcccataa ccatgaattt tggtgtcgac gaagtcaagc ggtttaacga cgccgtgaat    2400
tccgcgatcc ggatagacga gaatgtgaat gtcattggga ttgacagagg tgaacgcaat    2460
cttctttacg tggtggtgat agactctaaa gggaatatat tggagcaaat ttctctgaac    2520
tcaatcatta ataagaata cgatattgaa acagactatc atgcccttct cgacgagcgg    2580
gagggcggga gggataaagc acggaaggac tggaacacag ttgagaatat ccgggacctc    2640 aaaagccggat acctttccca ggtggtcaat gttgtcgcaa aattggtctt gaagtacaat    2700
gccattatat gccttgaaga tttgaacttt gggttcaaac gcggtaggca aaaagttgaa    2760
aaacaagttt accagaaatt cgaaaagatg cttatagata agctcaacta cctggttatt    2820
gacaagagta gagagcagac gtcgcccaaa gaactcgggg gggcgctgaa tgcgttgcaa    2880
ctgacctcga agttcaaatc gttcaaagaa ttggggaaac agtccggcgt tatctattac    2940
gtgcctgctt atctcacgtc taagatagat cctaccacag gcttcgcgaa tctttttat    3000 atgaagtgtg agaatgtcga gaagtctaag cggtttttcg atggatttga cttcatcagg    3060
ttcaatgcgc tcgaaaatgt ttttgagttt ggattcgact accggagctt tacacagaga    3120
gcgtgcggta taaacagtaa atggacagtc tgcacaaatg gggagagaat tataaagtat    3180
aggaaccccg ataaaaataa catgttcgac gaaaaggtgg tggttgttac tgatgaaatg    3240
aagaacctgt ttgaacagta caaaataacct tatgaggatg gaaggaacgt gaaggacatg    3300
```

```
attatttcaa acgaggaggc ggagttctac cgcagattgt accgcctgct tcagcagacc    3360
ctccaaatgc ggaattcgac ctcagatgga acgagagatt atattatatc accagtgaaa    3420
aacaagcgcg aggcgtattt caactctgag cttttccgatg gttcggttcc gaaagacgca    3480
gatgcaaacg gagcatacaa catcgcaagg aaagggttgt gggtgttgga acaaatccgc    3540
cagaaatccg aaggcgaaaa aattaacttg gctatgacca atgctgagtg gcttgaatac    3600
gcgcagacgc accttctg                                                  3618

<210> SEQ ID NO 2
<211> LENGTH: 3681
<212> TYPE: DNA
<213> ORGANISM: Artificial Sequence
<220> FEATURE:
<223> OTHER INFORMATION: Synthetic construct

<400> SEQUENCE: 2
atggacgcga aagagtttac tggacaatac ccactctcaa agactctccg ctttgagctg      60
agacccatcg ggaggacttg ggacaacttg gaagccagtg gctacttggc cgaggaccgc     120
caccgcgccg agtgctaccc gagagcaaaa gagctgctgg atgacaacca tagagcgttc     180
ctgaacaggg ttctcccgca gattgatatg gattggcatc ccatcgcaga agccttctgc     240
aaagtccata aaaatccagg aaacaaagag ctcgcgcaag attataatct tcagttgtcc     300
aagagacgca aagaaatctc ggcttatctt caggacgctg acggatataa aggtttgttt     360
gctaaacctg ctcttgacga ggcaatgaag atcgctaagg agaacggtaa cgaatcggat     420
attgaggtcc tcgaggcatt taacggcttt tccgtttatt tcacgggcta ccacgagtct     480
agagaaaata tctactcaga cgaagacatg gtctccgtgg cctacaggat cacagaggat     540
aattttcccc gcttcgtctc caacgcgttg atattcgaca gttgaatga atcacatcct      600 gatatcatct ctgaggtgtc tgggaatctc ggtgttgacg atataggcaa atactttgac     660
gtctcgaact acaataactt tctcagccag gcaggaattg atgactataa tcatattatt     720
ggtggacaca ccactgaaga tggtctgatt caggccttta atgtggtttt gaatctgcgc     780
caccagaagg atccagggtt cgaaaagatc caattcaaac agctctataa gcagattctc     840
tctgttcgga cgtccaaatc gtatattcca aaacaattcg acaattctaa ggaaatggtc     900
gattgcattt gcgattatgt ctcaaaaatc gagaaatcag agacggtcga aagggctttg     960
aagcttgtga gaaatatctc cagcttcgat cttcggggca tatttgtgaa caagaaaaac    1020
ctcaggatcc tctccaataa gttgataggg gattgggacg caatcgagac cgcgcttatg    1080
cattccagct cctcagaaaa tgataaaaaa tccgtctatg attcagccga agcctttact    1140
ttggacgata tattctcgtc agtgaaaaaa ttcagtgatg ctagcgccga ggatattggg    1200
aaccgcgccg aggacatatg cagggtgatc tctgaaacgg ctcccttat taacgacttg    1260 cgcgcggtgg acctggacag tctcaacgat gacggatatg aagcagcagt tagcaagatc    1320
cgggagtccc ttgagccgta catggatctt ttccatgaac ttgagatatt tagtgttggg    1380
gacgagttcc ctaaatgtgc ggcattttac tcggagttgg aagaggttag cgaacagctc    1440
atagaaatca taccgctgtt taataaggcc agatccttct gcacccggaa gaggtattcc    1500
actgacaaaa ttaaagtgaa tctcaagttc cctacattgg cagacggctg ggaccttaat    1560
aaggagcggg ataacaaagc cgctatattg agaaaagacg gcaagtacta tttggccatc    1620
ctggatatga gaaggatct gtcttcgata agaacgtcgg acgaagacga atcctccttc    1680
gaaaagatgg agtacaaact gcttccatcc ccggttaaga tgctccctaa aattttcgtt    1740
```

-continued

```
aagtcaaaag ccgcaaagga gaaatacggc cttactgata gaatgctgga atgctatgat    1800
aagggaatgc ataaaagtgg gagcgcattc gatctcggat tctgtcacga gctcattgac    1860
tattacaaaa ggtgcatcgc ggagtacccc ggctgggatg ttttttgattt taagttcaga   1920 gaaactagtg attacggatc tatgaaggaa ttcaacgaag atgtggcagg cgctgggtac    1980
tatatgtcgc tcaggaagat cccctgttcc gaagtgtatc ggctgttgga cgaaaagtcg    2040
atatatctgt ttcaaattta caacaaagat tatagtgaaa atgcgcatgg taataagaat    2100
atgcatacta tgtattggga agggctcttc tctccacaaa atcttgaatc tccggtcttt    2160
aagcttagcg gtggggcaga gctttttcttc agaaaaagca gcatcccaaa cgatgcaaaa    2220
acggtgcacc caaaggggag cgtgctggtt cctagaaacg atgttaatgg gcgccggata    2280
cctgacagca tatacagaga gctcacaagg tactttaacc ggggcgattg cagaatttcc    2340
gatgaggcga agtcgtacct ggataaagtc aaaaccaaga aagccgatca tgacatcgtc    2400
aaggaccggc gcttcacggt cgataaaatg atgttccatg tcccaattgc aatgaacttc    2460
aaagctatat ccaagccgaa tctgaacaag aaggtgatag atggaattat tgacgatcag    2520
gaccttaaaa ttatcgggat tgacaggggg gaacgcaact tgatatatgt gacgatggtg    2580
gatcgcaagg gcaatatcct ttatcaagat agccttaata tcttgaacgg atacgattac    2640
cggaaggcct tggatgttcg cgagtacgat aacaaagaag caaggaggaa ctggactaag    2700
gttgaaggaa taaggaagat gaaggaaggt tacctctcac ttgcggtctc caagcttgca    2760
gacatgatta tagagaacaa cgccataatt gttatggagg atctgaatca tgggtttaag    2820
gcaggtcgct ccaaaatcga gaaacaggtt taccaaaagt ttgagtccat gcttatcaat    2880
aagctcgggt acatggtgct caaagacaaa tcaatagatc agtccggcgg agctctgcac    2940
ggctaccaat tggcgaacca tgtgactaca cttgcctccg ttggtaaaca atgtggcgtc    3000 atctttttata ttccagctgc ctttactagt aagatagacc ccactaccgg ctttgccgat    3060
ctgtttgctt tgagcaacgt caagaacgtg gcgagtatga gagagtttttt tagcaagatg   3120 aaaagcgtca tatatgataa agccgaaggt aaatttgcgt tcactttcga ttatctggat    3180
tataacgtga aatcagagtg cgggcggaca ctgtggaccg tctataccgt gggtgagagg    3240
tttacatact cacgggtcaa tagggaatac gttcgcaaag tccccactga cataatttac    3300
gatgcgcttc aaaaggcagg tatctccgtt gagggcgact tgcgcgacag aattgcagag    3360
agtgatgggg acacgctgaa atcaattttttc tatgcgttca aatatgcgct tgatatgaga   3420
gtcgagaacc gcgaagaaga ttatattcag agtcctgtga agaacgctag tggcgaattt    3480
ttttgctcaa agaatgcagg taaaagcttg cctcaggact cggacgcgaa tggggcttac    3540
aatatagcac tcaaggggat cttgcagctc aggatgctta gcgagcagta tgacccgaac    3600
gcagaatcga tacggcttcc actgatcacc aacaaagctt ggctcacttt catgcaatca    3660
ggaatgaaga cctggaagaa c    3681
```

<210> SEQ ID NO 3
<211> LENGTH: 3681
<212> TYPE: DNA
<213> ORGANISM: Artificial Sequence
<220> FEATURE:
<223> OTHER INFORMATION: Synthetic construct

<400> SEQUENCE: 3

```
atggacgcga aagagtttac tggacaatac ccactctcaa agactctccg ctttgagctg      60
```

-continued

```
agacccatcg ggaggacttg ggacaacttg gaagccagtg gctacttggc cgaggaccgc    120
caccgcgccg agtgctaccc gagagcaaaa gagctgctgg atgacaacca tagagcgttc    180
ctgaacaggg ttctcccgca gattgatatg gattggcatc ccatcgcaga agccttctgc    240
aaagtccata aaaatccagg aaacaaagag ctcgcgcaag attataatct tcagttgtcc    300
aagagacgca aagaaatctc ggcttatctt caggacgctg acggatataa aggtttgttt    360
gctaaacctg ctcttgacga ggcaatgaag atcgctaagg agaacggtaa cgaatcggat    420
attgaggtcc tcgaggcatt taacggcttt tccgtttatt tcacgggcta ccacgagtct    480
agagaaaata tctactcaga cgaagacatg gtctccgtgg cctacaggat cacagaggat    540
aattttcccc gcttcgtctc caacgcgttg atattcgaca agttgaatga atcacatcct    600
gatatcatct ctgaggtgtc tgggaatctc ggtgttgacg atataggcaa atactttgac    660
gtctcgaact acaataactt tctcagccag gcaggaattg atgactataa tcatattatt    720
ggtggacaca ccactgaaga tggtctgatt caggccttta atgtggtttt gaatctgcgc    780
caccagaagg atccagggtt cgaaaagatc caattcaaac agctctataa gcagattctc    840
tctgttcgga cgtccaaatc gtatattcca aaacaattcg acaattctaa ggaaatggtc    900
gattgcattt gcgattatgt ctcaaaaatc gagaaatcag agacggtcga aagggctttg    960
aagcttgtga gaaatatctc cagcttcgat cttcggggca tatttgtgaa caagaaaaac   1020
ctcaggatcc tctccaataa gttgataggg gattgggacg caatcgagac cgcgcttatg   1080
cattccagct cctcagaaaa tgataaaaaa tccgtctatg attcagccga agcctttact   1140
ttggacgata tattctcgtc agtgaaaaaa ttcagtgatg ctagcgccga ggatattggg   1200
aaccgcgccg aggacatatg cagggtgatc tctgaaacgg ctccctttat taacgacttg   1260
cgcgcggtgg acctggacag tctcaacgat gacggatatg aagcagcagt tagcaagatc   1320
cgggagtccc ttgagccgta catggatctt ttccatgaac ttgagatatt tagtgttggg   1380
gacgagttcc ctaaatgtgc ggcattttac tcggagttgg aagaggttag cgaacagctc   1440
atagaaatca taccgctgtt taataaggcc agatccttct gcacccggaa gaggtattcc   1500
actgacaaaa ttaaagtgaa tctcaagttc cctacattgg cagacggctg ggaccttaat   1560
aaggagcggg ataacaaagc cgctatattg agaaaagacg gcaagtacta tttggccatc   1620
ctggatatga agaaggatct gtcttcgata agaacgtcgg acgaagacga atcctccttc   1680
gaaaagatgg agtacaaact gcttccatcc ccggttaaga tgctccctaa aattttcgtt   1740
aagtcaaaag ccgcaaagga gaaatacggc cttactgata gaatgctgga atgctatgat   1800
aagggaatgc ataaaagtgg gagcgcattc gatctcggat tctgtcacga gctcattgac   1860
tattacaaaa ggtgcatcgc ggagtacccc ggctgggatg tttttgattt taagttcaga   1920
gaaactagtg attacggatc tatgaaggaa ttcaacgaag atgtggcagg cgctgggtac   1980
tatatgtcgc tcaggaagat cccctgttcc gaagtgtatc ggctgttgga cgaaaagtcg   2040
atatatctgt ttcaaatttta caacaaagat tatagtgaaa atgcgcatgg taataagaat   2100
atgcatacta tgtattggga agggctcttc tctccacaaa atcttgaatc tccggtcttt   2160
aagcttagcg tggggcagag cttttcttc agaaaaagca gcatcccaaa cgatgcaaaa   2220
acggtgcacc caaaggggag cgtgctggtt cctagaaacg atgttaatgg gcgccggata   2280
cctgacagca tatacagaga gctcacaagg tactttaacc ggggcgattg cagaatttcc   2340
gatgaggcga agtcgtacct ggataaagtc aaaaccaaga aagccgatca tgacatcgtc   2400
aaggaccggc gcttcacggt cgataaaatg atgttccatg tcccaattgc aatgaacttc   2460
```

-continued

```
aaagctatat ccaagccgaa tctgaacaag aaggtgatag atggaattat tgacgatcag        2520
gaccttaaaa ttatcgggat tgacaggggg gaacgcaact tgatatatgt gacgatggtg        2580
gatcgcaagg gcaatatcct ttatcaagat agccttaata tcttgaacgg atacgattac        2640
cggaaggcct tggatgttcg cgagtacgat aacaaagaag caaggaggaa ctggactaag        2700
gttgaaggaa taaggaagat gaaggaaggt tacctctcac ttgcggtctc caagcttgca        2760
gacatgatta tagagaacaa cgccataatt gttatggagg atctgaatca tgggtttaag        2820
gcaggtcgct ccaaaatcga gaaacaggtt taccaaaagt ttgagtccat gcttatcaat        2880
aagctcgggt acatggtgct caaagacaaa tcaatagatc agtccggcgg agctctgcac        2940
ggctaccaat tggcgaacca tgtgactaca cttgcctccg ttggtaaaca atgtggcgtc        3000
atcttttata ttccagctgc ctttactagt aagatagacc ccactaccgg ctttgccgat        3060
ctgtttgctt tgagcaacgt caagaacgtg gcgagtatga gagagttttt tagcaagatg        3120
aaaagcgtca tatatgataa agccgaaggt aaatttgcgt tcactttcga ttatctggat        3180
tataacgtga aatcagagtg cgggcggaca ctgtggaccg tctataccgt gggtgagagg        3240
tttacatact cacgggtcaa tagggaatac gttcgcaaag tccccactga cataatttac        3300
gatgcgcttc aaaaggcagg tatctccgtt gagggcgact tgcgcgacag aattgcagag        3360
agtgatgggg acacgctgaa atcaattttc tatgcgttca aatatgcgct tgatatgaga        3420
gtcgagaacc gcgaagaaga ttatattcag agtcctgtga agaacgctag tggcgaattt        3480
ttttgctcaa agaatgcagg taaaagcttg cctcaggact cggacgcgaa tggggcttac        3540
aatatagcac tcaaggggat cttgcagctc aggatgctta gcgagcagta tgacccgaac        3600
gcagaatcga tacggcttcc actgatcacc aacaaagctt ggctcacttt catgcaatca        3660
ggaatgaaga cctggaagaa c                                                  3681
```

<210> SEQ ID NO 4
<211> LENGTH: 3786
<212> TYPE: DNA
<213> ORGANISM: Artificial Sequence
<220> FEATURE:
<223> OTHER INFORMATION: Synthetic construct

<400> SEQUENCE: 4

```
atgcggaagt ttaatgagtt cgttggcctt tacccaatta gtaaaacatt gagatttgaa          60 ttgaagcccca tagggaagac actcgaacat atccagcgga acaaactgct tgagcacgat         120
gcggtccggg ctgacgatta cgtgaaggtt aagaagataa tcgacaaata tcacaagtgt         180
ctcatcgatg aagcgttgtc ggggttcaca tttgatactg aggccgacgg gaggtctaat         240
aacagcttgt ccgagtatta tctttattac aatctgaaaa agcggaacga acaggagcag         300
aaaacgttca aaaccataca aaataatttg aggaaacaaa tagtcaataa gttgacgcaa         360
agcgagaagt acaaacggat cgacaagaaa gaactgatca ctactgacct ccccgatttc         420
ctcactaatg agtcggaaaa ggaattggtt gaaaaattta agaactttac aacttacttc         480
acggagttcc acaagaacag gaaaaatatg tattctaaag aggaaaagtc tacagcgata         540
gccttcaggc ttataaatga aaatttgccc aagttcgttg acaatatagc tgcgtttgaa         600
aaagtcgtgt cgagcccatt ggcggaaaaa attaatgctc tctacgagga ttttaaggaa         660
taccttaacg ttgaagagat ttctaggggtt tttagacttg actactatga cgaactgctg         720
actcagaagc agattgacct ttataacgct atagttggcg gcaggaccga ggaggataat         780
```

-continued

```
aaaattcaga ttaaaggact caaccaatat atcaacgaat acaatcagca gcagacagat    840
agatcgaaca gactcccgaa acttaagcca ctgtataaac agattctttc cgatagggaa    900
tccgtctcct ggctgcctcc gaaatttgac tcagacaaaa acctcctcat aaagattaaa    960
gaatgttacg acgcgctctc tgagaaagaa aaagttttg ataaactgga aagtattctt   1020
aaaagtctct caacttacga tttgtctaag atatatatat caaacgacag ccaattgagc   1080
tacatcagcc aaaagatgtt cgggaggtgg gacataataa gtaaagcaat tcgggaagac   1140
tgcgctaaaa ggaacccgca aaagtcaagg gagagtttgg agaagtttgc tgagcgcata   1200
gataaaaaat tgaagacgat agacagtatc tcgattgggg atgttgacga gtgtctggcg   1260
caactcggtg aaacatacgt gaaacgggtt gaggactact ttgtcgctat gggtgagtca   1320
gagatagacg acgaacaaac ggacacaact tcttttaaaa aaaatataga aggagcgtat   1380
gaatccgtca aggaacttct caataacgcg gacaacatta ctgataacaa tctgatgcaa   1440
gataaaggaa atgtggaaaa gattaaaacg ttgcttgacg ctataaagga cctccagcgc   1500
tttataaaac cccttctcgg caagggtgat gaggcggaca aagatggtgt cttttatggg   1560
gagttcacca gtctttggac taaattggat caagtcaccc cactctataa catggtgagg   1620
aattacctta cgtctaagcc gtatagtacc aaaaaaatta aacttaactt tgaaaactcg   1680
accctcatgg acggctggga cctcaataaa gaacccgata acactacagt tattttctgc   1740
aaagacggct tgtattacct cggcattatg ggcaagaagt acaacagggt tttcgtcgat   1800
agagaggacc tcccgcacga cggtgaatgc tacgacaaga tggagtataa gctgcttccg   1860
ggagcgaaca agatgcttcc taaggtgttc ttttctgaaa cgggcattca aagatttctt   1920
ccgtccgagg agttgttggg taaatacgag agggggacgc ataagaaagg agcaggattt   1980
gacttgggag attgtcgggc gcttatcgat ttttttcaaaa agagtattga gcgccacgat   2040
gattggaaga aattcgactt taagttctct gataccagca cctaccagga catttcagag   2100
ttctacagag aggtcgagca acagggatat aaaatgtcat tcagaaaggt tagtgtcgat   2160
tatatcaagt cactcgttga agaaggtaaa ctctatcttt tccagattta caataaggat   2220
ttctctgctc atagtaaggg gaccccgaat atgcacacct tgtactggaa aatgctgttt   2280
gacgaagaaa atcttaagga cgtcgtttac aagctgaatg gagaggcgga agtctttttt   2340
aggaaatcaa gtattacggt ccaatcgccc acgcatccgg cgaattctcc tataaagaat   2400
aagaataagg ataatcaaaa aaaagaaagt aagttcgagt acgatctgat taaagacaga   2460
cggtatactg ttgataagtt cctgtttcat gttcccatta ctatgaactt caaaagcgtc   2520
ggtggttcga atattaacca attggttaag cgccatatac gcagcgctac cgacttgcac   2580
ataatcggaa tcgaccgggg tgagaggcac ttgctttatc ttaccgttat agactctagg   2640
ggtaacataa aagaacaatt ctctcttaac gagatagtta atgaatataa cggaaatact   2700
taccgcacag attaccatga gctcctcgac acgcgcgagg gggagcggac ggaggctcgc   2760
aggaactggc agactataca aaatataagg gaactgaagg aaggctattt gtcccaggtg   2820
atacacaaga tttcggagtt ggcgattaag tataatgcag tcattgtgct ggaggatctg   2880
aattttgggt ttatgaggtc gcggcagaaa gttgaaaaac aagtctacca gaagttcgag   2940
aagatgctca tagacaaact gaattacttg gtcgataaga aaaagccggt tgctgaaacc   3000
ggagggctcc tcagggcgta ccagctcacc ggcgaatttg agagctttaa aacgctcggt   3060
aagcaatctg ggatcttgtt ctacgtccca gcttggaata cctcgaaaat cgatccagtg   3120
acgggctttg tgaatctttt tgatacgcac tacgagaata tagagaaagc aaaagttttc   3180
```

-continued

```
ttcgataaat ttaagtcgat ccggtataac agtgataagg actggtttga attcgtcgtc    3240
gatgactaca caagatttag tcccaaagcc gaagggacta gacgcgattg gaccatatgc    3300
acacagggga agaggataca aatttgtcgc aatcaccagc ggaataatga atgggaaggt    3360
caagagattg atctgacaaa agcgtttaag gaacattttg aggcctatgg cgtggacatc    3420
tcaaaggact tgcgcgaaca gattaacacg cagaataaaa aagagttttt tgaagaattg    3480
ctccggctgc tcaggctcac gttgcaaatg aggaactcta tgccatctag cgatattgat    3540
tacctcatat ctccagttgc caatgatacc ggttgcttct tcgatagtag aaaacaggca    3600
gaactgaaag agaacgctgt cttgcctatg aatgcagacg caaatggtgc ttacaatatt    3660
gcacgcaagg ggctcctcgc aatcagaaag atgaagcaag aggagaatga ctcagcgaaa    3720
atttctttgg caattagtaa taaagaatgg ctgaaattcg ctcagactaa gccttacttg    3780
gaagat                                                                3786

<210> SEQ ID NO 5
<211> LENGTH: 3753
<212> TYPE: DNA
<213> ORGANISM: Artificial Sequence
<220> FEATURE:
<223> OTHER INFORMATION: Synthetic construct

<400> SEQUENCE: 5
atgctgtttc aagatttcac acacctttac ccactgtcta aaacggtgcg gtttgagctt      60
aaacccatcg gaaaaacgct ggaacatatt catgcgaaga acttttttgtc gcaggatgag     120 acaatggcag acatgtacca aaaagtgaaa gccatactgg acgattacca tagagacttc     180
attacgaaga tgatgagtga ggtgactctt acaaagctcc cggagtttta cgaggtttac     240
ctcgctctga ggaagaatcc gaaagacgat accctccaga acaacttac cgaaattcag       300 accgcgctcc gggaggaagt tgtgaagccc atagattccg gaggtaaata caaggctggt      360
tatgagcgct gtttgggggc gaaactgttt aaagacggaa aagagttggg agatttggcg      420
aaatttgtca tcgcccagga aggggaatcg tctccgaaac ttccacagat cgcccacttt      480
gaaaagtttt caacatactt cacgggggttc cacgataacc gcaagaacat gtactcgtct      540
gacgataaac acacagctat tgcctacagg cttatccatg aaaatttgcc ccgctttatt      600
gataacttgc aaattttggt tactattaag cagaagcact cagtccttta cgatcagatt      660
gtgaacgagc tcaacgccaa tggcctggac gtgtctctcg cctcgcatct cgacggctac      720
cataaacttt tgactcaaga aggcattacc gcgtacaata ggattattgg cgaagtgaac      780
agttatacaa acaagcataa tcagatatgt cacaagtctg aaagaattgc aaagctgaga      840
ccgcttcata agcaaatact tagtgatggg atgggagtga gtttcctccc atctaaattt      900
gcagatgact cggaaatgtg tcaagcggtg aatgaattct acagacacta tgcccacgtg      960
ttcgccaaag tccaaagtct ctttgaccgg tttgacgatt accaaaaaga cggcatttat     1020
gttgaacaca agaatctcaa cgaattgagc aagcaggcct ttggagattt cgcactcctt     1080
ggcagggtcc ttgacggcta ctatgtcgac gttgtcaatc ctgagttcaa tgacaaattc     1140
gctaaggcta agacagataa cgccaaagag aaacttacca agaaaaaga caaattcatt      1200 aagggagtgc attcattggc ttctctcgag caggcaatcg aacactatat agcggggcat     1260
gatgacgaaa cgttcaggc gggaaaaactt ggccaatact tcaagcacgg cctcgctgga     1320
gttgataatc ctatacaaaa gattcataat agtcattcta cgataaaggg attccttgag     1380
```

-continued

```
agggagaggc cagccggaga acgcaccctc cctaaaataa aatcagataa gtctctggag     1440
atgactcaac tcagacagct gaaggagctg ctggacaacg ccctcaatgt cgtccacttc     1500
gcaaagctgc ttacaaccaa aacgaccctg gataaccaag atggaaattt ctacggagaa     1560
ttcggggccc tttatgatga gttggctaaa atcgcaacct tgtacaacaa ggtgcgggat     1620
tatcttagcc aaaaaccgtt cagtacagaa aaatacaaac ttaactttgg gaatccgact     1680
ctcttgaatg gatgggacct caataaggag aaggataatt ttggcgtcat cctgcagaag     1740
gacggctgct actatctcgc actgcttgat aaagctcaca aaaaagtctt tgataatgcg     1800
cccaacacgg gtaagtcggt gtatcagaaa atggtgtata aacttttgcc tggatcaaat     1860
aagatgctcc caaaagtttt ttttgcgaaa tcgaaccttg attactataa tcctagtgcc     1920
gaactcctcg acaagtatgc ccaaggcact cacaagaagg gagacaactt caacctgaaa     1980
gattgccatg cattgatcga cttttttcaaa gcgtccatta acaagcaccc cgaatggcaa     2040
catttcggtt ttgaatttag cttgacgagc tcttaccagg acctgtcaga cttctacagg     2100
gaggtggagc cgcaaggcta tcaagttaag ttcgtcgaca ttgatgctga ctacatcgac     2160
gaacttgtgg aacaaggtca actctacctg tttcaaatat ataacaagga ttttagtcct     2220
aaggcgcacg gaaaacccaa ccttcatacg ctctacttca aagctttgtt ctcagaagat     2280
aacctggcta acccaatata taagctcaac ggagaagccg aaatcttcta ccggaaagct     2340
tcgctcgata tgaacgagac aacgatccat cgcgcgggtg aggtgcttga aaataagaac     2400
ccggataacc cgaaagagag gcagtttgtg tacgatataa tcaaagacaa acgctacact     2460
caggataagt ttatgctgca tgttccaatt acaatgaact ttgggggttca aggaatgacg     2520 atcaaggagt ttaacaaaaa ggttaaccag tccatacaac agtatgacga agttaatgtc     2580
attggaatag acagaggcga gcgccatctc ctgtacctta cagttattaa ttctaaggga     2640
gaaatactcg agcaacggtc gctcaacgac atcataacta ccagcgcgaa cggcacccag     2700
atgacaacac catatcacaa gatcctggac aagagggaga tcgagcggct gaatgctagg     2760
gtgggttggg gagaaataga gacaatcaag gagttgaagt ctggttatct ttcgcatgtc     2820
gtgcaccaaa tatcgcagct gatgcttaaa tacaatgcta tagttgtcct tgaagatttg     2880
aattttggct tcaaacgggg tcgcttcaaa gttgaaaaac agatatatca gaattttgaa     2940
aacgctctta ttaagaaact gaatcatctg gttttgaagg ataaagcgga caatgaaatc     3000
ggctcttaca aaaatgcgct tcagttgact aacaatttta ccgatctcaa gtctataggg     3060
aagcagacag gtttcctctt ttacgtgcct gcttggaaca cgtcaaaaat tgatcccgtt     3120
accggttttg ttgacctgtt gaaaccgcgg tacgaaaata ttgcacaaag tcaagcattt     3180
tttgataagt tcgacaagat ttgctataat gctgacaaag ctacttcga gtttcatata     3240 gactatgcaa agttcacgga caaggcaaaa aactcgcgcc agatatggac gatttgctcg     3300
catggagaca agcgctatgt gtatgacaag acagccaatc agaacaaggg agcaactatt     3360
gggatcaatg ttaatgatga gctcaagtcg ttgtttgccc gctaccggat taacgacaag     3420
cagccaaacc tggtcatgga tatctgtcaa aataatgata aagagtttca caagtcgctc     3480
acgtaccttc ttaaagctct cttggcattg cggtacagca atgccagttc cgacgaagat     3540
tttatcctga gcccggtggc caacgataag ggggtgtttt tcaattctgc actggctgat     3600
gatacccagc cgcagaatgc ggacgcaaac ggagcatatc atatcgcgtt gaagggactt     3660
tggcttctca atgagcttaa gaactcggat gaccttgata aagtgaaact cgccatcgac     3720
aatcagacat ggcttaattt cgcacagaac aga                                 3753
```

-continued

```
<210> SEQ ID NO 6
<211> LENGTH: 3753
<212> TYPE: DNA
<213> ORGANISM: Artificial Sequence
<220> FEATURE:
<223> OTHER INFORMATION: Synthetic construct

<400> SEQUENCE: 6
atgctgtttc aagattttac acatctgtac ccgctgagta aaacagtgcg gttcgagctg      60
aaacccatag gaaggaccct cgagcacatc cacgcgaaga attttctgag ccaggatgaa     120
actatggctg atatgtatca aaaagttaag gtcattttgg acgactatca tcgcgatttt     180
attgccgaca tgatgggaga ggtgaaactc acgaagcttg ctgaatttta cgacgtctat     240
ctgaagttca ggaaaaatcc taaggacgat gggctgcaaa aacagcttaa agaccttcaa     300
gctgtccttc ggaaggaatc ggtgaagcct atagggtcag gtgggaagta caaaacaggc     360
tacgatagac tctttggggc aaaactcttc aaagatggaa aagagttggg tgacctcgca     420
aaattcgtta tagcccaaga aggtgagtct tctccgaagc tggctcatct tgctcatttt     480
gagaagttca gcacgtattt tactggattt cacgataatc ggaagaatat gtactcggat     540
gaagacaagc atactgcaat agcgtacagg ctcatccatg agaatttgcc gagattcatc     600
gacaatctgc aaatcttgac aacaatcaaa caaaagcata gcgccctcta tgatcagata     660
atcaacgagc tcacggcctc cgggctcgac gtctccttgg cttctcatct tgacgggtat     720
cacaagctcc ttacacaaga ggggatcacg gcatacaaca ggatcatagg agaggtgaat     780
ggatatacaa ataagcataa ccagatatgc cacaagagcg agcgcatagc gaaacttaga     840
cccttgcaca agcaaatcct ttctgacgga atgggagtgt cattccttcc gtctaagttc     900
gcggatgata gtgagatgtg ccaagcggtc aacgaatttt atcgccatta tactgacgtg     960
ttcgcaaagg tgcaaagtct ctttgacgga tttgatgatc accagaaaga cgggatctat    1020
gttgaacaca aaaaccttaa tgaactgagc aaacaggcgt tcggcgactt tgctttgctg    1080
gggagggtcc ttgatggata ctacgtggac gttgtcaatc cggagttcaa tgagcggttc    1140
gcaaaggcca agactgacaa tgcgaaagcc aagcttacaa aagaaaagga caaattcatt    1200
aaaggagtcc actcactggc ttccctcgaa caagcaatag aacaccatac agctagacac    1260
gacgatgaga gtgttcaagc cggaaaactt ggccagtact caaaacacgg tttggcgggg    1320
gttgacaacc cgattcagaa aattcacaat aaccattcga cgattaaagg gtttctggaa    1380
agggaaaggc tgctgggga acgggcgctc ccgaagatca agtcaggaaa aaacccagaa    1440
atgacacagc tcaggcagct gaaggaactt ttggacaacg cattgaatgt ggcgcacttc    1500
gctaagctgc tgacaactaa aacaaccttg gacaaccagg atggaaattt ttacggggag    1560 tttgggggtgc tttacgacga gctggctaaa attccaactc tctacaataa ggttagagat    1620
tatctctctc aaaagccctt ttctaccgaa aagtataagc tcaacttcgg caatccgacc    1680
cttctcaatg ggtgggacct gaacaaagag aaagataact ttggggttat acttcagaag    1740
gatggatgct attacttggc gcttcttgat aaggctcata aaaaagtttt cgacaacgcc    1800
cctaacactg gtaagaacgt ctaccaaaag atggtctaca aactgttgcc cggccccaac    1860
aaaatgcttc ctaaagtgtt tttcgcaaaa tcgaatctcg actattataa tccatctgcc    1920
gagctccttg acaaatatgc taaggggacc cataaaaagg gtgataattt caacctgaag    1980
gactgccacg cgcttatcga ctttttcaaa gccgggataa ataagcatcc ggagtggcaa    2040
```

-continued

```
cattttggtt ttaaatttc gccaacgtcg tcctatcgcg acctttccga tttctatagg      2100
gaagttgaac ctcaggggta ccaggtcaaa tttgttgaca ttaatgcgga ctacattgat      2160
gaattggtgg agcaagggaa gctctacctc tttcaaatat ataacaaaga tttctcgcca      2220
aaagcgcatg gtaaaccgaa tcttcatacc ttgtacttta aagcactttt ttcagaagat      2280
aacttggcgg acccgatcta caagctgaat ggggaagctc agatcttcta caggaaagct      2340
tcgttggaca tgaacgagac taccatacat cgcgcgggag aggtgcttga gaacaaaaat      2400
cccgacaacc cgaaaaagcg gcaattcgtt tacgacatca tcaaagacaa acggtacacg      2460
caggacaaat ttatgctcca cgtccccatt accatgaatt ttggagtcca aggcatgacc      2520
attaaggaat tcaacaaaaa ggtcaaccaa agtattcagc aatacgatga agtcaatgtc      2580
ataggcatag atcggggaga aaggcatctg ttgtatctta ccgtgattaa ctctaagggt      2640
gaaatactgg agcaacggtc acttaacgat ataaccacgg cgtccgcgaa cggtacacaa      2700
gtgaccactc cctaccacaa aatattggat aaaagggaga tagaacgctt gaatgcccgc      2760
gttggctggg gtgagattga gaccatcaaa gagcttaaat cgggatattt gtctcacgtc      2820
gttcatcaaa ttaaccaact catgcttaag tacaatgcaa tcgttgtgct cgaggacctg      2880
aactttggtt tcaaaagagg gaggttcaag gtggaaaaac aaatttacca gaactttgaa      2940
aacgcgctta tcaagaaatt gaatcacctt gttttgaaag ataaggcaga tgacgaaatc      3000
gggtcgtata aaaatgcact ccagttgaca aataatttca cggatttgaa gtcgatcggc      3060
aagcaaacag ggttcctctt ttatgtgcca gcgtggaata catcaaaaat tgatccggag      3120
acgggatttg tcgacttgct gaagcctagg tatgagaaca ttgcccaatc tcaggccttt      3180
ttcggcaaat tcgataaaat atgctacaac acagacaaag gttattttga atttcacatt      3240
gattacgcca aatttacaga taaggcgaaa aacagcagac agaaatgggc tatctgttct      3300
catggggaca aacgctatgt ctacgataag acggctaatc aaaataaagg cgccgcaaaa      3360
ggtattaatg tgaatgatga gctgaaaagc ttgtttgccc gctaccatat caatgataaa      3420
caaccaaact tggtgatgga catatgccag aacaatgaca agaattcca caagtcactc      3480 atgtgcctgc ttaaaaccct tttggcgctg cggtatagca atgcatctag cgatgaagac      3540 tttatttga gtcccgtggc caacgacgag ggcgtgtttt ttaattcagc cttggcggac      3600
gatacgcagc cccagaatgc ggacgcaaac ggcgcgtacc acattgcact gaagggactg      3660
tggcttctga acgagctgaa aaatagcgac gacctgaata aagtcaagtt ggccattgac      3720
aatcaaacct ggttgaattt cgctcaaaat aga                                   3753
```

<210> SEQ ID NO 7
<211> LENGTH: 4119
<212> TYPE: DNA
<213> ORGANISM: Artificial Sequence
<220> FEATURE:
<223> OTHER INFORMATION: Synthetic construct

<400> SEQUENCE: 7

```
atgctgttcc aagatttcac tcatctgtac cccctctcca aaacagtgcg gtttgaattg       60
aagccgatcg atcggacact tgaacacatt cacgcaaaaa acttcctctc tcaggatgag      120
accatggcag acatgcacca gaaagtcaaa gtcatactcg atgactacca tagggacttc      180
atagccgaca tgatgggtga ggttaaactg actaaactcg cggaatttta cgatgtgtac      240
ttgaaattca gaaaaaatcc caaggacgac gagttgcaaa agcaactcaa ggatctccag      300
gccgtcttgc gcaaagaaat tgttaagccg ataggtaacg gtggcaaata taggcagga       360
```

-continued

```
tacgacagac ttttcggtgc taaattgttc aaagacggta aagagctggg cgatttggca    420
aagtttgtga tagcgcaaga aggtgagtcg tctcccaaac tggcccatct tgcccacttc    480
gagaaatttt caacgtactt tacaggattt catgataaca gaaaaaacat gtacagcgac    540
gaggataaac acaccgctat tgcttatagg ttgatccatg aaaatctgcc gaggttcata    600
gataacctgc agatccttac gactattaaa cagaaacata gtgcacttta tgatcaaata    660
atcaacgaac tgactgcgtc cgggctggac gtgtcacttg cgtcacatct ggatggctat    720
cacaagttgt tgacccagga gggtatcacc gcttacaata cattgcttgg tggtatttca    780
ggggaggctg ggtcgccaaa aattcagggg atcaacgagc tcataaatag ccatcacaat    840
cagcactgcc acaaatcaga aaggattgcc aaactgcgcc ctctccacaa acaaatcttg    900
tcagatggaa tgtcggtctc ctttcttccg agcaagtttg cagacgactc ggagatgtgc    960
caagctgtga acgaatttta cagacattat gccgatgttt cgccaaggt ccaatcactc    1020 tttgatggat tcgatgatca tcagaaggat gggatctatg ttgaacacaa aaacctcaat    1080
gagctctcga agcaggcgtt cggggatttc gctctcttgg aagggttttt ggatgggtat    1140
tatgttgatg tggtgaatcc ggaattcaac gagcgcttcg ctaaagcgaa gacggacaac    1200
gcgaaagcta aactcacaaa ggagaaggac aagttcatca agggtgtcca ctcgttggcc    1260
agcctggaac aagcaataga acactatacc gcacgccacg atgatgagag tgtgcaagca    1320
gggaagcttg ggcaatactt taagcatggg ctcgcgggtg tggacaatcc tatccagaag    1380
atacacaaca accacagtac gatcaaaggg tttctggaaa gagaacgccc cgcgggagag    1440
cgggcgcttc cgaaaattaa gagcggtaaa aatcccgaaa tgacccagct tcgccagttg    1500
aaagaacttc tcgataatgc tttgaacgtt gcccactttg ctaaacttct gaccacgaaa    1560
acgacactcg ataatcaaga cggcaatttc tacggagagt ttggtgttct ttatgacgaa    1620
cttgcgaaaa tccctacact ctacaataaa gttcgggatt acctgtccca aaaaccattc    1680
tcgacggaga aatacaagct gaattttggc aatcccactc ttctgaacgg atgggacctg    1740
aacaaagaaa aggataattt cggagtgatt ctccagaagg acggctgcta ctatcttgcc    1800
ctcctggata aagctcataa aaaagtgttc gataatgccc cgaatactgg taaatctatt    1860
taccaaaaaa tgatatataa atatcttgag gttcggaagc agttcccgaa ggtttttttt    1920
agtaaggaag caatcgcgat aaactaccac ccgtcgaaag agctcgtcga aattaaagat    1980
aagggcaggc aaaggagtga cgacgaacgg cttaagctct atcggtttat cttggagtgt    2040
ctcaaaatcc acccgaagta cgacaagaaa tttgaaggcg ctattggtga catacagctc    2100
ttcaaaaagg ataaaaaggg aagagaagtg ccaatatcag agaaagattt gttcgataag    2160
ataaatggta tatttagtag taagccgaaa ttggagatgg aagacttctt catcggggag    2220
ttcaagagat ataatcccag ccaagatttg gttgatcaat acaacattta taaaaagata    2280
gactctaatg ataacagaaa gaaagaaaat ttctataata atcaccctaa attcaagaaa    2340
gatctcgtcc gctactatta tgagtctatg tgcaagcacg aggaatggga ggagtctttt    2400
gagttctcca agaagctcca agacataggt tgttatgtcg acgtgaacga acttttttacg    2460 gagatcgaga cccgccgcct gaactataag atctcatttt gcaatatcaa tgcggattat    2520
atagacgagc ttgtggaaca aggccagttg tatctttttc aaatctacaa caaagacttc    2580
tcgcctaagg ctcatggcaa gccgaatctc cacacgttgt attttaaggc acttttctct    2640
gaggacaact tggcggatcc gatatacaag ctcaacggcg aggcccagat cttttaccgc    2700
```

-continued

```
aaagcttcac tcgatatgaa tgaaacaacc attcacagag ctggtgaggt gctcgagaac    2760
aaaaaccccg acaatcccaa gaaaaggcag tttgtgtatg acataataaa agacaagcgc    2820
tatacccaag acaaatttat gcttcacgtt ccgatcacaa tgaacttcgg tgtgcagggt    2880
atgaccatta aggagttcaa taaaaaagtg aatcagtcca tccagcaata tgatgaagtc    2940
aatgttatcg gaatcgatcg gggagaacgc cacctgctct acctcacggt tattaatagc    3000
aaaggagaaa ttttggagca atgctcgctg aatgacatta cgacagcctc cgctaacgga    3060
actcagatga ctactccata tcataagata ctcgacaaaa gggaaataga gagattgaat    3120
gcaagggttg gatggggtga aattgaaacc attaaggagc tcaagtctgg ttatctgtct    3180
cacgttgttc accagatttc acagttgatg ttgaagtata acgcaattgt cgtgctggag    3240
gatcttaact tcggctttaa aaggggcagg tttaaggtgg agaaacaaat ttatcagaat    3300
ttcgaaaacg cgctcatcaa gaagctgaat catttggtcc tgaaagataa agcagacgac    3360
gaaatcggct catataaaaa tgctctgcag ctcactaata actttaccga cttgaaaagt    3420
ataggaaagc agacaggctt tctcttttac gtgcctgctt ggaacacttc aaaaatagat    3480
ccagaaactg gctttgttga cctcctgaaa cctagatatg agaacatcgc ccaatcccag    3540
gctttttttg gcaagttcga caaaatctgt tacaacgccg acaaagacta ttttgaattc    3600
catatagatt atgctaagtt tacagataag gcaaaaaatt ctagacagat atggaccatc    3660
tgttcacatg gggacaagag atacgtctat gataagactg ctaatcaaaa caaaggagca    3720
gctaaaggta tcaacgtcaa tgatgagctc aaaagtttgt tcgctcgcca tcacataaac    3780
gagaagcaac ctaatttggt tatggatata tgccaaaaca acgataagga atttcacaaa    3840
tcgctcatgt acctgcttaa gacgttgctg gccttgcgct actctaacgc atcctcagac    3900
gaagacttta ttctcagtcc tgtcgctaat gacgagggcg tttttttcaa ctctgcgttg    3960
gctgacgaca cacaaccgca aaacgcagat gccaatggcg cctaccacat cgctctgaag    4020
ggtctttggc tcttgaatga actcaagaac agtgatgatc ttaacaaggt gaaacttgca    4080
atcgataatc agacgtggtt gaattttgcg cagaatagg                          4119
```

```
<210> SEQ ID NO 8
<211> LENGTH: 3894
<212> TYPE: DNA
<213> ORGANISM: Artificial Sequence
<220> FEATURE:
<223> OTHER INFORMATION: Synthetic construct

<400> SEQUENCE: 8
atgaccaaaa ccttcgattc agaattcttt aatctttact cactccagaa aaccgtccgc     60
ttcgaattga aacccgttgg cgagactgca tcattcgtcg aagattttaa gaatgaggga    120
ttgaagcggg tcgtgagcga agacgagcgg agagcagtgg actatcagaa ggtgaaggag    180
attattgatg attaccatcg cgactttatt gaggagagcc ttaactactt cccagagcag    240
gtgtccaaag acgcacttga acaggcattt cacctctacc aaaagctgaa ggcagcgaag    300
gtggaggagc gggaaaaaagc tctgaaggaa tgggaagctt tgcagaagaa attgcgggag    360
aaagttgtca agtgcttctc agattcgaat aaagcgagat ttagcagaat tgacaaaaag    420
gagcttatca aggaggatct tattaactgg cttgtcgccc agaatcggga agacgatatt    480
ccgactgtcg agacgtttaa caattttacg acttacttca cgggctttca cgagaatagg    540
aagaatattt actccaagga cgatcacgct actgcgatta gttttcgcct catccatgaa    600
aatttgccca aattttttcga caatgttatc tcctttaata agctcaagga aggattcccg    660
```

-continued

```
gaactgaaat ttgataaagt taaggaagat ttggaggtcg attatgacct caaacacgca      720
ttcgagatag aatatttcgt caattttgtt acgcaggccg ggatagacca gtacaactac      780
ctgcttggcg gtaagacgct cgaagacgga accaaaaagc agggtatgaa tgaacagatc      840
aacctgttta aacagcagca gacccgcgac aaggcacggc agattcccaa gttgataccg      900
ctctttaagc agattttgag cgaacggaca gaatcgcaat cgttcatccc gaagcaattt      960
gagtccgatc aagagctctt cgactcattg cagaaattgc acaacaactg ccaggacaag     1020
ttcacagtcc ttcaacaggc catattggga ttggccgagg ccgatctcaa aaaggttttc     1080
ataaagacat cggacttgaa tgctctttcg aatacgatat tcggaaatta ttccgtgttt     1140
tccgacgcgc tcaacctcta taaagagagt cttaaaacga aaaaagccca agaagcgttt     1200
gaaaagctgc cggctcacag catacacgat ctgatacagt atctggaaca attcaattcc     1260
agcctcgacg ctgagaagca gcaatcaacg gacaccgttc tgaactattt tatcaagacc     1320
gatgaactgt attcgagatt cataaaaagt acatcagaag ccttcacgca ggtccagcca     1380
ttgttcgagt tggaagcctt gtcgtctaaa agacggcccc ctgagtctga agatgagggc     1440
gcaaaaggcc aagagggatt cgaacaaata aagcgcatca aggcctatct ggatactctt     1500
atggaagcgg ttcactttgc taagcccctc tatcttgtca aagggaggaa gatgattgag     1560
ggtctggata agaccaatc attttacgaa gcattcgaaa tggcgtacca ggagcttgaa     1620
agtttgatta taccgatata taacaaagca aggtcgtacc tttcaaggaa acctttttaag     1680 gcagataaat tcaagataaa tttcgataac aacactctct tgagcggttg ggatgctaat     1740
aaagagaccg ctaacgccag tatcttgttt aagaaagatg gcctttacta cctgggtatc     1800
atgcctaaag gaaaaacgtt tctcttcgat tattttgtga gttctgagga ttctgagaaa     1860
ttgaaacagc ggagacaaaa gactgcggag gaagctctcg cgcaagacgg tgagtcgtat     1920
tttgaaaaaa tcaggtacaa gttgttgccg ggagctagca agatgctgcc aaaagttttc     1980
ttctcgaata agaatatagg tttttacaac cctagcgatg acatcctccg gatcaggaac     2040
acagcgtccc acacaaagaa cggtacccca caaaagggac attccaaagt ggaattcaac     2100
ctgaacgatt gtcataagat gatagatttc tttaagtctt ctatacagaa acatcccgag     2160
tggggcagtt ttgggtttac tttcagcgac actagtgatt tcgaagatat gtctgctttc     2220
tacagggagg ttgaaaatca aggctatgtg atctcttttg ataaaattaa agaaacatat     2280
attcaatcgc aagtcgaaca agggaacctc tacctcttcc aaatctacaa taaggacttt     2340
agtccttatt ccaaggggaa acccaacctt cacacactct attggaaggc acttttcgaa     2400
gaggcgaatc ttaataatgt cgtggcaaaa ctgaacggcg aagcagaaat ttttttcaga     2460
agacattcca taaaagcaag cgacaaagtt gtgcaccctg ctaatcaagc aatagacaac     2520
aagaatccgc ataccgaaaa gacacaaagt accttcgagt acgatctggt gaaagataaa     2580
agatacacac aggacaagtt ttttttccac gttccaatct ccttgaactt taaggctcaa     2640
ggtgtttcga gtttaacga caaggttaac gggtttctca aagggaaccc ggacgtgaac      2700
atcattggca ttgatcgggg cgagcggcat ttgttgtact ttactgttgt gaaccagaag     2760
ggtgagatat tggttcagga gtcacttaat actctgatgt cagataaagg acacgtgaat     2820
gactaccaac agaagcttga taagaaagaa caagaacggg atgccgctag gaagtcatgg     2880
acaacagtcg aaaatattaa agaattgaag gagggttacc tgagccatgt tgttcataag     2940
ctggcacatc tcataatcaa atacaacgcg atcgtctgtc tggaagatct taatttcggt     3000
```

-continued

```
ttcaagaggg ggcgctttaa agtggaaaag caagtctacc agaaattcga aaaggccctt     3060
attgacaagc tgaactatct cgttttttaaa gagaaggaat tgggggaggt cgggcattat     3120
ctgactgcat accaactgac tgctcctttc gaatccttca aaaagttggg taagcagtct     3180
ggtatactct tttatgtgcc ggctgattac acctccaaga tcgaccccac cacaggattt     3240
gttaacttct tggatctgag atatcaaagc gtcgagaagg ctaagcaact tttgtccgat     3300
ttcaacgcta ttcgctttaa ttctgtccag aattatttcg agtttgaaat tgactacaaa     3360
aagctgactc ctaaacggaa agttggcacg cagagcaagt gggtcatttg tacttatggt     3420
gatgtcaggt accaaaatcg cagaaaccag aaaggccatt gggagaccga agaggtcaac     3480
gttacggaga aactcaaagc gctctttgcc agtgattcga agaccactac cgtcatcgac     3540
tatgccaatg atgataacct tatagatgtc atacttgagc aggataaagc gagcttcttt     3600
aaagaattgt tgtggctcct gaagctgaca atgaccttga ggcatagtaa aattaagagt     3660
gaagatgact ttattctgtc tccagtcaag aatgaacagg gcgagtttta cgactccagg     3720
aaagcggggg aagtctggcc taaagatgcc gacgctaatg gcgcatatca tattgctctg     3780
aaaggtcttt ggaatctcca acaaataaat caatgggaaa aaggcaaaac cttgaacttg     3840
gctattaaaa atcaagattg gttctccttc atccagaaa aaccctatca agag           3894
```

```
<210> SEQ ID NO 9
<211> LENGTH: 3792
<212> TYPE: DNA
<213> ORGANISM: Artificial Sequence
<220> FEATURE:
<223> OTHER INFORMATION: Synthetic construct

<400> SEQUENCE: 9
```

```
atgatgaata acggcacaaa taactttcaa aacttcatcg ggatttctag cctgcaaaaa       60
acacttcgga atgcactgat cccgacggag acaacacagc agttcattgt caaaaacggt      120
atcattaaag aagacgagct gcggggagag aatagacaaa tattgaagga cataatggat      180
gactattaca ggggatttat ctccgaaacc ctctctagca tagatgatat agattggaca      240
tcccttttcg agaaaatgga aattcagctc aagaatggag ataataagga cacactgatt      300
aaggagcaaa cggagtaccg gaaggccatc cacaaaaagt ttgctaacga cgatcggttc      360
aagaatatgt ttagtgcgaa acttatatct gatatactgc ccgagtttgt gattcacaac      420
aataactatt ccgcatctga aaaagaagag aaaacacaag tgattaaact cttttcgaga      480
ttcgccacct cgttcaaaga ctactttaaa aacagagcta actgctttag tgcagatgat      540
atatcctcgt cgtcttgcca caggattgtc aatgacaatg cggaaatatt cttttcgaac      600
gccctggtgt acagaagaat tgtgaaatct ttgagcaacg acgacattaa caagatcagt      660
ggggatatga aggactcttt gaaggaaatg tcgctcgagg agatttactc gtatgaaaaa      720
tatggtgaat tcattacaca agaaggcatt tcattttata atgatatttg cggcaaagtc      780
aatagcttta tgaatcttta ctgtcaaaaa aataaagaaa ataagaacct ctataaattg      840
cagaagctcc ataagcaaat tctctgcatc gccgatactt cttatgaagt gccttacaaa      900
ttcgagtccg atgaagaggt gtatcaatct gtgaatggat tcttggataa catatcctcg      960
aagcacattg tcgaacgctt gcgcaagatt ggcgacaact ataatgggta caatctcgac     1020
aaaatttaca tagttagcaa atttttacgaa tctgtctcac agaaaaccta tcgggattgg     1080
gagaccataa ataccgcact cgagattcat tataataata tactccccgg taacggaaag     1140
tccaaggctg acaaagttaa aaaggcagtt aaaaacgatc tccaaaaatc aataacggag     1200
```

```
atcaatgagt tggtgagtaa ttataagctt tgctccgacg acaatatcaa ggctgaaacg    1260
tatatccacg aaattagcca tattctcaac aacttcgaag cgcaggagtt gaaatacaac    1320
cctgagatac acctggttga gagcgagctt aaggccagcg agctcaaaaa tgtcctggat    1380
gtgattatga atgcgttcca ctggtgctca gtgttcatga cagaagaact ggttgacaaa    1440
gataataatt tctacgcgga acttgaggag atttatgatg agatctaccc tgttataagc    1500
ctgtataact tggtcagaaa ttatgtcacg caaaaaccgt actccacaaa aaagataaag    1560
ctgaatttcg gaatccctac tctcgcggat ggctggtcca aatctaaaga gtacagtaac    1620
aatgccatca tattgatgag ggacaacctt tactatttgg gaatctttaa tgcgaaaaat    1680
aaacctgaca aaaaaataat agagggtaac acctcggaga ataaaggcga ttataaaaaa    1740
atgatatata atctgctgcc cgggcccaat aagatgattc ccaaggtttt tcttagcagt    1800
aaaaccgggg tggagacgta taagccgtcg gcctacattt tggaaggcta taaacagaac    1860
aagcacatca aatcgagcaa ggactttgat attactttct gtcatgacct gatagactat    1920
tttaaaaact gcatagcgat tcacccagaa tggaagaact tcggtttcga cttctctgac    1980
acctctacat acgaggacat atcaggcttt tatagagagg tcgagctgca aggctacaag    2040
atagattgga cttatatctc agagaaggat atcgacctgc tccaagaaaa gggccaattg    2100
tatcttttcc aaatctacaa taaagatttt tctaaaaagt ccacagggaa cgataatctc    2160
cacacgatgt accttaaaaa cctcttttcg gaagaaaacc tgaaggacat tgtgcttaag    2220
ctgaatgggg aggccgagat attctttagg aagagtagca taaagaaccc gataatccat    2280
aaaaaaggtt ccatactggt taatcggacc tatgaggcag aagaaaaaga ccagttcgga    2340
aatatccaga ttgtcagaaa aaatatacca gagaatatct accaggaatt gtacaaatat    2400
ttcaacgata aatcagataa ggaactctcg gacgaagcag cgaaattgaa gaacgtcgtt    2460
ggacaccacg aggccgccac taatatcgtt aaagattaca ggtacacgta cgataagtat    2520
tttctccaca tgccaatcac tataaacttt aaagctaata agaccggctt tattaacgat    2580
cgcatccttc agtatatcgc taaggagaag gacctgcacg ttataggaat agaccgcggc    2640
gagcgcaatc ttatctacgt gagcgtgatc gatacctgtg ggaatatagt cgagcagaag    2700
tcttttaata tcgtgaacgg ctacgactat cagataaagc tgaagcagca agagggcgct    2760
agacagatcg ccaggaagga atggaaggag atcggtaaaa taaagaaat taaggagggt    2820 tacctcagtt tggttataca tgagatatca aaaatggtta ttaagtataa tgcgattatt    2880
gcgatggaag acctgtcata tgggtttaaa aaagggcggt tcaaggttga gcgccaggtc    2940
tatcaaaagt ttgagactat gctgattaat aagctcaatt atcttgtttt caaagacatc    3000
agtatcacgg aaaacggagg acttctcaag gggtaccagt tgacttatat cccagacaag    3060
cttaaaaatg ttggtcacca gtgtggatgt atattttatg tgcctgcggc ctacacatct    3120
aagatcgacc caacaactgg ctttgttaat attttttaaat tcaaagacct tacggtggat    3180
gcgaaaagag agttcataaa aaaattcgac tcgatcagat atgactctga gaagaatctc    3240
ttctgtttta ctttcgacta taataatttc ataacacaaa ataccgtcat gtcgaaatca    3300
agctggtcag tctacacata tggcgttcgc ataaagcgcc gcttcgttaa tggcaggttc    3360
tcgaatgagt ccgatacaat cgacattacg aaggatatgg agaaaacact cgagatgacg    3420
gatataaatt ggagggatgg gcatgatctg agacaggaca taatagacta tgagatagtt    3480
cagcacatat tcgagatctt cagactcact gttcagatgc ggaactccct cagtgaactt    3540
```

```
gaagacaggg attatgatag gcttatttct cctgtcctga acgaaaacaa tattttctac      3600
gactctgcta aagcagggga tgctcttcct aaggatgcag acgcaaatgg cgcatactgc      3660
atagctctta aagggctcta tgagatcaag cagattacag aaaactggaa agaagacggg      3720 aagtttttcca gagacaaatt gaagatctcc aacaaggact ggttcgattt tatacaaaat      3780
aaaaggtacc tt                                                          3792

<210> SEQ ID NO 10
<211> LENGTH: 6939
<212> TYPE: DNA
<213> ORGANISM: Artificial Sequence
<220> FEATURE:
<223> OTHER INFORMATION: Synthetic construct

<400> SEQUENCE: 10
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag       120
ctgtaatgca agtagcgtat cgcctcacgc aactggtcca gaaccttgac cgaacgcagc       180
ggtggtaacg cgcagtggc ggttttcatg gcttgttatg actgttttttt tggggtacag       240 tctatgcctc gggcatccaa gcagcaagcg cgttacgccg tgggtcgatg tttgatgtta       300
tggagcagca acgatgttac gcagcagggc agtcgcccta aaacaaagtt aaacatcatg       360
agggaagcgg tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca       540
acgcggcgag ctttgatcaa cgacctttg gaaacttcgg cttcccctgg agagagcgag       600
attctccgcg ctgtagaagt caccattgtt gtgcacgacg acatcattcc gtggcgttat       660
ccagctaagc gcgaactgca atttggagaa tggcagcgca atgacattct tgcaggtatc       720
ttcgagccag ccacgatcga cattgatctg gctatcttgc tgacaaaagc aagagaacat       780
agcgttgcct tggtaggtcc agcggcggag gaactctttg atccggttcc tgaacaggat       840
ctatttgagg cgctaaatga aaccttaacg ctatggaact cgccgcccga ctgggctggc       900
gatgagcgaa atgtagtgct tacgttgtcc cgcatttggt acagcgcagt aaccggcaaa       960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagacccgt agaaaagatc aaaggatctt cttgagatcc tttttttctg     1260
cgcgtaatct gctgcttgca acaaaaaaaa ccaccgctac cagcggtggt ttgtttgccg     1320
gatcaagagc taccaactct ttttccgaag gtaactggct tcagcagagc gcagatacca     1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg tcgggctga     1560 acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga     1800
```

```
tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat  aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgctttttta taatgccaac tttgtacaaa aaagcaggct ccgaattcgc ccttcaccat    2580
ggctcctaag aagaagcgga aggttggtat tcacggggtg cctgcggctt caaagctcga    2640
gaaattcacc aactgttatt cgttgagcaa aacactgcgg tttaaagcga ttccagtcgg    2700
caagactcaa gagaatatag acaataagcg gctgttggtg gaagatgaaa agcgcgcgga    2760
agactacaaa ggggtgaaga agttgttgga cagatactac ctctctttta tcaatgatgt    2820
cttgcactca atcaaattga agaatctgaa caactacatc tccctcttca gaaagaaaac    2880
aaggacagaa aaggagaata aggaacttga aaatttggag atcaatctga ggaaagagat    2940
cgcgaaagcc tttaaaggca acgaaggata caaaagtctg ttcaagaagg atataattga    3000
gacaattttg ccagagttcc tcgatgacaa ggacgagatt gcgctggtca attcgttcaa    3060
cggattcaca acagcattca caggcttctt tgataatcgg gaaaatatgt tctctgagga    3120
ggcaaagtcc acttctattg cgttcaggtg tatcaatgag aatctcacta ggtacatttc    3180
caacatggat atctttgaga aggttgacgc aattttttgac aagcacgaag ttcaggagat    3240
taaggagaag atcctcaatt ccgattatga cgttgaggac ttcttcgaag gtgagttttt    3300
taatttcgtg ctcactcaag agggtatcga cgtgtataat gcgatcatcg gtgggttcgt    3360
gactgagtcc ggtgaaaaga ttaagggatt gaacgagtat atcaacccttt acaaccaaaa    3420 gacgaaacag aagctgccaa agttcaagcc tctttacaaa caggttcttt cagaccgcga    3480
gtcactctcg ttctatgggg agggctacac ttcggatgag gaagtcctgg aggtgttcag    3540
gaatactctc aataagaatt cggagatttt ctcttctata aaaaaactgg aaaagttgtt    3600
taagaatttt gacgaatact ctagcgccgg catatttgtg aaaaacggcc cggccatatc    3660 aacgatagt  aaagatatct cggcgaatg  gaacgtgatc agagacaaat ggaacgcgga    3720
gtatgacgat attcacctga gaagaaggc  tgtcgtaacg gagaagtacg aggatgatcg    3780
caggaaaagc ttcaaaaaga tcggaagttt cagcctggaa cagttgcagg agtatgctga    3840
cgccgatctt agcgtcgtcg agaagttgaa ggagataatc atccaaaagg tcgacgagat    3900
atataaagtc tatggatcaa gtgaaaaact gttcgacgcc gacttcgttt tggagaagtc    3960
cctgaagaag aacgacgctg ttgttgccat tatgaaggat ctgctcgaca gcgtgaagag    4020
tttcgagaac tatattaagg cttttttcgg ggaggggaag gagactaaca gagatgagtc    4080
cttctacgga gacttcgtcc tcgcgtacga tatactcctt aaggtagacc acatctacga    4140
```

-continued

```
cgcaatcaga aattacgtga cacaaaagcc gtacagcaag gacaagttca aactctactt    4200
ccagaacccc cagttcatgg gcggctggga caaggacaag gaaacggatt acagggctac    4260
gatcctgagg tatggttcaa aatactactt ggcgattatg gacaagaagt acgccaagtg    4320
tctccagaag attgacaaag acgatgtcaa tggcaattat gagaagatca actacaagct    4380
gcttccgggt ccgaacaaga tgctcccaaa ggttttcttc agcaagaaat ggatggccta    4440
ctataaccca agcgaggaca tccagaagat ttataagaac ggtacgttca agaagggcga    4500
catgttcaat cttaacgact gtcacaagct gatcgacttc ttcaaagact caattagccg    4560
gtacccaaag tggtctaacg cctatgactt caacttttcg gaaaccgaga agtacaagga    4620
tatagccgga tttttatagag aggtggaaga gcagggctac aaggtgtcat tcgagtccgc    4680
cagcaagaag gaagtggaca agctcgtgga agagggtaag ctctacatgt tccagattta    4740
taataaagac tttagcgata agagccacgg gacacctaat ctccacacaa tgtatttcaa    4800
gctgctcttc gacgagaata accacggcca aatcaggttg tcaggagggg ctgaactctt    4860
catgcggcgc gctagcctta agaaggagga gcttgtagtc caccctgcga atagtccaat    4920
tgcgaataag aacccggaca atcctaaaaa gactacaaca ttgagctacg acgtgtacaa    4980
ggataagagg ttttccgagg atcagtacga gctccacatc ccgattgcga tcaacaagtg    5040
cccaaagaat attttcaaga taaacacaga ggtgcgtgta ctcctgaagc atgacgacaa    5100
tccttacgtc attgggattg atcggggcga gaggaacctc ctctatattg tggtggtgga    5160
cgggaagggg aacatagtcg aacagtactc ccttaacgaa ataattaaca atttcaacgg    5220
catccgtatc aagaccgact accattcgtt gctggacaag aaggagaagg agagatttga    5280
ggcgcggcaa aattggacaa gtatcgagaa catcaaggaa ctcaaagcag gttatatctc    5340
tcaagttgtg cataagatat gcgagctggt tgagaagtat gacgcagtga tcgctcttga    5400
ggacctcaac tcgggcttta agaattctag agttaaagtg gagaagcagg tctatcaaaa    5460
gttcgagaag atgcttatag ataagctcaa ctacatggtc gataagaaat cgaacccatg    5520
tgccaccggc ggcgcactca aaggttacca aataacaaac aaattcgagt ccttcaaatc    5580
gatgagtact cagaatgggt tcatatttta tataccggcg tggcttacgt ctaagatcga    5640
cccgtcaact ggttttgtca acctgttgaa gacgaaatac acgtccattg ccgattcgaa    5700
aaagttcata tctagttttg atcgtattat gtacgtccca gaggaagatc tttttcgagtt    5760 tgctctcgac tacaaaaact tttcgcggac cgatgcggat tacattaaaa aatggaaact    5820
ctattcgtac ggcaacagaa tcaggatttt tcgcaaccct aagaagaata acgtctttga    5880
ttgggaggaa gtttgcttga ctagcgcgta caaggagctc tttaataagt atggcattaa    5940
ctaccaacag ggtgatatca gagcactgct ttgcgaacaa tctgacaagg ctttctactc    6000
atccttcatg gctttgatga gcctgatgct ccagatgaga aattcaatta caggcagaac    6060
cgacgtggat ttcttgatct ccccggttaa aaattctgat ggcatctttt acgatagcag    6120
gaactatgaa gcgcaagaga atgcgattct gccaaaaaat gcagacgcca acggtgccta    6180
taacatcgcc aggaaagtcc tgtgggcgat cggccagttc aaaaaggccg aagacgaaaa    6240
attggacaag tcaaaatcg ctatcagcaa caaagagtgg ctggagtatg ctcagacatc    6300
cgtaaagcat aagcgtcctg ctgccaccaa aaaggccgga caggctaaga aaaagaagtg    6360
agacgactag tggcggccgc cgacgtccga tcgttcaaac atttggcaat aaagtttctt    6420
aagattgaat cctgttgccg gtcttgcgat gattatcata taatttctgt tgaattacgt    6480
taagcatgta ataattaaca tgtaatgcat gacgttattt atgagatggg tttttatgat    6540
```

```
tagagtcccg caattataca tttaatacgc gatagaaaac aaaatatagc gcgcaaacta    6600
ggataaatta tcgcgcgcgg tgtcatctat gttactagat cgggaattga tcccccctcg    6660
acagcttccg gaaagggcga attcgcaact ttgtatacaa aagttgaacg agaaacgtaa    6720
aatgatataa atatcaatat attaaattag attttgcata aaaaacagac tacataaatac    6780 tgtaaaacac aacatatcca gtcactatgc catccagctg atatcccta tagtgagtcg    6840 tattacatgg tcatagctgt ttcctggcag ctctggcccg tgtctcaaaa tctctgatgt    6900
tacattgcac aagataaaaa tatatcatca tgcctcctc    6939
```

```
<210> SEQ ID NO 11
<211> LENGTH: 7374
<212> TYPE: DNA
<213> ORGANISM: Artificial Sequence
<220> FEATURE:
<223> OTHER INFORMATION: Synthetic construct

<400> SEQUENCE: 11
tggaccagcc aggacagaaa tgcctcgact tcgctgctac ccaaggttgc cgggtgacgc     60
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg cgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcaggc agtcgcccta aaacaaagtt aaacatcatg    360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttccctgg agagagcgag    600 attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagacccgt agaaaagatc aaaggatctt cttgagatcc ttttttttctg    1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg tcgggctga    1560 acggggggtt cgtgcacaca gcccagcttg gagcgaacga cctacaccga actgagatac    1620
```

```
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga  1800 tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg gccgttgct tcacaacgtt caaatccgct cccggcggat    2280
ttgtcctact caggagagcg ttcaccgaca acaacagat aaaacgaaag gcccagtctt     2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc    2460
caaataatga tttatttttg actgatagtg acctgttcgt tgcaacaaat tgatgagcaa   2520 tgcttttttta taatgccaac tttgtacaaa aaagcaggct ccgaattcgc ccttcaccat   2580
ggctcctaag aagaagcgga aggttggtat tcacggggtg cctgcggctc tgttccaaga   2640
tttcactcat ctgtaccccc tctccaaaac agtgcggttt gaattgaagc cgatcgatcg   2700
gacacttgaa cacattcacg caaaaaactt cctctctcag gatgagacca tggcagacat   2760
gcaccagaaa gtcaaagtca tactcgatga ctaccatagg gacttcatag ccgacatgat   2820
gggtgaggtt aaactgacta aactcgcgga attttacgat gtgtacttga aattcagaaa   2880
aaatcccaag gacgacgagt tgcaaaagca actcaaggat ctccaggccg tcttgcgcaa   2940
agaaattgtt aagccgatag gtaacggtgg caaatataag gcaggatacg acagactttt   3000
cggtgctaaa ttgttcaaag acggtaaaga gctgggcgat ttggcaaagt ttgtgatagc   3060
gcaagaaggt gagtcgtctc ccaaactggc ccatcttgcc cacttcgaga aattttcaac   3120
gtactttaca ggatttcatg ataacagaaa aaacatgtac agcgacgagg ataaacacac   3180
cgctattgct tataggttga tccatgaaaa tctgccgagg ttcatagata acctgcagat   3240
ccttacgact attaaacaga aacatagtgc actttatgat caaataatca acgaactgac   3300
tgcgtccggg ctggacgtgt cacttgcgtc acatctggat ggctatcaca agttgttgac   3360
ccaggagggt atcaccgctt acaatacatt gcttggtggt atttcagggg aggctgggtc   3420
gccaaaaatt caggggatca acgagctcat aaatagccat cacaatcagc actgccacaa   3480
atcagaaagg attgccaaac tgcgccctct ccacaaacaa atcttgtcag atggaatgtc   3540
ggtctccttt cttccgagca agtttgcaga cgactcggag atgtgccaag ctgtgaacga   3600
attttacaga cattatgccg atgttttcgc caaggtccaa tcactctttg atggattcga   3660
tgatcatcag aaggatggga tctatgttga acacaaaaac ctcaatgagc tctcgaagca   3720
ggcgttcggg gatttcgctc tcttgggaag ggttttggat gggtattatg ttgatgtggt   3780
gaatccggaa ttcaacgagc gcttcgctaa agcgaagacg gacaacgcga aagctaaact   3840
cacaaaggag aaggacaagt tcatcaaggg tgtccactcg ttggccagcc tggaacaagc   3900
aatagaacac tataccgcac gccacgatga tgagagtgtg caagcaggga gcttgggca    3960 atactttaag catgggctcg cgggtgtgga caatcctatc cagaagatac acaacaacca   4020
```

-continued

```
cagtacgatc aaagggtttc tggaaagaga acgccccgcg ggagagcggg cgcttccgaa    4080
aattaagagc ggtaaaaatc ccgaaatgac ccagcttcgc cagttgaaag aacttctcga    4140
taatgctttg aacgttgccc actttgctaa acttctgacc acgaaaacga cactcgataa    4200
tcaagacggc aatttctacg gagagtttgg tgttctttat gacgaacttg cgaaaatccc    4260
tacactctac aataaagttc gggattacct gtcccaaaaa ccattctcga cggagaaata    4320
caagctgaat tttggcaatc ccactcttct gaacggatgg gacctgaaca aagaaaagga    4380
taatttcgga gtgattctcc agaaggacgg ctgctactat cttgccctcc tggataaagc    4440
tcataaaaaa gtgttcgata atgccccgaa tactggtaaa tctatttacc aaaaaatgat    4500
atataaatat cttgaggttc ggaagcagtt cccgaaggtt tttttttagta aggaagcaat    4560 cgcgataaac taccacccgt cgaaagagct cgtcgaaatt aaagataagg gcaggcaaag    4620
gagtgacgac gaacggctta agctctatcg gtttatcttg gagtgtctca aaatccaccc    4680
gaagtacgac aagaaatttg aaggcgctat tggtgacata cagctcttca aaaaggataa    4740
aaagggaaga gaagtgccaa tatcagagaa agatttgttc gataagataa atggtatatt    4800
tagtagtaag ccgaaattgg agatggaaga cttcttcatc ggggagttca agagagatat aa    4860 tcccagccaa gatttggttg atcaatacaa catttataaa aagatagact ctaatgataa    4920
cagaaagaaa gaaaatttct ataataatca ccctaaattc aagaaagatc tcgtccgcta    4980
ctattatgag tctatgtgca agcacgagga atgggaggag tcttttgagt tctccaagaa    5040
gctccaagac ataggttgtt atgtcgacgt gaacgaactt tttacggaga tcgagacccg    5100
ccgcctgaac tataagatct cattttgcaa tatcaatgcg gattatatag acgagcttgt    5160
ggaacaaggc cagttgtatc ttttttcaaat ctacaacaaa gacttctcgc ctaaggctca    5220
tggcaagccg aatctccaca cgttgtattt taaggcactt ttctctgagg acaacttggc    5280
ggatccgata tacaagctca acggcgaggc ccagatcttt taccgcaaag cttcactcga    5340
tatgaatgaa acaaccattc acagagctgg tgaggtgctc gagaacaaaa accccgacaa    5400
tcccaagaaa aggcagtttg tgtatgacat aataaaagac aagcgctata cccaagacaa    5460
atttatgctt cacgttccga tcacaatgaa cttcggtgtg cagggtatga ccattaagga    5520
gttcaataaa aaagtgaatc agtccatcca gcaatatgat gaagtcaatg ttatcggaat    5580
cgatcgggga gaacgccacc tgctctacct cacggttatt aatagcaaag agaaaatttt    5640
ggagcaatgc tcgctgaatg acattacgac agcctccgct aacggaactc agatgactac    5700
tccatatcat aagatactcg acaaaaggga aatagagaga ttgaatgcaa gggttggatg    5760
gggtgaaatt gaaaccatta aggagctcaa gtctggttat ctgtctcacg ttgttcacca    5820
gatttcacag ttgatgttga agtataacgc aattgtcgtg ctggaggatc ttaacttcgg    5880 cttttaaaagg ggcaggttta aggtggagaa acaaatttat cagaatttcg aaaacgcgct    5940
catcaagaag ctgaatcatt tggtcctgaa agataaagca gacgacgaaa tcggctcata    6000
taaaaatgct ctgcagctca ctaataactt taccgacttg aaaagtatag aaaagcagac    6060
aggctttctc tttttacgtgc ctgcttggaa cacttcaaaa atagatccag aaactggctt    6120
tgttgacctc ctgaaaccta gatatgagaa catcgcccaa tcccaggctt tttttggcaa    6180
gttcgacaaa atctgttaca acgccgacaa agactatttt gaattccata tagattatgc    6240
taagtttaca gataaggcaa aaaattctag acagatatgg accatctgtt cacatgggga    6300
caagagatac gtctatgata agactgctaa tcaaaacaaa ggagcagcta aaggtatcaa    6360
```

-continued

```
cgtcaatgat gagctcaaaa gtttgttcgc tcgccatcac ataaacgaga agcaacctaa      6420
tttggttatg gatatatgcc aaaacaacga taaggaattt cacaaatcgc tcatgtacct      6480
gcttaagacg ttgctggcct tgcgctactc taacgcatcc tcagacgaag actttattct      6540
cagtcctgtc gctaatgacg agggcgtttt tttcaactct gcgttggctg acgacacaca      6600
accgcaaaac gcagatgcca atggcgccta ccacatcgct ctgaagggtc tttggctctt      6660
gaatgaactc aagaacagtg atgatcttaa caaggtgaaa cttgcaatcg ataatcagac      6720
gtggttgaat tttgcgcaga ataggaagcg tcctgctgcc accaaaaagg ccggacaggc      6780
taagaaaaag aagtgagacg actagtggcg gccgccgacg tccgatcgtt caaacatttg      6840
gcaataaagt ttcttaagat tgaatcctgt tgccggtctt gcgatgatta tcatataatt      6900
tctgttgaat tacgttaagc atgtaataat taacatgtaa tgcatgacgt tatttatgag      6960
atgggttttt atgattagag tcccgcaatt atacatttaa tacgcgatag aaaacaaaat      7020
atagcgcgca aactaggata aattatcgcg cgcggtgtca tctatgttac tagatcggga      7080
attgatcccc cctcgacagc ttccggaaag ggcgaattcg caactttgta tacaaaagtt      7140
gaacgagaaa cgtaaaatga tataaatatc aatatattaa attagatttt gcataaaaaa      7200
cagactacat aatactgtaa aacacaacat atccagtcac tatgccatcc agctgatatc      7260
ccctatagtg agtcgtatta catggtcata gctgtttcct ggcagctctg gcccgtgtct      7320
caaaatctct gatgttacat tgcacaagat aaaaatatat catcatgcct cctc            7374
```

<210> SEQ ID NO 12
<211> LENGTH: 7149
<212> TYPE: DNA
<213> ORGANISM: Artificial Sequence
<220> FEATURE:
<223> OTHER INFORMATION: Synthetic construct

<400> SEQUENCE: 12

```
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag       120
ctgtaatgca agtagcgtat gcgctcacgc aactggtcca gaaccttgac cgaacgcagc       180
ggtggtaacg gcgcagtggc ggttttcatg gcttgttatg actgtttttt tggggtacag       240
tctatgcctc gggcatccaa gcagcaagcg cgttacgccg tgggtcgatg tttgatgtta       300
tggagcagca acgatgttac gcagcagggc agtcgcccta aaacaaagtt aaacatcatg       360
agggaagcgg tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca       540
acgcggcgag ctttgatcaa cgaccttttg gaaacttcgg cttcccctgg agagagcgag       600
attctccgcg ctgtagaagt caccattgtt gtgcacgacg acatcattcc gtggcgttat       660
ccagctaagc gcgaactgca atttggagaa tggcagcgca atgacattct tgcaggtatc       720
ttcgagccag ccacgatcga cattgatctg gctatcttgc tgacaaaagc aagagaacat       780
agcgttgcct tggtaggtcc agcggcggag gaactctttg atccggttcc tgaacaggat       840
ctatttgagg cgctaaatga aaccttaacg ctatggaact cgccgcccga ctgggctggc       900
gatgagcgaa atgtagtgct tacgttgtcc cgcatttggt acagcgcagt aaccggcaaa       960
atcgcgccga aggatgtcgc tgccgactgg gcaatggagc gcctgccggc ccagtatcag      1020
cccgtcatac ttgaagctag acaggcttat cttggacaag aagaagatcg cttggcctcg      1080
```

-continued

```
cgcgcagatc agttggaaga atttgtccac tacgtgaaag gcgagatcac caaggtagtc      1140
ggcaaataac cctcgagcca cccatgacca aaatccctta acgtgagtta cgcgtcgttc      1200
cactgagcgt cagaccccgt agaaaagatc aaaggatctt cttgagatcc ttttttttctg     1260 cgcgtaatct gctgcttgca aacaaaaaaa ccaccgctac cagcggtggt ttgtttgccg      1320
gatcaagagc taccaactct ttttccgaag gtaactggct tcagcagagc gcagatacca      1380
aatactgtcc ttctagtgta gccgtagtta ggccaccact tcaagaactc tgtagcaccg      1440
cctacatacc tcgctctgct aatcctgtta ccagtggctg ctgccagtgg cgataagtcg      1500
tgtcttaccg ggttggactc aagacgatag ttaccggata aggcgcagcg gtcgggctga      1560
acggggggtt cgtgcacaca gcccagcttg gagcgaacga cctacaccga actgagatac      1620
ctacagcgtg agctatgaga aagcgccacg cttcccgaag ggagaaaggc ggacaggtat      1680
ccggtaagcg gcagggtcgg aacaggagag cgcacgaggg agcttccagg gggaaacgcc      1740
tggtatcttt atagtcctgt cgggtttcgc cacctctgac ttgagcgtcg attttttgtga     1800 tgctcgtcag ggggggcggag cctatggaaa aacgccagca acgcggcctt tttacggttc     1860 ctggccttt gctggccttt tgctcacatg ttctttcctg cgttatcccc tgattctgtg       1920
gataaccgta ttaccgcctt tgagtgagct gataccgctc gccgcagccg aacgaccgag      1980
cgcagcgagt cagtgagcga ggaagcggaa gagcgcccaa tacgcaaacc gcctctcccc      2040
gcgcgttggc cgattcatta atgcagctgg cacgacaggt ttcccgactg gaaagcgggc      2100
agtgagcgca acgcaattaa tacgcgtacc gcgagccagg aagagtttgt agaaacgcaa      2160
aaaggccatc cgtcaggatg gccttctgct tagtttgatg cctggcagtt tatggcgggc      2220
gtcctgcccg ccaccctccg ggccgttgct tcacaacgtt caaatccgct cccggcggat      2280
ttgtcctact caggagagcg ttcaccgaca aacaacagat aaaacgaaag gcccagtctt      2340
ccgactgagc ctttcgtttt atttgatgcc tggcagttcc ctactctcgc gttaacgctt      2400
gcatggatgt tttcccagtc acgacgttgt aaaacgacgg ccagtcttaa gctcgggccc      2460
caaataatga tttattttg actgatagtg acctgttcgt tgcaacaaat tgatgagcaa       2520
tgctttttta taatgccaac tttgtacaaa aaagcaggct ccgaattcgc ccttcaccat      2580
ggctcctaag aagaagcgga aggttggtat tcacggggtg cctgcggcta ccaaaacctt      2640
cgattcagaa ttctttaatc tttactcact ccagaaaacc gtccgcttcg aattgaaacc      2700
cgttggcgag actgcatcat cgtcgaaga ttttaagaat gagggattga agcgggtcgt      2760
gagcgaagac gagcggagag cagtggacta tcagaaggtg aaggagatta ttgatgatta      2820
ccatcgcgac tttattgagg agagccttaa ctacttccca gagcaggtgt ccaaagacgc      2880
acttgaacag gcatttcacc tctaccaaaa gctgaaggca gcgaaggtgg aggagcggga      2940
aaaagctctg aaggaatggg aagctttgca gaagaaattg cgggagaaag ttgtcaagtg      3000
cttctcagat tcgaataaag cgagatttag cagaattgac aaaaaggagc ttatcaagga      3060
ggatcttatt aactggcttg tcgcccagaa tcgggaagac gatattccga ctgtcgagac      3120
gtttaacaat tttacgactt acttcacggg ctttcacgag aataggaaga atatttactc      3180
caaggacgat cacgctactg cgattagttt tcgcctcatc catgaaaatt gcccaaatt       3240 tttcgacaat gttatctcct ttaataagct caaggaagga ttcccggaac tgaaatttga      3300
taaagttaag gaagatttgg aggtcgatta tgacctcaaa cacgcattcg agatagaata      3360
tttcgtcaat tttgttacgc aggccgggat agaccagtac aactacctgc ttggcggtaa      3420
```

-continued

```
gacgctcgaa gacggaacca aaaagcaggg tatgaatgaa cagatcaacc tgtttaaaca    3480
gcagcagacc cgcgacaagg cacggcagat tcccaagttg ataccgctct ttaagcagat    3540
tttgagcgaa cggacagaat cgcaatcgtt catcccgaag caatttgagt ccgatcaaga    3600
gctcttcgac tcattgcaga aattgcacaa caactgccag gacaagttca cagtccttca    3660
acaggccata ttgggattgg ccgaggccga tctcaaaaag gttttcataa agacatcgga    3720
cttgaatgct ctttcgaata cgatattcgg aaattattcc gtgttttccg acgcgctcaa    3780
cctctataaa gagagtctta aaacgaaaaa agcccaagaa gcgtttgaaa agctgccggc    3840
tcacagcata cacgatctga tacagtatct ggaacaattc aattccagcc tcgacgctga    3900
gaagcagcaa tcaacggaca ccgttctgaa ctattttatc aagaccgatg aactgtattc    3960
gagattcata aaaagtacat cagaagcctt cacgcaggtc cagccattgt tcgagttgga    4020
agccttgtcg tctaaaagac ggccccctga gtctgaagat gagggcgcaa aaggccaaga    4080
gggattcgaa caaataaagc gcatcaaggc ctatctggat actcttatgg aagcggttca    4140
ctttgctaag cccctctatc ttgtcaaagg gaggaagatg attgagggtc tggataaaga    4200
ccaatcattt tacgaagcat tcgaaatggc gtaccaggag cttgaaagtt tgattatacc    4260
gatatataac aaagcaaggt cgtacctttc aaggaaacct tttaaggcag ataaattcaa    4320
gataaatttc gataacaaca ctctcttgag cggttgggat gctaataaag agaccgctaa    4380
cgccagtatc ttgtttaaga aagatggcct ttactacctg ggtatcatgc ctaaaggaaa    4440
aacgtttctc ttcgattatt ttgtgagttc tgaggattct gagaaattga aacagcggag    4500
acaaaagact gcggaggaag ctctcgcgca agacggtgag tcgtattttg aaaaaatcag    4560
gtacaagttg ttgccgggag ctagcaagat gctgccaaaa gttttcttct cgaataagaa    4620
tataggtttt tacaacccta gcgatgacat cctccggatc aggaacacag cgtcccacac    4680
aaagaacggt accccacaaa agggacattc caaagtggaa ttcaacctga acgattgtca    4740
taagatgata gatttcttta agtcttctat acagaaacat cccgagtggg gcagttttgg    4800
gtttactttc agcgacacta gtgatttcga agatatgtct gctttctaca gggaggttga    4860
aaatcaaggc tatgtgatct ctttttgataa aattaaagaa acatatattc aatcgcaagt    4920
cgaacaaggg aacctctacc tcttccaaat ctacaataag gactttagtc cttattccaa    4980
ggggaaaccc aaccttcaca cactctattg gaaggcactt ttcgaagagg cgaatcttaa    5040
taatgtcgtg gcaaaactga acggcgaagc agaaattttt ttcagaagac attccataaa    5100
agcaagcgac aaagttgtgc accctgctaa tcaagcaata gacaacaaga atccgcatac    5160
cgaaaagaca caaagtacct tcgagtacga tctggtgaaa gataaaagat acacacagga    5220
caagtttttt ttccacgttc caatctcctt gaactttaag gctcaaggtg tttcgaagtt    5280
taacgacaag gttaacgggt ttctcaaagg gaacccggac gtgaacatca ttggcattga    5340
tcggggcgag cggcatttgt tgtactttac tgttgtgaac cagaagggtg agatattggt    5400
tcaggagtca cttaatactc tgatgtcaga taaaggacac gtgaatgact accaacagaa    5460
gcttgataag aaagaacaag aacgggatgc cgctaggaag tcatggacaa cagtcgaaaa    5520
tattaaagaa ttgaaggagg gttacctgag ccatgttgtt cataagctgg cacatctcat    5580
aatcaaatac aacgcgatcg tctgtctgga agatcttaat ttcggtttca gagggggcg    5640 ctttaaagtg gaaaagcaag tctaccagaa attcgaaaag gcccttattg acaagctgaa    5700
ctatctcgtt tttaaagaga aggaattggg ggaggtcggg cattatctga ctgcatacca    5760
actgactgct cctttcgaat ccttcaaaaa gttgggtaag cagtctggta tactcttta    5820
```

-continued

```
tgtgccggct gattacacct ccaagatcga ccccaccaca ggatttgtta acttcttgga      5880
tctgagatat caaagcgtcg agaaggctaa gcaacttttg tccgatttca acgctattcg      5940 cttttaattct gtccagaatt atttcgagtt tgaaattgac tacaaaaagc tgactcctaa      6000
acggaaagtt ggcacgcaga gcaagtgggt catttgtact tatggtgatg tcaggtacca      6060
aaatcgcaga aaccagaaag gccattggga gaccgaagag gtcaacgtta cggagaaact      6120
caaagcgctc tttgccagtg attcgaagac cactaccgtc atcgactatg ccaatgatga      6180
taaccttata gatgtcatac ttgagcagga taaagcgagc ttctttaaag aattgttgtg      6240
gctcctgaag ctgacaatga ccttgaggca tagtaaaatt aagagtgaag atgactttat      6300
tctgtctcca gtcaagaatg aacagggcga gttttacgac tccaggaaag cggggggaagt      6360 ctggcctaaa gatgccgacg ctaatggcgc atatcatatt gctctgaaag gtctttggaa      6420
tctccaacaa ataaatcaat gggaaaaagg caaaaccttg aacttggcta ttaaaaatca      6480
agattggttc tccttcatcc aagaaaaacc ctatcaagag aagcgtcctg ctgccaccaa      6540
aaaggccgga caggctaaga aaagaagtg agacgactag tggcggccgc cgacgtccga      6600
tcgttcaaac atttggcaat aaagtttctt aagattgaat cctgttgccg gtcttgcgat      6660
gattatcata taatttctgt tgaattacgt taagcatgta ataattaaca tgtaatgcat      6720
gacgttattt atgagatggg tttttatgat tagagtcccg caattataca tttaatacgc      6780
gatagaaaac aaaatatagc gcgcaaacta ggataaatta tcgcgcgcgg tgtcatctat      6840
gttactagat cgggaattga tcccccctcg acagcttccg gaaagggcga attcgcaact      6900
ttgtatacaa aagttgaacg agaaacgtaa aatgatataa atatcaatat attaaattag      6960
attttgcata aaaaacagac tacataatac tgtaaaacac aacatatcca gtcactatgc      7020
catccagctg atatcccta tagtgagtcg tattacatgg tcatagctgt ttcctggcag      7080
ctctggcccg tgtctcaaaa tctctgatgt tacattgcac aagataaaaa tatatcatca      7140
tgcctcctc                                                                7149
```

```
<210> SEQ ID NO 13
<211> LENGTH: 7008
<212> TYPE: DNA
<213> ORGANISM: Artificial Sequence
<220> FEATURE:
<223> OTHER INFORMATION: Synthetic construct

<400> SEQUENCE: 13
```

```
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag       120
ctgtaatgca agtagcgtat gcgctcacgc aactggtcca gaaccttgac cgaacgcagc       180
ggtggtaacg gcgcagtggc ggttttcatg gcttgttatg actgtttttt tggggtacag       240
tctatgcctc gggcatccaa gcagcaagcg cgttacgccg tgggtcgatg tttgatgtta       300
tggagcagca acgatgttac gcagcagggc agtcgcccta aacaaagtt aaacatcatg        360 agggaagcgg tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca       540
acgcggcgag ctttgatcaa cgaccttttg gaaacttcgg cttcccctgg agagagcgag       600
attctccgcg ctgtagaagt caccattgtt gtgcacgacg acatcattcc gtggcgttat       660
```

-continued

```
ccagctaagc gcgaactgca atttggagaa tggcagcgca atgacattct tgcaggtatc      720
ttcgagccag ccacgatcga cattgatctg gctatcttgc tgacaaaagc aagagaacat      780
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagacccccgt agaaaagatc aaaggatctt cttgagatcc ttttttttctg     1260 cgcgtaatct gctgcttgca acaaaaaaa ccaccgctac cagcggtggt ttgtttgccg     1320
gatcaagagc taccaactct ttttccgaag gtaactggct tcagcagagc gcagatacca     1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg gtcgggctga     1560
acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga     1800 tgctcgtcag ggggggcggag cctatggaaa aacgccagca acgcggcctt tttacggttc     1860
ctggcctttt gctggccttt tgctcacatg ttctttcctg cgttatcccc tgattctgtg     1920
gataaccgta ttaccgcctt tgagtgagct gataccgctc gccgcagccg aacgaccgag     1980
cgcagcgagt cagtgagcga ggaagcggaa gagcgcccaa tacgcaaacc gcctctcccc     2040
gcgcgttggc cgattcatta atgcagctgg cacgacaggt ttcccgactg gaaagcgggc     2100
agtgagcgca acgcaattaa tacgcgtacc gcgagccagg aagagtttgt agaaacgcaa     2160
aaaggccatc cgtcaggatg gccttctgct tagtttgatg cctggcagtt tatggcgggc     2220
gtcctgcccg ccaccctccg ggccgttgct tcacaacgtt caaatccgct cccggcggat     2280
ttgtcctact caggagagcg ttcaccgaca aacaacagat aaaacgaaag gcccagtctt     2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga ttttattttg actgatagtg acctgttcgt tgcaacaaat tgatgagcaa     2520 tgcttttttta taatgccaac tttgtacaaa aaagcaggct ccgaattcgc ccttcaccat     2580
ggctcctaag aagaagcgga aggttggtat tcacggggtg cctgcggctc tgtttcaaga     2640
tttcacacac ctttacccac tgtctaaaac ggtgcggttt gagcttaaac ccatcggaaa     2700
aacgctggaa catattcatg cgaagaactt tttgtcgcag gatgagacaa tggcagacat     2760
gtaccaaaaa gtgaaagcca tactggacga ttaccataga gacttcatta cgaagatgat     2820
gagtgaggtg actcttacaa agctcccgga gtttttacgag gtttacctcg ctctgaggaa     2880
gaatccgaaa gacgataccc tccagaaaca acttaccgaa attcagaccg cgctccggga     2940
ggaagttgtg aagcccatag attccggagg taaatacaag gctggttatg agcgcttgtt     3000
tggggcgaaa ctgtttaaag acggaaaaga gttgggagat ttggcgaaat ttgtcatcgc     3060
```

```
ccaggaaggg gaatcgtctc cgaaacttcc acagatcgcc cactttgaaa agttttcaac   3120
atacttcacg gggttccacg ataaccgcaa gaacatgtac tcgtctgacg ataaacacac   3180
agctattgcc tacaggctta tccatgaaaa tttgccccgc tttattgata acttgcaaat   3240
tttggttact attaagcaga agcactcagt cctttacgat cagattgtga acgagctcaa   3300
cgccaatggc ctggacgtgt ctctcgcctc gcatctcgac ggctaccata aacttttgac   3360
tcaagaaggc attaccgcgt acaataggat tattggcgaa gtgaacagtt atacaaacaa   3420
gcataatcag atatgtcaca agtctgaaag aattgcaaag ctgagaccgc ttcataagca   3480
aatacttagt gatgggatgg gagtgagttt cctcccatct aaatttgcag atgactcgga   3540
aatgtgtcaa gcggtgaatg aattctacag acactatgcc cacgtgttcg ccaaagtcca   3600
aagtctcttt gaccggtttg acgattacca aaaagacggc atttatgttg aacacaagaa   3660
tctcaacgaa ttgagcaagc aggcctttgg agatttcgca ctccttggca gggtccttga   3720
cggctactat gtcgacgttg tcaatcctga gttcaatgac aaattcgcta aggctaagac   3780
agataacgcc aaagagaaac ttaccaaaga aaaagacaaa ttcattaagg gagtgcattc   3840
attggcttct ctcgagcagg caatcgaaca ctatatagcg gggcatgatg acgaaagcgt   3900
tcaggcggga aaacttggcc aatacttcaa gcacggcctc gctggagttg ataatcctat   3960
acaaaagatt cataatagtc attctacgat aaagggattc cttgagaggg agaggccagc   4020
cggagaacgc accctcccta aaataaaatc agataagtct ctggagatga ctcaactcag   4080
acagctgaag gagctgctgg acaacgccct caatgtcgtc cacttcgcaa agctgcttac   4140
aaccaaaacg accctggata accaagatgg aaatttctac ggagaattcg gggcccttta   4200
tgatgagttg gctaaaatcg caaccttgta caacaaggtg cgggattatc ttagccaaaa   4260
accgttcagt acagaaaaat acaaacttaa cttttgggaat ccgactctct tgaatggatg   4320
ggacctcaat aaggagaagg ataattttgg cgtcatcctg cagaaggacg gctgctacta   4380
tctcgcactg cttgataaag ctcacaaaaa agtctttgat aatgcgccca acacgggtaa   4440
gtcggtgtat cagaaaatgg tgtataaact tttgcctgga tcaaataaga tgctcccaaa   4500
agtttttttt gcgaaatcga accttgatta ctataatcct agtgccgaac tcctcgacaa   4560
gtatgcccaa ggcactcaca agaagggaga caacttcaac ctgaaagatt gccatgcatt   4620
gatcgacttt ttcaaagcgt ccattaacaa gcaccccgaa tggcaacatt tcggtttga   4680 atttagcttg acgagctctt accaggacct gtcagacttc tacagggagg tggagccgca   4740
aggctatcaa gttaagttcg tcgacattga tgctgactac atcgacgaac ttgtggaaca   4800
aggtcaactc tacctgtttc aaatatataa caaggatttt agtcctaagg cgcacggaaa   4860
acccaacctt catacgctct acttcaaagc tttgttctca gaagataacc tggctaaccc   4920
aatatataag ctcaacggag aagccgaaat cttctaccgg aaagcttcgc tcgatatgaa   4980
cgagacaacg atccatcgcg cgggtgaggt gcttgaaaat aagaaccggg ataacccgaa   5040
agagaggcag tttgtgtacg atataatcaa agacaaacgc tacactcagg ataagtttat   5100
gctgcatgtt ccaattacaa tgaactttgg ggttcaagga atgacgatca aggagtttaa   5160
caaaaaggtt aaccagtcca tacaacagta tgacgaagtt aatgtcattg gaatagacag   5220
aggcgagcgc catctcctgt accttacagt tattaattct aagggagaaa tactcgagca   5280
acggtcgctc aacgacatca taactaccag cgcgaacggc acccagatga caacaccata   5340
tcacaagatc ctggacaaga gggagatcga gcggctgaat gctagggtgg gttggggaga   5400
```

-continued

```
aatagagaca atcaaggagt tgaagtctgg ttatctttcg catgtcgtgc accaaatatc      5460
gcagctgatg cttaaataca atgctatagt tgtccttgaa gatttgaatt ttggcttcaa      5520
acggggtcgc ttcaaagttg aaaaacagat atatcagaat tttgaaaacg ctcttattaa      5580
gaaactgaat catctggttt tgaaggataa agcggacaat gaaatcggct cttacaaaaa      5640
tgcgcttcag ttgactaaca attttaccga tctcaagtct atagggaagc agacaggttt      5700
cctcttttac gtgcctgctt ggaacacgtc aaaaattgat cccgttaccg gttttgttga      5760
cctgttgaaa ccgcggtacg aaaatattgc acaaagtcaa gcatttttg ataagttcga      5820 caagatttgc tataatgctg acaaaggcta cttcgagttt catatagact atgcaaagtt      5880
cacggacaag gcaaaaaact cgcgccagat atggacgatt tgctcgcatg gagacaagcg      5940
ctatgtgtat gacaagacag ccaatcagaa caagggagca actattggga tcaatgttaa      6000
tgatgagctc aagtcgttgt ttgcccgcta ccggattaac gacaagcagc caaacctggt      6060
catggatatc tgtcaaaata atgataaaga gtttcacaag tcgctcacgt accttcttaa      6120
agctctcttg gcattgcggt acagcaatgc cagttccgac gaagatttta tcctgagccc      6180
ggtggccaac gataagggg tgttttcaa ttctgcactg gctgatgata cccagccgca      6240
gaatgcggac gcaaacggag catatcatat cgcgttgaag ggactttggc ttctcaatga      6300
gcttaagaac tcggatgacc ttgataaagt gaaactcgcc atcgacaatc agacatggct      6360
taatttcgca cagaacagaa agcgtcctgc tgccaccaaa aaggccggac aggctaagaa      6420
aaagaagtga gacgactagt ggcggccgcc gacgtccgat cgttcaaaca tttggcaata      6480
aagtttctta agattgaatc ctgttgccgg tcttgcgatg attatcatat aatttctgtt      6540
gaattacgtt aagcatgtaa taattaacat gtaatgcatg acgttattta tgagatgggt      6600
ttttatgatt agagtcccgc aattatacat ttaatacgcg atagaaaaca aaatatagcg      6660
cgcaaactag gataaattat cgcgcgcggt gtcatctatg ttactagatc gggaattgat      6720 ccccctcga cagcttccgg aaagggcgaa ttcgcaactt tgtatacaaa agttgaacga      6780
gaaacgtaaa atgatataaa tatcaatata ttaaattaga ttttgcataa aaaacagact      6840
acataatact gtaaaacaca acatatccag tcactatgcc atccagctga tatcccctat      6900
agtgagtcgt attacatggt catagctgtt tcctggcagc tctggcccgt gtctcaaaat      6960
ctctgatgtt acattgcaca agataaaaat atatcatcat gcctcctc                  7008
```

```
<210> SEQ ID NO 14
<211> LENGTH: 7008
<212> TYPE: DNA
<213> ORGANISM: Artificial Sequence
<220> FEATURE:
<223> OTHER INFORMATION: Synthetic construct

<400> SEQUENCE: 14
tggaccagcc aggacagaaa tgcctcgact tcgctgctac ccaaggttgc cgggtgacgc       60
acaccgtgga aacggatgaa ggcacgaacc cagtggacat aagcctgttc ggttcgtaag      120
ctgtaatgca agtagcgtat gcgctcacgc aactggtcca gaaccttgac cgaacgcagc      180
ggtggtaacg cgcagtggc ggttttcatg gcttgttatg actgtttttt tggggtacag      240
tctatgcctc gggcatccaa gcagcaagcg cgttacgccg tgggtcgatg tttgatgtta      300
tggagcagca acgatgttac gcagcagggc agtcgcccta aaacaaagtt aaacatcatg      360
agggaagcgg tgatcgccga agtatcgact caactatcag aggtagttgg cgtcatcgag      420
cgccatctcg aaccgacgtt gctggccgta catttgtacg gctccgcagt ggatggcggc      480
```

-continued

```
ctgaagccac acagtgatat tgatttgctg gttacggtga ccgtaaggct tgatgaaaca    540
acgcggcgag ctttgatcaa cgaccttttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatcccttq acgtgagtta cgcgtcgttc    1200
cactgagcgt cagacccggt agaaaagatc aaaggatctt cttgagatcc ttttttttctg    1260 cgcgtaatct gctgcttgca aacaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat a aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttttta taatgccaac tttgtacaaa aaagcaggct ccgaattcgc ccttcaccat    2580
ggctcctaag aagaagcgga aggttggtat tcacggggtg cctgcggctc tgtttcaaga    2640
ttttacacat ctgtacccgc tgagtaaaac agtgcggttc gagctgaaac ccataggaag    2700
gaccctcgag cacatccacg cgaagaattt tctgagccag gatgaaacta ggctgatat     2760 gtatcaaaaa gttaaggtca ttttggacga ctatcatcgc gattttattg ccgacatgat    2820
```

-continued

```
gggagaggtg aaactcacga agcttgctga attttacgac gtctatctga agttcaggaa      2880
aaatcctaag gacgatgggc tgcaaaaaca gcttaaagac cttcaagctg tccttcggaa      2940
ggaatcggtg aagcctatag ggtcaggtgg gaagtacaaa acaggctacg atagactctt      3000
tggggcaaaa ctcttcaaag atggaaaaga gttgggtgac ctcgcaaaat tcgttatagc      3060
ccaagaaggt gagtcttctc cgaagctggc tcatcttgct cattttgaga agttcagcac      3120
gtattttact ggatttcacg ataatcggaa gaatatgtac tcggatgaag acaagcatac      3180
tgcaatagcg tacaggctca tccatgagaa tttgccgaga ttcatcgaca atctgcaaat      3240
cttgacaaca atcaaacaaa agcatagcgc cctctatgat cagataatca acgagctcac      3300
ggcctccggg ctcgacgtct ccttggcttc tcatcttgac gggtatcaca agctccttac      3360
acaagagggg atcacggcat acaacaggat cataggagag gtgaatggat atacaaataa      3420
gcataaccag atatgccaca agagcgagcg catagcgaaa cttagaccct tgcacaagca      3480
aatcctttct gacggaatgg gagtgtcatt ccttccgtct aagttcgcgg atgatagtga      3540
gatgtgccaa gcggtcaacg aattttatcg ccattatact gacgtgttcg caaaggtgca      3600
aagtctcttt gacggatttg atgatcacca gaaagacggg atctatgttg aacacaaaaa      3660
ccttaatgaa ctgagcaaac aggcgttcgg cgactttgct ttgctgggga gggtccttga      3720
tggatactac gtggacgttg tcaatccgga gttcaatgag cggttcgcaa aggccaagac      3780
tgacaatgcg aaagccaagc ttacaaaaga aaaggacaaa ttcattaaag gagtccactc      3840
actggcttcc ctcgaacaag caatagaaca ccatacagct agacacgacg atgagagtgt      3900
tcaagccgga aaacttggcc agtacttcaa acacggtttg gcgggggttg acaacccgat      3960
tcagaaaatt cacaataacc attcgacgat taaagggttt ctggaaaggg aaaggcctgc      4020
tggggaacgg gcgctcccga agatcaagtc aggaaaaaac ccagaaatga cacagctcag      4080
gcagctgaag gaacttttgg acaacgcatt gaatgtggcg cacttcgcta agctgctgac      4140
aactaaaaca accttggaca accaggatgg aaatttttac ggggagtttg gggtgcttta      4200
cgacgagctg gctaaaattc caactctcta caataaggtt agagattatc tctctcaaaa      4260
gcccttttct accgaaaagt ataagctcaa cttcggcaat ccgacccttc tcaatgggtg      4320
ggacctgaac aaagagaaag ataactttgg ggttatactt cagaaggatg gatgctatta      4380
cttggcgctt cttgataagg ctcataaaaa agttttcgac aacgcccta acactggtaa        4440 gaacgtctac caaaagatgg tctacaaact gttgcccggc cccaacaaaa tgcttcctaa      4500
agtgtttttc gcaaaatcga atctcgacta ttataatcca tctgccgagc tccttgacaa      4560
atatgctaag gggacccata aaaagggtga taatttcaac ctgaaggact gccacgcgct      4620
tatcgacttt ttcaaagccg ggataaataa gcatccggag tggcaacatt ttggtttttaa     4680 attttcgcca acgtcgtcct atcgcgacct ttccgatttc tataggggaag ttgaacctca     4740 ggggtaccag gtcaaatttg ttgacattaa tgcggactac attgatgaat ggtggagca        4800 agggaagctc tacctctttc aaatatataa caaagatttc tcgccaaaag cgcatggtaa      4860
accgaatctt catacctttgt actttaaagc acttttttca gaagataact ggcggaccc       4920 gatctacaag ctgaatgggg aagctcagat cttctacagg aaagcttcgt tggacatgaa      4980
cgagactacc atacatcgcg cgggagaggt gcttgagaac aaaaatcccg acaacccgaa      5040
aaagcggcaa ttcgtttacg acatcatcaa agacaaacgg tacacgcagg acaaatttat      5100
gctccacgtc cccattacca tgaattttgg agtccaaggc atgaccatta aggaattcaa      5160
caaaaaggtc aaccaaagta ttcagcaata cgatgaagtc aatgtcatag gcatagatcg      5220
```

-continued

```
gggagaaagg catctgttgt atcttaccgt gattaactct aagggtgaaa tactggagca      5280
acggtcactt aacgatataa ccacggcgtc cgcgaacggt acacaagtga ccactcccta      5340
ccacaaaata ttggataaaa gggagataga acgcttgaat gcccgcgttg gctggggtga      5400
gattgagacc atcaaagagc ttaaatcggg atatttgtct cacgtcgttc atcaaattaa      5460
ccaactcatg cttaagtaca atgcaatcgt tgtgctcgag gacctgaact ttggtttcaa      5520
aagagggagg ttcaaggtgg aaaaacaaat ttaccagaac tttgaaaacg cgcttatcaa      5580
gaaattgaat caccttgttt tgaaagataa ggcagatgac gaaatcgggt cgtataaaaa      5640
tgcactccag ttgacaaata atttcacgga tttgaagtcg atcggcaagc aaacagggtt      5700 cctctttttat gtgccagcgt ggaatacatc aaaaattgat ccggagacgg gatttgtcga      5760
cttgctgaag cctaggtatg agaacattgc ccaatctcag gcctttttcg gcaaattcga      5820
taaaatatgc tacaacacag acaaaggtta ttttgaattt cacattgatt acgccaaatt      5880
tacagataag gcgaaaaaca gcagacagaa atgggctatc tgttctcatg gggacaaacg      5940
ctatgtctac gataagacgg ctaatcaaaa taaaggcgcc gcaaaaggta ttaatgtgaa      6000
tgatgagctg aaaagcttgt ttgcccgcta ccatatcaat gataaacaac caaacttggt      6060
gatggacata tgccagaaca atgacaaaga attccacaag tcactcatgt gcctgcttaa      6120
aacccttttg gcgctgcggt atagcaatgc atctagcgat gaagacttta tttttgagtcc      6180 cgtggccaac gacgagggcg tgtttttttaa ttcagccttg gcggacgata cgcagcccca      6240
gaatgcggac gcaaacggcg cgtaccacat tgcactgaag ggactgtggc ttctgaacga      6300
gctgaaaaat agcgacgacc tgaataaagt caagttggcc attgacaatc aaacctggtt      6360
gaatttcgct caaaatagaa agcgtcctgc tgccaccaaa aaggccggac aggctaagaa      6420
aaagaagtga gacgactagt ggcggccgcc gacgtccgat cgttcaaaca tttggcaata      6480
aagtttctta agattgaatc ctgttgccgg tcttgcgatg attatcatat aatttctgtt      6540
gaattacgtt aagcatgtaa taattaacat gtaatgcatg acgttattta tgagatgggt      6600
ttttatgatt agagtcccgc aattatacat ttaatacgcg atagaaaaca aaatatagcg      6660
cgcaaactag gataaattat cgcgcgcggt gtcatctatg ttactagatc gggaattgat      6720 ccccctcga cagcttccgg aaagggcgaa ttcgcaactt tgtatacaaa agttgaacga      6780
gaaacgtaaa atgatataaa tatcaatata ttaaattaga ttttgcataa aaaacagact      6840
acataatact gtaaaacaca acatatccag tcactatgcc atccagctga tatcccctat      6900
agtgagtcgt attacatggt catagctgtt tcctggcagc tctggcccgt gtctcaaaat      6960
ctctgatgtt acattgcaca agataaaaat atatcatcat gcctcctc                 7008
```

<210> SEQ ID NO 15
<211> LENGTH: 7008
<212> TYPE: DNA
<213> ORGANISM: Artificial Sequence
<220> FEATURE:
<223> OTHER INFORMATION: Synthetic construct
<400> SEQUENCE: 15

```
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag       120
ctgtaatgca agtagcgtat cgctcacgc aactggtcca gaaccttgac cgaacgcagc       180
ggtggtaacg cgcagtggc ggttttcatg gcttgttatg actgtttttt tggggtacag       240
```

-continued

```
tctatgcctc gggcatccaa gcagcaagcg cgttacgccg tgggtcgatg tttgatgtta    300
tggagcagca acgatgttac gcagcagggc agtcgcccta aaacaaagtt aaacatcatg    360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttccctgg agagagcgag    600 attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagaccccgt agaaaagatc aaaggatctt cttgagatcc tttttttctg    1260
cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttgtga    1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttttta taatgccaac tttgtacaaa aaagcaggcc ccgaattcgc ccttcaccat    2580
ggctcctaag aagaagcgga aggttggtat tcacggggtg cctgcggctc tgtttcaaga    2640
```

-continued

```
ttttacacat ctgtacccgc tgagtaaaac agtgcggttc gagctgaaac ccataggaag    2700
gaccctcgag cacatccacg cgaagaattt tctgagccag gatgaaacta tggctgatat    2760
gtatcaaaaa gttaaggtca ttttggacga ctatcatcgc gattttattg ccgacatgat    2820
gggagaggtg aaaactcacga agcttgctga attttacgac gtctatctga agttcaggaa    2880
aaatcctaag gacgatgggc tgcaaaaaca gcttaaagac cttcaagctg tccttcggaa    2940
ggaatcggtg aagcctatag ggtcaggtgg gaagtacaaa acaggctacg atagactctt    3000
tggggcaaaa ctcttcaaag atggaaaaga gttgggtgac ctcgcaaaat tcgttatagc    3060
ccaagaaggt gagtcttctc cgaagctggc tcatcttgct cattttgaga agttcagcac    3120
gtattttact ggatttcacg ataatcggaa gaatatgtac tcggatgaag acaagcatac    3180
tgcaatagcg tacaggctca tccatgagaa tttgccgaga ttcatcgaca atctgcaaat    3240
cttgacaaca atcaaacaaa agcatagcgc cctctatgat cagataatca acgagctcac    3300
ggcctccggg ctcgacgtct ccttggcttc tcatcttgac gggtatcaca agctccttac    3360
acaagagggg atcacggcat acaacaggat cataggagag gtgaatggat atacaaataa    3420
gcataaccag atatgccaca agagcgagcg catagcgaaa cttagaccct tgcacaagca    3480
aatcctttct gacggaatgg gagtgtcatt ccttccgtct aagttcgcgg atgatagtga    3540
gatgtgccaa gcggtcaacg aatttttatcg ccattatact gacgtgttcg caaaggtgca    3600
aagtctcttt gacggatttg atgatcacca gaaagacggg atctatgttg aacacaaaaa    3660
ccttaatgaa ctgagcaaac aggcgttcgg cgactttgct ttgctgggga gggtccttga    3720
tggatactac gtggacgttg tcaatccgga gttcaatgag cggttcgcaa aggccaagac    3780
tgacaatgcg aaagccaagc ttacaaaaga aaaggacaaa ttcattaaag gagtccactc    3840
actggcttcc ctcgaacaag caatagaaca ccatacagct agacacgacg atgagagtgt    3900
tcaagccgga aaacttggcc agtacttcaa acacggtttg gcgggggttg acaacccgat    3960
tcagaaaatt cacaataacc attcgacgat taaagggttt ctggaaaggg aaaggcctgc    4020
tggggaacgg gcgctcccga agatcaagtc aggaaaaaac ccagaaatga cacagctcag    4080
gcagctgaag gaacttttgg acaacgcatt gaatgtggcg cacttcgcta agctgctgac    4140
aactaaaaca accttggaca accaggatgg aaattttttac ggggagtttg gggtgcttta    4200
cgacgagctg gctaaaattc caactctcta caataaggtt agagattatc tctctcaaaa    4260
gcccttttct accgaaaagt ataagctcaa cttcggcaat ccgacccttc tccgcgggtg    4320
ggacctgaac gtggagaaag atcgctttgg ggttatactt cagaaggatg gatgctatta    4380
cttggcgctt cttgataagg ctcataaaaa agttttcgac aacgcccta acactggtaa    4440 gaacgtctac caaaagatgg tctacaaact gttgcccggc cccaacaaaa tgcttcctaa    4500
agtgtttttc gcaaatcga atctcgacta ttataatcca tctgccgagc tccttgacaa    4560
atatgctaag gggacccata aaaagggtga taatttcaac ctgaaggact gccacgcgct    4620
tatcgacttt ttcaaagccg ggataaataa gcatccggag tggcaacatt ttggtttttaa    4680 attttcgcca acgtcgtcct atcgcgacct ttccgatttc tataggggaag ttgaacctca    4740 ggggtaccag gtcaaatttg ttgacattaa tgcggactac attgatgaat ggtggagca    4800 agggaagctc tacctctttc aaatatataa caaagatttc tcgccaaaag cgcatggtaa    4860
accgaatctt cataccttgt actttaaagc actttttttca gaagataact ggcggaccc    4920 gatctacaag ctgaatgggg aagctcgat cttctacagg aaagcttcgt tggacatgaa    4980
```

-continued

```
cgagactacc atacatcgcg cgggagaggt gcttgagaac aaaaatcccg acaacccgaa    5040
aaagcggcaa ttcgtttacg acatcatcaa agacaaacgg tacacgcagg acaaatttat    5100
gctccacgtc cccattacca tgaattttgg agtccaaggc atgaccatta aggaattcaa    5160
caaaaaggtc aaccaaagta ttcagcaata cgatgaagtc aatgtcatag gcatagatcg    5220
gggagaaagg catctgttgt atcttaccgt gattaactct aagggtgaaa tactggagca    5280
acggtcactt aacgatataa ccacggcgtc cgcgaacggt acacaagtga ccactcccta    5340
ccacaaaata ttggataaaa gggagataga acgcttgaat gcccgcgttg gctggggtga    5400
gattgagacc atcaaagagc ttaaatcggg atatttgtct cacgtcgttc atcaaattaa    5460
ccaactcatg cttaagtaca atgcaatcgt tgtgctcgag gacctgaact ttggtttcaa    5520
aagagggagg ttcaaggtgg aaaaacaaat ttaccagaac tttgaaaacg cgcttatcaa    5580
gaaattgaat caccttgttt tgaaagataa ggcagatgac gaaatcgggt cgtataaaaa    5640
tgcactccag ttgacaaata atttcacgga tttgaagtcg atcggcaagc aaacagggtt    5700
cctcttttat gtgccagcgt ggaatacatc aaaaattgat ccggagacgg gatttgtcga    5760
cttgctgaag cctaggtatg agaacattgc ccaatctcag gccttttcg gcaaattcga    5820 taaaatatgc tacaacacag acaaaggtta ttttgaattt cacattgatt acgccaaatt    5880
tacagataag gcgaaaaaca gcagacagaa atgggctatc tgttctcatg gggacaaacg    5940
ctatgtctac gataagacgg ctaatcaaaa taaaggcgcc gcaaaggta ttaatgtgaa    6000 tgatgagctg aaaagcttgt ttgcccgcta ccatatcaat gataaacaac caaacttggt    6060
gatggacata tgccagaaca atgacaaaga attccacaag tcactcatgt gcctgcttaa    6120 aaccctttg gcgctgcggt atagcaatgc atctagcgat gaagacttta ttttgagtcc    6180
cgtggccaac gacgagggcg tgttttttaa ttcagccttg gcggacgata cgcagccca    6240 gaatgcggac gcaaacggcg cgtaccacat tgcactgaag ggactgtggc ttctgaacga    6300
gctgaaaaat agcgacgacc tgaataaagt caagttggcc attgacaatc aaacctggtt    6360
gaatttcgct caaaatagaa agcgtcctgc tgccaccaaa aaggccggac aggctaagaa    6420
aaagaagtga gacgactagt ggcggccgcc gacgtccgat cgttcaaaca tttggcaata    6480
aagtttctta agattgaatc ctgttgccgg tcttgcgatg attatcatat aatttctgtt    6540
gaattacgtt aagcatgtaa taattaacat gtaatgcatg acgttatta tgagatgggt    6600 ttttatgatt agagtcccgc aattatacat ttaatacgcg atagaaaaca aaatatagcg    6660
cgcaaactag gataaattat cgcgcgcggt gtcatctatg ttactagatc gggaattgat    6720 ccccctcga cagcttccgg aaagggcgaa ttcgcaactt tgtatacaaa agttgaacga    6780
gaaacgtaaa atgatataaa tatcaatata ttaaattaga ttttgcataa aaaacagact    6840
acataatact gtaaaacaca acatatccag tcactatgcc atccagctga tatcccctat    6900
agtgagtcgt attacatggt catagctgtt tcctggcagc tctggcccgt gtctcaaaat    6960
ctctgatgtt acattgcaca agataaaaat atatcatcat gcctcctc                 7008
```

<210> SEQ ID NO 16
<211> LENGTH: 6873
<212> TYPE: DNA
<213> ORGANISM: Artificial Sequence
<220> FEATURE:
<223> OTHER INFORMATION: Synthetic construct

<400> SEQUENCE: 16

```
tggaccagcc aggacagaaa tgcctcgact tcgctgctac ccaaggttgc cgggtgacgc     60
```

-continued

```
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg gcgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagacccccgt agaaaagatc aaaggatctt cttgagatcc ttttttttctg    1260 cgcgtaatct gctgcttgca acaaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca aacaacagat aaaacgaaag gcccagtctt    2340
ccgactgagc ctttcgtttt atttgatgcc tggcagttcc ctactctcgc gttaacgctt    2400
```

-continued

```
gcatggatgt tttcccagtc acgacgttgt aaaacgacgg ccagtcttaa gctcgggccc     2460
caaataatga ttttattttg actgatagtg acctgttcgt tgcaacaaat tgatgagcaa     2520
tgctttttta taatgccaac tttgtacaaa aaagcaggct ccgaattcgc ccttcaccat     2580
ggctcctaag aagaagcgga aggttggtat tcacggggtg cctgcggctt actatgaatc     2640
cctgaccaaa caataccctg tttccaaaac aatccgcaat gagctgattc ctataggtaa     2700
aaccctggat aacatccgcc aaaataacat cttggaatca gacgttaaaa gaaagcagaa     2760
ttacgaacat gtcaaaggta tacttgatga ataccacaaa cagctcataa acgaagcgtt     2820
ggataactgt acgcttccct cactgaaaat agcggctgag atctacctca aaaaccagaa     2880
ggaggtgtca gacagagaag atttcaacaa aacccaggat ctgttgcgca aggaggttgt     2940
ggagaaactc aaggcgcatg aaaattttac taagatagga aaaaaagata ttcttgattt     3000
gttggagaag cttcctagca tatccgagga cgactacaat gccctggaaa gtttcagaaa     3060
cttttacaca tacttcacat cgtataataa ggtccgggaa aatctgtata gcgataaaga     3120
gaaaagttct actgttgcgt acaggcttat caatgagaat tttccaaagt ttctcgacaa     3180
cgtcaaatca tatcggttcg tcaaaactgc gggcattttg gctgacggat tgggagagga     3240
ggagcaggac agcctgttca tagtggagac tttcaacaag acattgaccc aggatggcat     3300
tgatacatat aactcccagg tcggcaagat aaactcctcg ataaacctct acaaccagaa     3360
aaaccagaag gcaaacggct tccggaaaat cccaaagatg aaaatgcttt ataagcagat     3420
cttgagtgat cgggaggagt ctttcatcga tgaatttcag tcagacgaag ttcttatcga     3480
caacgttgag agttacggct ctgtgcttat tgagagcctc aagtcgtcaa aggtttctgc     3540
attttttgat gcacttcggg agagtaaagg taaaaacgtt tacgttaaga atgacctggc     3600
gaaaacagca atgtcaaaca tagttttttga gaactggagg accttcgatg accttctgaa     3660
tcaagagtac gatttggcga acgaaaataa aaagaaggac gacaagtact ttgagaagag     3720
gcaaaaggag ctgaaaaaga ataaatcgta ttcgttggaa catctttgca acctctctga     3780
ggattcctgc aacctgatag aaaactacat ccaccagatc agtgacgata ttgaaaacat     3840
tattattaac aatgaaacct ttttgcggat agtgattaat gagcacgatc gcagtagaaa     3900
acttgctaaa aatagaaaag ctgttaaagc aataaaggat ttccttgaca gtattaaggt     3960
gctcgagcgg gagttgaaac tgatcaattc ttcaggacaa gagttggaaa aagaccttat     4020
cgtctatagc gctcacgagg aacttctggt ggaactgaaa caagttgatt cgctttataa     4080
catgacgagg aactacctga ccaaaaaagcc cttttctact gagaaagtca aactcaattt     4140
taatcggtcg acgcttctga atggctggga ccgcaacaaa gagactgata acctcggggt     4200
tctcttgctg aaagatggca agtattatct gggtataatg aatacatcag caaataaggc     4260
attcgttaac ccgcctgtgg ctaaaaccga aaggtttttt aaaaaagtgg actacaagct     4320
gttgccagtg ccgaaccaga tgttgcccaa ggttttttttt gcgaaaagca atattgattt     4380
ctataatcca tcgagcgaga tatattccaa ctacaaaaaa ggtacccata aaaagggtaa     4440
catgttttca cttgaggact gccacaacct gattgatttc tttaaagaga gtattagtaa     4500
gcacgaagat tggagtaagt ttggattcaa attttctgat actgcgagtt acaatgatat     4560
aagtgaattc tatcgggaag tcgaaaaaca gggttacaag cttacgtaca ctgacataga     4620
tgaaacatac attaatgacc tgattgagcg caatgagttg tacctgtttc agatctataa     4680
caaagatttt tccatgtata gcaaaggcaa gctcaacttg cataccctgt attttatgat     4740
gctcttcgat caaaggaata tcgatgacgt tgtttataag ctgaatggtg aagcagaagt     4800
```

```
tttttaccgc ccagcctcga tcagtgaaga tgagctgatc attcacaaag cgggtgaaga    4860
gattaagaat aagaaccta atcgggccag gacgaaagaa acttcaacgt tttcctatga     4920
tattgtcaaa gacaaaaggt actcgaagga taagtttacc cttcacattc ccataaccat    4980
gaattttggt gtcgacgaag tcaagcggtt taacgacgcc gtgaattccg cgatccggat    5040
agacgagaat gtgaatgtca ttgggattga cagaggtgaa cgcaatcttc tttacgtggt    5100
ggtgatagac tctaaaggga atatattgga gcaaatttct ctgaactcaa tcattaataa    5160
agaatacgat attgaaacag actatcatgc ccttctcgac gagcgggagg gcgggaggga    5220
taaagcacgg aaggactgga acacagttga gaatatccgg gacctcaaag ccggatacct    5280
ttcccaggtg gtcaatgttg tcgcaaaatt ggtcttgaag tacaatgcca ttatatgcct    5340
tgaagatttg aactttgggt tcaaacgcgg taggcaaaaa gttgaaaaac aagtttacca    5400
gaaattcgaa aagatgctta tagataagct caactacctg gttattgaca gagtagaga     5460 gcagacgtcg cccaaagaac tcgggggggc gctgaatgcg ttgcaactga cctcgaagtt    5520
caaatcgttc aaagaattgg ggaaacagtc cggcgttatc tattacgtgc ctgcttatct    5580
cacgtctaag atagatccta ccacaggctt cgcgaatctt ttttatatga agtgtgagaa    5640
tgtcgagaag tctaagcggt ttttcgatgg atttgacttc atcaggttca atgcgctcga    5700
aaatgttttt gagtttggat tcgactaccg gagctttaca cagagagcgt gcggtataaa    5760
cagtaaatgg acagtctgca caaatgggga gagaattata aagtatagga accccgataa    5820
aaataacatg ttcgacgaaa aggtggtggt tgttactgat gaaatgaaga acctgtttga    5880
acagtacaaa ataccttatg aggatggaag gaacgtgaag gacatgatta tttcaaacga    5940
ggaggcggag ttctaccgca gattgtaccg cctgcttcag cagaccctcc aaatgcggaa    6000
ttcgacctca gatggaacga gagattatat tatatcacca gtgaaaaaca agcgcgaggc    6060
gtatttcaac tctgagcttt ccgatggttc ggttccgaaa gacgcagatg caaacgagc     6120 atacaacatc gcaaggaaag ggttgtgggt gttggaacaa atccgccaga aatccgaagg    6180
cgaaaaaatt aacttggcta tgaccaatgc tgagtggctt gaatacgcgc agacgcacct    6240
tctgaagcgt cctgctgcca ccaaaaaggc cggacaggct aagaaaaaga agtgagacga    6300
ctagtggcgg ccgccgacgt ccgatcgttc aaacatttgg caataaagtt tcttaagatt    6360
gaatcctgtt gccggtcttg cgatgattat catataattt ctgttgaatt acgttaagca    6420
tgtaataatt aacatgtaat gcatgacgtt atttatgaga tgggtttttta tgattagagt    6480 cccgcaatta tacatttaat acgcgataga aaacaaaata tagcgcgcaa actaggataa    6540
attatcgcgc gcggtgtcat ctatgttact agatcgggaa ttgatccccc ctcgacagct    6600 tccgaaagg gcgaattcgc aactttgtat acaaaagttg aacgagaaac gtaaaatgat    6660
ataaatatca atatattaaa ttagattttg cataaaaaac agactacata atactgtaaa    6720
acacaacata tccagtcact atgccatcca gctgatatcc cctatagtga gtcgtattac    6780
atggtcatag ctgtttcctg gcagctctgg cccgtgtctc aaaatctctg atgttacatt    6840
gcacaagata aaaatatatc atcatgcctc ctc                                 6873
```

<210> SEQ ID NO 17
<211> LENGTH: 6873
<212> TYPE: DNA
<213> ORGANISM: Artificial Sequence
<220> FEATURE:
<223> OTHER INFORMATION: Synthetic construct -continued

```
<400> SEQUENCE: 17
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg gcgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagacccccgt agaaaagatc aaaggatctt cttgagatcc ttttttttctg    1260 cgcgtaatct gctgcttgca acaaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800 tgctcgtcag ggggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg gcgcgttgct tcacaacgtt caaatccgct cccggcggat    2280
ttgtcctact caggagagcg ttcaccgaca aacaacagat aaaacgaaag gcccagtctt    2340
```

-continued

```
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttta taatgccaac tttgtacaaa aaagcaggct ccgaattcgc ccttcaccat    2580
ggctcctaag aagaagcgga aggttggtat tcacggggtg cctgcggctt actatgaatc    2640
cctgaccaaa caataccctg tttccaaaac aatccgcaat gagctgattc ctataggtaa    2700
aaccctggat aacatccgcc aaaataacat cttggaatca gacgttaaaa gaaagcagaa    2760
ttacgaacat gtcaaaggta tacttgatga ataccacaaa cagctcataa acgaagcgtt    2820
ggataactgt acgcttccct cactgaaaat agcggctgag atctacctca aaaaccagaa    2880
ggaggtgtca gacagagaag atttcaacaa aacccaggat ctgttgcgca aggaggttgt    2940
ggagaaactc aaggcgcatg aaaattttac taagatagga aaaaaagata ttcttgattt    3000
gttggagaag cttcctagca tatccgagga cgactacaat gccctggaaa gtttcagaaa    3060
cttttacaca tacttcacat cgtataataa ggtccgggaa aatctgtata gcgataaaga    3120
gaaaagttct actgttgcgt acaggcttat caatgagaat tttccaaagt ttctcgacaa    3180
cgtcaaatca tatcggttcg tcaaaactgc gggcattttg gctgacggat tgggagagga    3240
ggagcaggac agcctgttca tagtggagac tttcaacaag acattgaccc aggatggcat    3300
tgatacatat aactcccagg tcggcaagat aaactcctcg ataaacctct acaaccagaa    3360
aaaccagaag gcaaacggct tccggaaaat cccaaagatg aaaatgcttt ataagcagat    3420
cttgagtgat cgggaggagt ctttcatcga tgaatttcag tcagacgaag ttcttatcga    3480
caacgttgag agttacggct ctgtgcttat tgagagcctc aagtcgtcaa aggtttctgc    3540
attttttgat gcacttcggg agagtaaagg taaaaacgtt tacgttaaga atgacctggc    3600
gaaaacagca atgtcaaaca tagtttttga gaactggagg accttcgatg accttctgaa    3660
tcaagagtac gatttggcga acgaaaataa aaagaaggac gacaagtact ttgagaagag    3720
gcaaaaggag ctgaaaaaga ataaatcgta ttcgttggaa catctttgca acctctctga    3780
ggattcctgc aacctgatag aaaactacat ccaccagatc agtgacgata ttgaaaacat    3840
tattattaac aatgaaacct ttttgcggat agtgattaat gagcacgatc gcagtagaaa    3900
acttgctaaa aatagaaaag ctgttaaagc aataaaggat ttccttgaca gtattaaggt    3960
gctcgagcgg gagttgaaac tgatcaattc ttcaggacaa gagttggaaa aagaccttat    4020
cgtctatagc gctcacgagg aacttctggt ggaactgaaa caagttgatt cgctttataa    4080
catgacgagg aactacctga ccaaaaagcc cttttctact gagaaagtca aactcaattt    4140
taatcggtcg acgcttctgc gcggctggga ccgcaacgtg gagactgatc gcctcggggt    4200
tctcttgctg aaagatggca agtattatct gggtataatg aatacatcag caaataaggc    4260
attcgttaac ccgcctgtgg ctaaaaccga gaaggttttt aaaaaagtgg actacaagct    4320
gttgccagtg ccgaaccaga tgttgcccaa ggtttttttt gcgaaaagca atattgattt    4380
ctataatcca tcgagcgaga tatattccaa ctacaaaaaa ggtacccata aaaagggtaa    4440
catgttttca cttgaggact gccacaacct gattgatttc tttaaagaga gtattagtaa    4500
gcacgaagat tggagtaagt ttggattcaa attttctgat actgcgagtt acaatgatat    4560
aagtgaattc tatcgggaag tcgaaaaaca gggttacaag cttacgtaca ctgacataga    4620
tgaaacatac attaatgacc tgattgagcg caatgagttg tacctgtttc agatctataa    4680
```

-continued

```
caaagatttt tccatgtata gcaaaggcaa gctcaacttg cataccctgt attttatgat      4740
gctcttcgat caaaggaata tcgatgacgt tgtttataag ctgaatggtg aagcagaagt      4800
tttttaccgc ccagcctcga tcagtgaaga tgagctgatc attcacaaag cgggtgaaga      4860
gattaagaat aagaaccata atcgggccag gacgaaagaa acttcaacgt tttcctatga      4920
tattgtcaaa gacaaaaggt actcgaagga taagtttacc cttcacattc ccataaccat      4980
gaattttggt gtcgacgaag tcaagcggtt taacgacgcc gtgaattccg cgatccggat      5040
agacgagaat gtgaatgtca ttgggattga cagaggtgaa cgcaatcttc tttacgtggt      5100
ggtgatagac tctaaaggga atatattgga gcaaatttct ctgaactcaa tcattaataa      5160
agaatacgat attgaaacag actatcatgc ccttctcgac gagcgggagg gcgggaggga      5220
taaagcacgg aaggactgga acacagttga gaatatccgg gacctcaaag ccggatacct      5280
ttcccaggtg gtcaatgttg tcgcaaaatt ggtcttgaag tacaatgcca ttatatgcct      5340
tgaagatttg aactttgggt tcaaacgcgg taggcaaaaa gttgaaaaac aagtttacca      5400
gaaattcgaa aagatgctta tagataagct caactacctg gttattgaca agagtagaga      5460
gcagacgtcg cccaaagaac tcggggggggc gctgaatgcg ttgcaactga cctcgaagtt      5520
caaatcgttc aaagaattgg ggaaacagtc cggcgttatc tattacgtgc ctgcttatct      5580
cacgtctaag atagatccta ccacaggctt cgcgaatctt ttttatatga agtgtgagaa      5640
tgtcgagaag tctaagcggt ttttcgatgg atttgacttc atcaggttca atgcgctcga      5700
aaatgttttt gagtttggat tcgactaccg gagctttaca cagagagcgt gcggtataaa      5760
cagtaaatgg acagtctgca caaatgggga gagaattata aagtatagga accccgataa      5820
aaataacatg ttcgacgaaa aggtggtggt tgttactgat gaaatgaaga acctgtttga      5880
acagtacaaa ataccttatg aggatggaag gaacgtgaag gacatgatta tttcaaacga      5940
ggaggcggag ttctaccgca gattgtaccg cctgcttcag cagaccctcc aaatgcggaa      6000
ttcgacctca gatggaacga gagattatat tatatcacca gtgaaaaaca agcgcgaggc      6060
gtatttcaac tctgagcttt ccgatggttc ggttccgaaa gacgcagatg caaacggagc      6120
atacaacatc gcaaggaaag ggttgtgggt gttggaacaa atccgccaga aatccgaagg      6180
cgaaaaaatt aacttggcta tgaccaatgc tgagtggctt gaatacgcgc agacgcacct      6240
tctgaagcgt cctgctgcca ccaaaaaggc cggacaggct aagaaaaaga agtgagacga      6300
ctagtggcgg ccgccgacgt ccgatcgttc aaacatttgg caataaagtt tcttaagatt      6360
gaatcctgtt gccggtcttg cgatgattat catataattt ctgttgaatt acgttaagca      6420
tgtaataatt aacatgtaat gcatgacgtt atttatgaga tgggttttta tgattagagt      6480
cccgcaatta tacatttaat acgcgataga aaacaaaata tagcgcgcaa actaggataa      6540
attatcgcgc gcggtgtcat ctatgttact agatcgggaa ttgatccccc ctcgacagct      6600 tccgaaagg gcgaattcgc aactttgtat acaaaagttg aacgagaaac gtaaaatgat      6660
ataaatatca atatattaaa ttagattttg cataaaaaac agactacata atactgtaaa      6720
acacaacata tccagtcact atgccatcca gctgatatcc cctatagtga gtcgtattac      6780
atggtcatag ctgtttcctg gcagctctgg cccgtgtctc aaaatctctg atgttacatt      6840
gcacaagata aaaatatatc atcatgcctc ctc                                    6873
```

<210> SEQ ID NO 18
<211> LENGTH: 6936
<212> TYPE: DNA
<213> ORGANISM: Artificial Sequence -continued
<220> FEATURE:
<223> OTHER INFORMATION: Synthetic construct

<400> SEQUENCE: 18

```
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg gcgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagaccccgt agaaaagatc aaaggatctt cttgagatcc ttttttttctg    1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg atttttgtga    1800
tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
```

-continued

```
gtcctgcccg ccaccctccg ggccgttgct tcacaacgtt caaatccgct cccggcggat     2280
ttgtcctact caggagagcg ttcaccgaca aacaacagat aaaacgaaag gcccagtctt     2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga ttttattttg actgatagtg acctgttcgt tgcaacaaat tgatgagcaa     2520
tgctttttta taatgccaac tttgtacaaa aaagcaggct ccgaattcgc ccttcaccat     2580
ggctcctaag aagaagcgga aggttggtat tcacggggtg cctgcggctg acgcgaaaga     2640
gtttactgga caatacccac tctcaaagac tctccgcttt gagctgagac ccatcgggag     2700
gacttgggac aacttggaag ccagtggcta cttggccgag gaccgccacc gcgccgagtg     2760
ctacccgaga gcaaaagagc tgctggatga caaccataga gcgttcctga acagggttct     2820
cccgcagatt gatatggatt ggcatcccat cgcagaagcc ttctgcaaag tccataaaaa     2880
tccaggaaac aaagagctcg cgcaagatta taatcttcag ttgtccaaga gacgcaaaga     2940
aatctcggct tatcttcagg acgctgacgg atataaaggt ttgtttgcta aacctgctct     3000
tgacgaggca atgaagatcg ctaaggagaa cggtaacgaa tcggatattg aggtcctcga     3060
ggcatttaac ggcttttccg tttatttcac gggctaccac gagtctagag aaaatatcta     3120
ctcagacgaa gacatggtct ccgtggccta caggatcaca gaggataatt ttccccgctt     3180
cgtctccaac gcgttgatat tcgacaagtt gaatgaatca catcctgata tcatctctga     3240
ggtgtctggg aatctcggtg ttgacgatat aggcaaatac tttgacgtct cgaactacaa     3300
taactttctc agccaggcag gaattgatga ctataatcat attattggtg gacacaccac     3360
tgaagatggt ctgattcagg cctttaatgt ggttttgaat ctgcgccacc agaaggatcc     3420
agggttcgaa aagatccaat tcaaacagct ctataagcag attctctctg ttcggacgtc     3480
caaatcgtat attccaaaac aattcgacaa ttctaaggaa atggtcgatt gcatttgcga     3540
ttatgtctca aaaatcgaga aatcagagac ggtcgaaagg gctttgaagc ttgtgagaaa     3600
tatctccagc ttcgatcttc ggggcatatt tgtgaacaag aaaaacctca ggatcctctc     3660
caataagttg ataggggatt gggacgcaat cgagaccgcg cttatgcatt ccagctcctc     3720
agaaaatgat aaaaaatccg tctatgattc agccgaagcc tttactttgg acgatatatt     3780
ctcgtcagtg aaaaaattca gtgatgctag cgccgaggat attgggaacc gcgccgagga     3840
catatgcagg gtgatctctg aaacggctcc ctttattaac gacttgcgcg cggtggacct     3900
ggacagtctc aacgatgacg gatatgaagc agcagttagc aagatccggg agtcccttga     3960
gccgtacatg gatcttttcc atgaacttga gatatttagt gttggggacg agttccctaa     4020
atgtgcggca ttttactcgg agttggaaga ggttagcgaa cagctcatag aaatcatacc     4080
gctgtttaat aaggccagat ccttctgcac ccggaagagg tattccactg acaaaattaa     4140
agtgaatctc aagttcccta cattggcaga cggctgggac cttaataagg agcgggataa     4200
caaagccgct atattgagaa aagacggcaa gtactatttg gccatcctgg atatgaagaa     4260
ggatctgtct tcgataagaa cgtcggacga agacgaatcc tccttcgaaa agatggagta     4320
caaactgctt ccatccccgg ttaagatgct ccctaaaatt ttcgttaagt caaaagccgc     4380
aaaggagaaa tacggcctta ctgatagaat gctggaatgc tatgataagg gaatgcataa     4440
aagtgggagc gcattcgatc tcggattctg tcacgagctc attgactatt acaaaaggtg     4500
catcgcggag tacccCggct gggatgtttt tgattttaag ttcagagaaa ctagtgatta     4560
cggatctatg aaggaattca acgaagatgt ggcaggcgct gggtactata tgtcgctcag     4620
```

-continued

```
gaagatcccc tgttccgaag tgtatcggct gttggacgaa aagtcgatat atctgtttca      4680
aatttacaac aaagattata gtgaaaatgc gcatggtaat aagaatatgc atactatgta      4740
ttgggaaggg ctcttctctc cacaaaatct tgaatctccg gtctttaagc ttagcggtgg      4800
ggcagagctt ttcttcagaa aaagcagcat cccaaacgat gcaaaaacgg tgcacccaaa      4860
ggggagcgtg ctggttccta gaaacgatgt taatgggcgc cggatacctg acagcatata      4920
cagagagctc acaaggtact ttaaccgggg cgattgcaga atttccgatg aggcgaagtc      4980
gtacctggat aaagtcaaaa ccaagaaagc cgatcatgac atcgtcaagg accggcgctt      5040
cacggtcgat aaaatgatgt tccatgtccc aattgcaatg aacttcaaag ctatatccaa      5100
gccgaatctg aacaagaagg tgatagatgg aattattgac gatcaggacc ttaaaattat      5160
cgggattgac aggggggaac gcaacttgat atatgtgacg atggtggatc gcaagggcaa      5220
tatcctttat caagatagcc ttaatatctt gaacggatac gattaccgga aggccttgga      5280
tgttcgcgag tacgataaca aagaagcaag gaggaactgg actaaggttg aaggaataag      5340
gaagatgaag gaaggttacc tctcacttgc ggtctccaag cttgcagaca tgattataga      5400
gaacaacgcc ataattgtta tggaggatct gaatcatggg tttaaggcag gtcgctccaa      5460
aatcgagaaa caggtttacc aaaagtttga gtccatgctt atcaataagc tcgggtacat      5520
ggtgctcaaa gacaaatcaa tagatcagtc cggcggagct ctgcacggct accaattggc      5580
gaaccatgtg actacacttg cctccgttgg taaacaatgt ggcgtcatct tttatattcc      5640
agctgccttt actagtaaga tagaccccac taccggcttt gccgatctgt ttgctttgag      5700
caacgtcaag aacgtggcga gtatgagaga gtttttttagc aagatgaaaa gcgtcatata      5760
tgataaagcc gaaggtaaat ttgcgttcac tttcgattat ctggattata acgtgaaatc      5820
agagtgcggg cggacactgt ggaccgtcta taccgtgggt gagaggttta catactcacg      5880
ggtcaatagg gaatacgttc gcaaagtccc cactgacata atttacgatg cgcttcaaaa      5940
ggcaggtatc tccgttgagg gcgacttgcg cgacagaatt gcagagagtg atggggacac      6000
gctgaaatca attttctatg cgttcaaata tgcgcttgat atgagagtcg agaaccgcga      6060
agaagattat attcagagtc ctgtgaagaa cgctagtggc gaattttttt gctcaaagaa      6120
tgcaggtaaa agcttgcctc aggactcgga cgcgaatggg gcttacaata tagcactcaa      6180
ggggatcttg cagctcagga tgcttagcga gcagtatgac ccgaacgcag aatcgatacg      6240
gcttccactg atcaccaaca aagcttggct cactttcatg caatcaggaa tgaagacctg      6300
gaagaacaag cgtcctgctg ccaccaaaaa ggccggacag gctaagaaaa agaagtgaga      6360
cgactagtgg cggccgccga cgtccgatcg ttcaaacatt tggcaataaa gtttcttaag      6420
attgaatcct gttgccggtc ttgcgatgat tatcatataa tttctgttga attacgttaa      6480
gcatgtaata attaacatgt aatgcatgac gttatttatg agatgggttt ttatgattag      6540
agtcccgcaa ttatacattt aatacgcgat agaaaacaaa atatagcgcg caaactagga      6600
taaattatcg cgcgcggtgt catctatgtt actagatcgg gaattgatcc cccctcgaca      6660
gcttccggaa agggcgaatt cgcaactttg tatacaaaag ttgaacgaga aacgtaaaat      6720
gatataaata tcaatatatt aaattagatt ttgcataaaa aacagactac ataatactgt      6780
aaaacacaac atatccagtc actatgccat ccagctgata tcccctatag tgagtcgtat      6840
tacatggtca tagctgtttc ctggcagctc tggcccgtgt ctcaaaatct ctgatgttac      6900
attgcacaag ataaaaatat atcatcatgc ctcctc                               6936
```

-continued

```
<210> SEQ ID NO 19
<211> LENGTH: 6873
<212> TYPE: DNA
<213> ORGANISM: Artificial Sequence
<220> FEATURE:
<223> OTHER INFORMATION: Synthetic construct

<400> SEQUENCE: 19
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg cgcagtggc ggttttcatg gcttgttatg actgtttttt tggggtacag      240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagacccgt agaaaagatc aaaggatctt cttgagatcc tttttttctg     1260
cgcgtaatct gctgcttgca aacaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg tcgggctga     1560 acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga   1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
```

-continued

```
agtgagcgca  acgcaattaa  tacgcgtacc  gcgagccagg  aagagtttgt  agaaacgcaa       2160
aaaggccatc  cgtcaggatg  gccttctgct  tagtttgatg  cctggcagtt  tatggcgggc       2220
gtcctgcccg  ccaccctccg  ggccgttgct  tcacaacgtt  caaatccgct  cccggcggat       2280
ttgtcctact  caggagagcg  ttcaccgaca  aacaacagat  aaaacgaaag  gcccagtctt       2340
ccgactgagc  ctttcgtttt  atttgatgcc  tggcagttcc  ctactctcgc  gttaacgctt       2400
gcatggatgt  tttcccagtc  acgacgttgt  aaaacgacgg  ccagtcttaa  gctcgggccc       2460
caaataatga  ttttattttg  actgatagtg  acctgttcgt  tgcaacaaat  tgatgagcaa       2520 tgcttttttta taatgccaac  tttgtacaaa  aaagcaggct  ccgaattcgc  ccttcaccat       2580
ggctcctaag  aagaagcgga  aggttggtat  tcacggggtg  cctgcggctt  actatcagaa       2640
tctcactaag  aagtacccag  tcagcaaaac  tatcagaaat  gaacttattc  caataggaaa       2700
aacgcttgaa  aacattagga  aaaacaacat  actggaaagc  gacgtgaaaa  ggaagcagga       2760
ctatgaacac  gttaagggga  tcatggacga  atatcacaag  cagctcatta  acgaagcact       2820
tgataactat  atgcttcctt  cgctcaatca  agccgccgaa  atttacctca  agaaacacgt       2880
ggacgtcgag  gatagagagg  agtttaagaa  aacgcaagat  ctgctcaggc  gggaggtgac       2940
gggaagactg  aaggaacatg  agaattacac  taagattgga  aaaaaggaca  ttctcgatct       3000
cctcgaaaaa  ctgccatcta  tttctgagga  agactacaat  gctctggagt  cctttagaaa       3060
cttttataca  tatttcacct  cctataataa  agttcgggag  aatctgtata  gcgacgaaga       3120
gaagagtagc  acggtggcct  atagactgat  aaacgagaac  ttgccaaagt  tcttggataa       3180
catcaaatct  tatgcatttg  ttaaagcggc  tggcgtgctc  gctgattgta  ttgaagagga       3240
ggaacaggat  gccctgttta  tggtcgaaac  tttcaacatg  acgctcacgc  aagaaggtat       3300
tgacatgtat  aattatcaga  tcggaaaagt  caattcggct  attaatctct  ataaccagaa       3360
gaatcacaag  gtcgaggaat  ttaagaaaat  cccaaaaatg  aaagttcttt  ataaacagat       3420
cctctctgat  cgcgaagaag  tcttcatcgg  tgaattcaag  gatgatgaga  ctctcctttc       3480
cagcataggc  gcatatggca  atgtttttgat gacatacctc  aaatccgaga  aaataaatat       3540
tttcttcgac  gctctgaggg  aaagcgaggg  aaaaaacgtc  tacgttaaga  acgatctgtc       3600
gaaaactacg  atgtcaaata  tagtctttgg  ctcgtggtcg  gcctttgatg  aacttctgaa       3660
tcaggaatac  gacctggcca  atgagaacaa  aaagaaagat  gataaatact  ttgagaagag       3720
acagaaggaa  ctcaaaaaaa  ataagagcta  cacgttggag  caaatgagca  atctttcgaa       3780
ggaggatatt  tcgccgatag  agaactacat  agagaggatt  tcagaggaca  tagagaagat       3840
atgcatctat  aatggcgagt  tcgaaaagat  tgtcgtgaac  gaacatgatt  cgagtagaaa       3900
gctctcgaag  aacatcaagg  cggttaaggt  gattaaagac  tacctcgatt  ccattaaaga       3960
acttgaacat  gatattaaac  tcataaatgg  atctggtcag  gagcttgaaa  agaacttggt       4020
tgtttacgtc  gggcaggaag  aagcgcttga  acagctgcgc  ccgtcgatt   ccctgtataa       4080 cctcacacgc  aattatctga  cgaagaagcc  attttcaacg  gaaaaagtga  aactgaattt       4140
taataaatct  actctcctca  atggctggga  caaaaataag  gaaacggata  acctcggtat       4200
actgtttttt  aaggacggta  aatactacct  cggaataatg  aacaccacag  caaacaaggc       4260
gtttgtcaac  ccacctgctg  ccaaaacaga  gaatgttttc  aaaaaggtgg  actacaagct       4320
gctgcctggc  tcgaacaaaa  tgctcccaaa  ggttttcttt  gcgaaatcga  atattggata       4380
ttataatccc  tcgaccgaac  tctattccaa  ctacaaaaaa  ggcactcaca  agaaaggccc       4440
```

-continued

```
ttccttctct atagatgatt gccacaatct tattgatttt tttaaagaat cgattaagaa   4500
gcatgaagac tggtccaaat ttggatttga attcagtgac actgcagatt acagagacat   4560
ttcggagttt taccgggaag tggagaagca ggggtataag ttgactttca ccgacataga   4620
tgagtcatac atcaacgatc tgatagaaaa gaacgaactg tatctttttc agatttataa   4680
caaagatttc tctgaatatt cgaagggtaa gctgaacctc cacacactct attttatgat   4740
gctgttcgac cagagaaacc ttgacaacgt cgtgtataag ctgaatggag aggccgaggt   4800
cttctataga ccagcatcta tagccgaaaa cgaacttgtg atacacaaag cgggcgaagg   4860
cataaagaac aaaaaccta atcgggcgaa agttaaagag actagtacat tcagttacga   4920
cattgtcaaa gataagcggt attcaaagta caagttcaca ctgcatattc ctatcacaat   4980
gaatttcgga gttgacgagg tccgcagatt taacgacgtt atcaataacg cactgcgcac   5040
agacgataac gtgaatgtta tcggtatcga ccggggcgaa cgcaatctgt tgtatgtcgt   5100
ggtgatcaat tcagagggta agatcttgga gcaaatttcc ttgaatagta taattaacaa   5160
agagtatgac atagagacta attatcatgc cctgttggac gaacgcgaag acgatagaaa   5220
taaagcaaga aaagattgga acactatcga aaacattaaa gaattgaaaa caggttatct   5280
gagtcaagtc gtcaacgttg tcgccaaact cgtcctgaaa tataacgcga taatctgctt   5340
ggaagacctt aattttggtt tcaagcgcgg acggcagaag gtcgaaaaac aggtctatca   5400
aaaatttgag aaaatgctca tagagaaact taattatttg gttattgata agagtagaga   5460
gcaggtgtcc cccgaaaaga tggggggtgc cctcaacgct ctccaattga cttcaaaatt   5520
taagagcttt gcggaacttg ggaagcagag tggtatcatt tactatgttc ccgcgtactt   5580
gacttctaag attgatccta ccacgggttt tgtgaatctg ttctacatca agtatgagaa   5640
catagaaaag gcaaagcaat ttttcgatgg ttttgatttc attcggttta ataagaaaga   5700
cgacatgttt gaatttagct ttgactacaa gtcattcacc cagaaggcgt gcgggatacg   5760
gtcgaaatgg atagtctaca caaatggaga gcgcatcata aaatatccga accctgagaa   5820
gaataacctg ttcgacgaaa aggttattaa cgtcacggac gagattaaag gtcttttttaa   5880 gcaataccgg attccgtacg agaacggaga agacattaag gaaataatca tttcgaaggc   5940
agaggctgac ttctataaac ggttgttccg cctgcttcat caaacgctgc aaatgagaaa   6000
ttcaactagc gatggcacca gggattacat catcagtccg gtgaagaacg accggggaga   6060 attttttctgc tctgaatttt cggagggcac aatgcctaaa gatgccgacg cgaacggtgc   6120
atacaatata gccagaaagg ggctttgggt cctcgagcag attcgccaga aagatgaggg   6180
agagaaagtt aatttgtcaa tgacgaatgc cgaatggctt aaatacgccc aattgcacct   6240
cctgaagcgt cctgctgcca ccaaaaaggc cggacaggct aagaaaaaga agtgagacga   6300
ctagtggcgg ccgccgacgt ccgatcgttc aaacatttgg caataaagtt tcttaagatt   6360
gaatcctgtt gccggtcttg cgatgattat catataattt ctgttgaatt acgttaagca   6420
tgtaataatt aacatgtaat gcatgacgtt atttatgaga tgggttttta tgattagagt   6480
cccgcaatta tacatttaat acgcgataga aaacaaaata tagcgcgcaa actaggataa   6540
attatcgcgc gcggtgtcat ctatgttact agatcgggaa ttgatccccc ctcgacagct   6600
tccggaaagg gcgaattcgc aactttgtat acaaaagttg aacgagaaac gtaaaatgat   6660
ataaatatca atatattaaa ttagattttg cataaaaaac agactacata atactgtaaa   6720
acacaacata tccagtcact atgccatcca gctgatatcc cctatagtga gtcgtattac   6780
atggtcatag ctgtttcctg gcagctctgg cccgtgtctc aaaatctctg atgttacatt   6840
```

-continued gcacaagata aaaatatatc atcatgcctc ctc                                    6873

<210> SEQ ID NO 20
<211> LENGTH: 6873
<212> TYPE: DNA
<213> ORGANISM: Artificial Sequence
<220> FEATURE:
<223> OTHER INFORMATION: Synthetic construct

<400> SEQUENCE: 20
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg cgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgacctttg gaaacttcgg cttcccctgg agagagcgag      600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagaccccgt agaaaagatc aaaggatctt cttgagatcc tttttttctg    1260
cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttgtga    1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980

-continued

```
cgcagcgagt cagtgagcga ggaagcggaa gagcgcccaa tacgcaaacc gcctctcccc       2040
gcgcgttggc cgattcatta atgcagctgg cacgacaggt ttcccgactg gaaagcgggc       2100
agtgagcgca acgcaattaa tacgcgtacc gcgagccagg aagagtttgt agaaacgcaa       2160
aaaggccatc cgtcaggatg gccttctgct tagtttgatg cctggcagtt tatggcgggc       2220
gtcctgcccg ccaccctccg ggccgttgct tcacaacgtt caaatccgct cccggcggat       2280
ttgtcctact caggagagcg ttcaccgaca aacaacagat aaaacgaaag gcccagtctt       2340
ccgactgagc ctttcgtttt atttgatgcc tggcagttcc ctactctcgc gttaacgctt       2400
gcatggatgt tttcccagtc acgacgttgt aaaacgacgg ccagtcttaa gctcgggccc       2460
caaataatga ttttattttg actgatagtg acctgttcgt tgcaacaaat tgatgagcaa       2520 tgcttttta taatgccaac tttgtacaaa aaagcaggct ccgaattcgc ccttcaccat       2580
ggctcctaag aagaagcgga aggttggtat tcacggggtg cctgcggctt actatcagaa       2640
tctcactaag aagtacccag tcagcaaaac tatcagaaat gaacttattc aataggaaa       2700 aacgcttgaa aacattagga aaacaacat actggaaagc gacgtgaaaa ggaagcagga       2760
ctatgaacac gttaaggga tcatggacga atatcacaag cagctcatta acgaagcact       2820
tgataactat atgcttcctt cgctcaatca agccgccgaa atttacctca agaaacacgt       2880
ggacgtcgag gatagagagg agtttaagaa aacgcaagat ctgctcaggc gggaggtgac       2940
gggaagactg aaggaacatg agaattacac taagattgga aaaaggaca ttctcgatct       3000 cctcgaaaaa ctgccatcta tttctgagga agactacaat gctctggagt cctttagaaa       3060
cttttataca tatttcacct cctataataa agttcgggag aatctgtata gcgacgaaga       3120
gaagagtagc acggtggcct atagactgat aaacgagaac ttgccaaagt cttggataa       3180 catcaaatct tatgcatttg ttaaagcggc tggcgtgctc gctgattgta ttgaagagga       3240
ggaacaggat gccctgttta tggtcgaaac tttcaacatg acgctcacgc aagaaggtat       3300
tgacatgtat aattatcaga tcggaaaagt caattcggct attaatctct ataaccagaa       3360
gaatcacaag gtcgaggaat ttaagaaaat cccaaaaatg aaagttcttt ataaacagat       3420
cctctctgat cgcgaagaag tcttcatcgg tgaattcaag gatgatgaga ctctcctttc       3480
cagcataggc gcatatggca atgttttgat gacatacctc aaatccgaga aaataaatat       3540
tttcttcgac gctctgaggg aaagcgaggg aaaaaacgtc tacgttaaga acgatctgtc       3600
gaaaactacg atgtcaaata tagtctttgg ctcgtggtcg gccttgatg aacttctgaa       3660 tcaggaatac gacctggcca atgagaacaa aagaaagat gataaatact ttgagaagag       3720
acagaaggaa ctcaaaaaaa ataagagcta cacgttggag caaatgagca atctttcgaa       3780
ggaggatatt tcgccgatag agaactacat agagaggatt tcagaggaca tagagaagat       3840
atgcatctat aatggcgagt tcgaaaagat tgtcgtgaac gaacatgatt cgagtagaaa       3900
gctctcgaag aacatcaagg cggttaaggt gattaaagac tacctcgatt ccattaaaga       3960
acttgaacat gatattaaac tcataaatgg atctggtcag gagcttgaaa agaacttggt       4020
tgtttacgtc gggcaggaag aagcgcttga acagctgcgc ccgtcgatt ccctgtataa       4080 cctcacacgc aattatctga cgaagaagcc attttcaacg gaaaaagtga aactgaattt       4140
taataaatct actctcctcc gcggctggga caaaaatgtg gaaacggatc gcctcggtat       4200 actgttttt aaggacggta aatactacct cggaataatg aacaccacag caaacaaggc       4260
gtttgtcaac ccacctgctg ccaaaacaga gaatgttttc aaaaaggtgg actacaagct       4320
gctgcctggc tcgaacaaaa tgctcccaaa ggttttcttt gcgaaatcga atattggata       4380
```

-continued

```
ttataatccc tcgaccgaac tctattccaa ctacaaaaaa ggcactcaca agaaaggccc     4440
ttccttctct atagatgatt gccacaatct tattgatttt tttaaagaat cgattaagaa     4500
gcatgaagac tggtccaaat ttggatttga attcagtgac actgcagatt acagagacat     4560
ttcggagttt taccgggaag tggagaagca ggggtataag ttgactttca ccgacataga     4620
tgagtcatac atcaacgatc tgatagaaaa gaacgaactg tatcttttc agatttataa      4680 caaagatttc tctgaatatt cgaagggtaa gctgaacctc cacacactct attttatgat     4740
gctgttcgac cagagaaacc ttgacaacgt cgtgtataag ctgaatggag aggccgaggt     4800
cttctataga ccagcatcta tagccgaaaa cgaacttgtg atacacaaag cgggcgaagg     4860
cataaagaac aaaaacccta atcgggcgaa agttaaagag actagtacat tcagttacga     4920
cattgtcaaa gataagcggt attcaaagta caagttcaca ctgcatattc ctatcacaat     4980
gaatttcgga gttgacgagg tccgcagatt taacgacgtt atcaataacg cactgcgcac     5040
agacgataac gtgaatgtta tcggtatcga ccggggcgaa cgcaatctgt tgtatgtcgt     5100
ggtgatcaat tcagagggta agatcttgga gcaaatttcc ttgaatagta taattaacaa     5160
agagtatgac atagagacta attatcatgc cctgttggac gaacgcgaag acgatagaaa     5220
taaagcaaga aaagattgga acactatcga aaacattaaa gaattgaaaa caggttatct     5280
gagtcaagtc gtcaacgttg tcgccaaact cgtcctgaaa tataacgcga taatctgctt     5340
ggaagacctt aattttggtt tcaagcgcgg acggcagaag gtcgaaaaac aggtctatca     5400
aaaatttgag aaaatgctca tagagaaact taattatttg gttattgata agagtagaga     5460
gcaggtgtcc cccgaaaaga tgggggggtgc cctcaacgct ctccaattga cttcaaaatt    5520
taagagcttt gcggaacttg ggaagcagag tggtatcatt tactatgttc ccgcgtactt     5580
gacttctaag attgatccta ccacgggttt tgtgaatctg ttctacatca agtatgagaa     5640
catagaaaag gcaaagcaat ttttcgatgg ttttgatttc attcggttta ataagaaaga     5700
cgacatgttt gaatttagct ttgactacaa gtcattcacc cagaaggcgt gcgggatacg     5760
gtcgaaatgg atagtctaca caaatggaga gcgcatcata aaatatccga accctgagaa     5820
gaataacctg ttcgacgaaa aggttattaa cgtcacggac gagattaaag gtcttttaa      5880 gcaataccgg attccgtacg agaacggaga agacattaag gaaataatca tttcgaaggc     5940
agaggctgac ttctataaac ggttgttccg cctgcttcat caaacgctgc aaatgagaaa     6000
ttcaactagc gatggcacca gggattacat catcagtccg gtgaagaacg accggggaga     6060 attttttctgc tctgaatttt cggagggcac aatgcctaaa gatgccgacg cgaacggtgc     6120
atacaatata gccagaaagg ggctttgggt cctcgagcag attcgccaga aagatgaggg     6180
agagaaagtt aatttgtcaa tgacgaatgc cgaatggctt aaatacgccc aattgcacct     6240
cctgaagcgt cctgctgcca ccaaaaaggc cggacaggct aagaaaaaga agtgagacga     6300
ctagtggcgg ccgccgacgt ccgatcgttc aaacatttgg caataaagtt tcttaagatt     6360
gaatcctgtt gccggtcttg cgatgattat catataattt ctgttgaatt acgttaagca     6420
tgtaataatt aacatgtaat gcatgacgtt atttatgaga tgggtttttta tgattagagt     6480 cccgcaatta tacatttaat acgcgataga aaacaaaata tagcgcgcaa actaggataa     6540
attatcgcgc gcggtgtcat ctatgttact agatcgggaa ttgatccccc ctcgacagct     6600
tccggaaagg gcgaattcgc aactttgtat acaaaagttg aacgagaaac gtaaaatgat     6660
ataaatatca atatattaaa ttagattttg cataaaaaac agactacata atactgtaaa     6720
```

```
acacaacata tccagtcact atgccatcca gctgatatcc cctatagtga gtcgtattac      6780
atggtcatag ctgtttcctg gcagctctgg cccgtgtctc aaaatctctg atgttacatt      6840
gcacaagata aaaatatatc atcatgcctc ctc                                    6873

<210> SEQ ID NO 21
<211> LENGTH: 7041
<212> TYPE: DNA
<213> ORGANISM: Artificial Sequence
<220> FEATURE:
<223> OTHER INFORMATION: Synthetic construct

<400> SEQUENCE: 21
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag       120
ctgtaatgca agtagcgtat gcgctcacgc aactggtcca gaaccttgac cgaacgcagc       180
ggtggtaacg cgcagtggc ggttttcatg gcttgttatg actgtttttt tggggtacag       240
tctatgcctc gggcatccaa gcagcaagcg cgttacgccg tgggtcgatg tttgatgtta       300
tggagcagca acgatgttac gcagcagggc agtcgcccta aaacaaagtt aaacatcatg       360
agggaagcgg tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca       540
acgcggcgag ctttgatcaa cgaccttttg gaaacttcgg cttcccctgg agagagcgag       600
attctccgcg ctgtagaagt caccattgtt gtgcacgacg acatcattcc gtggcgttat       660
ccagctaagc gcgaactgca atttggagaa tggcagcgca atgacattct tgcaggtatc       720
ttcgagccag ccacgatcga cattgatctg gctatcttgc tgacaaaagc aagagaacat       780
agcgttgcct tggtaggtcc agcggcggag gaactctttg atccggttcc tgaacaggat       840
ctatttgagg cgctaaatga aaccttaacg ctatggaact cgccgcccga ctgggctggc       900
gatgagcgaa atgtagtgct tacgttgtcc cgcatttggt acagcgcagt aaccggcaaa       960
atcgcgccga aggatgtcgc tgccgactgg gcaatggagc gcctgccggc ccagtatcag      1020
cccgtcatac ttgaagctag acaggcttat cttggacaag aagaagatcg cttggcctcg      1080
cgcgcagatc agttggaaga atttgtccac tacgtgaaag gcgagatcac caaggtagtc      1140
ggcaaataac cctcgagcca cccatgacca aaatccctta acgtgagtta cgcgtcgttc      1200
cactgagcgt cagaccccgt agaaaagatc aaaggatctt cttgagatcc tttttttctg      1260
cgcgtaatct gctgcttgca acaaaaaaa ccaccgctac cagcggtggt ttgtttgccg      1320
gatcaagagc taccaactct ttttccgaag gtaactggct tcagcagagc gcagatacca      1380
aatactgtcc ttctagtgta gccgtagtta ggccaccact tcaagaactc tgtagcaccg      1440
cctacatacc tcgctctgct aatcctgtta ccagtggctg ctgccagtgg cgataagtcg      1500
tgtcttaccg ggttggactc aagacgatag ttaccggata aggcgcagcg gtcgggctga      1560
acggggggtt cgtgcacaca gcccagcttg gagcgaacga cctacaccga actgagatac      1620
ctacagcgtg agctatgaga aagcgccacg cttcccgaag ggagaaaggc ggacaggtat      1680
ccggtaagcg gcagggtcgg aacaggagag cgcacgaggg agcttccagg gggaaacgcc      1740
tggtatcttt atagtcctgt cgggtttcgc cacctctgac ttgagcgtcg attttttgtga      1800 tgctcgtcag gggggcggag cctatggaaa aacgccagca acgcggcctt ttacggttc       1860 ctggcctttt gctggccttt tgctcacatg ttctttcctg cgttatcccc tgattctgtg      1920
```

-continued

```
gataaccgta ttaccgcctt tgagtgagct gataccgctc gccgcagccg aacgaccgag      1980
cgcagcgagt cagtgagcga ggaagcggaa gagcgcccaa tacgcaaacc gcctctcccc      2040
gcgcgttggc cgattcatta atgcagctgg cacgacaggt ttcccgactg gaaagcgggc      2100
agtgagcgca acgcaattaa tacgcgtacc gcgagccagg aagagtttgt agaaacgcaa      2160
aaaggccatc cgtcaggatg gccttctgct tagtttgatg cctggcagtt tatggcgggc      2220
gtcctgcccg ccaccctccg ggccgttgct tcacaacgtt caaatccgct cccggcggat      2280
ttgtcctact caggagagcg ttcaccgaca acaacagat aaaacgaaag gcccagtctt      2340
ccgactgagc ctttcgtttt atttgatgcc tggcagttcc ctactctcgc gttaacgctt      2400
gcatggatgt tttcccagtc acgacgttgt aaaacgacgg ccagtcttaa gctcgggccc      2460
caaataatga tttttattttg actgatagtg acctgttcgt tgcaacaaat tgatgagcaa      2520
tgctttttta taatgccaac tttgtacaaa aaagcaggct ccgaattcgc ccttcaccat      2580
ggctcctaag aagaagcgga aggttggtat tcacggggtg cctgcggctc ggaagtttaa      2640
tgagttcgtt ggcctttacc caattagtaa aacattgaga tttgaattga agcccatagg      2700
gaagacactc gaacatatcc agcggaacaa actgcttgag cacgatgcgg tccgggctga      2760
cgattacgtg aaggttaaga agataatcga caaatatcac aagtgtctca tcgatgaagc      2820
gttgtcgggg ttcacatttg atactgaggc cgacgggagg tctaataaca gcttgtccga      2880
gtattatctt tattacaatc tgaaaaagcg gaacgaacag gagcagaaaa cgttcaaaac      2940
catacaaaat aatttgagga aacaaatagt caataagttg acgcaaagcg agaagtacaa      3000
acggatcgac aagaaagaac tgatcactac tgacctcccc gatttcctca ctaatgagtc      3060
ggaaaaggaa ttggttgaaa aatttaagaa ctttacaact tacttcacgg agttccacaa      3120
gaacaggaaa aatatgtatt ctaaagagga aaagtctaca gcgatagcct tcaggcttat      3180
aaatgaaaat ttgcccaagt tcgttgacaa tatagctgcg tttgaaaaag tcgtgtcgag      3240
cccattggcg gaaaaaatta atgctctcta cgaggatttt aaggaatacc ttaacgttga      3300
agagatttct agggttttta gacttgacta ctatgacgaa ctgctgactc agaagcagat      3360
tgacctttat aacgctatag ttggcggcag gaccgaggag gataataaaa ttcagattaa      3420
aggactcaac caatatatca acgaatacaa tcagcagcag acagatagat cgaacagact      3480
cccgaaactt aagccactgt ataaacagat tctttccgat agggaatccg tctcctggct      3540
gcctccgaaa tttgactcag acaaaaacct cctcataaag attaaagaat gttacgacgc      3600
gctctctgag aaagaaaaag ttttttgataa actggaaagt attcttaaaa gtctctcaac      3660
ttacgatttg tctaagatat atatatcaaa cgacagccaa ttgagctaca tcagccaaaa      3720
gatgttcggg aggtgggaca taataagtaa agcaattcgg gaagactgcg ctaaaaggaa      3780
cccgcaaaag tcaagggaga gtttggagaa gtttgctgag cgcatagata aaaaattgaa      3840
gacgatagac agtatctcga ttggggatgt tgacgagtgt ctggcgcaac tcggtgaaac      3900
atacgtgaaa cgggttgagg actactttgt cgctatgggt gagtcagaga tagacgacga      3960
acaaacggac acaacttctt ttaaaaaaaa tatagaagga gcgtatgaat ccgtcaagga      4020
acttctcaat aacgcggaca acattactga taacaatctg atgcaagata aaggaaatgt      4080
ggaaaagatt aaaacgttgc ttgacgctat aaaggacctc cagcgcttta taaaacccct      4140
tctcggcaag ggtgatgagg cggacaaaga tggtgtcttt tatggggagt tcaccagtct      4200
ttggactaaa ttggatcaag tcacccccact ctataacatg gtgaggaatt accttacgtc      4260
```

-continued

```
taagccgtat agtaccaaaa aaattaaact taactttgaa aactcgaccc tcatggacgg    4320
ctgggacctc aataaagaac ccgataacac tacagttatt ttctgcaaag acggcttgta    4380
ttacctcggc attatgggca agaagtacaa cagggttttc gtcgatagag aggacctccc    4440
gcacgacggt gaatgctacg acaagatgga gtataagctg cttccgggag cgaacaagat    4500
gcttcctaag gtgttctttt ctgaaacggg cattcaaaga tttcttccgt ccgaggagtt    4560
gttgggtaaa tacgagaggg ggacgcataa gaaaggagca ggatttgact tgggagattg    4620
tcgggcgctt atcgattttt tcaaaaagag tattgagcgc cacgatgatt ggaagaaatt    4680
cgactttaag ttctctgata ccagcaccta ccaggacatt tcagagttct acagagaggt    4740
cgagcaacag ggatataaaa tgtcattcag aaaggttagt gtcgattata tcaagtcact    4800
cgttgaagaa ggtaaactct atcttttcca gatttacaat aaggatttct ctgctcatag    4860
taaggggacc ccgaatatgc acaccttgta ctggaaaatg ctgtttgacg aagaaaatct    4920
taaggacgtc gtttacaagc tgaatggaga ggcggaagtc tttttttagga aatcaagtat    4980 tacggtccaa tcgcccacgc atccggcgaa ttctcctata aagaataaga ataaggataa    5040
tcaaaaaaaa gaaagtaagt tcgagtacga tctgattaaa gacagacggt atactgttga    5100
taagttcctg tttcatgttc ccattactat gaacttcaaa agcgtcggtg gttcgaatat    5160
taaccaattg gttaagcgcc atatacgcag cgctaccgac ttgcacataa tcggaatcga    5220
ccggggtgag aggcacttgc tttatcttac cgttatagac tctagggggta acataaaaga    5280 acaattctct cttaacgaga tagttaatga atataacgga aatacttacc gcacagatta    5340
ccatgagctc ctcgacacgc gcgaggggga gcggacggag gctcgcagga actggcagac    5400
tatacaaaat ataagggaac tgaaggaagg ctatttgtcc caggtgatac acaagatttc    5460
ggagttggcg attaagtata atgcagtcat tgtgctggag gatctgaatt ttgggtttat    5520
gaggtcgcgg cagaaagttg aaaaacaagt ctaccagaag ttcgagaaga tgctcataga    5580
caaactgaat tacttggtcg ataagaaaaa gccggttgct gaaaccggag ggctcctcag    5640
ggcgtaccag ctcaccggcg aatttgagag ctttaaaacg ctcggtaagc aatctgggat    5700
cttgttctac gtcccagctt ggaatacctc gaaaatcgat ccagtgacgg gctttgtgaa    5760 tcttttttgat acgcactacg agaatataga gaaagcaaaa gtttttcttcg ataaatttaa    5820 gtcgatccgg tataacagtg ataaggactg gtttgaattc gtcgtcgatg actacacaag    5880
atttagtccc aaagccgaag ggactagacg cgattggacc atatgcacac aggggaagag    5940
gatacaaatt tgtcgcaatc accagcggaa taatgaatgg gaaggtcaag agattgatct    6000
gacaaaagcg tttaaggaac attttgaggc ctatggcgtg gacatctcaa aggacttgcg    6060
cgaacagatt aacacgcaga ataaaaaaga gttttttgaa gaattgctcc ggctgctcag    6120
gctcacgttg caaatgagga actctatgcc atctagcgat attgattacc tcatatctcc    6180
agttgccaat gataccggtt gcttcttcga tagtagaaaa caggcagaac tgaaagagaa    6240
cgctgtcttg cctatgaatg cagacgcaaa tggtgcttac aatattgcac gcaagggct    6300 cctcgcaatc agaaagatga agcaagagga gaatgactca gcgaaaattt ctttggcaat    6360
tagtaataaa gaatggctga aattcgctca gactaagcct tacttggaag ataagcgtcc    6420
tgctgccacc aaaaaggccg gacaggctaa gaaaaagaag tgagacgact agtggcggcc    6480
gccgacgtcc gatcgttcaa acatttggca ataaagtttc ttaagattga atcctgttgc    6540
cggtcttgcg atgattatca tataatttct gttgaattac gttaagcatg taataattaa    6600
catgtaatgc atgacgttat ttatgagatg ggtttttatg attagagtcc cgcaattata    6660
```

```
catttaatac gcgatagaaa acaaaatata gcgcgcaaac taggataaat tatcgcgcgc    6720
ggtgtcatct atgttactag atcgggaatt gatccccct cgacagcttc cggaaagggc     6780
gaattcgcaa ctttgtatac aaaagttgaa cgagaaacgt aaaatgatat aaatatcaat    6840
atattaaatt agattttgca taaaaaacag actacataat actgtaaaac acaacatatc    6900
cagtcactat gccatccagc tgatatcccc tatagtgagt cgtattacat ggtcatagct    6960
gtttcctggc agctctggcc cgtgtctcaa aatctctgat gttacattgc acaagataaa    7020
aatatatcat catgcctcct c                                               7041
```

```
<210> SEQ ID NO 22
<211> LENGTH: 7047
<212> TYPE: DNA
<213> ORGANISM: Artificial Sequence
<220> FEATURE:
<223> OTHER INFORMATION: Synthetic construct

<400> SEQUENCE: 22
```

```
tggaccagcc aggacagaaa tgcctcgact tcgctgctac ccaaggttgc cgggtgacgc     60
acaccgtgga aacggatgaa ggcacgaacc cagtggacat aagcctgttc ggttcgtaag    120
ctgtaatgca agtagcgtat gcgctcacgc aactggtcca gaaccttgac cgaacgcagc    180
ggtggtaacg cgcagtggc ggttttcatg gcttgttatg actgtttttt tggggtacag     240
tctatgcctc gggcatccaa gcagcaagcg cgttacgccg tgggtcgatg tttgatgtta    300
tggagcagca acgatgttac gcagcagggc agtcgcccta aaacaaagtt aaacatcatg    360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgacctttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct ggtaggtcc agcggcggag gaactctttg atccggttcc tgaacaggat    840
ctatttgagg cgctaaatga aaccttaacg ctatggaact cgccgcccga ctgggctggc    900
gatgagcgaa atgtagtgct tacgttgtcc cgcatttggt acagcgcagt aaccggcaaa    960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag gcgagatcac caaggtagtc   1140
ggcaaataac cctcgagcca cccatgacca aaatccctta acgtgagtta cgcgtcgttc   1200
cactgagcgt cagacccgt agaaaagatc aaaggatctt cttgagatcc ttttttctg    1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg tcgggctga    1560 acggggggtt cgtgcacaca gcccagcttg gagcgaacga cctacaccga actgagatac   1620
```

-continued

```
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgctttttta taatgccaac tttgtacaaa aaagcaggct ccgaattcgc ccttcaccat    2580
ggctcctaag aagaagcgga aggttggtat tcacggggtg cctgcggcta tgaataacgg    2640
cacaaataac tttcaaaact tcatcgggat ttctagcctg caaaaaacac ttcggaatgc    2700
actgatcccg acggagacaa cacagcagtt cattgtcaaa aacggtatca ttaaagaaga    2760
cgagctgcgg ggagagaata gacaaatatt gaaggacata atggatgact attacagggg    2820
atttatctcc gaaaccctct ctagcataga tgatatagat tggacatccc tttttcgagaa    2880 aatggaaatt cagctcaaga atggagataa taaggacaca ctgattaagg agcaaacgga    2940
gtaccggaag gccatccaca aaaagtttgc taacgacgat cggttcaaga atatgtttag    3000
tgcgaaactt atatctgata tactgcccga gtttgtgatt cacaacaata actattccgc    3060
atctgaaaaa gaagagaaaa cacaagtgat taaactcttt tcgagattcg ccacctcgtt    3120
caaagactac tttaaaaaca gagctaactg ctttagtgca gatgatatat cctcgtcgtc    3180
ttgccacagg attgtcaatg acaatgcgga aatattcttt tcgaacgccc tggtgtacag    3240
aagaattgtg aaatctttga gcaacgacga cattaacaag atcagtgggg atatgaagga    3300
ctctttgaag gaaatgtcgc tcgaggagat ttactcgtat gaaaaatatg gtgaattcat    3360
tacacaagaa ggcatttcat tttataatga tatttgcggc aaagtcaata gctttatgaa    3420
tctttactgt caaaaaaata aagaaaataa gaacctctat aaaattgcaga agctccataa    3480 gcaaattctc tgcatcgccg atacttctta tgaagtgcct tacaaattcg agtccgatga    3540
agaggtgtat caatctgtga atggattctt ggataacata tcctcgaagc acattgtcga    3600
acgcttgcgc aagattggcg acaactataa tgggtacaat ctcgacaaaa tttacatagt    3660
tagcaaattt tacgaatctg tctcacagaa aacctatcgg gattgggaga ccataaatac    3720
cgcactcgag attcattata ataatatact ccccggtaac ggaaagtcca aggctgacaa    3780
agttaaaaag gcagttaaaa acgatctcca aaaatcaata acggagatca atgagttggt    3840
gagtaattat aagctttgct ccgacgacaa tatcaaggct gaaacgtata tccacgaaat    3900
tagccatatt ctcaacaact tcgaagcgca ggagttgaaa tacaaccctg agatacacct    3960
ggttgagagc gagcttaagg ccagcgagct caaaaaatgtc ctggatgtga ttatgaatgc    4020
```

-continued

```
gttccactgg tgctcagtgt tcatgacaga agaactggtt gacaaagata ataatttcta   4080
cgcggaactt gaggagattt atgatgagat ctaccctgtt ataagcctgt ataacttggt   4140
cagaaattat gtcacgcaaa aaccgtactc cacaaaaaag ataaagctga atttcggaat   4200
ccctactctc gcggatggct ggtccaaatc taaagagtac agtaacaatg ccatcatatt   4260
gatgagggac aacctttact atttgggaat ctttaatgcg aaaaataaac ctgacaaaaa   4320
aataatagag ggtaacacct cggagaataa aggcgattat aaaaaaatga tatataatct   4380
gctgcccggg cccaataaga tgattcccaa ggtttttctt agcagtaaaa ccggggtgga   4440
gacgtataag ccgtcggcct acattttgga aggctataaa cagaacaagc acatcaaatc   4500
gagcaaggac tttgatatta ctttctgtca tgacctgata gactatttta aaaactgcat   4560
agcgattcac ccagaatgga agaacttcgg tttcgacttc tctgacacct ctacatacga   4620
ggacatatca ggcttttata gagaggtcga gctgcaaggc tacaagatag attggactta   4680
tatctcagag aaggatatcg acctgctcca agaaaagggc caattgtatc ttttccaaat   4740
ctacaataaa gattttttcta aaaagtccac agggaacgat aatctccaca cgatgtacct   4800
taaaaacctc ttttcggaag aaaacctgaa ggacattgtg cttaagctga atggggaggc   4860
cgagatattc tttaggaaga gtagcataaa gaacccgata atccataaaa aaggttccat   4920
actggttaat cggaccctatg aggcagaaga aaaagaccag ttcggaaata tccagattgt   4980
cagaaaaaat ataccagaga atatctacca ggaattgtac aaatatttca acgataaatc   5040
agataaggaa ctctcggacg aagcagcgaa attgaagaac gtcgttggac accacgaggc   5100
cgccactaat atcgttaaag attacaggta cacgtacgat aagtattttc tccacatgcc   5160
aatcactata aactttaaag ctaataagac cggctttatt aacgatcgca tccttcagta   5220
tatcgctaag gagaaggacc tgcacgttat aggaatagac cgcggcgagc gcaatcttat   5280
ctacgtgagc gtgatcgata cctgtgggaa tatagtcgag cagaagtctt ttaatatcgt   5340
gaacggctac gactatcaga taaagctgaa gcagcaagag ggcgctagac agatcgccag   5400
gaaggaatgg aaggagatcg gtaaaataaa agaaattaag gagggttacc tcagtttggt   5460
tatacatgag atatcaaaaa tggttattaa gtataatgcg attattgcga tggaagacct   5520
gtcatatggg tttaaaaaag ggcggttcaa ggttgagcgc caggtctatc aaaagtttga   5580
gactatgctg attaataagc tcaattatct tgttttcaaa gacatcagta tcacggaaaa   5640
cggaggactt ctcaaggggt accagttgac ttatatccca gacaagctta aaaatgttgg   5700
tcaccagtgt ggatgtatat tttatgtgcc tgcggcctac acatctaaga tcgacccaac   5760
aactggcttt gttaatattt ttaaattcaa agaccttacg gtggatgcga aaagagagtt   5820
cataaaaaaa ttcgactcga tcagatatga ctctgagaa aatctcttct gttttacttt   5880
cgactataat aatttcataa cacaaaatac cgtcatgtcg aaatcaagct ggtcagtcta   5940
cacatatggc gttcgcataa agcgccgctt cgttaatggc aggttctcga atgagtccga   6000
tacaatcgac attacgaagg atatggagaa aacactcgag atgacggata taaattggag   6060
ggatgggcat gatctgagac aggacataat agactatgag atagttcagc acatattcga   6120
gatcttcaga ctcactgttc agatgcggaa ctccctcagt gaacttgaag acagggatta   6180
tgataggctt atttctcctg tcctgaacga aaacaatatt ttctacgact ctgctaaagc   6240
aggggatgct cttcctaagg atgcagacgc aaatggcgca tactgcatag ctcttaaagg   6300
gctctatgag atcaagcaga ttacagaaaa ctggaaagaa gacgggaagt tttccagaga   6360
```

```
caaattgaag atctccaaca aggactggtt cgatttata caaaataaaa ggtaccttaa     6420
gcgtcctgct gccaccaaaa aggccggaca ggctaagaaa aagaagtgag acgactagtg     6480
gcggccgccg acgtccgatc gttcaaacat ttggcaataa agtttcttaa gattgaatcc     6540
tgttgccggt cttgcgatga ttatcatata atttctgttg aattacgtta agcatgtaat     6600
aattaacatg taatgcatga cgttatttat gagatgggtt tttatgatta gagtcccgca     6660
attatacatt taatacgcga tagaaaacaa aatatagcgc gcaaactagg ataaattatc     6720
gcgcgcggtg tcatctatgt tactagatcg ggaattgatc ccccctcgac agcttccgga     6780
aagggcgaat tcgcaacttt gtatacaaaa gttgaacgag aaacgtaaaa tgatataaat     6840
atcaatatat taaattagat tttgcataaa aaacagacta cataatactg taaaacacaa     6900
catatccagt cactatgcca tccagctgat atcccctata gtgagtcgta ttacatggtc     6960
atagctgttt cctggcagct ctggcccgtg tctcaaaatc tctgatgtta cattgcacaa     7020
gataaaaata tatcatcatg cctcctc                                        7047
```

<210> SEQ ID NO 23
<211> LENGTH: 7047
<212> TYPE: DNA
<213> ORGANISM: Artificial Sequence
<220> FEATURE:
<223> OTHER INFORMATION: Synthetic construct

<400> SEQUENCE: 23

```
tggaccagcc aggacagaaa tgcctcgact tcgctgctac ccaaggttgc cgggtgacgc       60
acaccgtgga aacggatgaa ggcacgaacc cagtggacat aagcctgttc ggttcgtaag      120
ctgtaatgca agtagcgtat gcgctcacgc aactggtcca gaaccttgac cgaacgcagc      180
ggtggtaacg cgcagtggc ggttttcatg gcttgttatg actgtttttt tggggtacag      240
tctatgcctc gggcatccaa gcagcaagcg cgttacgccg tgggtcgatg tttgatgtta      300
tggagcagca acgatgttac gcagcagggc agtcgcccta aaacaaagtt aaacatcatg      360
agggaagcgg tgatcgccga agtatcgact caactatcag aggtagttgg cgtcatcgag      420
cgccatctcg aaccgacgtt gctggccgta catttgtacg gctccgcagt ggatggcggc      480
ctgaagccac acagtgatat tgatttgctg gttacggtga ccgtaaggct tgatgaaaca      540
acgcggcgag ctttgatcaa cgaccttttg gaaacttcgg cttcccctgg agagagcgag      600
attctccgcg ctgtagaagt caccattgtt gtgcacgacg acatcattcc gtggcgttat      660
ccagctaagc gcgaactgca atttggagaa tggcagcgca atgacattct tgcaggtatc      720
ttcgagccag ccacgatcga cattgatctg gctatcttgc tgacaaaagc aagagaacat      780
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagacccgt agaaaagatc aaaggatctt cttgagatcc tttttttctg     1260
cgcgtaatct gctgcttgca acaaaaaaaa ccaccgctac cagcggtggt ttgtttgccg     1320
gatcaagagc taccaactct ttttccgaag gtaactggct tcagcagagc gcagatacca     1380
```

```
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg atttttgtga   1800
tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca acaacagat aaaacgaaag gcccagtctt   2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520
tgctttttta taatgccaac tttgtacaaa aaagcaggct ccgaattcgc ccttcaccat   2580
ggctcctaag aagaagcgga aggttggtat tcacggggtg cctgcggcta tgaataacgg   2640
cacaaataac tttcaaaact tcatcgggat ttctagcctg caaaaaacac ttcggaatgc   2700
actgatcccg acggagacaa cacagcagtt cattgtcaaa aacggtatca ttaaagaaga   2760
cgagctgcgg ggagagaata gacaaatatt gaaggacata atggatgact attacagggg   2820
atttatctcc gaaaccctct ctagcataga tgatatagat tggacatccc ttttcgagaa   2880
aatggaaatt cagctcaaga atggagataa taaggacaca ctgattaagg agcaaacgga   2940
gtaccggaag gccatccaca aaaagtttgc taacgacgat cggttcaaga atatgtttag   3000
tgcgaaactt atatctgata tactgcccga gtttgtgatt cacaacaata actattccgc   3060
atctgaaaaa gaagagaaaa cacaagtgat taaactcttt tcgagattcg ccacctcgtt   3120
caaagactac tttaaaaaca gagctaactg ctttagtgca gatgatatat cctcgtcgtc   3180
ttgccacagg attgtcaatg acaatgcgga aatattcttt tcgaacgccc tggtgtacag   3240
aagaattgtg aaatctttga gcaacgacga cattaacaag atcagtgggg atatgaagga   3300
ctctttgaag gaaatgtcgc tcgaggagat ttactcgtat gaaaaatatg gtgaattcat   3360
tacacaagaa ggcatttcat tttataatga tatttgcggc aaagtcaata gctttatgaa   3420
tctttactgt caaaaaaata aagaaaataa gaacctctat aaattgcaga agctccataa   3480
gcaaattctc tgcatcgccg atacttctta tgaagtgcct tacaaattcg agtccgatga   3540
agaggtgtat caatctgtga atggattctt ggataacata tcctcgaagc acattgtcga   3600
acgcttgcgc aagattggcg acaactataa tgggtacaat ctcgacaaaa tttacatagt   3660
tagcaaattt tacgaatctg tctcacagaa aacctatcgg gattgggaga ccataaatac   3720
```

-continued

```
cgcactcgag attcattata ataatatact ccccggtaac ggaaagtcca aggctgacaa   3780
agttaaaaag gcagttaaaa acgatctcca aaaatcaata acggagatca atgagttggt   3840
gagtaattat aagctttgct ccgacgacaa tatcaaggct gaaacgtata tccacgaaat   3900
tagccatatt ctcaacaact tcgaagcgca ggagttgaaa tacaaccctg agatacacct   3960
ggttgagagc gagcttaagg ccagcgagct caaaaatgtc ctggatgtga ttatgaatgc   4020
gttccactgg tgctcagtgt tcatgacaga agaactggtt gacaaagata ataatttcta   4080
cgcggaactt gaggagattt atgatgagat ctaccctgtt ataagcctgt ataacttggt   4140
cagaaattat gtcacgcaaa aaccgtactc cacaaaaaag ataaagctga atttcggaat   4200
ccctactctc gcgcgcggct ggtccaaatc tgtggagtac agtcgcaatg ccatcatatt   4260
gatgagggac aacctttact atttgggaat cttttaatgcg aaaaataaac ctgacaaaaa   4320
aataatagag ggtaacacct cggagaataa aggcgattat aaaaaaatga tatataatct   4380
gctgcccggg cccaataaga tgattcccaa ggttttttctt agcagtaaaa ccggggtgga   4440
gacgtataag ccgtcggcct acattttgga aggctataaa cagaacaagc acatcaaatc   4500
gagcaaggac tttgatatta ctttctgtca tgacctgata gactatttta aaaactgcat   4560
agcgattcac ccagaatgga agaacttcgg tttcgacttc tctgacacct ctacatacga   4620
ggacatatca ggctttttata gagaggtcga gctgcaaggc tacaagatag attggactta   4680
tatctcagag aaggatatcg acctgctcca agaaaagggc caattgtatc ttttccaaat   4740
ctacaataaa gatttttcta aaaagtccac agggaacgat aatctccaca cgatgtacct   4800
taaaaacctc ttttcggaag aaaacctgaa ggacattgtg cttaagctga atggggaggc   4860
cgagatattc tttaggaaga gtagcataaa gaacccgata atccataaaa aaggttccat   4920
actggttaat cggaccctatg aggcagaaga aaaagaccag ttcggaaata tccagattgt   4980
cagaaaaaat ataccagaga atatctacca ggaattgtac aaatatttca cgataaaatc   5040
agataaggaa ctctcggacg aagcagcgaa attgaagaac gtcgttggac accacgaggc   5100
cgccactaat atcgttaaag attacaggta cacgtacgat aagtattttc tccacatgcc   5160
aatcactata aactttaaag ctaataagac cggctttatt aacgatcgca tccttcagta   5220
tatcgctaag gagaaggacc tgcacgttat aggaatagac cgcggcgagc gcaatcttat   5280
ctacgtgagc gtgatcgata cctgtgggaa tatagtcgag cagaagtctt ttaatatcgt   5340
gaacggctac gactatcaga taaagctgaa gcagcaagag ggcgctagac agatcgccag   5400
gaaggaatgg aaggagatcg gtaaaataaa agaaattaag gagggttacc tcagtttggt   5460
tatacatgag atatcaaaaa tggttattaa gtataatgcg attattgcga tggaagacct   5520
gtcatatggg tttaaaaaag ggcggttcaa ggttgagcgc caggtctatc aaaagtttga   5580
gactatgctg attaataagc tcaattatct tgttttcaaa gacatcagta tcacggaaaa   5640
cggaggactt ctcaaggggt accagttgac ttatatccca gacaagctta aaaatgttgg   5700
tcaccagtgt ggatgtatat tttatgtgcc tgcggcctac acatctaaga tcgacccaac   5760
aactggcttt gttaatattt ttaaattcaa agaccttacg gtggatgcga aaagagagtt   5820
cataaaaaaa ttcgactcga tcagatatga ctctgagaag aatctcttct gttttacttt   5880
cgactataat aatttcataa cacaaaatac cgtcatgtcg aaatcaagct ggtcagtcta   5940
cacatatggc gttcgcataa agcgccgctt cgttaatggc aggttctcga atgagtccga   6000
tacaatcgac attacgaagg atatggagaa aacactcgag atgacggata taaattggag   6060
ggatgggcat gatctgagac aggacataat agactatgag atagttcagc acatattcga   6120
```

-continued

```
gatcttcaga ctcactgttc agatgcggaa ctccctcagt gaacttgaag acagggatta    6180
tgataggctt atttctcctg tcctgaacga aaacaatatt ttctacgact ctgctaaagc    6240
aggggatgct cttcctaagg atgcagacgc aaatggcgca tactgcatag ctcttaaagg    6300
gctctatgag atcaagcaga ttacagaaaa ctggaaagaa gacgggaagt tttccagaga    6360
caaattgaag atctccaaca aggactggtt cgattttata caaaataaaa ggtaccttaa    6420
gcgtcctgct gccaccaaaa aggccggaca ggctaagaaa aagaagtgag acgactagtg    6480
gcggccgccg acgtccgatc gttcaaacat ttggcaataa agtttcttaa gattgaatcc    6540
tgttgccggt cttgcgatga ttatcatata atttctgttg aattacgtta agcatgtaat    6600
aattaacatg taatgcatga cgttatttat gagatgggtt tttatgatta gagtcccgca    6660
attatacatt taatacgcga tagaaaacaa aatatagcgc gcaaactagg ataaattatc    6720
gcgcgcggtg tcatctatgt tactagatcg ggaattgatc cccctcgac agcttccgga    6780 aagggcgaat cgcaactttt gtatacaaaa gttgaacgag aaacgtaaaa tgatataaat    6840
atcaatatat taaattagat tttgcataaa aaacagacta cataatactg taaaacacaa    6900
catatccagt cactatgcca tccagctgat atcccctata gtgagtcgta ttacatggtc    6960
atagctgttt cctggcagct ctggcccgtg tctcaaaatc tctgatgtta cattgcacaa    7020
gataaaaata tatcatcatg cctcctc                                        7047
```

```
<210> SEQ ID NO 24
<211> LENGTH: 3181
<212> TYPE: DNA
<213> ORGANISM: Artificial Sequence
<220> FEATURE:
<223> OTHER INFORMATION: Synthetic construct

<400> SEQUENCE: 24
ctgcattaat gaatcggcca acgcgcgggg agaggcggtt tgcgtattgg gcgctcttcc      60
gcttcctcgc tcactgactc gctgcgctcg tcgttcggc tgcggcgagc ggtatcagct     120
cactcaaagg cggtaatacg gttatccaca gaatcagggg ataacgcagg aaagaacatg     180
aattaattct catgtttgac agcttatcat cgattagctt taatgcggta gtttatcaca     240
gttaaattgc taacgcagtc aggcaccgtg tatgaaatct aacaatgcgc tcatcgtcat     300
cctcggcacc gtcaccctgg atgctgtagg cataggcttg gttatgccgg tactgccggg     360
cctcttgcgg gatatcgtcc attccgacag catcgccagt cactatggcg tgctgctagc     420
gctatatgcg ttgatgcaat ttctatgcgc acccgttctc ggagcactgt ccgaccgctt     480
tggccgccgc ccagtcctgc tcgcttcgct acttggagcc actatcgact acgcgatcat     540
ggcgaccaca cccgtcctgt ggattctcta cgccggacgc atcgtggccg gcatcaccgg     600
cgccacaggt gcggttgctg gcgcctatat cgccgacatc accgatgggg aagatcgggc     660
tcgccacttc gggctcatga gcgcttgttt cggcgtgggt atggtggcag gccccgtggc     720
cgggggactg ttgggcgcca tctccttaca tgcaccattc cttgcggcgg cggtgctcaa     780
cggcctcaac ctactactgg gctgcttcct aatgcaggag tcgcataagg gagagcgccg     840
acccatgccc ttgagagcct tcaacccagt cagctcctc cggtgggcgc ggggcatgac     900
tatcgtcgcc gcacttatga ctgtcttctt tatcatgcaa ctcgtaggac aggtgccggc     960
agcgctctgg gtcattttcg gcgaggaccg ctttcgctgg agcgcgacga tgatcggcct    1020
gtcgcttgcg gtattcggaa tcttgcacgc cctcgctcaa gccttcgtca ctggtcccgc    1080
```

-continued

```
caccaaacgt ttcggcgaga agcaggccat tatcgccggc atggcggccg acgcgctggg     1140
ctacgtcttg ctggcgttcg cgacgcgagg ctggatggcc ttccccatta tgattcttct     1200
cgcttccggc ggcatcggga tgcccgcgtt gcaggccatg ctgtccaggc aggtagatga     1260
cgaccatcag ggacagcttc aaggatcgct cgcggctctt accagcctaa cttcgatcat     1320
tggaccgctg atcgtcacgg cgatttatgc cgcctcggcg agcacatgga acgggttggc     1380
atggattgta ggcgccgccc tataccttgt ctgcctcccc gcgttgcgtc gcggtgcatg     1440
gagccgggcc acctcgacct gaatggaagc cggcggcacc tcgctaacgg attcaccact     1500
ccaagaattg gagccaatca attcttgcgg agaactgtga atgcgcaaac caacccttga     1560
tcggggaaga acagtatgtc gagctatttt ttgacttact ggggatcaag cctgattggg     1620
agaaaataaa atatcccta tagtgagtcg tattacatgg tcatagctgt ttcctggcag     1680
ctctggcccg tgtctcaaaa tctctgatgt tacattgcac aagataaaaa tatatcatca     1740
tgcctcctct agaggtctcg ctataaatta ctgatgagtc cgtgaggacg aaacgagtaa     1800
gctcgtctaa tttctactaa gtgtagatga gacggagctc agtctgaccg cggcgtctct     1860
ggccggcatg gtcccagcct cctcgctggc gccggctggg caacatgctt cggcatggcg     1920
aatgggacca tgggagaccc tcgagccacc catgaccaaa atcccttaac gtgagttacg     1980
cgtcgttcca ctgagcgtca gaccccgtag aaaagatcaa aggatcttct tgagatcctt     2040
tttttctgcg cgtaatctgc tgcttgcaaa caaaaaaacc accgctacca gcggtggttt     2100
gtttgccgga tcaagagcta ccaactcttt ttccgaaggt aactggcttc agcagagcgc     2160
agataccaaa tactgttctt ctagtgtagc cgtagttagg ccaccacttc aagaactctg     2220
tagcaccgcc tacatacctc gctctgctaa tcctgttacc agtggctgct gccagtggcg     2280
ataagtcgtg tcttaccggg ttggactcaa gacgatagtt accggataag cgcagcggt     2340 cgggctgaac ggggggttcg tgcacacagc ccagcttgga gcgaacgacc tacaccgaac     2400
tgagatacct acagcgtgag ctatgagaaa gcgccacgct tcccgaaggg agaaaggcgg     2460
acaggtatcc ggtaagcggc agggtcggaa caggagagcg cacgagggag cttccagggg     2520
gaaacgcctg gtatctttat agtcctgtcg ggtttcgcca cctctgactt gagcgtcgat     2580
ttttgtgatg ctcgtcaggg gggcggagcc tatggaaaaa cgccagcaac gcggcctttt     2640
tacggttcct ggccttttgc tggccttttg ctcacatgtt ctttcctgcg ttatcccctg     2700
attctgtgga taaccgtatt accgcctttg agtgagctga taccgctcgc cgcagccgaa     2760
cgaccgagcg cagcgagtca gtgagcgagg aagcggaaga gcgcccaata cgcaaaccgc     2820
ctctccccgc gcgttggccg attcattaat gcagctggca cgacaggttt cccgactgga     2880
aagcgggcag tgagcgcaac gcaattaata cgcgtaccgc tagccaggaa gagtttgtag     2940
aaacgcaaaa aggccatccg tcaggatggc cttctgctta gtttgatgcc tggcagttta     3000
tggcgggcgt cctgcccgcc accctccggg ccgttgcttc acaacgttca aatccgctcc     3060
cggcggattt gtcctactca ggagagcgtt caccgacaaa caacagataa aacgaaaggc     3120
ccagtcttcc gactgagcct ttcgttttat ttgatgcctg gcagttccct actctcgcgt     3180
t                                                                     3181
```

<210> SEQ ID NO 25
<211> LENGTH: 3181
<212> TYPE: DNA
<213> ORGANISM: Artificial Sequence
<220> FEATURE:
<223> OTHER INFORMATION: Synthetic construct -continued

<400> SEQUENCE: 25

```
ctgcattaat gaatcggcca acgcgcgggg agaggcggtt tgcgtattgg gcgctcttcc      60
gcttcctcgc tcactgactc gctgcgctcg gtcgttcggc tgcggcgagc ggtatcagct     120
cactcaaagg cggtaatacg gttatccaca gaatcagggg ataacgcagg aaagaacatg     180
aattaattct catgtttgac agcttatcat cgattagctt taatgcggta gtttatcaca     240
gttaaattgc taacgcagtc aggcaccgtg tatgaaatct aacaatgcgc tcatcgtcat     300
cctcggcacc gtcaccctgg atgctgtagg cataggcttg gttatgccgg tactgccggg     360
cctcttgcgg gatatcgtcc attccgacag catcgccagt cactatggcg tgctgctagc     420
gctatatgcg ttgatgcaat ttctatgcgc acccgttctc ggagcactgt ccgaccgctt     480
tggccgccgc ccagtcctgc tcgcttcgct acttggagcc actatcgact acgcgatcat     540
ggcgaccaca cccgtcctgt ggattctcta cgccggacgc atcgtggccg gcatcaccgg     600
cgccacaggt gcggttgctg gcgcctatat cgccgacatc accgatgggg aagatcgggc     660
tcgccacttc gggctcatga gcgcttgttt cggcgtgggt atggtggcag gccccgtggc     720
cgggggactg ttgggcgcca tctccttaca tgcaccattc cttgcggcgg cggtgctcaa     780
cggcctcaac ctactactgg gctgcttcct aatgcaggag tcgcataagg gagagcgccg     840
acccatgccc ttgagagcct tcaacccagt cagctccttc cggtgggcgc ggggcatgac     900
tatcgtcgcc gcacttatga ctgtcttctt tatcatgcaa ctcgtaggac aggtgccggc     960
agcgctctgg gtcattttcg gcgaggaccg ctttcgctgg agcgcgacga tgatcggcct    1020
gtcgcttgcg gtattcggaa tcttgcacgc cctcgctcaa gccttcgtca ctggtcccgc    1080
caccaaacgt ttcggcgaga agcaggccat tatcgccggc atggcggccg acgcgctggg    1140
ctacgtcttg ctggcgttcg cgacgcgagg ctggatggcc ttccccatta tgattcttct    1200
cgcttccggc ggcatcggga tgcccgcgtt gcaggccatg ctgtccaggc aggtagatga    1260
cgaccatcag ggacagcttc aaggatcgct cgcggctctt accagcctaa cttcgatcat    1320
tggaccgctg atcgtcacgg cgatttatgc cgcctcggcg agcacatgga acgggttggc    1380
atggattgta ggcgccgccc tataccttgt ctgcctcccc gcgttgcgtc gcggtgcatg    1440
gagccgggcc acctcgacct gaatggaagc cggcggcacc tcgctaacgg attcaccact    1500
ccaagaattg gagccaatca attcttgcgg agaactgtga atgcgcaaac caaccccttga    1560 tcggggaaga acagtatgtc gagctatttt ttgacttact ggggatcaag cctgattggg    1620
agaaaataaa atatcccta tagtgagtcg tattacatgg tcatagctgt ttcctggcag    1680
ctctggcccg tgtctcaaaa tctctgatgt tacattgcac aagataaaaa tatatcatca    1740
tgcctcctct agaggtctcc catgaaatta ctgatgagtc cgtgaggacg aaacgagtaa    1800
gctcgtctaa tttctactaa gtgtagatga cggagctc agtctgaccg cggcgtctct    1860
ggccggcatg gtcccagcct cctcgctggc gccggctggg caacatgctt cggcatggcg    1920
aatgggacgg accgagaccc tcgagccacc catgaccaaa atcccttaac gtgagttacg    1980
cgtcgttcca ctgagcgtca gaccccgtag aaaagatcaa aggatcttct tgagatcctt    2040
tttttctgcg cgtaatctgc tgcttgcaaa caaaaaaacc accgctacca gcggtggttt    2100
gtttgccgga tcaagagcta ccaactcttt ttccgaaggt aactggcttc agcagagcgc    2160
agataccaaa tactgttctt ctagtgtagc cgtagttagg ccaccacttc aagaactctg    2220
tagcaccgcc tacatacctc gctctgctaa tcctgttacc agtggctgct gccagtggcg    2280
```

-continued

```
ataagtcgtg tcttaccggg ttggactcaa gacgatagtt accggataag gcgcagcggt      2340
cgggctgaac gggggttcg tgcacacagc ccagcttgga gcgaacgacc tacaccgaac       2400
tgagatacct acagcgtgag ctatgagaaa gcgccacgct tcccgaaggg agaaaggcgg      2460
acaggtatcc ggtaagcggc agggtcggaa caggagagcg cacgagggag cttccagggg      2520
gaaacgcctg gtatctttat agtcctgtcg ggtttcgcca cctctgactt gagcgtcgat      2580
ttttgtgatg ctcgtcaggg gggcggagcc tatggaaaaa cgccagcaac gcggcctttt      2640
tacggttcct ggccttttgc tggccttttg ctcacatgtt ctttcctgcg ttatcccctg      2700
attctgtgga taaccgtatt accgcctttg agtgagctga taccgctcgc cgcagccgaa      2760
cgaccgagcg cagcgagtca gtgagcgagg aagcggaaga gcgcccaata cgcaaaccgc      2820
ctctccccgc gcgttggccg attcattaat gcagctggca cgacaggttt cccgactgga      2880
aagcgggcag tgagcgcaac gcaattaata cgcgtaccgc tagccaggaa gagtttgtag      2940
aaacgcaaaa aggccatccg tcaggatggc cttctgctta gtttgatgcc tggcagttta      3000
tggcgggcgt cctgcccgcc accctccggg ccgttgcttc acaacgttca aatccgctcc      3060
cggcggattt gtcctactca ggagagcgtt caccgacaaa caacagataa aacgaaaggc      3120
ccagtcttcc gactgagcct ttcgttttat ttgatgcctg gcagttccct actctcgcgt      3180
t                                                                      3181

<210> SEQ ID NO 26
<211> LENGTH: 3181
<212> TYPE: DNA
<213> ORGANISM: Artificial Sequence
<220> FEATURE:
<223> OTHER INFORMATION: Synthetic construct

<400> SEQUENCE: 26
ctgcattaat gaatcggcca acgcgcgggg agaggcggtt tgcgtattgg gcgctcttcc        60
gcttcctcgc tcactgactc gctgcgctcg gtcgttcggc tgcggcgagc ggtatcagct       120
cactcaaagg cggtaatacg gttatccaca gaatcagggg ataacgcagg aaagaacatg       180
aattaattct catgtttgac agcttatcat cgattagctt taatgcggta gtttatcaca       240
gttaaattgc taacgcagtc aggcaccgtg tatgaaatct aacaatgcgc tcatcgtcat       300
cctcggcacc gtcaccctgg atgctgtagg cataggcttg gttatgccgg tactgccggg       360
cctcttgcgg gatatcgtcc attccgacag catcgccagt cactatggcg tgctgctagc       420
gctatatgcg ttgatgcaat ttctatgcgc acccgttctc ggagcactgt ccgaccgctt       480
tggccgccgc ccagtcctgc tcgcttcgct acttggagcc actatcgact acgcgatcat       540
ggcgaccaca cccgtcctgt ggattctcta cgccggacgc atcgtggccg gcatcaccgg       600
cgccacaggt gcggttgctg gcgcctatat cgccgacatc accgatgggg aagatcgggc       660
tcgccacttc gggctcatga gcgcttgttt cggcgtgggt atggtggcag ccccgtggc       720 cgggggactg ttgggcgcca tctccttaca tgcaccattc cttgcggcgg cggtgctcaa       780
cggcctcaac ctactactgg gctgcttcct aatgcaggag tcgcataagg gagagcgccg       840
acccatgccc ttgagagcct tcaacccagt cagctcctc cggtgggcgc ggggcatgac       900
tatcgtcgcc gcacttatga ctgtcttctt tatcatgcaa ctcgtaggac aggtgccggc       960
agcgctctgg gtcattttcg gcgaggaccg ctttcgctgg agcgcgacga tgatcggcct      1020
gtcgcttgcg gtattcggaa tcttgcacgc cctcgctcaa gccttcgtca ctggtcccgc      1080
caccaaacgt ttcggcgaga gcaggccat tatcgccggc atggcggccg acgcgctggg      1140
```

```
ctacgtcttg ctggcgttcg cgacgcgagg ctggatggcc ttccccatta tgattcttct      1200
cgcttccggc ggcatcggga tgcccgcgtt gcaggccatg ctgtccaggc aggtagatga      1260
cgaccatcag ggacagcttc aaggatcgct cgcggctctt accagcctaa cttcgatcat      1320
tggaccgctg atcgtcacgg cgatttatgc cgcctcggcg agcacatgga acgggttggc      1380
atggattgta ggcgccgccc tataccttgt ctgcctcccc gcgttgcgtc gcggtgcatg      1440
gagccgggcc acctcgacct gaatggaagc cggcggcacc tcgctaacgg attcaccact      1500
ccaagaattg gagccaatca attcttgcgg agaactgtga atgcgcaaac caacccttga      1560
tcggggaaga acagtatgtc gagctatttt ttgacttact ggggatcaag cctgattggg      1620
agaaaataaa atatcccta tagtgagtcg tattacatgg tcatagctgt ttcctggcag      1680
ctctggcccg tgtctcaaaa tctctgatgt tacattgcac aagataaaaa tatatcatca      1740
tgcctcctct agaggtctca ggacaaatta ctgatgagtc cgtgaggacg aaacgagtaa      1800
gctcgtctaa tttctactaa gtgtagatga gacggagctc agtctgaccg cggcgtctct      1860
ggccggcatg gtcccagcct cctcgctggc gccggctggg caacatgctt cggcatggcg      1920
aatgggaccc agggagaccc tcgagccacc catgaccaaa atcccttaac gtgagttacg      1980
cgtcgttcca ctgagcgtca gacccegtag aaaagatcaa aggatcttct tgagatcctt      2040
tttttctgcg cgtaatctgc tgcttgcaaa caaaaaaacc accgctacca gcggtggttt      2100
gtttgccgga tcaagagcta ccaactcttt ttccgaaggt aactggcttc agcagagcgc      2160
agataccaaa tactgttctt ctagtgtagc cgtagttagg ccaccacttc aagaactctg      2220
tagcaccgcc tacatacctc gctctgctaa tcctgttacc agtggctgct gccagtggcg      2280
ataagtcgtg tcttaccggg ttggactcaa gacgatagtt accggataag gcgcagcggt      2340
cgggctgaac ggggggttcg tgcacacagc ccagcttgga gcgaacgacc tacaccgaac      2400
tgagatacct acagcgtgag ctatgagaaa gcgccacgct tcccgaaggg agaaaggcgg      2460
acaggtatcc ggtaagcggc agggtcggaa caggagagcg cacgagggag cttccagggg      2520
gaaacgcctg gtatctttat agtcctgtcg ggtttcgcca cctctgactt gagcgtcgat      2580
ttttgtgatg ctcgtcaggg gggcggagcc tatggaaaaa cgccagcaac gcggcctttt      2640
tacggttcct ggccttttgc tggccttttg ctcacatgtt ctttcctgcg ttatcccctg      2700
attctgtgga taaccgtatt accgcctttg agtgagctga taccgctcgc cgcagccgaa      2760
cgaccgagcg cagcgagtca gtgagcgagg aagcggaaga gcgcccaata cgcaaaccgc      2820
ctctccccgc gcgttggccg attcattaat gcagctggca cgacaggttt cccgactgga      2880
aagcgggcag tgagcgcaac gcaattaata cgcgtaccgc tagccaggaa gagtttgtag      2940
aaacgcaaaa aggccatccg tcaggatggc cttctgctta gtttgatgcc tggcagttta      3000
tggcgggcgt cctgcccgcc accctccggg ccgttgcttc acaacgttca aatccgctcc      3060
cggcggattt gtcctactca ggagagcgtt caccgacaaa caacagataa aacgaaaggc      3120
ccagtcttcc gactgagcct ttcgtttat ttgatgcctg gcagttccct actctcgcgt      3180
t                                                                      3181
```

```
<210> SEQ ID NO 27
<211> LENGTH: 3181
<212> TYPE: DNA
<213> ORGANISM: Artificial Sequence
<220> FEATURE:
<223> OTHER INFORMATION: Synthetic construct
```

-continued

```
<400> SEQUENCE: 27
ctgcattaat gaatcggcca acgcgcgggg agaggcggtt tgcgtattgg gcgctcttcc      60
gcttcctcgc tcactgactc gctgcgctcg gtcgttcggc tgcggcgagc ggtatcagct     120
cactcaaagg cggtaatacg gttatccaca gaatcagggg ataacgcagg aaagaacatg     180
aattaattct catgtttgac agcttatcat cgattagctt taatgcggta gtttatcaca     240
gttaaattgc taacgcagtc aggcaccgtg tatgaaatct aacaatgcgc tcatcgtcat     300
cctcggcacc gtcaccctgg atgctgtagg cataggcttg gttatgccgg tactgccggg     360
cctcttgcgg gatatcgtcc attccgacag catcgccagt cactatggcg tgctgctagc     420
gctatatgcg ttgatgcaat ttctatgcgc acccgttctc ggagcactgt ccgaccgctt     480
tggccgccgc ccagtcctgc tcgcttcgct acttggagcc actatcgact acgcgatcat     540
ggcgaccaca cccgtcctgt ggattctcta cgccggacgc atcgtggccg gcatcaccgg     600
cgccacaggt gcggttgctg cgcctatat cgccgacatc accgatgggg aagatcgggc      660
tcgccacttc gggctcatga gcgcttgttt cggcgtgggt atggtggcag gccccgtggc     720 cggggggactg ttgggcgcca ctcccttaca tgcaccattc cttgcggcgg cggtgctcaa    780
cggcctcaac ctactactgg gctgcttcct aatgcaggag tcgcataagg gagagcgccg     840
acccatgccc ttgagagcct tcaacccagt cagctccttc cggtgggcgc ggggcatgac     900
tatcgtcgcc gcacttatga ctgtcttctt tatcatgcaa ctcgtaggac aggtgccggc     960
agcgctctgg gtcattttcg gcgaggaccg ctttcgctgg agcgcgacga tgatcggcct    1020
gtcgcttgcg gtattcggaa tcttgcacgc cctcgctcaa gccttcgtca ctggtcccgc    1080
caccaaacgt ttcggcgaga agcaggccat tatcgccggc atggcggccg acgcgctggg    1140
ctacgtcttg ctggcgttcg cgacgcgagg ctggatggcc ttccccatta tgattcttct    1200
cgcttccggc ggcatcggga tgcccgcgtt gcaggccatg ctgtccaggc aggtagatga    1260
cgaccatcag ggacagcttc aaggatcgct cgcggctctt accagcctaa cttcgatcat    1320
tggaccgctg atcgtcacgg cgatttatgc cgcctcggcg agcacatgga acgggttggc    1380
atggattgta ggcgccgccc tataccttgt ctgcctcccc gcgttgcgtc gcggtgcatg    1440
gagccgggcc acctcgacct gaatggaagc cggcggcacc tcgctaacgg attcaccact    1500
ccaagaattg gagccaatca attcttgcgg agaactgtga atgcgcaaac caaccccttga   1560 tcggggaaga acagtatgtc gagctatttt ttgacttact ggggatcaag cctgattggg    1620
agaaaataaa atatcccccta tagtgagtcg tattacatgg tcatagctgt ttcctggcag    1680
ctctggcccg tgtctcaaaa tctctgatgt tacattgcac aagataaaaa tatatcatca    1740
tgcctcctct agaggtctcg ccagaaatta ctgatgagtc cgtgaggacg aaacgagtaa    1800
gctcgtctaa tttctactaa gtgtagatga cacggagctc agtctgaccg cggcgtctct    1860
ggccggcatg gtcccagcct cctcgctggc gccggctggg caacatgctt cggcatggcg    1920
aatgggactg ttggagaccc tcgagccacc catgaccaaa atcccttaac gtgagttacg    1980
cgtcgttcca ctgagcgtca gaccccgtag aaaagatcaa aggatcttct tgagatcctt    2040 ttttctgcg cgtaatctgc tgcttgcaaa caaaaaaacc accgctacca gcggtggttt     2100
gtttgccgga tcaagagcta ccaactcttt ttccgaaggt aactggcttc agcagagcgc    2160
agataccaaa tactgttctt ctagtgtagc cgtagttagg ccaccacttc aagaactctg    2220
tagcaccgcc tacatacctc gctctgctaa tcctgttacc agtggctgct gccagtggcg    2280
ataagtcgtg tcttaccggg ttggactcaa gacgatagtt accggataag gcgcagcggt    2340
```

-continued cgggctgaac gggggttcg tgcacacagc ccagcttgga gcgaacgacc tacaccgaac        2400
tgagatacct acagcgtgag ctatgagaaa gcgccacgct tcccgaaggg agaaaggcgg        2460
acaggtatcc ggtaagcggc agggtcggaa caggagagcg cacgagggag cttccagggg        2520
gaaacgcctg gtatctttat agtcctgtcg ggtttcgcca cctctgactt gagcgtcgat        2580
ttttgtgatg ctcgtcaggg gggcggagcc tatggaaaaa cgccagcaac gcggcctttt        2640
tacggttcct ggccttttgc tggccttttg ctcacatgtt ctttcctgcg ttatcccctg        2700
attctgtgga taaccgtatt accgcctttg agtgagctga taccgctcgc cgcagccgaa        2760
cgaccgagcg cagcgagtca gtgagcgagg aagcggaaga gcgcccaata cgcaaaccgc        2820
ctctccccgc gcgttggccg attcattaat gcagctggca cgacaggttt cccgactgga        2880
aagcgggcag tgagcgcaac gcaattaata cgcgtaccgc tagccaggaa gagtttgtag        2940
aaacgcaaaa aggccatccg tcaggatggc cttctgctta gtttgatgcc tggcagttta        3000
tggcgggcgt cctgcccgcc accctccggg ccgttgcttc acaacgttca aatccgctcc        3060
cggcggattt gtcctactca ggagagcgtt caccgacaaa caacagataa aacgaaaggc        3120
ccagtcttcc gactgagcct ttcgttttat ttgatgcctg gcagttccct actctcgcgt        3180
t                                                                       3181

<210> SEQ ID NO 28
<211> LENGTH: 3180
<212> TYPE: DNA
<213> ORGANISM: Artificial Sequence
<220> FEATURE:
<223> OTHER INFORMATION: Synthetic construct

<400> SEQUENCE: 28
ctgcattaat gaatcggcca acgcgcgggg agaggcggtt tgcgtattgg gcgctcttcc          60
gcttcctcgc tcactgactc gctgcgctcg tcgttcggc tgcggcgagc ggtatcagct         120
cactcaaagg cggtaatacg gttatccaca gaatcagggg ataacgcagg aaagaacatg        180
aattaattct catgtttgac agcttatcat cgattagctt taatgcggta gtttatcaca        240
gttaaattgc taacgcagtc aggcaccgtg tatgaaatct aacaatgcgc tcatcgtcat        300
cctcggcacc gtcaccctgg atgctgtagg cataggcttg gttatgccgg tactgccggg        360
cctcttgcgg gatatcgtcc attccgacag catcgccagt cactatggcg tgctgctagc        420
gctatatgcg ttgatgcaat ttctatgcgc acccgttctc ggagcactgt ccgaccgctt        480
tggccgccgc ccagtcctgc tcgcttcgct acttggagcc actatcgact acgcgatcat        540
ggcgaccaca cccgtcctgt ggattctcta cgccggacgc atcgtggccg gcatcaccgg        600
cgccacaggt gcggttgctg gcgcctatat cgccgacatc accgatgggg aagatcgggc        660
tcgccacttc gggctcatga gcgcttgttt cggcgtgggt atggtggcag gccccgtggc        720
cgggggactg ttgggcgcca tctccttaca tgcaccattc cttgcggcgg cggtgctcaa        780
cggcctcaac ctactactgg gctgcttcct aatgcaggag tcgcataagg gagagcgccg        840
acccatgccc ttgagagcct tcaacccagt cagctccttc cggtgggcgc ggggcatgac        900
tatcgtcgcc gcacttatga ctgtcttctt tatcatgcaa ctcgtaggac aggtgccggc        960
agcgctctgg gtcattttcg gcgaggaccg ctttcgctgg agcgcgacga tgatcggcct       1020
gtcgcttgcg gtattcggaa tcttgcacgc cctcgctcaa gccttcgtca ctggtcccgc       1080
caccaaacgt ttcggcgaga gcaggccat atcgccggc atggcggccg acgcgctggg        1140

-continued

```
ctacgtcttg ctggcgttcg cgacgcgagg ctggatggcc ttccccatta tgattcttct      1200
cgcttccggc ggcatcggga tgcccgcgtt gcaggccatg ctgtccaggc aggtagatga      1260
cgaccatcag ggacagcttc aaggatcgct cgcggctctt accagcctaa cttcgatcat      1320
tggaccgctg atcgtcacgg cgatttatgc cgcctcggcg agcacatgga acgggttggc      1380
atggattgta ggcgccgccc tataccttgt ctgcctcccc gcgttgcgtc gcggtgcatg      1440
gagccgggcc acctcgacct gaatggaagc cggcggcacc tcgctaacgg attcaccact      1500
ccaagaattg gagccaatca attcttgcgg agaactgtga atgcgcaaac caaccccttga      1560 tcggggaaga acagtatgtc gagctatttt ttgacttact ggggatcaag cctgattggg      1620
agaaaataaa atatcccta tagtgagtcg tattacatgg tcatagctgt ttcctggcag      1680
ctctggcccg tgtctcaaaa tctctgatgt tacattgcac aagataaaaa tatatcatca      1740
tgcctcctct agaggtctcg ctataaatta ctgatgagtc cgtgaggacg aaacgagtaa      1800
gctcgtctaa tttctactct tgtagatgag acggagctca gtctgaccgc ggcgtctctg      1860
gccggcatgg tcccagcctc ctcgctggcg ccggctgggc aacatgcttc ggcatggcga      1920
atgggaccat gggagaccct cgagccaccc atgaccaaaa tcccttaacg tgagttacgc      1980
gtcgttccac tgagcgtcag accccgtaga aaagatcaaa ggatcttctt gagatccttt      2040
ttttctgcgc gtaatctgct gcttgcaaac aaaaaaacca ccgctaccag cggtggtttg      2100
tttgccggat caagagctac caactctttt tccgaaggta actggcttca gcagagcgca      2160
gataccaaat actgttcttc tagtgtagcc gtagttaggc caccacttca agaactctgt      2220
agcaccgcct acatacctcg ctctgctaat cctgttacca gtggctgctg ccagtggcga      2280
taagtcgtgt cttaccgggt tggactcaag acgatagtta ccggataagg cgcagcggtc      2340
gggctgaacg gggggttcgt gcacacagcc cagcttggag cgaacgacct acaccgaact      2400
gagataccta cagcgtgagc tatgagaaag cgccacgctt cccgaaggga gaaaggcgga      2460
caggtatccg gtaagcggca gggtcggaac aggagagcgc acgagggagc ttccaggggg      2520
aaacgcctgg tatctttata gtcctgtcgg gtttcgccac ctctgacttg agcgtcgatt      2580
tttgtgatgc tcgtcagggg ggcggagcct atggaaaaac gccagcaacg cggcctttt      2640 acggttcctg gccttttgct ggccttttgc tcacatgttc tttcctgcgt tatcccctga      2700
ttctgtggat aaccgtatta ccgcctttga gtgagctgat accgctcgcc gcagccgaac      2760
gaccgagcgc agcgagtcag tgagcgagga agcggaagag cgcccaatac gcaaaccgcc      2820
tctccccgcg cgttggccga ttcattaatg cagctggcac gacaggtttc ccgactggaa      2880
agcgggcagt gagcgcaacg caattaatac gcgtaccgct agccaggaag agtttgtaga      2940
aacgcaaaaa ggccatccgt caggatggcc ttctgcttag tttgatgcct ggcagtttat      3000
ggcgggcgtc ctgcccgcca ccctccgggc cgttgcttca caacgttcaa atccgctccc      3060
ggcggatttg tcctactcag gagagcgttc accgacaaac aacagataaa acgaaaggcc      3120
cagtcttccg actgagcctt tcgttttatt tgatgcctgg cagttcccta ctctcgcgtt      3180
```

<210> SEQ ID NO 29
<211> LENGTH: 3180
<212> TYPE: DNA
<213> ORGANISM: Artificial Sequence
<220> FEATURE:
<223> OTHER INFORMATION: Synthetic construct

<400> SEQUENCE: 29

```
ctgcattaat gaatcggcca acgcgcgggg agaggcggtt tgcgtattgg gcgctcttcc       60
```

-continued

```
gcttcctcgc tcactgactc gctgcgctcg gtcgttcggc tgcggcgagc ggtatcagct    120
cactcaaagg cggtaatacg gttatccaca gaatcagggg ataacgcagg aaagaacatg    180
aattaattct catgtttgac agcttatcat cgattagctt taatgcggta gtttatcaca    240
gttaaattgc taacgcagtc aggcaccgtg tatgaaatct aacaatgcgc tcatcgtcat    300
cctcggcacc gtcaccctgg atgctgtagg cataggcttg gttatgccgg tactgccggg    360
cctcttgcgg gatatcgtcc attccgacag catcgccagt cactatggcg tgctgctagc    420
gctatatgcg ttgatgcaat ttctatgcgc acccgttctc ggagcactgt ccgaccgctt    480
tggccgccgc ccagtcctgc tcgcttcgct acttggagcc actatcgact acgcgatcat    540
ggcgaccaca cccgtcctgt ggattctcta cgccggacgc atcgtggccg gcatcaccgg    600
cgccacaggt gcggttgctg gcgcctatat cgccgacatc accgatgggg aagatcgggc    660
tcgccacttc gggctcatga gcgcttgttt cggcgtgggt atggtggcag gccccgtggc    720 cggggggactg ttgggcgcca tctccttaca tgcaccattc cttgcggcgg cggtgctcaa    780
cggcctcaac ctactactgg gctgcttcct aatgcaggag tcgcataagg gagagcgccg    840
acccatgccc ttgagagcct tcaacccagt cagctccttc cggtgggcgc ggggcatgac    900
tatcgtcgcc gcacttatga ctgtcttctt tatcatgcaa ctcgtaggac aggtgccggc    960
agcgctctgg gtcattttcg gcgaggaccg ctttcgctgg agcgcgacga tgatcggcct   1020
gtcgcttgcg gtattcggaa tcttgcacgc cctcgctcaa gccttcgtca ctggtcccgc   1080
caccaaacgt ttcggcgaga agcaggccat tatcgccggc atggcggccg acgcgctggg   1140
ctacgtcttg ctggcgttcg cgacgcgagg ctggatggcc ttccccatta tgattcttct   1200
cgcttccggc ggcatcggga tgcccgcgtt gcaggccatg ctgtccaggc aggtagatga   1260
cgaccatcag ggacagcttc aaggatcgct cgcggctctt accagcctaa cttcgatcat   1320
tggaccgctg atcgtcacgg cgatttatgc cgcctcggcg agcacatgga acgggttggc   1380
atggattgta ggcgccgccc tataccttgt ctgcctcccc gcgttgcgtc gcggtgcatg   1440
gagccgggcc acctcgacct gaatggaagc cggcggcacc tcgctaacgg attcaccact   1500
ccaagaattg gagccaatca attcttgcgg agaactgtga atgcgcaaac caaccccttga  1560 tcggggaaga acagtatgtc gagctatttt ttgacttact ggggatcaag cctgattggg   1620 agaaataaa atatcccta tagtgagtcg tattacatgg tcatagctgt ttcctggcag    1680
ctctggcccg tgtctcaaaa tctctgatgt tacattgcac aagataaaaa tatatcatca   1740
tgcctcctct agaggtctcc catgaaatta ctgatgagtc cgtgaggacg aaacgagtaa   1800
gctcgtctaa tttctactct tgtagatgag acggagctca gtctgaccgc ggcgtctctg   1860
gccggcatgt cccagcctc ctcgctggcg ccggctgggc aacatgcttc ggcatggcga   1920
atgggacgga ccgagaccct cgagccaccc atgaccaaaa tcccttaacg tgagttacgc   1980
gtcgttccac tgagcgtcag accccgtaga aaagatcaaa ggatcttctt gagatccttt   2040
ttttctgcgc gtaatctgct gcttgcaaac aaaaaaacca ccgctaccag cggtggtttg   2100
tttgccggat caagagctac caactctttt tccgaaggta actggcttca gcagagcgca   2160
gataccaaat actgttcttc tagtgtagcc gtagttaggc caccacttca agaactctgt   2220
agcaccgcct acatacctcg ctctgctaat cctgttacca gtggctgctg ccagtggcga   2280
taagtcgtgt cttaccgggt tggactcaag acgatagtta ccggataagg cgcagcggtc   2340
gggctgaacg gggggttcgt gcacacagcc cagcttggag cgaacgacct acaccgaact   2400
```

-continued

```
gagataccta cagcgtgagc tatgagaaag cgccacgctt cccgaaggga gaaaggcgga    2460
caggtatccg gtaagcggca gggtcggaac aggagagcgc acgagggagc ttccaggggg    2520
aaacgcctgg tatctttata gtcctgtcgg gtttcgccac ctctgacttg agcgtcgatt    2580
tttgtgatgc tcgtcagggg ggcggagcct atggaaaaac gccagcaacg cggccttttt    2640
acggttcctg gccttttgct ggccttttgc tcacatgttc tttcctgcgt tatcccctga    2700
ttctgtggat aaccgtatta ccgcctttga gtgagctgat accgctcgcc gcagccgaac    2760
gaccgagcgc agcgagtcag tgagcgagga agcggaagag cgcccaatac gcaaaccgcc    2820
tctccccgcg cgttggccga ttcattaatg cagctggcac gacaggtttc ccgactggaa    2880
agcgggcagt gagcgcaacg caattaatac gcgtaccgct agccaggaag agtttgtaga    2940
aacgcaaaaa ggccatccgt caggatggcc ttctgcttag tttgatgcct ggcagtttat    3000
ggcgggcgtc ctgcccgcca ccctccgggc cgttgcttca caacgttcaa atccgctccc    3060
ggcggatttg tcctactcag gagagcgttc accgacaaac aacagataaa acgaaaggcc    3120
cagtcttccg actgagcctt tcgtttttt tgatgcctgg cagttcccta ctctcgcgtt    3180
```

```
<210> SEQ ID NO 30
<211> LENGTH: 3180
<212> TYPE: DNA
<213> ORGANISM: Artificial Sequence
<220> FEATURE:
<223> OTHER INFORMATION: Synthetic construct

<400> SEQUENCE: 30
ctgcattaat gaatcggcca acgcgcgggg agaggcggtt tgcgtattgg gcgctcttcc      60
gcttcctcgc tcactgactc gctgcgctcg tcgttcggc tgcggcgagc ggtatcagct     120
cactcaaagg cggtaatacg gttatccaca gaatcagggg ataacgcagg aaagaacatg     180
aattaattct catgtttgac agcttatcat cgattagctt taatgcggta gtttatcaca     240
gttaaattgc taacgcagtc aggcaccgtg tatgaaatct aacaatgcgc tcatcgtcat     300
cctcggcacc gtcaccctgg atgctgtagg cataggcttg gttatgccgg tactgccggg     360
cctcttgcgg gatatcgtcc attccgacag catcgccagt cactatggcg tgctgctagc     420
gctatatgcg ttgatgcaat ttctatgcgc acccgttctc ggagcactgt ccgaccgctt     480
tggccgccgc ccagtcctgc tcgcttcgct acttggagcc actatcgact acgcgatcat     540
ggcgaccaca cccgtcctgt ggattctcta cgccggacgc atcgtggccg gcatcaccgg     600
cgccacaggt gcggttgctg gcgcctatat cgccgacatc accgatgggg aagatcgggc     660
tcgccacttc gggctcatga gcgcttgttt cggcgtgggt atggtggcag gccccgtggc     720
cgggggactg ttgggcgcca tctccttaca tgcaccattc cttgcggcgg cggtgctcaa     780
cggcctcaac ctactactgg gctgcttcct aatgcaggag tcgcataagg gagagcgccg     840
acccatgccc ttgagagcct tcaacccagt cagctccttc cggtgggcgc ggggcatgac     900
tatcgtcgcc gcacttatga ctgtcttctt tatcatgcaa ctcgtaggac aggtgccggc     960
agcgctctgg gtcattttcg gcgaggaccg ctttcgctgg agcgcgacga tgatcggcct    1020
gtcgcttgcg gtattcggaa tcttgcacgc cctcgctcaa gccttcgtca ctggtcccgc    1080
caccaaacgt ttcggcgaga gcaggccat tatcgccggc atggcggccg acgcgctggg    1140
ctacgtcttg ctggcgttcg cgacgcgagg ctggatggcc ttccccatta tgattcttct    1200
cgcttccggc ggcatcggga tgcccgcgtt gcaggccatg ctgtccaggc aggtagatga    1260
cgaccatcag ggacagcttc aaggatcgct cgcggctctt accagcctaa cttcgatcat    1320
```

-continued

```
tggaccgctg atcgtcacgg cgatttatgc cgcctcggcg agcacatgga acgggttggc    1380
atggattgta ggcgccgccc tataccttgt ctgcctcccc gcgttgcgtc gcggtgcatg    1440
gagccgggcc acctcgacct gaatggaagc cggcggcacc tcgctaacgg attcaccact    1500
ccaagaattg gagccaatca attcttgcgg agaactgtga atgcgcaaac caacccttga    1560
tcggggaaga acagtatgtc gagctatttt ttgacttact ggggatcaag cctgattggg    1620
agaaaataaa atatcccta tagtgagtcg tattacatgg tcatagctgt ttcctggcag    1680
ctctggcccg tgtctcaaaa tctctgatgt tacattgcac aagataaaaa tatatcatca    1740
tgcctcctct agaggtctca ggacaaatta ctgatgagtc cgtgaggacg aaacgagtaa    1800
gctcgtctaa tttctactct tgtagatgag acggagctca gtctgaccgc ggcgtctctg    1860
gccggcatgg tcccagcctc ctcgctggcg ccggctgggc aacatgcttc ggcatggcga    1920
atgggaccca gggagaccct cgagccaccc atgaccaaaa tcccttaacg tgagttacgc    1980
gtcgttccac tgagcgtcag accccgtaga aaagatcaaa ggatcttctt gagatccttt    2040
ttttctgcgc gtaatctgct gcttgcaaac aaaaaaacca ccgctaccag cggtggtttg    2100
tttgccggat caagagctac caactctttt tccgaaggta actggcttca gcagagcgca    2160
gataccaaat actgttcttc tagtgtagcc gtagttaggc caccacttca agaactctgt    2220
agcaccgcct acatacctcg ctctgctaat cctgttacca gtggctgctg ccagtggcga    2280
taagtcgtgt cttaccgggt tggactcaag acgatagtta ccggataagg cgcagcggtc    2340
gggctgaacg gggggttcgt gcacacagcc cagcttggag cgaacgacct acaccgaact    2400
gagataccta cagcgtgagc tatgagaaag cgccacgctt cccgaaggga gaaaggcgga    2460
caggtatccg gtaagcggca gggtcggaac aggagagcgc acgagggagc ttccaggggg    2520
aaacgcctgg tatctttata gtcctgtcgg gtttcgccac ctctgacttg agcgtcgatt    2580
tttgtgatgc tcgtcagggg ggcggagcct atggaaaaac gccagcaacg cggccttttt    2640
acggttcctg gccttttgct ggccttttgc tcacatgttc tttcctgcgt tatcccctga    2700
ttctgtggat aaccgtatta ccgcctttga gtgagctgat accgctcgcc gcagccgaac    2760
gaccgagcgc agcgagtcag tgagcgagga agcggaagag cgcccaatac gcaaaccgcc    2820
tctccccgcg cgttggccga ttcattaatg cagctggcac gacaggtttc ccgactggaa    2880
agcgggcagt gagcgcaacg caattaatac gcgtaccgct agccaggaag agtttgtaga    2940
aacgcaaaaa ggccatccgt caggatggcc ttctgcttag tttgatgcct ggcagtttat    3000
ggcgggcgtc ctgcccgcca ccctccgggc cgttgcttca caacgttcaa atccgctccc    3060
ggcggatttg tcctactcag gagagcgttc accgacaaac aacagataaa acgaaaggcc    3120
cagtcttccg actgagcctt tcgtttattt tgatgcctgg cagttcccta ctctcgcgtt    3180
```

```
<210> SEQ ID NO 31
<211> LENGTH: 3180
<212> TYPE: DNA
<213> ORGANISM: Artificial Sequence
<220> FEATURE:
<223> OTHER INFORMATION: Synthetic construct

<400> SEQUENCE: 31
ctgcattaat gaatcggcca acgcgcgggg agaggcggtt tgcgtattgg gcgctcttcc     60
gcttcctcgc tcactgactc gctgcgctcg gtcgttcggc tgcggcgagc ggtatcagct    120
cactcaaagg cggtaatacg gttatccaca gaatcagggg ataacgcagg aaagaacatg    180
```

-continued

```
aattaattct catgtttgac agcttatcat cgattagctt taatgcggta gtttatcaca      240
gttaaattgc taacgcagtc aggcaccgtg tatgaaatct aacaatgcgc tcatcgtcat      300
cctcggcacc gtcaccctgg atgctgtagg cataggcttg gttatgccgg tactgccggg      360
cctcttgcgg gatatcgtcc attccgacag catcgccagt cactatggcg tgctgctagc      420
gctatatgcg ttgatgcaat ttctatgcgc acccgttctc ggagcactgt ccgaccgctt      480
tggccgccgc ccagtcctgc tcgcttcgct acttggagcc actatcgact acgcgatcat      540
ggcgaccaca cccgtcctgt ggattctcta cgccggacgc atcgtggccg gcatcaccgg      600
cgccacaggt gcggttgctg gcgcctatat cgccgacatc accgatgggg aagatcgggc      660
tcgccacttc gggctcatga gcgcttgttt cggcgtgggt atggtggcag gccccgtggc      720
cgggggactg ttgggcgcca tctccttaca tgcaccattc cttgcggcgg cggtgctcaa      780
cggcctcaac ctactactgg gctgcttcct aatgcaggag tcgcataagg gagagcgccg      840
acccatgccc ttgagagcct tcaacccagt cagctccttc cggtgggcgc ggggcatgac      900
tatcgtcgcc gcacttatga ctgtcttctt tatcatgcaa ctcgtaggac aggtgccggc      960
agcgctctgg gtcattttcg gcgaggaccg ctttcgctgg agcgcgacga tgatcggcct     1020
gtcgcttgcg gtattcggaa tcttgcacgc cctcgctcaa gccttcgtca ctggtcccgc     1080
caccaaacgt ttcggcgaga agcaggccat tatcgccggc atggcggccg acgcgctggg     1140
ctacgtcttg ctggcgttcg cgacgcgagg ctggatggcc ttccccatta tgattcttct     1200
cgcttccggc ggcatcggga tgcccgcgtt gcaggccatg ctgtccaggc aggtagatga     1260
cgaccatcag ggacagcttc aaggatcgct cgcggctctt accagcctaa cttcgatcat     1320
tggaccgctg atcgtcacgg cgatttatgc cgcctcggcg agcacatgga acgggttggc     1380
atggattgta ggcgccgccc tataccttgt ctgcctcccc gcgttgcgtc gcggtgcatg     1440
gagccgggcc acctcgacct gaatggaagc cggcggcacc tcgctaacgg attcaccact     1500
ccaagaattg gagccaatca attcttgcgg agaactgtga atgcgcaaac caacccttga     1560
tcggggaaga acagtatgtc gagctatttt ttgacttact ggggatcaag cctgattggg     1620
agaaaataaa atatccccta tagtgagtcg tattacatgg tcatagctgt ttcctggcag     1680
ctctggcccg tgtctcaaaa tctctgatgt tacattgcac aagataaaaa tatatcatca     1740
tgcctcctct agaggtctcg ccagaaatta ctgatgagtc cgtgaggacg aaacgagtaa     1800
gctcgtctaa tttctactct tgtagatgag acggagctca gtctgaccgc ggcgtctctg     1860
gccggcatgg tcccagcctc ctcgctggcg ccggctgggc aacatgcttc ggcatggcga     1920
atgggactgt tggagaccct cgagccaccc atgaccaaaa tcccttaacg tgagttacgc     1980
gtcgttccac tgagcgtcag accccgtaga aaagatcaaa ggatcttctt gagatccttt     2040
ttttctgcgc gtaatctgct gcttgcaaac aaaaaaacca ccgctaccag cggtggtttg     2100
tttgccggat caagagctac caactctttt tccgaaggta actggcttca gcagagcgca     2160
gataccaaat actgttcttc tagtgtagcc gtagttaggc caccacttca agaactctgt     2220
agcaccgcct acatacctcg ctctgctaat cctgttacca gtggctgctg ccagtggcga     2280
taagtcgtgt cttaccgggt tggactcaag acgatagtta ccggataagg cgcagcggtc     2340
gggctgaacg gggggttcgt gcacacagcc cagcttggag cgaacgacct acaccgaact     2400 gagatacota cagcgtgagc tatgagaaag cgccacgctt cccgaaggga aaaggcggga     2460
caggtatccg gtaagcggca gggtcggaac aggagagcgc acgagggagc ttccaggggg     2520
aaacgcctgg tatctttata gtcctgtcgg gtttcgccac ctctgacttg agcgtcgatt     2580
```

-continued

```
tttgtgatgc tcgtcagggg ggcggagcct atggaaaaac gccagcaacg cggccttttt     2640
acggttcctg gcctttttgct ggcctttttgc tcacatgttc tttcctgcgt tatcccctga    2700
ttctgtggat aaccgtatta ccgcctttga gtgagctgat accgctcgcc gcagccgaac      2760
gaccgagcgc agcgagtcag tgagcgagga agcggaagag cgcccaatac gcaaaccgcc      2820
tctccccgcg cgttggccga ttcattaatg cagctggcac gacaggtttc ccgactggaa      2880
agcgggcagt gagcgcaacg caattaatac gcgtaccgct agccaggaag agtttgtaga      2940
aacgcaaaaa ggccatccgt caggatggcc ttctgcttag tttgatgcct ggcagtttat      3000
ggcgggcgtc ctgcccgcca ccctccgggc cgttgcttca caacgttcaa atccgctccc      3060
ggcggatttg tcctactcag gagagcgttc accgacaaac aacagataaa acgaaaggcc      3120
cagtcttccg actgagcctt tcgtttatt tgatgcctgg cagttcccta ctctcgcgtt       3180
```

<210> SEQ ID NO 32
<211> LENGTH: 3180
<212> TYPE: DNA
<213> ORGANISM: Artificial Sequence
<220> FEATURE:
<223> OTHER INFORMATION: Synthetic construct

<400> SEQUENCE: 32

```
ctgcattaat gaatcggcca acgcgcgggg agaggcggtt tgcgtattgg gcgctcttcc      60
gcttcctcgc tcactgactc gctgcgctcg tcgttcggc tgcggcgagc ggtatcagct       120
cactcaaagg cggtaatacg gttatccaca gaatcagggg ataacgcagg aaagaacatg      180
aattaattct catgtttgac agcttatcat cgattagctt taatgcggta gtttatcaca      240
gttaaattgc taacgcagtc aggcaccgtg tatgaaatct aacaatgcgc tcatcgtcat      300
cctcggcacc gtcaccctgg atgctgtagg cataggcttg gttatgccgg tactgccggg      360
cctcttgcgg gatatcgtcc attccgacag catcgccagt cactatggcg tgctgctagc      420
gctatatgcg ttgatgcaat ttctatgcgc accgttctc ggagcactgt ccgaccgctt       480
tggccgccgc ccagtcctgc tcgcttcgct acttggagcc actatcgact acgcgatcat      540
ggcgaccaca cccgtcctgt ggattctcta cgccggacg atcgtggccg gcatcaccgg       600
cgccacaggt gcggttgctg gcgcctatat cgccgacatc accgatgggg aagatcgggc      660
tcgccacttc gggctcatga gcgcttgttt cggcgtgggt atggtggcag gccccgtggc      720
cgggggactg ttgggcgcca tctccttaca tgcaccattc cttgcggcgg cggtgctcaa      780
cggcctcaac ctactactgg gctgcttcct aatgcaggag tcgcataagg gagagcgccg      840
acccatgccc ttgagagcct tcaacccagt cagctccttc cggtgggcgc ggggcatgac      900
tatcgtcgcc gcacttatga ctgtcttctt tatcatgcaa ctcgtaggac aggtgccggc      960
agcgctctgg gtcattttcg gcgaggaccg ctttcgctgg agcgcgacga tgatcggcct      1020
gtcgcttgcg gtattcggaa tcttgcacgc cctcgctcaa gccttcgtca ctggtcccgc      1080
caccaaacgt ttcggcgaga gcaggccat tatcgccggc atggcggccg acgcgctggg      1140
ctacgtcttg ctggcgttcg cgacgcgagg ctggatggcc ttccccatta tgattcttct     1200
cgcttccggc ggcatcggga tgcccgcgtt gcaggccatg ctgtccaggc aggtagatga      1260
cgaccatcag ggacagcttc aaggatcgct cgcggctctt accagcctaa cttcgatcat      1320
tggaccgctg atcgtcacgg cgatttatgc cgcctcggcg agcacatgga acgggttggc      1380
atggattgta ggcgccgccc tataccttgt ctgcctcccc gcgttgcgtc gcggtgcatg      1440
```

-continued

```
gagccgggcc acctcgacct gaatggaagc cggcggcacc tcgctaacgg attcaccact    1500
ccaagaattg gagccaatca attcttgcgg agaactgtga atgcgcaaac caacccttga    1560
tcggggaaga acagtatgtc gagctatttt ttgacttact ggggatcaag cctgattggg    1620
agaaaataaa atatcccta tagtgagtcg tattacatgg tcatagctgt ttcctggcag    1680
ctctggcccg tgtctcaaaa tctctgatgt tacattgcac aagataaaaa tatatcatca    1740
tgcctcctct agaggtctcg ctataaatta ctgatgagtc cgtgaggacg aaacgagtaa    1800
gctcgtctaa tttctactgt tgtagatgag acggagctca gtctgaccgc ggcgtctctg    1860
gccggcatgg tcccagcctc ctcgctggcg ccggctgggc aacatgcttc ggcatggcga    1920
atgggaccat gggagaccct cgagccaccc atgaccaaaa tcccttaacg tgagttacgc    1980
gtcgttccac tgagcgtcag accccgtaga aaagatcaaa ggatcttctt gagatccttt    2040
ttttctgcgc gtaatctgct gcttgcaaac aaaaaaacca ccgctaccag cggtggtttg    2100
tttgccggat caagagctac caactctttt tccgaaggta actggcttca gcagagcgca    2160
gataccaaat actgttcttc tagtgtagcc gtagttaggc caccacttca agaactctgt    2220
agcaccgcct acatacctcg ctctgctaat cctgttacca gtggctgctg ccagtggcga    2280
taagtcgtgt cttaccgggt tggactcaag acgatagtta ccggataagg cgcagcggtc    2340
gggctgaacg gggggttcgt gcacacagcc cagcttggag cgaacgacct acaccgaact    2400
gagatacCta cagcgtgagc tatgagaaag cgccacgctt cccgaaggga gaaaggcgga    2460
caggtatccg gtaagcggca gggtcggaac aggagagcgc acgagggagc ttccaggggg    2520
aaacgcctgg tatctttata gtcctgtcgg gtttcgccac ctctgacttg agcgtcgatt    2580
tttgtgatgc tcgtcagggg ggcggagcct atggaaaaac gccagcaacg cggccttttt    2640
acggttcctg gccttttgct ggccttttgc tcacatgttc tttcctgcgt tatcccctga    2700
ttctgtggat aaccgtatta ccgcctttga gtgagctgat accgctcgcc gcagccgaac    2760
gaccgagcgc agcgagtcag tgagcgagga agcggaagag cgcccaatac gcaaaccgcc    2820
tctccccgcg cgttggccga ttcattaatg cagctggcac gacaggtttc ccgactggaa    2880
agcgggcagt gagcgcaacg caattaatac gcgtaccgct agccaggaag agtttgtaga    2940
aacgcaaaaa ggccatccgt caggatggcc ttctgcttag tttgatgcct ggcagtttat    3000
ggcgggcgtc ctgcccgcca ccctccgggc cgttgcttca caacgttcaa atccgctccc    3060
ggcggatttg tcctactcag gagagcgttc accgacaaac aacagataaa acgaaaggcc    3120
cagtcttccg actgagcctt tcgttttatt tgatgcctgg cagttcccta ctctcgcgtt    3180
```

<210> SEQ ID NO 33
<211> LENGTH: 3180
<212> TYPE: DNA
<213> ORGANISM: Artificial Sequence
<220> FEATURE:
<223> OTHER INFORMATION: Synthetic construct

<400> SEQUENCE: 33

```
ctgcattaat gaatcggcca acgcgcgggg agaggcggtt tgcgtattgg gcgctcttcc    60
gcttcctcgc tcactgactc gctgcgctcg tcgttcggc tgcggcgagc ggtatcagct    120
cactcaaagg cggtaatacg gttatccaca gaatcagggg ataacgcagg aaagaacatg    180
aattaattct catgtttgac agcttatcat cgattagctt taatgcggta gtttatcaca    240
gttaaattgc taacgcagtc aggcaccgtg tatgaaatct aacaatgcgc tcatcgtcat    300
cctcggcacc gtcaccctgg atgctgtagg cataggcttg gttatgccgg tactgccggg    360
```

-continued

```
cctcttgcgg gatatcgtcc attccgacag catcgccagt cactatggcg tgctgctagc      420
gctatatgcg ttgatgcaat ttctatgcgc acccgttctc ggagcactgt ccgaccgctt      480
tggccgccgc ccagtcctgc tcgcttcgct acttggagcc actatcgact acgcgatcat      540
ggcgaccaca cccgtcctgt ggattctcta cgccggacgc atcgtggccg gcatcaccgg      600
cgccacaggt gcggttgctg gcgcctatat cgccgacatc accgatgggg aagatcgggc      660
tcgccacttc gggctcatga gcgcttgttt cggcgtgggt atggtggcag gccccgtggc      720 cggggggactg ttgggcgcca tctccttaca tgcaccattc cttgcggcgg cggtgctcaa      780
cggcctcaac ctactactgg gctgcttcct aatgcaggag tcgcataagg gagagcgccg      840
acccatgccc ttgagagcct tcaacccagt cagctccttc cggtgggcgc ggggcatgac      900
tatcgtcgcc gcacttatga ctgtcttctt tatcatgcaa ctcgtaggac aggtgccggc      960
agcgctctgg gtcattttcg gcgaggaccg ctttcgctgg agcgcgacga tgatcggcct     1020
gtcgcttgcg gtattcggaa tcttgcacgc cctcgctcaa gccttcgtca ctggtcccgc     1080
caccaaacgt ttcggcgaga agcaggccat tatcgccggc atggcggccg acgcgctggg     1140
ctacgtcttg ctggcgttcg cgacgcgagg ctggatggcc ttccccatta tgattcttct     1200
cgcttccggc ggcatcggga tgcccgcgtt gcaggccatg ctgtccaggc aggtagatga     1260
cgaccatcag ggacagcttc aaggatcgct cgcggctctt accagcctaa cttcgatcat     1320
tggaccgctg atcgtcacgg cgatttatgc cgcctcggcg agcacatgga acgggttggc     1380
atggattgta ggcgccgccc tataccttgt ctgcctcccc gcgttgcgtc gcggtgcatg     1440
gagccgggcc acctcgacct gaatggaagc cggcggcacc tcgctaacgg attcaccact     1500
ccaagaattg gagccaatca attcttgcgg agaactgtga atgcgcaaac caacccttga     1560
tcggggaaga acagtatgtc gagctatttt ttgacttact ggggatcaag cctgattggg     1620
agaaaataaa atatcccta tagtgagtcg tattacatgg tcatagctgt ttcctggcag     1680
ctctggcccg tgtctcaaaa tctctgatgt tacattgcac aagataaaaa tatatcatca     1740
tgcctcctct agaggtctcc catgaaatta ctgatgagtc cgtgaggacg aaacgagtaa     1800
gctcgtctaa tttctactgt tgtagatgag acggagctca gtctgaccgc ggcgtctctg     1860
gccggcatgg tcccagcctc ctcgctggcg ccggctgggc aacatgcttc ggcatggcga     1920
atgggacgga ccgagaccct cgagccaccc atgaccaaaa tcccttaacg tgagttacgc     1980
gtcgttccac tgagcgtcag accccgtaga aaagatcaaa ggatcttctt gagatccttt     2040
ttttctgcgc gtaatctgct gcttgcaaac aaaaaaacca ccgctaccag cggtggtttg     2100
tttgccggat caagagctac caactctttt tccgaaggta actggcttca gcagagcgca     2160
gataccaaat actgttcttc tagtgtagcc gtagttaggc caccacttca agaactctgt     2220
agcaccgcct acatacctcg ctctgctaat cctgttacca gtggctgctg ccagtggcga     2280
taagtcgtgt cttaccgggt tggactcaag acgatagtta ccggataagg cgcagcggtc     2340
gggctgaacg gggggttcgt gcacacagcc cagcttggag cgaacgacct acaccgaact     2400
gagataccta cagcgtgagc tatgagaaag cgccacgctt cccgaaggga gaaaggcgga     2460
caggtatccg gtaagcggca gggtcggaac aggagagcgc acgagggagc ttccaggggg     2520
aaacgcctgg tatctttata gtcctgtcgg gtttcgccac ctctgacttg agcgtcgatt     2580
tttgtgatgc tcgtcagggg ggcggagcct atggaaaaac gccagcaacg cggccttttt     2640
acggttcctg gccttttgct ggccttttgc tcacatgttc tttcctgcgt tatcccctga     2700
```

-continued

```
ttctgtggat aaccgtatta ccgcctttga gtgagctgat accgctcgcc gcagccgaac      2760
gaccgagcgc agcgagtcag tgagcgagga agcggaagag cgcccaatac gcaaaccgcc      2820
tctccccgcg cgttggccga ttcattaatg cagctggcac gacaggtttc ccgactggaa      2880
agcgggcagt gagcgcaacg caattaatac gcgtaccgct agccaggaag agtttgtaga      2940
aacgcaaaaa ggccatccgt caggatggcc ttctgcttag tttgatgcct ggcagtttat      3000
ggcgggcgtc ctgcccgcca ccctccgggc cgttgcttca caacgttcaa atccgctccc      3060
ggcggatttg tcctactcag gagagcgttc accgacaaac aacagataaa acgaaaggcc      3120
cagtcttccg actgagcctt tcgttttatt tgatgcctgg cagttcccta ctctcgcgtt      3180
```

<210> SEQ ID NO 34
<211> LENGTH: 3180
<212> TYPE: DNA
<213> ORGANISM: Artificial Sequence
<220> FEATURE:
<223> OTHER INFORMATION: Synthetic construct

<400> SEQUENCE: 34

```
ctgcattaat gaatcggcca acgcgcgggg agaggcggtt tgcgtattgg gcgctcttcc        60
gcttcctcgc tcactgactc gctgcgctcg gtcgttcggc tgcggcgagc ggtatcagct       120
cactcaaagg cggtaatacg gttatccaca gaatcagggg ataacgcagg aaagaacatg       180
aattaattct catgtttgac agcttatcat cgattagctt taatgcggta gtttatcaca       240
gttaaattgc taacgcagtc aggcaccgtg tatgaaatct aacaatgcgc tcatcgtcat       300
cctcggcacc gtcaccctgg atgctgtagg cataggcttg gttatgccgg tactgccggg       360
cctcttgcgg gatatcgtcc attccgacag catcgccagt cactatggcg tgctgctagc       420
gctatatgcg ttgatgcaat ttctatgcgc accgttctc ggagcactgt ccgaccgctt       480
tggccgccgc ccagtcctgc tcgcttcgct acttggagcc actatcgact acgcgatcat       540
ggcgaccaca cccgtcctgt ggattctcta cgccggacgc atcgtggccg gcatcaccgg       600
cgccacaggt gcggttgctg gcgcctatat cgccgacatc accgatgggg aagatcgggc       660
tcgccacttc gggctcatga gcgcttgttt cggcgtgggt atggtggcag ccccgtggc       720 cggggactg ttgggcgcca tctccttaca tgcaccattc cttgcggcgg cggtgctcaa       780
cggcctcaac ctactactgg gctgcttcct aatgcaggag tcgcataagg gagagcgccg       840
acccatgccc ttgagagcct tcaacccagt cagctccttc cggtgggcgc ggggcatgac       900
tatcgtcgcc gcacttatga ctgtcttctt tatcatgcaa ctcgtaggac aggtgccggc       960
agcgctctgg gtcattttcg gcgaggaccg ctttcgctgg agcgcgacga tgatcggcct      1020
gtcgcttgcg gtattcggaa tcttgcacgc cctcgctcaa gccttcgtca ctggtcccgc      1080
caccaaacgt ttcggcgaga gcaggccat tatcgccggc atggcggccg acgcgctggg      1140
ctacgtcttg ctggcgttcg cgacgcgagg ctggatggcc ttccccatta tgattcttct      1200
cgcttccggc ggcatcggga tgcccgcgtt gcaggccatg ctgtccaggc aggtagatga      1260
cgaccatcag ggacagcttc aaggatcgct cgcggctctt accagcctaa cttcgatcat      1320
tggaccgctg atcgtcacgg cgatttatgc cgcctcggcg agcacatgga acgggttggc      1380
atggattgta ggcgccgccc tataccttgt ctgcctcccc gcgttgcgtc gcggtgcatg      1440
gagccgggcc acctcgacct gaatggaagc cggcggcacc tcgctaacgg attcaccact      1500
ccaagaattg gagccaatca attcttgcgg agaactgtga atgcgcaaac caaccccttga     1560 tcggggaaga acagtatgtc gagctatttt ttgacttact ggggatcaag cctgattggg     1620
```

-continued

```
agaaaataaa atatcccta tagtgagtcg tattacatgg tcatagctgt ttcctggcag      1680
ctctggcccg tgtctcaaaa tctctgatgt tacattgcac aagataaaaa tatatcatca      1740
tgcctcctct agaggtctca ggacaaatta ctgatgagtc cgtgaggacg aaacgagtaa      1800
gctcgtctaa tttctactgt tgtagatgag acggagctca gtctgaccgc ggcgtctctg      1860
gccggcatgg tcccagcctc ctcgctggcg ccggctgggc aacatgcttc ggcatggcga      1920
atgggaccca gggagaccct cgagccaccc atgaccaaaa tcccttaacg tgagttacgc      1980
gtcgttccac tgagcgtcag accccgtaga aaagatcaaa ggatcttctt gagatccttt      2040
ttttctgcgc gtaatctgct gcttgcaaac aaaaaaacca ccgctaccag cggtggtttg      2100
tttgccggat caagagctac caactctttt tccgaaggta actggcttca gcagagcgca      2160
gataccaaat actgttcttc tagtgtagcc gtagttaggc caccacttca agaactctgt      2220
agcaccgcct acatacctcg ctctgctaat cctgttacca gtggctgctg ccagtggcga      2280
taagtcgtgt cttaccgggt tggactcaag acgatagtta ccggataagg cgcagcggtc      2340
gggctgaacg gggggttcgt gcacacagcc cagcttggag cgaacgacct acaccgaact      2400
gagataccta cagcgtgagc tatgagaaag cgccacgctt cccgaaggga gaaaggcgga      2460
caggtatccg gtaagcggca gggtcggaac aggagagcgc acgagggagc ttccaggggg      2520
aaacgcctgg tatctttata gtcctgtcgg gtttcgccac ctctgacttg agcgtcgatt      2580
tttgtgatgc tcgtcagggg ggcggagcct atggaaaaac gccagcaacg cggccttttt      2640
acggttcctg gccttttgct ggcctttttgc tcacatgttc tttcctgcgt tatcccctga      2700
ttctgtggat aaccgtatta ccgcctttga gtgagctgat accgctcgcc gcagccgaac      2760
gaccgagcgc agcgagtcag tgagcgagga agcggaagag cgcccaatac gcaaaccgcc      2820
tctccccgcg cgttggccga ttcattaatg cagctggcac gacaggtttc ccgactggaa      2880
agcgggcagt gagcgcaacg caattaatac gcgtaccgct agccaggaag agtttgtaga      2940
aacgcaaaaa ggccatccgt caggatggcc ttctgcttag tttgatgcct ggcagtttat      3000
ggcgggcgtc ctgcccgcca ccctccgggc cgttgcttca caacgttcaa atccgctccc      3060
ggcggatttg tcctactcag gagagcgttc accgacaaac aacagataaa acgaaaggcc      3120
cagtcttccg actgagcctt tcgtttattt tgatgcctgg cagttcccta ctctcgcgtt      3180
```

<210> SEQ ID NO 35
<211> LENGTH: 3180
<212> TYPE: DNA
<213> ORGANISM: Artificial Sequence
<220> FEATURE:
<223> OTHER INFORMATION: Synthetic construct

<400> SEQUENCE: 35

```
ctgcattaat gaatcggcca acgcgcgggg agaggcggtt tgcgtattgg gcgctcttcc        60
gcttcctcgc tcactgactc gctgcgctcg gtcgttcggc tgcggcgagc ggtatcagct       120
cactcaaagg cggtaatacg gttatccaca gaatcagggg ataacgcagg aaagaacatg       180
aattaattct catgtttgac agcttatcat cgattagctt taatgcggta gtttatcaca       240
gttaaattgc taacgcagtc aggcaccgtg tatgaaatct aacaatgcgc tcatcgtcat       300
cctcggcacc gtcaccctgg atgctgtagg cataggcttg gttatgccgg tactgccggg       360
cctcttgcgg gatatcgtcc attccgacag catcgccagt cactatggcg tgctgctagc       420
gctatatgcg ttgatgcaat ttctatgcgc acccgttctc ggagcactgt ccgaccgctt       480
```

-continued

```
tggccgccgc ccagtcctgc tcgcttcgct acttggagcc actatcgact acgcgatcat      540
ggcgaccaca cccgtcctgt ggattctcta cgccggacgc atcgtggccg gcatcaccgg      600
cgccacaggt gcggttgctg gcgcctatat cgccgacatc accgatgggg aagatcgggc      660
tcgccacttc gggctcatga gcgcttgttt cggcgtgggt atggtggcag gccccgtggc      720 cggggggactg ttgggcgcca tctccttaca tgcaccattc cttgcggcgg cggtgctcaa      780
cggcctcaac ctactactgg gctgcttcct aatgcaggag tcgcataagg gagagcgccg      840
acccatgccc ttgagagcct tcaacccagt cagctccttc cggtgggcgc ggggcatgac      900
tatcgtcgcc gcacttatga ctgtcttctt tatcatgcaa ctcgtaggac aggtgccggc      960
agcgctctgg gtcattttcg gcgaggaccg ctttcgctgg agcgcgacga tgatcggcct     1020
gtcgcttgcg gtattcggaa tcttgcacgc cctcgctcaa gccttcgtca ctggtcccgc     1080
caccaaacgt ttcggcgaga agcaggccat tatcgccggc atggcggccg acgcgctggg     1140
ctacgtcttg ctggcgttcg cgacgcgagg ctggatggcc ttccccatta tgattcttct     1200
cgcttccggc ggcatcggga tgcccgcgtt gcaggccatg ctgtccaggc aggtagatga     1260
cgaccatcag ggacagcttc aaggatcgct cgcggctctt accagcctaa cttcgatcat     1320
tggaccgctg atcgtcacgg cgatttatgc cgcctcggcg agcacatgga acgggttggc     1380
atggattgta ggcgccgccc tataccttgt ctgcctcccc gcgttgcgtc gcggtgcatg     1440
gagccgggcc acctcgacct gaatggaagc cggcggcacc tcgctaacgg attcaccact     1500
ccaagaattg gagccaatca attcttgcgg agaactgtga atgcgcaaac caacccttga     1560
tcggggaaga acagtatgtc gagctatttt ttgacttact ggggatcaag cctgattggg     1620
agaaaataaa atatcccta tagtgagtcg tattacatgg tcatagctgt ttcctggcag     1680
ctctggcccg tgtctcaaaa tctctgatgt tacattgcac aagataaaaa tatatcatca     1740
tgcctcctct agaggtctcg ccagaaatta ctgatgagtc cgtgaggacg aaacgagtaa     1800
gctcgtctaa tttctactgt tgtagatgag acggagctca gtctgaccgc ggcgtctctg     1860
gccggcatgg tcccagcctc ctcgctggcg ccggctgggc aacatgcttc ggcatggcga     1920
atgggactgt tggagaccct cgagccaccc atgaccaaaa tcccttaacg tgagttacgc     1980
gtcgttccac tgagcgtcag accccgtaga aaagatcaaa ggatcttctt gagatccttt     2040
ttttctgcgc gtaatctgct gcttgcaaac aaaaaaacca ccgctaccag cggtggtttg     2100
tttgccggat caagagctac caactctttt tccgaaggta actggcttca gcagagcgca     2160
gataccaaat actgttcttc tagtgtagcc gtagttaggc caccacttca agaactctgt     2220
agcaccgcct acatacctcg ctctgctaat cctgttacca gtggctgctg ccagtggcga     2280
taagtcgtgt cttaccgggt tggactcaag acgatagtta ccggataagg cgcagcggtc     2340
gggctgaacg gggggttcgt gcacacagcc cagcttggag cgaacgacct acaccgaact     2400
gagataccta cagcgtgagc tatgagaaag cgccacgctt cccgaaggga aaaggcgga     2460 caggtatccg gtaagcggca gggtcggaac aggagagcgc acgagggagc ttccaggggg     2520
aaacgcctgg tatctttata gtcctgtcgg gtttcgccac ctctgacttg agcgtcgatt     2580
tttgtgatgc tcgtcagggg ggcggagcct atggaaaaac gccagcaacg cggccttttt     2640
acggttcctg gccttttgct ggccttttgc tcacatgttc tttcctgcgt tatcccctga     2700
ttctgtggat aaccgtatta ccgcctttga gtgagctgat accgctcgcc gcagccgaac     2760
gaccgagcgc agcgagtcag tgagcgagga agcggaagag cgcccaatac gcaaaccgcc     2820
tctccccgcg cgttggccga ttcattaatg cagctggcac gacaggtttc ccgactggaa     2880
```

-continued

```
agcgggcagt gagcgcaacg caattaatac gcgtaccgct agccaggaag agtttgtaga     2940
aacgcaaaaa ggccatccgt caggatggcc ttctgcttag tttgatgcct ggcagtttat     3000
ggcgggcgtc ctgcccgcca ccctccgggc cgttgcttca caacgttcaa atccgctccc     3060
ggcggatttg tcctactcag gagagcgttc accgacaaac aacagataaa acgaaaggcc     3120
cagtcttccg actgagcctt tcgttttatt tgatgcctgg cagttcccta ctctcgcgtt     3180
```

<210> SEQ ID NO 36
<211> LENGTH: 3313
<212> TYPE: DNA
<213> ORGANISM: Artificial Sequence
<220> FEATURE:
<223> OTHER INFORMATION: Synthetic construct

<400> SEQUENCE: 36

```
ctagataacg caggatcccc aagtggtggc tatcgagacc ggcgccgcta cagggcgcgt       60
cccattcgcc attcaggctg cgcaactgtt gggaagggcg atcggtgcgg gcctcttcgc      120
tattacgcca gctggcgaaa gggggatgtg ctgcaaggcg attaagttgg gtaacgccag      180
ggttttccca gtcacgacgt tgtaaaacga cggccagtga gcgcgcgtaa tacgactcac      240
tatagggcga attgggtacc gggccccccc tcgaggtcct ccagcttttg ttccctttag      300
tgagggttaa ttgcgcgctt ggcgtaatca tggtcatagc tgtttcctgt gtgaaattgt      360
tatccgctca caattccaca caacatacga gccggaagca taaagtgtaa agcctggggt      420
gcctaatgag tgagctaact cacattaatt gcgttgcgct cactgcccgc tttccaccgg      480
tggtctctgg acactagtaa gggcgaattc gacccagctt tcttgtacaa agttggcatt      540
ataaaaaata attgctcatc aatttgttgc aacgaacagg tcactatcag tcaaaataaa      600
atcattattt gccatccagc tgatatcccc tatagtgagt cgtattacat ggtcatagct      660
gtttcctggc agctctggcc cgtgtctcaa aatctctgat gttacattgc acaagataaa      720
aatatatcat catgcctcct ctggaccagc caggacagaa atgcctcgac ttcgctgctg      780
cccaaggttg ccgggtgacg cacaccgtgg aaacggatga aggcacgaac ccagtggaca      840
taagcctgtt cggttcgtaa ctgtaatgc aagtagcgta tgcgctcacg caactggtcc      900
agaaccttga ccgaacgcag cggtggtaac ggcgcagtgg cggttttcat ggcttgttat      960
gactgttttt ttggggtaca gtctatgcct cgggcatcca agcagcaagc gcgttacgcc     1020
gtgggtcgat gtttgatgtt atggagcagc aacgatgtta cgcagcaggg cagtcgccct     1080
aaaacaaagt taaacatcat gagggaagcg gtgatcgccg aagtatcgac tcaactatca     1140
gaggtagttg gcgtcatcga gcgccatctc gaaccgacgt tgctggccgt acatttgtac     1200
ggctccgcag tggatggcgg cctgaagcca cacagtgata ttgatttgct ggttacggtg     1260
accgtaaggc ttgatgaaac aacgcggcga gctttgatca cgacctttt ggaaacttcg     1320 gcttcccctg gagagagcga gattctccgc gctgtagaag tcaccattgt tgtgcacgac     1380
gacatcattc cgtggcgtta ccagctaag cgcgaactgc aatttggaga atggcagcgc     1440
aatgacattc ttgcaggtat cttcgagcca gccacgatcg acattgatct ggctatcttg     1500
ctgacaaaag caagagaaca tagcgttgcc ttggtaggtc cagcggcgga ggaactcttt     1560
gatccggttc ctgaacagga tctatttgag gcgctaaatg aaaccttaac gctatggaac     1620 tcgccgccg actgggctgg cgatgagcga aatgtagtgc ttacgttgtc ccgcatttgg     1680
tacagcgcag taaccggcaa aatcgcgccg aaggatgtcg ctgccgactg ggcaatggag     1740
```

-continued

```
cgcctgccgg cccagtatca gcccgtcata cttgaagcta gacaggctta tcttggacaa     1800
gaagaagatc gcttggcctc gcgcgcagat cagttggaag aatttgtcca ctacgtgaaa     1860
ggcgagatca ccaaggtagt cggcaaataa ccctcgagcc acccatgacc aaaatccctt     1920
aacgtgagtt acgcgtcgtt ccactgagcg tcagaccccg tagaaaagat caaaggatct     1980
tcttgagatc cttttttttct gcgcgtaatc tgctgcttgc aaacaaaaaa accaccgcta     2040
ccagcggtgg tttgtttgcc ggatcaagag ctaccaactc tttttccgaa ggtaactggc     2100
ttcagcagag cgcagatacc aaatactgtc cttctagtgt agccgtagtt aggccaccac     2160
ttcaagaact ctgtagcacc gcctacatac ctcgctctgc taatcctgtt accagtggct     2220
gctgccagtg gcgataagtc gtgtcttacc gggttggact caagacgata gttaccggat     2280
aaggcgcagc ggtcgggctg aacggggggt tcgtgcacac agcccagctt ggagcgaacg     2340
acctacaccg aactgagata cctacagcgt gagcattgag aaagcgccac gcttcccgaa     2400
gggagaaagg cggacaggta tccggtaagc ggcagggtcg aacaggaga gcgcacgagg     2460 gagcttccag ggggaaacgc ctggtatctt tatagtcctg tcgggtttcg ccacctctga     2520
cttgagcgtc gatttttgtg atgctcgtca gggggggcgga gcctatggaa aaacgccagc     2580
aacgcggcct ttttacggtt cctggccttt tgctggcctt ttgctcacat gttctttcct     2640
gcgttatccc ctgattctgt ggataaccgt attaccgcct ttgagtgagc tgataccgct     2700
cgccgcagcc gaacgaccga gcgcagcgag tcagtgagcg aggaagcgga agagcgccca     2760
atacgcaaac cgcctctccc cgcgcgttgg ccgattcatt aatgcagctg gcacgacagg     2820
tttcccgact ggaaagcggg cagtgagcgc aacgcaatta atacgcgtac cgctcgccag     2880
gaagagtttg tagaaacgca aaaaggccat ccgtcaggat ggccttctgc ttagtttgat     2940
gcctggcagt ttatggcggg cgtcctgccc gccaccctcc gggccgttgc ttcacaacgt     3000
tcaaatccgc tcccggcgga tttgtcctac tcaggagagc gttcaccgac aaacaacaga     3060
taaaacgaaa ggcccagtct tccgactgag cctttcgttt tatttgatgc ctggcagttc     3120
cctactctcg cgttaacgct tgcatggatg ttttcccagt cacgacgttg taaaacgacg     3180
gccagtctta agctcgggcc caaataatga ttttattttg actgatagtg acctgttcgt     3240
tgcaacaaat tgatgagcaa tgctttttta taatgccaac tttgtataca aaagttgccc     3300
catggcgttc cct                                                          3313
```

```
<210> SEQ ID NO 37
<211> LENGTH: 3313
<212> TYPE: DNA
<213> ORGANISM: Artificial Sequence
<220> FEATURE:
<223> OTHER INFORMATION: Synthetic construct

<400> SEQUENCE: 37
```

```
ctagataacg caggatcccc aagtggtggc tatcgagacc ggcgccgcta cagggcgcgt       60
cccattcgcc attcaggctg cgcaactgtt gggaagggcg atcggtgcgg gcctcttcgc      120
tattacgcca gctggcgaaa gggggatgtg ctgcaaggcg attaagttgg gtaacgccag      180
ggttttccca gtcacgacgt tgtaaaacga cggccagtga gcgcgcgtaa tacgactcac      240 tataggggcga attgggtacc gggccccccc tcgaggtcct ccagcttttg ttccctttat      300
tgagggttaa ttgcgcgctt ggcgtaatca tggtcatagc tgtttcctgt gtgaaattgt      360
tatccgctca caattccaca caacatacca gccggaagca taaagtgtaa agcctggggt      420
gcctaatgag tgagctaact cacattaatt gcgttgcgct cactgcccgc tttccaccgg      480
```

-continued

```
tggtctctcc agactagtaa gggcaaattc gacccagctt tcttgtacaa agttggcatt      540
ataaaaaata attgctcatc aatttgttgc aacgaacagg tcactatcag tcaaaataaa      600
atcattattt gccatccagc tgatatcccc tatagtgagt cgtattacat ggtcatagct      660
gtttcctggc agctctggcc cgtgtctcaa aatctctgat gttacattgc acaagataaa      720
aatatatcat catgcctcct ctggaccagc caggacagaa atgcctcgac ttcgctgctg      780
cccaaggttg ccgggtgacg cacaccgtgg aaacggatga aggcacgaac ccagtggaca      840
taagcctgtt cggttcgtaa gctgtaatgc aagtagcgta tgcgctcacg caactggtcc      900
agaaccttga ccgaacgcag cggtggtaac ggcgcagtgg cggttttcat ggcttgttat      960
gactgttttt ttggggtaca gtctatgcct cgggcatcca agcagcaagc gcgttacgcc     1020
gtgggtcgat gtttgatgtt atggagcagc aacgatgtta cgcagcaggg cagtcgccct     1080
aaaacaaagt taaacatcat gagggaagcg gtgatcgccg aagtatcgac tcaactatca     1140
gaggtagttg gcgtcatcga gcgccatctc gaaccgacgt tgctggccgt acatttgtac     1200
ggctccgcag tggatggcgg cctgaagcca cacagtgata ttgatttgct ggttacggtg     1260
accgtaaggc ttgatgaaac aacgcggcga gctttgatca acgacctttt ggaaacttcg     1320
gcttcccctg gagagagcga gattctccgc gctgtagaag tcaccattgt tgtgcacgac     1380
gacatcattc cgtggcgtta tccagctaag cgcgaactgc aatttggaga atggcagcgc     1440
aatgacattc ttgcaggtat cttcgagcca gccacgatcg acattgatct ggctatcttg     1500
ctgacaaaag caagagaaca tagcgttgcc ttggtaggtc cagcggcgga ggaactcttt     1560
gatccggttc ctgaacagga tctatttgag gcgctaaatg aaaccttaac gctatggaac     1620
tcgccgcccg actgggctgg cgatgagcga aatgtagtgc ttacgttgtc ccgcatttgg     1680
tacagcgcag taaccggcaa aatcgcgccg aaggatgtcg ctgccgactg ggcaatggag     1740
cgcctgccgg cccagtatca gcccgtcata cttgaagcta gacaggctta tcttggacaa     1800
gaagaagatc gcttggcctc gcgcgcagat cagttggaag aatttgtcca ctacgtgaaa     1860
ggcgagatca ccaaggtagt cggcaaataa ccctcgagcc acccatgacc aaaatccctt     1920
aacgtgagtt acgcgtcgtt ccactgagcg tcagaccccg tagaaaagat caaaggatct     1980
tcttgagatc cttttttct gcgcgtaatc tgctgcttgc aaacaaaaaa accaccgcta     2040
ccagcggtgg tttgtttgcc ggatcaagag ctaccaactc ttttttccgaa ggtaactggc     2100 ttcagcagag cgcagatacc aaatactgtc cttctagtgt agccgtagtt aggccaccac     2160
ttcaagaact ctgtagcacc gcctacatac ctcgctctgc taatcctgtt accagtggct     2220
gctgccagtg gcgataagtc gtgtcttacc gggttggact caagacgata gttaccggat     2280
aaggcgcagc ggtcgggctg aacggggggt tcgtgcacac agcccagctt ggagcgaacg     2340
acctacaccg aactgagata cctacagcgt gagcattgag aaagcgccac gcttcccgaa     2400
gggagaaagg cggacaggta tccggtaagc ggcaggtcg gaacaggaga gcgcacgagg     2460
gagcttccag ggggaaacgc ctggtatctt tatagtcctg tcgggtttcg ccacctctga     2520
cttgagcgtc gatttttgtg atgctcgtca gggggggcgga gcctatggaa aaacgccagc     2580
aacgcggcct ttttacggtt cctggccttt tgctggcctt ttgctcacat gttctttcct     2640
gcgttatccc ctgattctgt ggataaccgt attaccgcct ttgagtgagc tgataccgct     2700
cgccgcagcc gaacgaccga gcgcagcgag tcagtgagcg aggaagcgga agagcgccca     2760
atacgcaaac cgcctctccc cgcgcgttgg ccgattcatt aatgcagctg gcacgacagg     2820
```

-continued

```
tttcccgact ggaaagcggg cagtgagcgc aacgcaatta atacgcgtac cgctcgccag      2880
gaagagtttg tagaaacgca aaaaggccat ccgtcaggat ggccttctgc ttagtttgat      2940
gcctggcagt ttatggcggg cgtcctgccc gccaccctcc gggccgttgc ttcacaacgt      3000
tcaaatccgc tcccggcgga tttgtcctac tcaggagagc gttcaccgac aaacaacaga      3060
taaaacgaaa ggcccagtct tccgactgag cctttcgttt tatttgatgc ctggcagttc      3120
cctactctcg cgttaacgct tgcatggatg ttttcccagt cacgacgttg taaaacgacg      3180
gccagtctta agctcgggcc caaataatga ttttattttg actgatagtg acctgttcgt      3240
tgcaacaaat tgatgagcaa tgcttttttta taatgccaac tttgtataca aaagttgccc      3300
catggcgttc cct                                                          3313

<210> SEQ ID NO 38
<211> LENGTH: 3313
<212> TYPE: DNA
<213> ORGANISM: Artificial Sequence
<220> FEATURE:
<223> OTHER INFORMATION: Synthetic construct

<400> SEQUENCE: 38
ctagataacg caggatcccc aagtggtggc tatcgagacc ggcgccgcta cagggcgcgt        60
cccattcgcc attcaggctg cgcaactgtt gggaagggcg atcggtgcgg gcctcttcgc       120
tattacgcca gctggcgaaa gggggatgtg ctgcaaggcg attaagttgg gtaacgccag       180
ggttttccca gtcacgacgt tgtaaaacga cggccagtga gcgcgcgtaa tacgactcac       240
tatagggcga attgggtacc gggccccccc tcgaggtcct ccagcttttg ttccctttag       300
tgagggttaa ttgcgcgctt ggcgtaatca tggtcatagc tgtttcctgt gtgaaattgt       360
tatccgctca caattccaca caacatacga gccggaagca taaagtgtaa agcctggggt       420
gcctaatgag tgagctaact cacattaatt gcgttgcgct cactgcccgc tttccaccgg       480
tggtctcttg ttactagtaa gggcgaattc gacccagctt tcttgtacaa agttggcatt       540
ataaaaaata attgctcatc aatttgttgc aacgaacagg tcactatcag tcaaaataaa       600
atcattattt gccatccagc tgatatcccc tatagtgagt cgtattacat ggtcatagct       660
gtttcctggc agctctggcc cgtgtctcaa aatctctgat gttacattgc acaagataaa       720
aatatatcat catgcctcct ctggaccagc caggacagaa atgcctcgac ttcgctgctg       780
cccaaggttg ccgggtgacg cacaccgtgg aaacggatga aggcacgaac ccagtggaca       840
taagcctgtt cggttcgtaa gctgtaatgc aagtagcgta tgcgctcacg caactggtcc       900
agaaccttga ccgaacgcag cggtggtaac ggcgcagtgg cggttttcat ggcttgttat       960
gactgttttt ttggggtaca gtctatgcct cgggcatcca agcagcaagc gcgttacgcc      1020
gtgggtcgat gtttgatgtt atggagcagc aacgatgtta cgcagcaggg cagtcgccct      1080
aaaacaaagt taaacatcat gagggaagcg gtgatcgccg aagtatcgac tcaactatca      1140
gaggtagttg gcgtcatcga gcgccatctc gaaccgacgt tgctggccgt acatttgtac      1200
ggctccgcag tggatggcgg cctgaagcca cacagtgata ttgatttgct ggttacggtg      1260
accgtaaggc ttgatgaaac aacgcggcga gctttgatca acgacctttt ggaaacttcg      1320
gcttcccctg gagagagcga gattctccgc gctgtagaag tcaccattgt tgtgcacgac      1380
gacatcattc cgtggcgtta tccagctaag cgcgaactgc aatttggaga atggcagcgc      1440
aatgacattc ttgcaggtat cttcgagcca gccacgatcg acattgatct ggctatcttg      1500
ctgacaaaag caagagaaca tagcgttgcc ttggtaggtc cagcggcgga ggaactcttt      1560
```

-continued

```
gatccggttc ctgaacagga tctatttgag gcgctaaatg aaaccttaac gctatggaac      1620
tcgccgcccg actgggctgg cgatgagcga aatgtagtgc ttacgttgtc ccgcatttgg      1680
tacagcgcag taaccggcaa aatcgcgccg aaggatgtcg ctgccgactg ggcaatggag      1740
cgcctgccgg cccagtatca gcccgtcata cttgaagcta gacaggctta tcttggacaa      1800
gaagaagatc gcttggcctc gcgcgcagat cagttggaag aatttgtcca ctacgtgaaa      1860
ggcgagatca ccaaggtagt cggcaaataa ccctcgagcc acccatgacc aaaatccctt      1920
aacgtgagtt acgcgtcgtt ccactgagcg tcagaccccg tagaaaagat caaaggatct      1980
tcttgagatc cttttttct gcgcgtaatc tgctgcttgc aaacaaaaaa accaccgcta      2040
ccagcggtgg tttgtttgcc ggatcaagag ctaccaactc tttttccgaa ggtaactggc      2100
ttcagcagag cgcagatacc aaatactgtc cttctagtgt agccgtagtt aggccaccac      2160
ttcaagaact ctgtagcacc gcctacatac ctcgctctgc taatcctgtt accagtggct      2220
gctgccagtg gcgataagtc gtgtcttacc gggttggact caagacgata gttaccggat      2280
aaggcgcagc ggtcgggctg aacggggggt tcgtgcacac agcccagctt ggagcgaacg      2340
acctacaccg aactgagata cctacagcgt gagcattgag aaagcgccac gcttcccgaa      2400
gggagaaagg cggacaggta tccggtaagc ggcagggtcg aacaggaga gcgcacgagg      2460 gagcttccag gggggaaacgc ctggtatctt tatagtcctg tcgggtttcg ccacctctga      2520
cttgagcgtc gatttttgtg atgctcgtca gggggggcgga gcctatggaa aaacgccagc      2580
aacgcggcct ttttacggtt cctggccttt tgctggcctt ttgctcacat gttctttcct      2640
gcgttatccc ctgattctgt ggataaccgt attaccgcct ttgagtgagc tgataccgct      2700
cgccgcagcc gaacgaccga gcgcagcgag tcagtgagcg aggaagcgga agagcgccca      2760
atacgcaaac cgcctctccc cgcgcgttgg ccgattcatt aatgcagctg gcacgacagg      2820
tttcccgact ggaaagcggg cagtgagcgc aacgcaatta atacgcgtac cgctcgccag      2880
gaagagtttg tagaaacgca aaaaggccat ccgtcaggat ggccttctgc ttagtttgat      2940
gcctggcagt ttatggcggg cgtcctgccc gccaccctcc gggccgttgc ttcacaacgt      3000
tcaaatccgc tcccggcgga tttgtcctac tcaggagagc gttcaccgac aaacaacaga      3060
taaaacgaaa ggcccagtct tccgactgag cctttcgttt tatttgatgc ctggcagttc      3120
cctactctcg cgttaacgct tgcatggatg ttttcccagt cacgacgttg taaaacgacg      3180
gccagtctta agctcgggcc caaataatga ttttattttg actgatagtg acctgttcgt      3240
tgcaacaaat tgatgagcaa tgcttttttta taatgccaac tttgtataca aaagttgccc      3300
catggcgttc cct                                                        3313
```

<210> SEQ ID NO 39
<211> LENGTH: 5311
<212> TYPE: DNA
<213> ORGANISM: Artificial Sequence
<220> FEATURE:
<223> OTHER INFORMATION: Synthetic construct

<400> SEQUENCE: 39

```
cccaagtggt ggctatcgag accggcgccg ctacagggcg cgtcccattc gccattcagg       60
ctgcgcaact gttgggaagg gcgatcggtg cgggcctctt cgctattacg ccagctggcg      120 aaaggggggat gtgctgcaag gcgattaagt tgggtaacgc cagggttttc ccagtcacga      180
cgttgtaaaa cgacggccag tgagcgcgcg taatacgact cactataggg cgaattgggt      240
```

-continued

```
accgggcccc ccctcgaggt cctccagctt ttgttccctt tagtgagggt taattgcgcg     300
cttggcgtaa tcatggtcat agctgtttcc tgtgtgaaat tgttatccgc tcacaattcc     360
acacaacata cgagccggaa gcataaagtg taaagcctgg ggtgcctaat gagtgagcta     420
actcacatta attgcgttgc gctcactgcc cgctttccac cggtggtctc tggacactag     480
taagggcgaa ttcgacccag ctttcttgta caaagttggc attataaaaa ataattgctc     540
atcaatttgt tgcaacgaac aggtcactat cagtcaaaat aaaatcatta tttgccatcc     600
agctgatatc ccctatagtg agtcgtatta catggtcata gctgtttcct ggcagctctg     660
gcccgtgtct caaaatctct gatgttacat tgcacaagat aaaaatatat catcatgcct     720
cctctggacc agccaggaca gaaatgcctc gacttcgctg ctgcccaagg ttgccgggtg     780
acgcacaccg tggaaacgga tgaaggcacg aacccagtgg acataagcct gttcggttcg     840
taagctgtaa tgcaagtagc gtatgcgctc acgcaactgg tccagaacct tgaccgaacg     900
cagcggtggt aacggcgcag tggcggtttt catggcttgt tatgactgtt tttttggggt     960
acagtctatg cctcgggcat ccaagcagca agcgcgttac gccgtgggtc gatgtttgat    1020
gttatggagc agcaacgatg ttacgcagca gggcagtcgc cctaaaacaa agttaaacat    1080
catgagggaa gcggtgatcg ccgaagtatc gactcaacta tcagaggtag ttggcgtcat    1140
cgagcgccat ctcgaaccga cgttgctggc cgtacatttg tacggctccg cagtggatgg    1200
cggcctgaag ccacacagtg atattgattt gctggttacg gtgaccgtaa ggcttgatga    1260
aacaacgcgg cgagctttga tcaacgacct tttggaaact tcggcttccc ctggagagag    1320
cgagattctc cgcgctgtag aagtcaccat tgttgtgcac gacgacatca ttccgtggcg    1380
ttatccagct aagcgcgaac tgcaatttgg agaatggcag cgcaatgaca ttcttgcagg    1440
tatcttcgag ccagccacga tcgacattga tctggctatc ttgctgacaa aagcaagaga    1500
acatagcgtt gccttggtag gtccagcggc ggaggaactc tttgatccgg ttcctgaaca    1560
ggatctattt gaggcgctaa atgaaacctt aacgctatgg aactcgccgc ccgactgggc    1620
tggcgatgag cgaaatgtag tgcttacgtt gtcccgcatt tggtacagcg cagtaaccgg    1680
caaaatcgcg ccgaaggatg tcgctgccga ctgggcaatg gagcgcctgc cggcccagta    1740
tcagcccgtc atacttgaag ctagacaggc ttatcttgga caagaagaag atcgcttggc    1800
ctcgcgcgca gatcagttgg aagaatttgt ccactacgtg aaaggcgaga tcaccaaggt    1860
agtcggcaaa taaccctcga gccacccatg accaaaatcc cttaacgtga gttacgcgtc    1920
gttccactga cgtcagacc ccgtagaaaa gatcaaagga tcttcttgag atcctttttt    1980
tctgcgcgta atctgctgct tgcaaacaaa aaaaccaccg ctaccagcgg tggtttgttt    2040
gccggatcaa gagctaccaa ctcttttttcc gaaggtaact ggcttcagca gagcgcagat    2100
accaaatact gtccttctag tgtagccgta gttaggccac cacttcaaga actctgtagc    2160
accgcctaca tacctcgctc tgctaatcct gttaccagtg gctgctgcca gtggcgataa    2220
gtcgtgtctt accgggttgg actcaagacg atagttaccg gataaggcgc agcggtcggg    2280
ctgaacgggg ggttcgtgca cacagcccag cttggagcga acgacctaca ccgaactgag    2340
atacctacag cgtgagcatt gagaaagcgc cacgcttccc gaaggagaa aggcggacag    2400 gtatccggta agcggcaggg tcggaacagg agagcgcacg agggagcttc caggggggaaa    2460 cgcctggtat ctttatagtc ctgtcgggtt cgccacctc tgacttgagc gtcgattttt    2520
gtgatgctcg tcaggggggc ggagcctatg gaaaaacgcc agcaacgcgg cctttttacg    2580
gttcctggcc ttttgctggc cttttgctca catgttcttt cctgcgttat cccctgattc    2640
```

-continued

```
tgtggataac cgtattaccg cctttgagtg agctgatacc gctcgccgca gccgaacgac    2700
cgagcgcagc gagtcagtga gcgaggaagc ggaagagcgc ccaatacgca aaccgcctct    2760
ccccgcgcgt tggccgattc attaatgcag ctggcacgac aggtttcccg actggaaagc    2820
gggcagtgag cgcaacgcaa ttaatacgcg taccgctcgc caggaagagt ttgtagaaac    2880
gcaaaaaggc catccgtcag gatggccttc tgcttagttt gatgcctggc agtttatggc    2940
gggcgtcctg cccgccaccc tccgggccgt tgcttcacaa cgttcaaatc cgctcccggc    3000
ggatttgtcc tactcaggag agcgttcacc gacaaacaac agataaaacg aaaggcccag    3060
tcttccgact gagcctttcg ttttatttga tgcctggcag ttccctactc tcgcgttaac    3120
gcttgcatgg atgttttccc agtcacgacg ttgtaaaacg acggccagtc ttaagctcgg    3180
gcccaaataa tgattttatt ttgactgata gtgacctgtt cgttgcaaca aattgatgag    3240
caatgctttt ttataatgcc aactttgtat acaaaagttg ccccatggcg ttccctctag    3300
ataacgcact gcagtgcagc gtgacccggt cgtgcccctc tctagagata atgagcattg    3360
catgtctaag ttataaaaaa ttaccacata ttttttttgt cacacttgtt tgaagtgcag    3420
tttatctatc tttatacata tatttaaact ttactctacg aataatataa tctatagtac    3480
tacaataata tcagtgtttt agagaatcat ataaatgaac agttagacat ggtctaaagg    3540
acaattgagt attttgacaa caggactcta cagtttatc tttttagtgt gcatgtgttc    3600
tccttttttt ttgcaaatag cttcacctat ataatacttc atccatttta ttagtacatc    3660
catttagggt ttagggttaa tggttttat agactaattt ttttagtaca tctattttat    3720
tctattttag cctctaaatt aagaaaacta aaactctatt ttagtttttt tatttaataa    3780
tttagatata aaatagaata aaataaagtg actaaaaatt aaacaaatac cctttaagaa    3840
attaaaaaaa ctaaggaaac attttttcttg tttcgagtag ataatgccag cctgttaaac    3900
gccgtcgacg agtctaacgg acaccaacca gcgaaccagc agcgtcgcgt cgggccaagc    3960
gaagcagacg gcacggcatc tctgtcgctg cctctggacc cctctcgaga gttccgctcc    4020
accgttggac ttgctccgct gtcggcatcc agaaattgcg tggcggagcg gcagacgtga    4080
gccggcacgg caggcggcct cctcctcctc tcacggcacc ggcagctacg ggggattcct    4140
ttcccaccgc tccttcgctt tcccttcctc gcccgccgta ataaatagac accccctcca    4200
caccctcttt ccccaacctc gtgttgttcg gagcgcacac acacacaacc agatctcccc    4260
caaatccacc cgtcggcacc tccgcttcaa ggtacgccgc tcgtcctccc ccccccccc    4320 ctctctacct tctctagatc ggcgttccgg tccatggtta gggcccggta gttctacttc    4380
tgttcatgtt tgtgttagat ccgtgtttgt gttagatccg tgctgctagc gttcgtacac    4440
ggatgcgacc tgtacgtcag acacgttctg attgctaact tgccagtgtt tctctttggg    4500
gaatcctggg atggctctag ccgttccgca gacgggatcg atttcatgat tttttttgtt    4560
tcgttgcata gggtttggtt tgccctttc ctttatttca atatatgccg tgcacttgtt    4620
tgtcgggtca tcttttcatg cttttttttg tcttggttgt gatgatgtgg tctggttggg    4680
cggtcgttct agatcggagt agaattaatt ctgtttcaaa ctacctggtg gatttattaa    4740
ttttggatct gtatgtgtgt gccatacata ttcatagtta cgaattgaag atgatggatg    4800
gaaatatcga tctaggatag gtatacatgt tgatgcgggt tttactgatg catatacaga    4860
gatgcttttt gttcgcttgg ttgtgatgat gtggtgtggt tgggcggtcg ttcattcgtt    4920
ctagatcgga gtagaatact gtttcaaact acctggtgta tttattaatt ttggaactgt    4980
```

```
atgtgtgtgt catacatctt catagttacg agtttaagat ggatggaaat atcgatctag    5040
gataggtata catgttgatg tgggtttttac tgatgcatat acatgatggc atatgcagca    5100
tctattcata tgctctaacc ttgagtacct atctattata ataaacaagt atgttttata    5160
attattttga tcttgatata cttggatgat ggcatatgca gcagctatat gtggattttt    5220
ttagccctgc cttcatacgc tatttatttg cttggtactg tttcttttgt cgatgctcac    5280
cctgttgttt ggtgttactt ctgcagggat c                                    5311
```

<210> SEQ ID NO 40
<211> LENGTH: 5311
<212> TYPE: DNA
<213> ORGANISM: Artificial Sequence
<220> FEATURE:
<223> OTHER INFORMATION: Synthetic construct

<400> SEQUENCE: 40

```
cccaagtggt ggctatcgag accggcgccg ctacagggcg cgtcccattc gccattcagg      60
ctgcgcaact gttgggaagg gcgatcggtg cgggcctctt cgctattacg ccagctggcg     120 aaaggggggat gtgctgcaag gcgattaagt tgggtaacgc cagggttttc ccagtcacga    180
cgttgtaaaa cgacggccag tgagcgcgcg taatacgact cactataggg cgaattgggt     240
accgggcccc ccctcgaggt cctccagctt ttgttccctt tattgagggt taattgcgcg     300
cttggcgtaa tcatggtcat agctgtttcc tgtgtgaaat tgttatccgc tcacaattcc     360
acacaacata ccagccggaa gcataaagtg taaagcctgg ggtgcctaat gagtgagcta     420
actcacatta attgcgttgc gctcactgcc cgctttccac cggtggtctc tccagactag     480
taagggcaaa ttcgacccag ctttcttgta caaagttggc attataaaaa ataattgctc     540
atcaatttgt tgcaacgaac aggtcactat cagtcaaaat aaaatcatta tttgccatcc     600
agctgatatc ccctatagtg agtcgtatta catggtcata gctgtttcct ggcagctctg     660
gcccgtgtct caaaatctct gatgttacat tgcacaagat aaaaatatat catcatgcct     720
cctctggacc agccaggaca gaaatgcctc gacttcgctg ctgcccaagg ttgccgggtg     780
acgcacaccg tggaaacgga tgaaggcacg aacccagtgg acataagcct gttcggttcg     840
taagctgtaa tgcaagtagc gtatgcgctc acgcaactgg tccagaacct tgaccgaacg     900
cagcggtggt aacggcgcag tggcggtttt catggcttgt tatgactgtt ttttttgggt     960
acagtctatg cctcgggcat ccaagcagca agcgcgttac gccgtgggtc gatgtttgat    1020
gttatggagc agcaacgatg ttacgcagca gggcagtcgc cctaaaacaa agttaaacat    1080
catgagggaa gcggtgatcg ccgaagtatc gactcaacta tcagaggtag ttggcgtcat    1140
cgagcgccat ctcgaaccga cgttgctggc cgtacatttg tacggctccg cagtggatgg    1200
cggcctgaag ccacacagtg atattgattt gctggttacg gtgaccgtaa ggcttgatga    1260
aacaacgcgg cgagctttga tcaacgacct tttggaaact tcggcttccc ctggagagag    1320
cgagattctc cgcgctgtag aagtcaccat tgttgtgcac gacgacatca ttccgtggcg    1380
ttatccagct aagcgcgaac tgcaatttgg agaatggcag cgcaatgaca ttcttgcagg    1440
tatcttcgag ccagccacga tcgacattga tctggctatc ttgctgacaa aagcaagaga    1500
acatagcgtt gccttggtag gtccagcggc ggaggaactc tttgatccgg ttcctgaaca    1560
ggatctattt gaggcgctaa atgaaacctt aacgctatgg aactcgccgc ccgactgggc    1620
tggcgatgag cgaaatgtag tgcttacgtt gtcccgcatt tggtacagcg cagtaaccgg    1680
caaaatcgcg ccgaaggatg tcgctgccga ctgggcaatg gagcgcctgc cggcccagta    1740
```

-continued

```
tcagcccgtc atacttgaag ctagacaggc ttatcttgga caagaagaag atcgcttggc     1800
ctcgcgcgca gatcagttgg aagaatttgt ccactacgtg aaaggcgaga tcaccaaggt     1860
agtcggcaaa taaccctcga gccacccatg accaaaatcc cttaacgtga gttacgcgtc     1920
gttccactga gcgtcagacc ccgtagaaaa gatcaaagga tcttcttgag atcctttttt     1980
tctgcgcgta atctgctgct tgcaaacaaa aaaaccaccg ctaccagcgg tggtttgttt     2040
gccggatcaa gagctaccaa ctcttttttcc gaaggtaact ggcttcagca gagcgcagat     2100
accaaatact gtccttctag tgtagccgta gttaggccac cacttcaaga actctgtagc     2160
accgcctaca tacctcgctc tgctaatcct gttaccagtg gctgctgcca gtggcgataa     2220
gtcgtgtctt accgggttgg actcaagacg atagttaccg gataaggcgc agcggtcggg     2280
ctgaacgggg ggttcgtgca cacagcccag cttggagcga acgacctaca ccgaactgag     2340
atacctacag cgtgagcatt gagaaagcgc cacgcttccc gaagggagaa aggcggacag     2400
gtatccggta agcggcaggg tcggaacagg agagcgcacg agggagcttc caggggggaaa     2460 cgcctggtat ctttatagtc ctgtcgggtt cgccacctc tgacttgagc gtcgattttt     2520
gtgatgctcg tcaggggggc ggagcctatg gaaaaacgcc agcaacgcgg ccttttttacg     2580 gttcctggcc ttttgctggc cttttgctca catgttcttt cctgcgttat cccctgattc     2640
tgtggataac cgtattaccg cctttgagtg agctgatacc gctcgccgca gccgaacgac     2700
cgagcgcagc gagtcagtga gcgaggaagc ggaagagcgc ccaatacgca aaccgcctct     2760
ccccgcgcgt tggccgattc attaatgcag ctggcacgac aggtttcccg actggaaagc     2820
gggcagtgag cgcaacgcaa ttaatacgcg taccgctcgc caggaagagt ttgtagaaac     2880
gcaaaaaggc catccgtcag gatggccttc tgcttagttt gatgcctggc agtttatggc     2940
gggcgtcctg cccgccaccc tccgggccgt tgcttcacaa cgttcaaatc cgctcccggc     3000
ggatttgtcc tactcaggag agcgttcacc gacaaacaac agataaaacg aaaggcccag     3060
tcttccgact gagcctttcg ttttatttga tgcctggcag ttccctactc tcgcgttaac     3120
gcttgcatgg atgttttccc agtcacgacg ttgtaaaacg acggccagtc ttaagctcgg     3180
gcccaaataa tgattttatt ttgactgata gtgacctgtt cgttgcaaca aattgatgag     3240
caatgctttt ttataatgcc aactttgtat acaaaagttg ccccatggcg ttccctctag     3300
ataacgcact gcagtgcagc gtgacccggt cgtgcccctc tctagagata atgagcattg     3360
catgtctaag ttataaaaaa ttaccacata ttttttttgt cacacttgtt tgaagtgcag     3420
tttatctatc tttatacata tatttaaact ttactctacg aataatataa tctatagtac     3480
tacaataata tcagtgtttt agagaatcat ataaatgaac agttagacat ggtctaaagg     3540
acaattgagt attttgacaa caggactcta cagtttatc tttttagtgt gcatgtgttc     3600
tccttttttt ttgcaaatag cttcacctat ataatacttc atccatttta ttagtacatc     3660
catttagggt ttagggttaa tggttttat agactaattt ttttagtaca tctattttat     3720
tctattttag cctctaaatt aagaaaacta aaactctatt ttagtttttt tatttaataa     3780
tttagatata aaatagaata aaataaagtg actaaaaatt aaacaaatac cctttaagaa     3840
attaaaaaaa ctaaggaaac attttttctg tttcgagtag ataatgccag cctgttaaac     3900
gccgtcgacg agtctaacgg acaccaacca gcgaaccagc agcgtcgcgt cgggccaagc     3960
gaagcagacg gcacggcatc tctgtcgctg cctctcggacc cctctcgaga gttccgctcc     4020
accgttggac ttgctccgct gtcggcatcc agaaattgcg tggcggagcg gcagacgtga     4080
```

-continued

```
gccggcacgg caggcggcct cctcctcctc tcacggcacc ggcagctacg ggggattcct    4140
ttcccaccgc tccttcgctt tcccttcctc gcccgccgta ataaatagac acccctcca    4200 caccctcttt ccccaacctc gtgttgttcg gagcgcacac acacacaacc agatctcccc    4260
caaatccacc cgtcggcacc tccgcttcaa ggtacgccgc tcgtcctccc cccccccccc    4320
ctctctacct tctctagatc ggcgttccgg tccatggtta gggcccggta gttctacttc    4380
tgttcatgtt tgtgttagat ccgtgtttgt gttagatccg tgctgctagc gttcgtacac    4440
ggatgcgacc tgtacgtcag acacgttctg attgctaact tgccagtgtt tctctttggg    4500
gaatcctggg atggctctag ccgttccgca gacgggatcg atttcatgat ttttttttgtt    4560 tcgttgcata gggtttggtt tgcccttttc ctttatttca atatatgccg tgcacttgtt    4620
tgtcgggtca tcttttcatg cttttttttg tcttggttgt gatgatgtgg tctggttggg    4680
cggtcgttct agatcggagt agaattaatt ctgtttcaaa ctacctggtg gatttattaa    4740
ttttggatct gtatgtgtgt gccatacata ttcatagtta cgaattgaag atgatggatg    4800
gaaatatcga tctaggatag gtatacatgt tgatgcgggt tttactgatg catatacaga    4860
gatgcttttt gttcgcttgg ttgtgatgat gtggtgtggt tgggcggtcg ttcattcgtt    4920
ctagatcgga gtagaatact gtttcaaact acctggtgta tttattaatt ttggaactgt    4980
atgtgtgtgt catacatctt catagttacg agtttaagat ggatggaaat atcgatctag    5040
gataggtata catgttgatg tgggtttac tgatgcatat acatgatggc atatgcagca    5100
tctattcata tgctctaacc ttgagtacct atctattata ataaacaagt atgttttata    5160
attattttga tcttgatata cttggatgat ggcatatgca gcagctatat gtggatttt    5220 ttagccctgc cttcatacgc tatttatttg cttggtactg tttcttttgt cgatgctcac    5280
cctgttgttt ggtgttactt ctgcagggat c    5311
```

```
<210> SEQ ID NO 41
<211> LENGTH: 5286
<212> TYPE: DNA
<213> ORGANISM: Artificial Sequence
<220> FEATURE:
<223> OTHER INFORMATION: Synthetic construct

<400> SEQUENCE: 41
gatccccaag tggtggctat cgagaccggc gccgctacag ggcgcgtccc attcgccatt     60
caggctgcgc aactgttggg aagggcgatc ggtgcgggcc tcttcgctat tacgccagct    120
ggcgaaaggg ggatgtgctg caaggcgatt aagttgggta acgccagggt tttcccagtc    180
acgacgttgt aaaacgacgg ccagtgagcg cgcgtaatac gactcactat agggcgaatt    240
gggtaccggg ccccccctcg aggtcctcca gcttttgttc cctttagtga gggttaattg    300
cgcgcttggc gtaatcatgg tcatagctgt ttcctgtgtg aaattgttat ccgctcacaa    360
ttccacacaa catacgagcc ggaagcataa agtgtaaagc ctggggtgcc taatgagtga    420
gctaactcac attaattgcg ttgcgctcac tgcccgcttt ccaccggtgg tctcttgtta    480
ctagtttttt tgctagcaga tctaagggcg aattcgaccc agctttcttg tacaaagttg    540
gcattataaa aaataattgc tcatcaattt gttgcaacga acaggtcact atcagtcaaa    600
ataaaatcat tatttgccat ccagctgata tcccctatag tgagtcgtat tacatggtca    660
tagctgtttc ctggcagctc tggcccgtgt ctcaaaatct ctgatgttac attgcacaag    720
ataaaaatat atcatcatgc ctcctctgga ccagccagga cagaaatgcc tcgacttcgc    780
tgctgcccaa ggttgccggg tgacgcacac cgtggaaacg gatgaaggca cgaacccagt    840
```

```
ggacataagc ctgttcggtt cgtaagctgt aatgcaagta gcgtatgcgc tcacgcaact        900
ggtccagaac cttgaccgaa cgcagcggtg gtaacggcgc agtggcggtt ttcatggctt        960
gttatgactg tttttttggg gtacagtcta tgcctcgggc atccaagcag caagcgcgtt       1020
acgccgtggg tcgatgtttg atgttatgga gcagcaacga tgttacgcag cagggcagtc       1080
gccctaaaac aaagttaaac atcatgaggg aagcggtgat cgccgaagta tcgactcaac       1140
tatcagaggt agttggcgtc atcgagcgcc atctcgaacc gacgttgctg gccgtacatt       1200
tgtacggctc cgcagtggat ggcggcctga agccacacag tgatattgat ttgctggtta       1260
cggtgaccgt aaggcttgat gaaacaacgc ggcgagcttt gatcaacgac cttttggaaa       1320
cttcggcttc ccctggagag agcgagattc tccgcgctgt agaagtcacc attgttgtgc       1380
acgacgacat cattccgtgg cgttatccag ctaagcgcga actgcaattt ggagaatggc       1440
agcgcaatga cattcttgca ggtatcttcg agccagccac gatcgacatt gatctggcta       1500
tcttgctgac aaaagcaaga gaacatacgc ttgccttggt aggtccagcg gcggaggaac       1560
tctttgatcc ggttcctgaa caggatctat ttgaggcgct aaatgaaacc ttaacgctat       1620
ggaactcgcc gcccgactgg gctggcgatg agcgaaatgt agtgcttacg ttgtcccgca       1680
tttggtacag cgcagtaacc ggcaaaatcg cgccgaagga tgtcgctgcc gactgggcaa       1740
tggagcgcct gccggcccag tatcagcccg tcatacttga agctagacag gcttatcttg       1800
gacaagaaga agatcgcttg gcctcgcgcg cagatcagtt ggaagaattt gtccactacg       1860
tgaaaggcga gatcaccaag gtagtcggca ataaccctc gagccaccca tgaccaaaat       1920
cccttaacgt gagttacgcg tcgttccact gagcgtcaga ccccgtagaa aagatcaaag       1980
gatcttcttg agatcctttt tttctgcgcg taatctgctg cttgcaaaca aaaaaaccac       2040
cgctaccagc ggtggtttgt ttgccggatc aagagctacc aactcttttt ccgaaggtaa       2100
ctggcttcag cagagcgcag ataccaaata ctgtccttct agtgtagccg tagttaggcc       2160
accacttcaa gaactctgta gcaccgccta catacctcgc tctgctaatc ctgttaccag       2220
tggctgctgc cagtggcgat aagtcgtgtc ttaccgggtt ggactcaaga cgatagttac       2280
cggataaggc gcagcggtcg ggctgaacgg ggggttcgtg cacacagccc agcttggagc       2340
gaacgaccta caccgaactg agatacctac agcgtgagca ttgagaaagc gccacgcttc       2400
ccgaagggag aaaggcggac aggtatccgg taagcggcag ggtcggaaca ggagagcgca       2460
cgagggagct tccaggggga aacgcctggt atctttatag tcctgtcggg tttcgccacc       2520
tctgacttga gcgtcgattt ttgtgatgct cgtcaggggg gcggagccta tggaaaaacg       2580
ccagcaacgc ggcctttta cggttcctgg ccttttgctg gccttttgct cacatgttct       2640
ttcctgcgtt atcccctgat tctgtggata accgtattac cgcctttgag tgagctgata       2700
ccgctcgccg cagccgaacg accgagcgca gcgagtcagt gagcgaggaa gcggaagagc       2760
gcccaatacg caaaccgcct ctccccgcgc gttggccgat tcattaatgc agctggcacg       2820
acaggtttcc cgactggaaa gcgggcagtg agcgcaacgc aattaatacg cgtaccgctc       2880
gccaggaaga gtttgtagaa acgcaaaaag gccatccgtc aggatggcct tctgcttagt       2940
ttgatgcctg gcagtttatg gcgggcgtcc tgcccgccac cctccgggcc gttgcttcac       3000
aacgttcaaa tccgctcccg gcggatttgt cctactcagg agagcgttca ccgacaaaca       3060
acagataaaa cgaaaggccc agtcttccga ctgagccttt cgttttattt gatgcctggc       3120
agttccctac tctcgcgtta acgcttgcat ggatgttttc ccagtcacga cgttgtaaaa       3180
```

-continued

```
cgacggccag tcttaagctc gggcccaaat aatgatttta ttttgactga tagtgacctg    3240
ttcgttgcaa caaattgatg agcaatgctt ttttataatg ccaactttgt atacaaaagt    3300
tgccccatgg cgttccctct agagagataa tgagcattgc atgtctaagt tataaaaaat    3360
taccacatat tttttttgtc acacttgttt gaagtgcagt ttatctatct ttatacatat    3420
atttaaactt tactctacga ataatataat ctatagtact acaataatat cagtgtttta    3480
gagaatcata taaatgaaca gttagacatg gtctaaagga caattgagta ttttgacaac    3540
aggactctac agttttatct ttttagtgtg catgtgttct cctttttttt tgcaaatagc    3600
ttcacctata taatacttca tccattttat tagtacatcc atttagggtt tagggttaat    3660 ggttttttata gactaatttt tttagtacat ctattttatt ctattttagc ctctaaatta    3720
agaaaactaa aactctattt tagttttttt atttaataat ttagatataa aatagaataa    3780
aataaagtga ctaaaaatta aacaaatacc ctttaagaaa ttaaaaaaac taaggaaaca    3840
tttttcttgt ttcgagtaga taatgccagc ctgttaaacg ccgtcgacga gtctaacgga    3900
caccaaccag cgaaccagca gcgtcgcgtc gggccaagcg aagcagacgg cacggcatct    3960
ctgtcgctgc ctctggaccc ctctcgagag ttccgctcca ccgttggact tgctccgctg    4020
tcggcatcca gaaattgcgt ggcggagcgg cagacgtgag ccggcacggc aggcggcctc    4080
ctcctcctct cacggcaccg gcagctacgg gggattcctt tcccaccgct ccttcgcttt    4140
cccttcctcg cccgccgtaa taaatagaca cccccctccac accctctttc cccaacctcg    4200
tgttgttcgg agcgcacaca cacacaacca gatctccccc aaatccaccc gtcggcacct    4260
ccgcttcaag gtacgccgct cgtcctcccc ccccccccc tctctacctt ctctagatcg    4320
gcgttccggt ccatggttag ggcccggtag ttctacttct gttcatgttt gtgttagatc    4380
cgtgtttgtg ttagatccgt gctgctagcg ttcgtacacg gatgcgacct gtacgtcaga    4440
cacgttctga ttgctaactt gccagtgttt ctctttgggg aatcctggga tggctctagc    4500
cgttccgcag acgggatcga tttcatgatt ttttttgttt cgttgcatag ggtttggttt    4560
gcccttttcc tttatttcaa tatatgccgt gcacttgttt gtcgggtcat cttttcatgc    4620
ttttttttgt cttggttgtg atgatgtggt ctggttgggc ggtcgttcta gatcggagta    4680
gaattaattc tgtttcaaac tacctggtgg atttattaat tttggatctg tatgtgtgtg    4740
ccatacatat tcatagttac gaattgaaga tgatggatgg aaatatcgat ctaggatagg    4800
tatacatgtt gatgcgggtt ttactgatgc atatacagag atgctttttg ttcgcttggt    4860
tgtgatgatg tggtgtggtt gggcggtcgt tcattcgttc tagatcggag tagaatactg    4920
tttcaaacta cctggtgtat ttattaattt tggaactgta tgtgtgtgtc atacatcttc    4980
atagttacga gtttaagatg gatggaaata tcgatctagg ataggtatac atgttgatgt    5040 gggtttttact gatgcatata catgatggca tatgcagcat ctattcatat gctctaacct    5100
tgagtaccta tctattataa taaacaagta tgttttataa ttattttgat cttgatatac    5160
ttggatgatg gcatatgcag cagctatatg tggattttt tagccctgcc ttcatacgct    5220
atttatttgc ttggtactgt ttcttttgtc gatgctcacc ctgttgtttg gtgttacttc    5280
tgcagg                                                                 5286
```

<210> SEQ ID NO 42
<211> LENGTH: 7069
<212> TYPE: DNA
<213> ORGANISM: Artificial Sequence
<220> FEATURE:
<223> OTHER INFORMATION: Synthetic construct -continued

```
<400> SEQUENCE: 42
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg gcgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagacccc gt agaaaagatc aaaggatctt cttgagatcc ttttttttctg    1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800 tgctcgtcag ggggggggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
```

-continued

```
ttgtcctact caggagagcg ttcaccgaca aacaacagat aaaacgaaag gcccagtctt   2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520
tgctttttta taatgccaac tttgtacaaa aaagcaggct ccgaattcgc ccttcaccat   2580
ggctcctaag aagaagcgga aggttggtat tcacggggtg cctgcggctt caaagctcga   2640
gaaattcacc aactgttatt cgttgagcaa aacactgcgg tttaaagcga ttccagtcgg   2700
caagactcaa gagaatatag acaataagcg gctgttggtg gaagatgaaa agcgcgcgga   2760
agactacaaa ggggtgaaga agttgttgga cagatactac ctctctttta tcaatgatgt   2820
cttgcactca atcaaattga agaatctgaa caactacatc tccctcttca gaaagaaaac   2880
aaggacagaa aaggagaata aggaacttga aaatttggag atcaatctga ggaaagagat   2940
cgcgaaagcc tttaaaggca acgaaggata caaaagtctg ttcaagaagg atataattga   3000
gacaattttg ccagagttcc tcgatgacaa ggacgagatt gcgctggtca attcgttcaa   3060
cggattcaca acagcattca caggcttctt tgataatcgg gaaaatatgt tctctgagga   3120
ggcaaagtcc acttctattg cgttcaggtg tatcaatgag aatctcacta ggtacatttc   3180
caacatggat atctttgaga aggttgacgc aattttttgac aagcacgaag ttcaggagat   3240
taaggagaag atcctcaatt ccgattatga cgttgaggac ttcttcgaag gtgagttttt   3300
taatttcgtg ctcactcaag agggtatcga cgtgtataat gcgatcatcg gtgggttcgt   3360
gactgagtcc ggtgaaaaga ttaagggatt gaacgagtat atcaacccttt acaaccaaaa   3420 gacgaaacag aagctgccaa agttcaagcc tctttacaaa caggttcttt cagaccgcga   3480
gtcactctcg ttctatgggg agggctacac ttcggatgag gaagtcctgg aggtgttcag   3540
gaatactctc aataagaatt cggagatttt ctcttctata aaaaaactgg aaaagttgtt   3600
taagaatttt gacgaatact ctagcgccgg catatttgtg aaaaacggcc cggccatatc   3660
aacgataagt aaagatatct cggcgaatg gaacgtgatc agagacaaat ggaacgcgga   3720
gtatgacgat attcacctga agaagaaggc tgtcgtaacg gagaagtacg aggatgatcg   3780
caggaaaagc ttcaaaaaga tcggaagttt cagcctggaa cagttgcagg agtatgctga   3840
cgccgatctt agcgtcgtcg agaagttgaa ggagataatc atccaaaagg tcgacgagat   3900
atataaagtc tatggatcaa gtgaaaaact gttcgacgcc gacttcgttt tggagaagtc   3960
cctgaagaag aacgacgctg ttgttgccat tatgaaggat ctgctcgaca gcgtgaagag   4020
tttcgagaac tatattaagg cttttttcgg ggaggggaag gagactaaca gagatgagtc   4080
cttctacgga gacttcgtcc tcgcgtacga tatactcctt aaggtagacc acatctacga   4140
cgcaatcaga aattacgtga cacaaaagcc gtacagcaag gacaagttca aactctactt   4200
ccagaacccc cagttcatgg gcggctggga caaggacaag gaaacggatt acaggctac    4260 gatcctgagg tatggttcaa aatactactt ggcgattatg gacaagaagt acgccaagtg   4320
tctccagaag attgacaaag acgatgtcaa tggcaattat gagaagatca actacaagct   4380
gcttccgggt ccgaacaaga tgctcccaaa ggttttcttc agcaagaaat ggatggccta   4440 ctataacca agcgaggaca tccagaagat ttataagaac ggtacgttca agaagggcga   4500
catgttcaat cttaacgact gtcacaagct gatcgacttc ttcaaagact caattagccg   4560
gtacccaaag tggtctaacg cctatgactt caactttttcg gaaaccgaga gtacaagga   4620 tatagccgga tttttatagag aggtggaaga gcagggctac aaggtgtcat tcgagtccgc   4680
```

-continued

```
cagcaagaag gaagtggaca agctcgtgga agagggtaag ctctacatgt tccagattta   4740
taataaagac tttagcgata agagccacgg gacacctaat ctccacacaa tgtatttcaa   4800
gctgctcttc gacgagaata accacggcca aatcaggttg tcaggagggg ctgaactctt   4860
catgcggcgc gctagcctta agaaggagga gcttgtagtc caccctgcga atagtccaat   4920
tgcgaataag aacccggaca atcctaaaaa gactacaaca ttgagctacg acgtgtacaa   4980
ggataagagg ttttccgagg atcagtacga gctccacatc ccgattgcga tcaacaagtg   5040
cccaaagaat attttcaaga taaacacaga ggtgcgtgta ctcctgaagc atgacgacaa   5100
tccttacgtc attgggattg ctcggggcga gaggaacctc ctctatattg tggtggtgga   5160
cgggaagggg aacatagtcg aacagtactc ccttaacgaa ataattaaca atttcaacgg   5220
catccgtatc aagaccgact accattcgtt gctggacaag aaggagaagg agagatttga   5280
ggcgcggcaa aattggacaa gtatcgagaa catcaaggaa ctcaaagcag gttatatctc   5340
tcaagttgtg cataagatat gcgagctggt tgagaagtat gacgcagtga tcgctcttga   5400
ggacctcaac tcgggcttta agaattctag agttaaagtg gagaagcagg tctatcaaaa   5460
gttcgagaag atgcttatag ataagctcaa ctacatggtc gataagaaat cgaacccatg   5520
tgccaccggc ggcgcactca aaggttacca aataacaaac aaattcgagt ccttcaaatc   5580
gatgagtact cagaatgggt tcatatttta tataccggcg tggcttacgt ctaagatcga   5640
cccgtcaact ggttttgtca acctgttgaa gacgaaatac acgtccattg ccgattcgaa   5700
aaagttcata tctagttttg atcgtattat gtacgtccca gaggaagatc ttttcgagtt   5760
tgctctcgac tacaaaaact tttcgcggac cgatgcggat tacattaaaa aatggaaact   5820
ctattcgtac ggcaacagaa tcaggatttt tcgcaaccct aagaagaata acgtctttga   5880
ttgggaggaa gtttgcttga ctagcgcgta caaggagctc tttaataagt atggcattaa   5940
ctaccaacag ggtgatatca gagcactgct ttgcgaacaa tctgacaagg ctttctactc   6000
atccttcatg gctttgatga gcctgatgct ccagatgaga aattcaatta caggcagaac   6060
cgacgtggat ttcttgatct ccccggttaa aaattctgat ggcatctttt acgatagcag   6120
gaactatgaa gcgcaagaga atgcgattct gccaaaaaat gcagacgcca acggtgccta   6180
taacatcgcc aggaaagtcc tgtgggcgat cggccagttc aaaaaggccg aagacgaaaa   6240
attggacaag gtcaaaatcg ctatcagcaa caaagagtgg ctggagtatg ctcagacatc   6300
cgtaaagcat aagcgtcctg ctgccaccaa aaaggccgga caggctaaga aaaagaaggg   6360
agacggctct ggatcggggt cgggttctgg ctcagtcgac cttgatcttg acctcgaact   6420
cagacttgga tttgctctcg atctcgacct tgaacttaga ctcggatttg ctcttgacct   6480
cgatcttgag cttagactcg gattcgctta ggacgtccga tcgttcaaac atttggcaat   6540
aaagtttctt aagattgaat cctgttgccg gtcttgcgat gattatcata taatttctgt   6600
tgaattacgt taagcatgta ataattaaca tgtaatgcat gacgttattt atgagatggg   6660 ttttttatgat tagagtcccg caattataca tttaatacgc gatagaaaac aaaatatagc   6720
gcgcaaacta ggataaatta tcgcgcgcgg tgtcatctat gttactagat cgggaattga   6780 tccccctcg acagcttccg gaaagggcga attcgcaact ttgtatacaa aagttgaacg   6840
agaaacgtaa aatgatataa atatcaatat attaaattag attttgcata aaaaacagac   6900
tacataatac tgtaaaacac aacatatcca gtcactatgc catccagctg atatcccta    6960 tagtgagtcg tattacatgg tcatagctgt ttcctggcag ctctggcccg tgtctcaaaa   7020
```

-continued

```
tctctgatgt tacattgcac aagataaaaa tatatcatca tgcctcctc          7069

<210> SEQ ID NO 43
<211> LENGTH: 7306
<212> TYPE: DNA
<213> ORGANISM: Artificial Sequence
<220> FEATURE:
<223> OTHER INFORMATION: Synthetic construct

<400> SEQUENCE: 43
tggaccagcc aggacagaaa tgcctcgact tcgctgctac ccaaggttgc cggggtgacgc    60 acaccgtgga aacggatgaa ggcacgaacc cagtggacat aagcctgttc ggttcgtaag   120
ctgtaatgca agtagcgtat gcgctcacgc aactggtcca gaaccttgac cgaacgcagc   180
ggtggtaacg cgcagtggc ggttttcatg gcttgttatg actgtttttt tggggtacag   240
tctatgcctc gggcatccaa gcagcaagcg cgttacgccg tgggtcgatg tttgatgtta   300
tggagcagca acgatgttac gcagcagggc agtcgcccta aaacaaagtt aaacatcatg   360
agggaagcgg tgatcgccga agtatcgact caactatcag aggtagttgg cgtcatcgag   420
cgccatctcg aaccgacgtt gctggccgta catttgtacg gctccgcagt ggatggcggc   480
ctgaagccac acagtgatat tgatttgctg gttacggtga ccgtaaggct tgatgaaaca   540
acgcggcgag ctttgatcaa cgaccttttg gaaacttcgg cttcccctgg agagagcgag   600
attctccgcg ctgtagaagt caccattgtt gtgcacgacg acatcattcc gtggcgttat   660
ccagctaagc gcgaactgca atttggagaa tggcagcgca atgacattct tgcaggtatc   720
ttcgagccag ccacgatcga cattgatctg gctatcttgc tgacaaaagc aagagaacat   780
agcgttgcct tggtaggtcc agcggcggag gaactctttg atccggttcc tgaacaggat   840
ctatttgagg cgctaaatga aaccttaacg ctatggaact cgccgcccga ctgggctggc   900
gatgagcgaa atgtagtgct tacgttgtcc cgcatttggt acagcgcagt aaccggcaaa   960
atcgcgccga aggatgtcgc tgccgactgg gcaatggagc gcctgccggc ccagtatcag   1020
cccgtcatac ttgaagctag acaggcttat cttggacaag aagaagatcg cttggcctcg   1080
cgcgcagatc agttggaaga atttgtccac tacgtgaaag gcgagatcac caaggtagtc   1140
ggcaaataac cctcgagcca cccatgacca aaatccctta acgtgagtta cgcgtcgttc   1200
cactgagcgt cagaccccgt agaaaagatc aaaggatctt cttgagatcc ttttttttctg   1260 cgcgtaatct gctgcttgca acaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg tcgggctga   1560 acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga   1800 tgctcgtcag ggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
```

-continued

```
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520
tgctttttta taatgccaac tttgtacaaa aaagcaggct ccgaattcgc ccttcaccat    2580
ggctcctaag aagaagcgga aggttggtat tcacgggtg cctgcggcta cgcagttcga    2640
ggggttcacc aacctctacc aggtcagcaa gacgctgcgg ttcgagctga ttccgcaggg    2700
caagaccctc aagcacatcc aggagcaggg ctttatcgag gaggacaaag cgcggaacga    2760
ccactacaag gagctcaagc cgatcatcga ccggatctac aagacctacg cggaccagtg    2820
cctgcagctc gtgcagctcg actgggagaa cctctcggcc gccatcgact cctaccgcaa    2880
ggagaagacg gaggagacac gcaacgcgct catcgaagaa caggctacgt atcgcaacgc    2940
tatccacgac tacttcatcg ggcgcacaga taatctcacc gacgccatca acaagcgcca    3000
cgccgaaatc tataaggggc tgtttaaggc cgagctgttc aatggcaaag tgctgaagca    3060
actgggcacc gtcacgacca cagagcatga gaacgccctc ctccggtcgt tcgacaagtt    3120
tacgacatac tttagcggct tttacgagaa ccgcaaaaac gtgttcagcg ccgaggacat    3180
tagcaccgcc atcccgcata ggatcgtgca agacaacttc ccgaagttca aggagaactg    3240
ccacatcttc acccgcctca tcacggccgt gccgtccctc cgcgagcact cgagaacgt    3300 gaagaaggcc atcgggatct tcgtgtccac ctcgatcgaa gaggtgttct ccttcccctt    3360
ctacaatcag ctgctgacgc agaccagat cgacctctac aaccagctcc tcggcggcat    3420
ctcccgcgag gccggcaccg agaagatcaa gggcctgaac gaggtgctca atctcgccat    3480
ccagaagaac gacgaaaccg cgcacatcat tgcctcactc ccacataggt ttatcccct    3540 gtttaagcag atcctctccg accgcaacac gttgtccttc atcctcgagg agttcaagag    3600
cgacgaggag gtcatccagt ccttctgcaa gtacaagacc ctcctccgca cgagaatgt    3660 gctcgaaacc gccgaggcgc tgttcaatga gctcaatagc atcgatctca cccacatctt    3720
catctcccat aagaagctgg aaaccatctc cagcgccctg tgcgaccact gggacaccct    3780
ccgcaacgcc ctctacgagc ggcgcatcag cgagctcacc ggcaagatca cgaagtcggc    3840
gaaagagaaa gtgcaaagga gcctcaagca cgaggacatt aacctgcagg agatcatctc    3900
cgccgcgggc aaggagctgt ccgaggcttt caagcagaag acctcggaga tcctctctca    3960
cgcccacgcg gccctggacc agccgctgcc gacgaccctg aaaaagcaag aggaaaaggga    4020 aatcctcaag tcccagctgg acagcctcct ggggctgtac caccttctcg actggttcgc    4080
cgtggacgag tccaacgagg tcgatccgga gtttagcgcc cgcctcaccg ggatcaagct    4140
tgagatggaa cctagcttga gcttctataa taaggcgcgc aattacgcga ccaagaagcc    4200
gtattccgtg gagaagttca agctgaactt ccaaatgccc accctggcca gcgggtggga    4260
cgttaacaaa gagaagaaca acggagccat tcttttcgtg aaaaatgggt tgtattattt    4320
gggaattatg ccgaaacaaa aaggcaggta caaggcgctc agcttcgagc caactgagaa    4380
```

-continued

```
gacctccgag ggcttcgaca agatgtacta cgattatttt cctgacgctg caaagatgat    4440
accgaagtgc agcactcagc ttaaggcggt gacggcgcac tttcagaccc ataccacccc    4500
catcctcctc tccaacaact tcatcgagcc gctcgagatc accaaggaga tatacgatct    4560
gaataatcca gaaaaggaac ccaagaagtt ccagaccgcc tacgccaaga agacgggcga    4620
tcaaaagggg tatagagagg cgctctgcaa gtggatcgac ttcacgcgcg atttcctcag    4680
caagtacacc aagacaacct ccatcgatct ctcttccctc cgccctctt cccagtacaa     4740 ggacctcggg gagtactacg ccgaactcaa cccactcctg tatcacatct cgtttcagcg    4800
tatcgcggaa aaggagatca tggacgccgt cgaaaccggc aagttgtatc ttttccaaat    4860
ctataacaag gacttcgcga agggccacca cgggaagcca aacctgcaca ccctctactg    4920
gacaggcctc ttcagcccgg aaaatctcgc gaagacgagc ataaagctga acggccaggc    4980
agaactcttc tacaggccga agtccaggat gaagcgcatg gctcatcgcc tcggtgagaa    5040
gatgctgaac aagaagctga agatcaaaa gacgccaatc cctgatacac tgtatcagga     5100
gctgtacgat tacgtgaacc accgcctctc acacgacctc agcgacgagg cccgcgcgct    5160
cctgccaaac gtcatcacga aggaggtcag ccacgagatc ataaaggatc ggcggtttac    5220
ctctgacaag ttcttttttcc atgtccccat cacgctgaac taccaggccg cgaatagccc    5280
gtccaagttc aaccagcggg tcaacgcgta tctcaaggag cacccagaga cacccataat    5340
cgggattgcc cgggggggagc ggaacctcat ctacatcacc gtcatcgact ccaccggaaa    5400
gattctcgag caacggtcgc tcaataccat ccagcagttc gactaccaga agaagctcga    5460
caaccgggag aaggaacgcg tcgccgcgag gcaggcctgg tccgtagtgg gcacgatcaa    5520
agacctgaag cagggctatc tcagccaggt catccatgag atagtggatc tcatgatcca    5580
ctaccaagcc gtcgtggtcc tcgagaatct caatttcgga ttcaaatcca agcgcacagg    5640
catcgccgag aaggcggtgt accaacagtt cgagaaaatg cttatcgaca agctcaattg    5700
cctggtgctc aaggactatc cggcggagaa ggtcgggggg gtcctcaatc cgtatcagct    5760
gaccgaccag tttacgtcat ttgcgaagat gggcacccag agcggcttcc ttttctatgt    5820 cccgcccca tatacctcaa agattgatcc cttgaccgga ttcgtggacc cgtttgtctg      5880
gaagaccatc aagaaccatg agtcgcgtaa gcatttcctg gagggtttcg acttcctgca     5940
ctatgatgta aaaaccggag acttcatcct gcatttcaag atgaatcgga acctctcctt      6000
ccagcgggga ctccctggct tcatgcccgc ttgggatatc gttttttgaga aaaatgaaac    6060 ccaattcgac gccaaaggca cgcctttcat cgcgggcaag aggattgtcc ctgtaattga     6120
gaaccataga ttcaccgggc gttaccgtga cctgtacccc gcaaacgaac tcatcgccct     6180
cctggaggag aaaggcatcg tttttccgcga cgggtcaaat atcctcccca aactgctcga     6240
gaacgatgat agccacgcta ttgacacgat ggtagcgctc atcagatccg tgctgcaaat     6300
gagaaattca aatgctgcca ctggggagga ttacatcaac tcccctgtgc gtgatctcaa     6360
tggcgtgtgc ttcgattcta gatttcagaa tcctgagtgg ccgatggatg ccgatgctaa    6420
cggcgcatac cacatagcat tgaaaggaca actgttgttg aaccatctca aggagagcaa     6480
ggaccttaag ctgcagaacg gcatcagcaa ccaggattgg cttgcctata tccaagagct     6540
ccgcaataag cgtcctgctg ccaccaaaaa ggccggacag gctaagaaaa agaagggaga     6600
cggctctgga tcggggtcgg gttctggctc agtcgacctt gatcttgacc tcgaactcag     6660
acttggattt gctctcgatc tcgaccttga acttagactc ggatttgctc ttgacctcga     6720
tcttgagctt agactcggat tcgcttagga cgtccgatcg ttcaaacatt tggcaataaa    6780
```

```
gtttcttaag attgaatcct gttgccggtc ttgcgatgat tatcatataa tttctgttga    6840
attacgttaa gcatgtaata attaacatgt aatgcatgac gttatttatg agatgggttt    6900
ttatgattag agtcccgcaa ttatacattt aatacgcgat agaaaacaaa atatagcgcg    6960
caaactagga taaattatcg cgcgcggtgt catctatgtt actagatcgg gaattgatcc    7020
cccctcgaca gcttccggaa agggcgaatt cgcaactttg tatacaaaag ttgaacgaga    7080
aacgtaaaat gatataaata tcaatatatt aaattagatt ttgcataaaa aacagactac    7140
ataatactgt aaaacacaac atatccagtc actatgccat ccagctgata tcccctatag    7200
tgagtcgtat tacatggtca tagctgtttc ctggcagctc tggcccgtgt ctcaaaatct    7260
ctgatgttac attgcacaag ataaaaatat atcatcatgc ctcctc    7306
```

<210> SEQ ID NO 44
<211> LENGTH: 7155
<212> TYPE: DNA
<213> ORGANISM: Artificial Sequence
<220> FEATURE:
<223> OTHER INFORMATION: Synthetic construct

<400> SEQUENCE: 44

```
tggaccagcc aggacagaaa tgcctcgact tcgctgctac ccaaggttgc cgggtgacgc      60
acaccgtgga aacggatgaa ggcacgaacc cagtggacat aagcctgttc ggttcgtaag     120
ctgtaatgca agtagcgtat gcgctcacgc aactggtcca gaaccttgac cgaacgcagc     180
ggtggtaacg gcgcagtggc ggttttcatg gcttgttatg actgtttttt tggggtacag     240
tctatgcctc gggcatccaa gcagcaagcg cgttacgccg tgggtcgatg tttgatgtta     300
tggagcagca acgatgttac gcagcagggc agtcgcccta aaacaaagtt aaacatcatg     360
agggaagcgg tgatcgccga agtatcgact caactatcag aggtagttgg cgtcatcgag     420
cgccatctcg aaccgacgtt gctggccgta catttgtacg gctccgcagt ggatggcggc     480
ctgaagccac acagtgatat tgatttgctg gttacggtga ccgtaaggct tgatgaaaca     540
acgcggcgag ctttgatcaa cgaccttttg gaaacttcgg cttcccctgg agagagcgag     600
attctccgcg ctgtagaagt caccattgtt gtgcacgacg acatcattcc gtggcgttat     660
ccagctaagc gcgaactgca atttggagaa tggcagcgca atgacattct tgcaggtatc     720
ttcgagccag ccacgatcga cattgatctg gctatcttgc tgacaaaagc aagagaacat     780
agcgttgcct tggtaggtcc agcggcggag gaactctttg atccggttcc tgaacaggat     840
ctatttgagg cgctaaatga aaccttaacg ctatggaact cgccgcccga ctgggctggc     900
gatgagcgaa atgtagtgct tacgttgtcc cgcatttggt acagcgcagt aaccggcaaa     960
atcgcgccga aggatgtcgc tgccgactgg gcaatggagc gcctgccggc ccagtatcag    1020
cccgtcatac ttgaagctag acaggcttat cttggacaag aagaagatcg cttggcctcg    1080
cgcgcagatc agttggaaga atttgtccac tacgtgaaag gcgagatcac caaggtagtc    1140
ggcaaataac cctcgagcca cccatgacca aaatccctta acgtgagtta cgcgtcgttc    1200
cactgagcgt cagacccgt agaaaagatc aaaggatctt cttgagatcc ttttttttctg    1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
```

-continued

```
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agctatgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga    1800 tgctcgtcag ggggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gcgagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgctt    2400
gcatggatgt tttcccagtc acgacgttgt aaaacgacgg ccagtcttaa gctcgggccc    2460
caaataatga tttttatttttg actgatagtg acctgttcgt tgcaacaaat tgatgagcaa    2520 tgcttttttta taatgccaac tttgtacaaa aaagcaggct ccgaattcgc ccttcaccat    2580
ggctcctaag aagaagcgga aggttggtat tcacggggtg cctgcggctt cgatctatca    2640
agaattcgtt aataagtatt cgctttctaa aacactgaga ttcgaactca tacctcaagg    2700
aaagacactc gagaacataa aggctagggg cctcatattg gatgatgaaa agagagccaa    2760
ggactataaa aaagccaaac agataatcga caagtaccac caattcttca tagaagaaat    2820
cctttccagc gtctgcatta gcgaggattt gttgcaaaat tacagcgatg tctacttcaa    2880
gcttaagaag agcgatgacg acaatctcca gaaagacttc aaatcagcga aggacacaat    2940
taagaagcag atcagcgagt atatcaaaga tagtgaaaaa ttcaagaacc ttttcaatca    3000
gaacctgata gacgcaaaaa aaggacaaga aagcgacctc attctttggt tgaagcagtc    3060
taaggacaac gggattgagc ttttttaaggc gaatagcgat ataaccgaca tcgacgaggc    3120
gcttgagatc ataaagtcgt ttaagggatg gacaacatac ttcaaaggct tccatgagaa    3180
tcgcaaaaac gtctactcca gcaacgacat tccaacgtcg attatataca gaattgttga    3240
tgataacctc cctaaattcc tcgaaaataa ggcaaaatat gaaagcctta aagataaagc    3300
gcctgaagca atcaattatg aacaaatcaa aaaggatctt gctgaagaat tgacgtttga    3360
tatagactac aagacgtcag aagttaacca gagggtgttt tcactcgacg aggtgtttga    3420
gattgctaat ttcaacaact acctcaatca gagtgggatc acgaagttca acactattat    3480
aggtggtaag ttcgtgaatg gtgagaacac taaaagaaaa gggattaacg aatatataaa    3540
cctttatagt caacagatca acgacaagac tttgaagaaa tataagatga gcgtcctctt    3600
caagcagata ctcagtgaca cggaatccaa gagctttgtg atcgacaagc tcgaagatga    3660
ctcggatgtg gtcactacca tgcaatcctt ctacgagcaa attgccgctt tcaaaactgt    3720
ggaggagaag agtataaagg agacactgtc tctgcttttt gacgatctta aggcccagaa    3780
attggatctt tccaaaatat atttcaagaa tgataagtca cttacggacc tttcccaaca    3840 agttttttgac gattattcag ttattggtac ggcggttctt gagtacatta cgcagcagat    3900
```

-continued

```
agcccccaag aatctggaca acccctctaa gaaagaacag gagttgatag cgaagaagac      3960
agagaaggcg aaatacctct cgctggagac cataaaattg gcactggaag aatttaacaa      4020
gcatcgcgac atagataaac agtgccgctt cgaggaaatt ttggcaaatt ttgcagccat      4080
tccaatgatt ttcgacgaga tagcgcaaaa caaggataat ttggcacaaa tttcaataaa      4140
atatcaaaac cagggcaaga aggacctctt gcaggcttcg gcagaggatg atgttaaggc      4200
tattaaagac ttgttggacc aaacgaacaa tctgttgcac aagttgaaaa ttttccacat      4260
tagtcaaagc gaggataaag caaacatatt ggacaaagac gagcactttt atctggtgtt      4320
tgaggagtgc tacttcgagc ttgctaatat tgtcccactt tataataaaa taagaaacta      4380
cattacgcaa aagccatatt cagatgaaaa gtttaagctc aatttcgaaa atagtactct      4440
tgccaacggc tgggacaaga ataaggagcc agataatacc gccatacttt ttatcaaaga      4500
tgataaatat tatcttgggg tgatgaataa gaagaataat aagatcttcg atgataaagc      4560
gataaaggaa aataagggtg aaggctataa aaaaattgtt tacaaactgt tgccgggagc      4620
aaataaaatg ctccccaagg ttttttttc ggcaaagagc attaaatttt acaatccttc      4680
agaagacatt ctgcgcataa gaaatcattc gacacacact aaaaatggtt cgccacaaaa      4740
gggctacgag aaatttgaat tcaacattga ggactgtcgg aagttcattg atttctacaa      4800
gcagtccatc tccaagcacc cggagtggaa agattttggg tttcggtttt ccgacacgca      4860
gagatacaac agcattgatg aattttatag agaggtcgag aatcaaggtt ataagcttac      4920
ctttgaaaac atttctgaat catacattga ttcagtggtc aatcagggca aactctatct      4980
ttttcaaata tacaacaagg actttagtgc ttatagtaaa gggcggccca atttgcatac      5040
tctctattgg aaagcgctgt ttgatgagcg gaaccttcaa gacgtcgtgt ataagctcaa      5100
cggggaagcc gagctctttt accgcaagca gtccataccg aaaaaaataa cacaccctgc      5160
caaagaagcc atcgccaaca agaataaaga caatcctaaa aaagagtccg tcttcgaata      5220
tgatcttatt aaggacaaga ggtttacaga agataaattt ttcttccatt gtcccataac      5280 tatcaattc aaaagctctg gcgcgaacaa atttaacgac gaaatcaatc tcttgttgaa      5340
agaaaaagcc aacgatgtgc acattctgtc gatcgacagg ggagagcgcc acttggcata      5400
ctacaccctt gttgatggga aaggaaatat tattaaacag gacacattta atatcatcgg      5460
caacgatcgc atgaagacca actatcatga caaactggca gcaattgaaa aggaccgcga      5520
ctcagcgaga aaagactgga agaagatcaa taatatcaaa gaaatgaaag agggttattt      5580
gtctcaagtg gtccatgaga tcgcgaagtt ggtcattgaa tataatgcca tagtggtctt      5640
cgaagatctg aattttggat ttaagcgcgg caggttcaaa gtcgaaaaac aggtctacca      5700
aaagttggaa aagatgctca tcgaaaagct gaattacctt gtcttcaaag ataacgaatt      5760
cgataaaacc ggggggggtct tgagggccta ccaactgact gcacccttg agacttttaa      5820 aaagatgggt aaacagacag gaataattta ctatgttcct gccggtttca ctagcaagat      5880
ttgccccgtt accggattcg tgaatcaact ctatcccaaa tacgaatccg tgagcaagag      5940
tcaggaattc ttctccaaat ttgataaaat atgctataat ctcgacaaag gttatttcga      6000
gttctcgttc gactataaga acttcggga taaggctgcc aagggaaagt ggactatagc      6060
aagctttggt agtcgcctta taaattttag gaacagcgac aagaatcaca actgggacac      6120 tcggaagtc tacccaacaa aagaactgga gaaactcttg aaggattata gtatcgagta      6180
tgggcatggg gagtgtatca aggcagcgat ttgtggagag tccgacaaaa agttttttgc      6240
```

-continued

```
taaactcacc tcggtgctca acactatcct ccagatgaga aattcaaaaa cagggacaga      6300
gctcgattac ctcattagcc ccgttgccga cgtcaatgga aactttttcg actcaagaca      6360
ggctccaaaa aacatgccgc aagatgcgga cgcgaatggg gcctatcaca taggcctgaa      6420
agggcttatg ctccttggga gaattaaaaa taaccaagaa ggcaaaaaac tcaacctcgt      6480
cattaagaac gaagaatact tcgaatttgt tcagaacagg aataacaagc gtcctgctgc      6540
caccaaaaag gccggacagg ctaagaaaaa gaagtgagac gactagtggc ggccgccgac      6600
gtccgatcgt tcaaacattt ggcaataaag tttcttaaga ttgaatcctg ttgccggtct      6660
tgcgatgatt atcatataat ttctgttgaa ttacgttaag catgtaataa ttaacatgta      6720
atgcatgacg ttatttatga gatgggtttt tatgattaga gtcccgcaat tatacattta      6780
atacgcgata gaaaacaaaa tatagcgcgc aaactaggat aaattatcgc gcgcggtgtc      6840
atctatgtta ctagatcggg aattgatccc ccctcgacag cttccggaaa gggcgaattc      6900
gcaactttgt atacaaaagt tgaacgagaa acgtaaaatg atataaatat caatatatta      6960
aattagattt tgcataaaaa acagactaca taatactgta aaacacaaca tatccagtca      7020
ctatgccatc cagctgatat cccctatagt gagtcgtatt acatggtcat agctgtttcc      7080
tggcagctct ggcccgtgtc tcaaaatctc tgatgttaca ttgcacaaga taaaaatata      7140
tcatcatgcc tcctc                                                     7155
```

<210> SEQ ID NO 45
<211> LENGTH: 7099
<212> TYPE: DNA
<213> ORGANISM: Artificial Sequence
<220> FEATURE:
<223> OTHER INFORMATION: Synthetic construct

<400> SEQUENCE: 45

```
tggaccagcc aggacagaaa tgcctcgact tcgctgctac ccaaggttgc cgggtgacgc       60
acaccgtgga aacggatgaa ggcacgaacc cagtggacat aagcctgttc ggttcgtaag      120
ctgtaatgca agtagcgtat gcgctcacgc aactggtcca gaaccttgac cgaacgcagc      180
ggtggtaacg gcgcagtggc ggttttcatg gcttgttatg actgtttttt tggggtacag      240
tctatgcctc gggcatccaa gcagcaagcg cgttacgccg tgggtcgatg tttgatgtta      300
tggagcagca acgatgttac gcagcagggc agtcgcccta aaacaaagtt aaacatcatg      360
agggaagcgg tgatcgccga agtatcgact caactatcag aggtagttgg cgtcatcgag      420
cgccatctcg aaccgacgtt gctggccgta catttgtacg gctccgcagt ggatggcggc      480
ctgaagccac acagtgatat tgatttgctg gttacggtga ccgtaaggct tgatgaaaca      540
acgcggcgag ctttgatcaa cgaccttttg gaaacttcgg cttcccctgg agagagcgag      600
attctccgcg ctgtagaagt caccattgtt gtgcacgacg acatcattcc gtggcgttat      660
ccagctaagc gcgaactgca atttggagaa tggcagcgca atgacattct tgcaggtatc      720
ttcgagccag ccacgatcga cattgatctg gctatcttgc tgacaaaagc aagagaacat      780
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
```

-continued

```
ggcaaataac cctcgagcca cccatgacca aaatcccotta acgtgagtta cgcgtcgttc   1200
cactgagcgt cagaccccgt agaaaagatc aaaggatctt cttgagatcc ttttttttctg   1260 cgcgtaatct gctgcttgca aacaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agctatgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga   1800 tgctcgtcag gggggcggag cctatggaaa aacgccagca acgcggcctt tttacggttc   1860 ctggccttttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gcgagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca acaacagat aaaacgaaag gcccagtctt   2340
ccgactgagc ctttcgtttt atttgatgcc tggcagttcc ctactctcgc gttaacgctt   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520
tgctttttta taatgccaac tttgtacaaa aaagcaggct ccgaattcgc ccttcaccat   2580
ggctcctaag aagaagcgga aggttggtat tcacggggtg cctgcggcta cgcagttcga   2640
ggggttcacc aacctctacc aggtcagcaa gacgctgcgg ttcgagctga ttccgcaggg   2700
caagaccctc aagcacatcc aggagcaggg ctttatcgag gaggacaaag cgcggaacga   2760
ccactacaag gagctcaagc cgatcatcga ccggatctac aagacctacg cggaccagtg   2820
cctgcagctc gtgcagctcg actgggagaa cctctcggcc gccatcgact cctaccgcaa   2880
ggagaagacg gaggagacac gcaacgcgct catcgaagaa caggctacgt atcgcaacgc   2940
tatccacgac tacttcatcg ggcgcacaga taatctcacc gacgccatca acaagcgcca   3000
cgccgaaatc tataaggggc tgtttaaggc cgagctgttc aatggcaaag tgctgaagca   3060
actgggcacc gtcacgacca cagagcatga gaacgccctc ctccggtcgt cgacaagtt   3120 tacgacatac tttagcggct tttacgagaa ccgcaaaaac gtgttcagcg ccgaggacat   3180
tagcaccgcc atcccgcata ggatcgtgca agacaacttc ccgaagttca aggagaactg   3240
ccacatcttc acccgcctca tcacggccgt gccgtccctc cgcgagcact cgagaacgt   3300 gaagaaggcc atcgggatct tcgtgtccac ctcgatcgaa gaggtgttct ccttcccctt   3360
ctacaatcag ctgctgacgc agaccccagat cgacctctac aaccagctcc tcggcggcat   3420
ctcccgcgag gccggcaccg agaagatcaa gggcctgaac gaggtgctca atctcgccat   3480
```

-continued

```
ccagaagaac gacgaaaccg cgcacatcat tgcctcactc ccacataggt ttatccccct    3540
gtttaagcag atcctctccg accgcaacac gttgtccttc atcctcgagg agttcaagag    3600
cgacgaggag gtcatccagt ccttctgcaa gtacaagacc ctcctccgca acgagaatgt    3660
gctcgaaacc gccgaggcgc tgttcaatga gctcaatagc atcgatctca cccacatctt    3720
catctcccat aagaagctgg aaaccatctc cagcgccctg tgcgaccact gggacaccct    3780
ccgcaacgcc ctctacgagc ggcgcatcag cgagctcacc ggcaagatca cgaagtcggc    3840
gaaagagaaa gtgcaaagga gcctcaagca cgaggacatt aacctgcagg agatcatctc    3900
cgccgcgggc aaggagctgt ccgaggcttt caagcagaag acctcggaga tcctctctca    3960
cgcccacgcg gccctggacc agccgctgcc gacgaccctg aaaaagcaag aggaaaagga    4020
aatcctcaag tcccagctgg acagcctcct ggggctgtac caccttctcg actggttcgc    4080
cgtggacgag tccaacgagg tcgatccgga gtttagcgcc cgcctcaccg ggatcaagct    4140
tgagatggaa cctagcttga gcttctataa taaggcgcgc aattacgcga ccaagaagcc    4200
gtattccgtg gagaagttca agctgaactt ccaaatgccc accctggcca gcgggtggga    4260
cgttaacaaa gagaagaaca acggagccat tcttttcgtg aaaaatgggt tgtattattt    4320
gggaattatg ccgaaacaaa aaggcaggta caaggcgctc agcttcgagc caactgagaa    4380
gacctccgag ggcttcgaca agatgtacta cgattatttt cctgacgctg caaagatgat    4440
accgaagtgc agcactcagc ttaaggcggt gacggcgcac tttcagaccc ataccacccc    4500
catcctcctc tccaacaact tcatcgagcc gctcgagatc accaaggaga tatacgatct    4560
gaataatcca gaaaaggaac ccaagaagtt ccagaccgcc tacgccaaga agacgggcga    4620
tcaaaagggg tatagagagg cgctctgcaa gtggatcgac ttcacgcgcg atttcctcag    4680
caagtacacc aagacaacct ccatcgatct ctcttccctc cgccctctt cccagtacaa    4740 ggacctcggg gagtactacg ccgaactcaa cccactcctg tatcacatct cgtttcagcg    4800
tatcgcggaa aaggagatca tggacgccgt cgaaaccggc aagttgtatc ttttccaaat    4860
ctataacaag gacttcgcga agggccacca cgggaagcca aacctgcaca ccctctactg    4920
gacaggcctc ttcagcccgg aaaatctcgc gaagacgagc ataaagctga acggccaggc    4980
agaactcttc tacaggccga agtccaggat gaagcgcatg gctcatcgcc tcggtgagaa    5040
gatgctgaac aagaagctga agatcaaaaa gacgccaatc cctgatacac tgtatcagga    5100
gctgtacgat tacgtgaacc accgcctctc acacgacctc agcgacgagg cccgcgcgct    5160
cctgccaaac gtcatcacga aggaggtcag ccacgagatc ataaaggatc ggcggtttac    5220
ctctgacaag ttctttttcc atgtccccat cacgctgaac taccaggccg cgaatagccc    5280
gtccaagttc aaccagcggg tcaacgcgta tctcaaggag cacccagaga cacccataat    5340
cgggattgcc cggggggagc ggaacctcat ctacatcacc gtcatcgact ccaccggaaa    5400
gattctcgag caacggtcgc tcaataccat ccagcagttc gactaccaga gaagctcga    5460 caaccgggag aaggaacgcg tcgccgcgag gcaggcctgg tccgtagtgg gcacgatcaa    5520
agacctgaag cagggctatc tcagccaggt catccatgag atagtggatc tcatgatcca    5580
ctaccaagcc gtcgtggtcc tcgagaatct caatttcgga ttcaaatcca agcgcacagg    5640
catcgccgag aaggcggtgt accaacagtt cgagaaaatg cttatcgaca agctcaattg    5700
cctggtgctc aaggactatc cggcggagaa ggtcgggggg gtcctcaatc cgtatcagct    5760
gaccgaccag tttacgtcat ttgcgaagat gggcacccag agcggcttcc tttttctatgt    5820 cccggcccca tataccteaa agattgatcc cttgaccgga ttcgtggacc cgtttgtctg    5880
```

-continued

```
gaagaccatc aagaaccatg agtcgcgtaa gcatttcctg gagggtttcg acttcctgca      5940
ctatgatgta aaaaccggag acttcatcct gcatttcaag atgaatcgga acctctcctt      6000
ccagcgggga ctccctggct tcatgcccgc ttgggatatc gtttttgaga aaaatgaaac      6060
ccaattcgac gccaaaggca cgcctttcat cgcgggcaag aggattgtcc ctgtaattga      6120
gaaccataga ttcaccgggc gttaccgtga cctgtacccc gcaaacgaac tcatcgccct      6180
cctggaggag aaaggcatcg ttttccgcga cgggtcaaat atcctcccca aactgctcga      6240
gaacgatgat agccacgcta ttgacacgat ggtagcgctc atcagatccg tgctgcaaat      6300
gagaaattca aatgctgcca ctggggagga ttacatcaac tcccctgtgc gtgatctcaa      6360
tggcgtgtgc ttcgattcta gatttcagaa tcctgagtgg ccgatggatg ccgatgctaa      6420
cggcgcatac cacatagcat tgaaaggaca actgttgttg aaccatctca aggagagcaa      6480
ggaccttaag ctgcagaacg gcatcagcaa ccaggattgg cttgcctata tccaagagct      6540
ccgcaataag cgtcctgctg ccaccaaaaa ggccggacag gctaagaaaa agaagggaga      6600
cggctctgga tcggggtcgg gttctggctc agtcgacctt gatcttgacc tcgaactcag      6660
acttggattt gctctcgatc tcgaccttga acttagactc ggatttgctc ttgacctcga      6720
tcttgagctt agactcggat tcgcttagga cgtcctaaga aaagaagta ggatccaaaa      6780 aaaaaaaaaa aaaaaaaaaa aaaaaaaaaa aaaaaaaaaa aaaaaatccg gaaagggcga      6840
attcgcaact ttgtatacaa aagttgaacg agaaacgtaa aatgatataa atatcaatat      6900
attaaattag attttgcata aaaaacagac tacataatac tgtaaaacac aacatatcca      6960
gtcactatgc catccagctg atatccccta tagtgagtcg tattacatgg tcatagctgt      7020
ttcctggcag ctctggcccg tgtctcaaaa tctctgatgt tacattgcac aagataaaaa      7080
tatatcatca tgcctcctc                                                   7099
```

<210> SEQ ID NO 46
<211> LENGTH: 6732
<212> TYPE: DNA
<213> ORGANISM: Artificial Sequence
<220> FEATURE:
<223> OTHER INFORMATION: Synthetic construct

<400> SEQUENCE: 46

```
tggaccagcc aggacagaaa tgcctcgact tcgctgctac ccaaggttgc cgggtgacgc        60
acaccgtgga aacggatgaa ggcacgaacc cagtggacat aagcctgttc ggttcgtaag       120
ctgtaatgca agtagcgtat gcgctcacgc aactggtcca gaaccttgac cgaacgcagc       180
ggtggtaacg gcgcagtggc ggttttcatg gcttgttatg actgtttttt tggggtacag       240
tctatgcctc gggcatccaa gcagcaagcg cgttacgccg tgggtcgatg tttgatgtta       300
tggagcagca acgatgttac gcagcagggc agtcgcccta aaacaaagtt aaacatcatg       360
agggaagcgt tgatcgccga agtatcgact caactatcag aggtagttgg cgtcatcgag       420
cgccatctcg aaccgacgtt gctggccgta catttgtacg gctccgcagt ggatggcggc       480
ctgaagccac acagtgatat tgatttgctg gttacggtga ccgtaaggct tgatgaaaca       540
acgcggcgag ctttgatcaa cgaccttttg gaaacttcgg cttcccctgg agagagcgag       600
attctccgcg ctgtagaagt caccattgtt gtgcacgacg acatcattcc gtggcgttat       660
ccagctaagc gcgaactgca atttggagaa tggcagcgca atgacattct tgcaggtatc       720
ttcgagccag ccacgatcga cattgatctg gctatcttgc tgacaaaagc aagagaacat      780
```

-continued

```
agcgttgcct tggtaggtcc agcggcggag gaactctttg atccggttcc tgaacaggat      840
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatcccttaa cgtgagtta cgcgtcgttc     1200 cactgagcgt cagaccccgt agaaaagatc aaaggatctt cttgagatcc ttttttttctg     1260 cgcgtaatct gctgcttgca acaaaaaaaa ccaccgctac cagcggtggt ttgtttgccg     1320
gatcaagagc taccaactct ttttccgaag gtaactggct tcagcagagc gcagatacca     1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg gtcgggctga     1560
acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga     1800 tgctcgtcag ggggcggag cctatggaaa aacgccagca acgcggcctt tttacggttc     1860
ctggcctttt gctggccttt tgctcacatg ttctttcctg cgttatcccc tgattctgtg     1920
gataaccgta ttaccgcctt tgagtgagct gataccgctc gccgcagccg aacgaccgag     1980
cgcagcgagt cagtgagcga ggaagcggaa gagcgcccaa tacgcaaacc gcctctcccc     2040
gcgcgttggc cgattcatta atgcagctgg cacgacaggt ttcccgactg gaaagcgggc     2100
agtgagcgca acgcaattaa tacgcgtacc gcgagccagg aagagtttgt agaaacgcaa     2160
aaaggccatc cgtcaggatg gccttctgct tagtttgatg cctggcagtt tatggcgggc     2220
gtcctgcccg ccaccctccg ggccgttgct tcacaacgtt caaatccgct cccggcggat     2280
ttgtcctact caggagagcg ttcaccgaca acaacagat aaaacgaaag gcccagtctt     2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga ttttattttg actgatagtg acctgttcgt tgcaacaaat tgatgagcaa     2520
tgctttttta taatgccaac tttgtacaaa aaagcaggct ccgaattcgc ccttcaccat     2580
ggctcctaag aagaagcgga aggttggtat tcacggggtg cctgcggctt caaagctcga     2640
gaaattcacc aactgttatt cgttgagcaa aacactgcgg tttaaagcga ttccagtcgg     2700
caagactcaa gagaatatag acaataagcg gctgttggtg gaagatgaaa gcgcgcgga     2760 agactacaaa ggggtgaaga agttgttgga cagatactac ctctcttta tcaatgatgt     2820 cttgcactca atcaaattga agaatctgaa caactacatc tccctcttca gaaagaaaac     2880
aaggacagaa aaggagaata aggaacttga aaatttggag atcaatctga ggaaagagat     2940
cgcgaaagcc tttaaaggca acgaaggata caaaagtctg ttcaagaagg atataattga     3000
gacaattttg ccagagttcc tcgatgacaa ggacgagatt cgctggtca attcgttcaa     3060 cggattcaca acagcattca caggcttctt tgataatcgg gaaaatatgt tctctgagga     3120
ggcaaagtcc acttctattg cgttcaggtg tatcaatgag aatctcacta ggtacattc     3180
```

-continued

```
caacatggat atctttgaga aggttgacgc aatttttgac aagcacgaag ttcaggagat   3240
taaggagaag atcctcaatt ccgattatga cgttgaggac ttcttcgaag gtgagttttt   3300
taatttcgtg ctcactcaag agggtatcga cgtgtataat gcgatcatcg gtgggttcgt   3360
gactgagtcc ggtgaaaaga ttaagggatt gaacgagtat atcaaccttt acaaccaaaa   3420
gacgaaacag aagctgccaa agttcaagcc tctttacaaa caggttcttt cagaccgcga   3480
gtcactctcg ttctatgggg agggctacac ttcggatgag gaagtcctgg aggtgttcag   3540
gaatactctc aataagaatt cggagatttt ctcttctata aaaaaactgg aaaagttgtt   3600
taagaatttt gacgaatact ctagcgccgg catatttgtg aaaaacggcc cggccatatc   3660
aacgataagt aaagatatct tcggcgaatg aacgtgatc agagacaaat ggaacgcgga   3720
gtatgacgat attcacctga agaagaaggc tgtcgtaacg gagaagtacg aggatgatcg   3780
caggaaaagc ttcaaaaaga tcggaagttt cagcctggaa cagttgcagg agtatgctga   3840
cgccgatctt agcgtcgtcg agaagttgaa ggagataatc atccaaaagg tcgacgagat   3900
atataaagtc tatggatcaa gtgaaaaact gttcgacgcc gacttcgttt tggagaagtc   3960
cctgaagaag aacgacgctg ttgttgccat tatgaaggat ctgctcgaca gcgtgaagag   4020
tttcgagaac tatattaagg ctttttttcgg ggaggggaag gagactaaca gagatgagtc   4080
cttctacgga gacttcgtcc tcgcgtacga tatactcctt aaggtagacc acatctacga   4140
cgcaatcaga aattacgtga cacaaaagcc gtacagcaag gacaagttca aactctactt   4200
ccagaacccc cagttcatgg gcggctggga caaggacaag gaaacggatt acagggctac   4260
gatcctgagg tatggttcaa aatactactt ggcgattatg gacaagaagt acgccaagtg   4320
tctccagaag attgacaaag acgatgtcaa tggcaattat gagaagatca actacaagct   4380
gcttccgggt ccgaacaaga tgctcccaaa ggttttcttc agcaagaaat ggatggccta   4440
ctataaccca agcgaggaca tccagaagat ttataagaac ggtacgttca agaagggcga   4500
catgttcaat cttaacgact gtcacaagct gatcgacttc ttcaaagact caattagccg   4560
gtacccaaag tggtctaacg cctatgactt caacttttcg gaaaccgaga agtacaagga   4620
tatagccgga ttttatagag aggtggaaga gcagggctac aaggtgtcat tcgagtccgc   4680
cagcaagaag gaagtggaca agctcgtgga agagggtaag ctctacatgt tccagattta   4740
taataaagac tttagcgata agagccacgg gacacctaat ctccacacaa tgtatttcaa   4800
gctgctcttc gacgagaata accacggcca aatcaggttg tcaggagggg ctgaactctt   4860
catgcggcgc gctagcctta agaaggagga gcttgtagtc caccctgcga atagtccaat   4920
tgcgaataag aacccggaca atcctaaaaa gactacaaca ttgagctacg acgtgtacaa   4980
ggataagagg ttttccgagg atcagtacga gctccacatc ccgattgcga tcaacaagtg   5040
cccaaagaat attttcaaga taaacacaga ggtgcgtgta ctcctgaagc atgacgacaa   5100
tccttacgtc attgggattg atcggggcga gaggaacctc ctctatattg tggtggtgga   5160
cgggaagggg aacatagtcg aacagtactc ccttaacgaa ataattaaca atttcaacgg   5220
catccgtatc aagaccgact accattcgtt gctggacaag aaggagaagg agagatttga   5280
ggcgcggcaa aattggacaa gtatcgagaa catcaaggaa ctcaaagcag gttatatctc   5340
tcaagttgtg cataagatat gcgagctggt tgagaagtat gacgcagtga tcgctcttga   5400
ggacctcaac tcgggcttta agaattctag agttaaagtg gagaagcagg tctatcaaaa   5460
gttcgagaag atgcttatag ataagctcaa ctacatggtc gataagaaat cgaacccatg   5520
```

-continued

```
tgccaccggc ggcgcactca aaggttacca aataacaaac aaattcgagt ccttcaaatc   5580
gatgagtact cagaatgggt tcatatttta tataccggcg tggcttacgt ctaagatcga   5640
cccgtcaact ggttttgtca acctgttgaa gacgaaatac acgtccattg ccgattcgaa   5700
aaagttcata tctagttttg atcgtattat gtacgtccca gaggaagatc ttttcgagtt   5760
tgctctcgac tacaaaaact tttcgcggac cgatgcggat tacattaaaa aatggaaact   5820
ctattcgtac ggcaacagaa tcaggatttt tcgcaaccct aagaagaata acgtctttga   5880
ttgggaggaa gtttgcttga ctagcgcgta caaggagctc tttaataagt atggcattaa   5940
ctaccaacag ggtgatatca gagcactgct ttgcgaacaa tctgacaagg ctttctactc   6000
atccttcatg gctttgatga gcctgatgct ccagatgaga aattcaatta caggcagaac   6060
cgacgtggat ttcttgatct ccccggttaa aaattctgat ggcatctttt acgatagcag   6120
gaactatgaa gcgcaagaga atgcgattct gccaaaaaat gcagacgcca acggtgccta   6180
taacatcgcc aggaaagtcc tgtgggcgat cggccagttc aaaaaggccg aagacgaaaa   6240
attggacaag gtcaaaatcg ctatcagcaa caaagagtgg ctggagtatg ctcagacatc   6300
cgtaaagcat aagcgtcctg ctgccaccaa aaaggccgga caggctaaga aaaagaagtg   6360
agacgactag tggcggccgc cgacgtccta agaaaaagaa gtaggatcca aaaaaaaaa   6420 aaaaaaaaaa aaaaaaaaaa aaaaaaaaaa aaaaaaaat ccggaaaggg cgaattcgca   6480
actttgtata caaaagttga acgagaaacg taaaatgata taaatatcaa tatattaaat   6540
tagattttgc ataaaaaaca gactacataa tactgtaaaa cacaacatat ccagtcacta   6600
tgccatccag ctgatatccc ctatagtgag tcgtattaca tggtcatagc tgtttcctgg   6660
cagctctggc ccgtgtctca aaatctctga tgttacattg cacaagataa aaatatatca   6720
tcatgcctcc tc                                                       6732
```

<210> SEQ ID NO 47
<211> LENGTH: 6862
<212> TYPE: DNA
<213> ORGANISM: Artificial Sequence
<220> FEATURE:
<223> OTHER INFORMATION: Synthetic construct

<400> SEQUENCE: 47

```
tggaccagcc aggacagaaa tgcctcgact tcgctgctac ccaaggttgc cgggtgacgc     60
acaccgtgga aacggatgaa ggcacgaacc cagtggacat aagcctgttc ggttcgtaag    120
ctgtaatgca agtagcgtat cgctcacgc aactggtcca gaaccttgac cgaacgcagc    180
ggtggtaacg cgcagtggc ggttttcatg gcttgttatg actgtttttt tggggtacag    240
tctatgcctc gggcatccaa gcagcaagcg cgttacgccg tgggtcgatg tttgatgtta    300
tggagcagca acgatgttac gcagcagggc agtcgcccta aaacaaagtt aaacatcatg    360
agggaagcgg tgatcgccga agtatcgact caactatcag aggtagttgg cgtcatcgag    420
cgccatctcg aaccgacgtt gctggccgta catttgtacg gctccgcagt ggatggcggc    480
ctgaagccac acagtgatat tgatttgctg gttacggtga ccgtaaggct tgatgaaaca    540
acgcggcgag ctttgatcaa cgaccttttg gaaacttcgg cttcccctgg agagagcgag    600
attctccgcg ctgtagaagt caccattgtt gtgcacgacg acatcattcc gtggcgttat    660
ccagctaagc gcgaactgca atttggagaa tggcagcgca atgacattct tgcaggtatc    720
ttcgagccag ccacgatcga cattgatctg gctatcttgc tgacaaaagc aagagaacat    780
agcgttgcct tggtaggtcc agcggcggag gaactctttg atccggttcc tgaacaggat    840
```

-continued

```
ctatttgagg cgctaaatga aaccttaacg ctatggaact cgccgcccga ctgggctggc      900
gatgagcgaa atgtagtgct tacgttgtcc cgcatttggt acagcgcagt aaccggcaaa      960
atcgcgccga aggatgtcgc tgccgactgg gcaatggagc gcctgccggc ccagtatcag     1020
cccgtcatac ttgaagctag acaggcttat cttggacaag aagaagatcg cttggcctcg     1080
cgcgcagatc agttggaaga atttgtccac tacgtgaaag gcgagatcac caaggtagtc     1140
ggcaaataac cctcgagcca cccatgacca aaatccctta acgtgagtta cgcgtcgttc     1200
cactgagcgt cagaccccgt agaaaagatc aaaggatctt cttgagatcc tttttttctg     1260
cgcgtaatct gctgcttgca aacaaaaaaa ccaccgctac cagcggtggt ttgtttgccg     1320
gatcaagagc taccaactct ttttccgaag gtaactggct tcagcagagc gcagatacca     1380
aatactgtcc ttctagtgta gccgtagtta ggccaccact tcaagaactc tgtagcaccg     1440
cctacatacc tcgctctgct aatcctgtta ccagtggctg ctgccagtgg cgataagtcg     1500
tgtcttaccg ggttggactc aagacgatag ttaccggata aggcgcagcg gtcgggctga     1560
acggggggtt cgtgcacaca gcccagcttg gagcgaacga cctacaccga actgagatac     1620
ctacagcgtg agctatgaga aagcgccacg cttcccgaag ggagaaaggc ggacaggtat     1680
ccggtaagcg gcagggtcgg aacaggagag cgcacgaggg agcttccagg gggaaacgcc     1740
tggtatcttt atagtcctgt cgggtttcgc cacctctgac ttgagcgtcg attttttgtga     1800 tgctcgtcag ggggcggag cctatggaaa aacgccagca acgcggcctt tttacggttc      1860
ctggcctttt gctggccttt tgctcacatg ttctttcctg cgttatcccc tgattctgtg     1920
gataaccgta ttaccgcctt tgagtgagct gataccgctc gccgcagccg aacgaccgag     1980
cgcagcgagt cagtgagcga ggaagcggaa gagcgcccaa tacgcaaacc gcctctcccc     2040
gcgcgttggc cgattcatta atgcagctgg cacgacaggt ttcccgactg gaaagcgggc     2100
agtgagcgca acgcaattaa tacgcgtacc gcgagccagg aagagtttgt agaaacgcaa     2160
aaaggccatc cgtcaggatg gccttctgct tagtttgatg cctggcagtt tatggcgggc     2220
gtcctgcccg ccaccctccg ggccgttgct tcacaacgtt caaatccgct cccggcggat     2280
ttgtcctact caggagagcg ttcaccgaca aacaacagat aaaacgaaag gcccagtctt     2340
ccgactgagc ctttcgtttt atttgatgcc tggcagttcc ctactctcgc gttaacgctt     2400
gcatggatgt tttcccagtc acgacgttgt aaaacgacgg ccagtcttaa gctcgggccc     2460
caaataatga tttatttttg actgatagtg acctgttcgt tgcaacaaat tgatgagcaa     2520
tgctttttta taatgccaac tttgtacaaa aaagcaggct ccgaattcgc ccttcaccat     2580
ggctcctaag aagaagcgga aggttggtat tcacggggtg cctgcggctt caaagctcga     2640
gaaattcacc aactgttatt cgttgagcaa aacactgcgg tttaaagcga ttccagtcgg     2700
caagactcaa gagaatatag acaataagcg gctgttggtg gaagatgaaa agcgcgcgga     2760
agactacaaa ggggtgaaga agttgttgga cagatactac ctctctttta tcaatgatgt     2820
cttgcactca atcaaattga agaatctgaa caactacatc tccctcttca gaaagaaaac     2880
aaggacagaa aaggagaata aggaacttga aaatttggag atcaatctga ggaaagagat     2940
cgcgaaagcc tttaaaggca acgaaggata caaaagtctg ttcaagaagg atataattga     3000
gacaattttg ccagagttcc tcgatgacaa ggacgagatt gcgctggtca attcgttcaa     3060
cggattcaca acagcattca caggcttctt tgataatcgg gaaaatatgt tctctgagga     3120
ggcaaagtcc acttctattg cgttcaggtg tatcaatgag aatctcacta ggtacatttc     3180
```

-continued

```
caacatggat atctttgaga aggttgacgc aatttttgac aagcacgaag ttcaggagat   3240
taaggagaag atcctcaatt ccgattatga cgttgaggac ttcttcgaag gtgagttttt   3300
taatttcgtg ctcactcaag agggtatcga cgtgtataat gcgatcatcg gtgggttcgt   3360
gactgagtcc ggtgaaaaga ttaagggatt gaacgagtat atcaaccttt acaaccaaaa   3420
gacgaaacag aagctgccaa agttcaagcc tctttacaaa caggttcttt cagaccgcga   3480
gtcactctcg ttctatgggg agggctacac ttcggatgag gaagtcctgg aggtgttcag   3540
gaatactctc aataagaatt cggagatttt ctcttctata aaaaaactgg aaaagttgtt   3600
taagaatttt gacgaatact ctagcgccgg catatttgtg aaaaacggcc cggccatatc   3660
aacgataagt aaagatatct tcggcgaatg gaacgtgatc agagacaaat ggaacgcgga   3720
gtatgacgat attcacctga agaagaaggc tgtcgtaacg gagaagtacg aggatgatcg   3780
caggaaaagc ttcaaaaaga tcggaagttt cagcctggaa cagttgcagg agtatgctga   3840
cgccgatctt agcgtcgtcg agaagttgaa ggagataatc atccaaaagg tcgacgagat   3900
atataaagtc tatggatcaa gtgaaaaact gttcgacgcc gacttcgttt tggagaagtc   3960
cctgaagaag aacgacgctg ttgttgccat tatgaaggat ctgctcgaca gcgtgaagag   4020
tttcgagaac tatattaagg cttttttcgg ggaggggaag gagactaaca gagatgagtc   4080
cttctacgga gacttcgtcc tcgcgtacga tatactcctt aaggtagacc acatctacga   4140
cgcaatcaga aattacgtga cacaaaagcc gtacagcaag gacaagttca aactctactt   4200
ccagaacccc cagttcatgg gcggctggga caaggacaag gaaacggatt acagggctac   4260
gatcctgagg tatggttcaa aatactactt ggcgattatg gacaagaagt acgccaagtg   4320
tctccagaag attgacaaag acgatgtcaa tggcaattat gagaagatca actacaagct   4380
gcttccgggt ccgaacaaga tgctcccaaa ggttttcttc agcaagaaat ggatggccta   4440
ctataaccca agcgaggaca tccagaagat ttataagaac ggtacgttca agaagggcga   4500
catgttcaat cttaacgact gtcacaagct gatcgacttc ttcaaagact caattagccg   4560
gtacccaaag tggtctaacg cctatgactt caacttttcg gaaaccgaga gtacaagga   4620 tatagccgga ttttatagag aggtggaaga gcagggctac aaggtgtcat tcgagtccgc   4680
cagcaagaag gaagtggaca agctcgtgga agagggtaag ctctacatgt tccagattta   4740
taataaagac tttagcgata agagccacgg gacacctaat ctccacacaa tgtatttcaa   4800
gctgctcttc gacgagaata accacggcca aatcaggttg tcaggagggg ctgaactctt   4860
catgcggcgc gctagcctta agaaggagga gcttgtagtc caccctgcga atagtccaat   4920
tgcgaataag aacccggaca atcctaaaaa gactacaaca ttgagctacg acgtgtacaa   4980
ggataagagg ttttccgagg atcagtacga gctccacatc ccgattgcga tcaacaagtg   5040
cccaaagaat attttcaaga taaacacaga ggtgcgtgta ctcctgaagc atgacgacaa   5100
tccttacgtc attgggattg ctcggggcga gaggaacctc ctctatattg tggtggtgga   5160
cgggaagggg aacatagtcg aacagtactc ccttaacgaa ataattaaca atttcaacgg   5220
catccgtatc aagaccgact accattcgtt gctggacaag aaggagaagg agagatttga   5280
ggcgcggcaa aattggacaa gtatcgagaa catcaaggaa ctcaaagcag gttatatctc   5340
tcaagttgtg cataagatat gcgagctggt tgagaagtat gacgcagtga tcgctcttga   5400
ggacctcaac tcgggcttta agaattctag agttaaagtg gagaagcagg tctatcaaaa   5460
gttcgagaag atgcttatag ataagctcaa ctacatggtc gataagaaat cgaacccatg   5520
tgccaccggc ggcgcactca aaggttacca aataacaaac aaattcgagt ccttcaaatc   5580
```

```
gatgagtact cagaatgggt tcatatttta tataccggcg tggcttacgt ctaagatcga      5640
cccgtcaact ggttttgtca acctgttgaa gacgaaatac acgtccattg ccgattcgaa      5700
aaagttcata tctagttttg atcgtattat gtacgtccca gaggaagatc ttttcgagtt      5760
tgctctcgac tacaaaaact tttcgcggac cgatgcggat tacattaaaa aatggaaact      5820
ctattcgtac ggcaacagaa tcaggatttt tcgcaaccct aagaagaata acgtctttga      5880
ttgggaggaa gtttgcttga ctagcgcgta caaggagctc tttaataagt atggcattaa      5940
ctaccaacag ggtgatatca gagcactgct ttgcgaacaa tctgacaagg ctttctactc      6000
atccttcatg gctttgatga gcctgatgct ccagatgaga aattcaatta caggcagaac      6060
cgacgtggat ttcttgatct ccccggttaa aaattctgat ggcatctttt acgatagcag      6120
gaactatgaa gcgcaagaga atgcgattct gccaaaaaat gcagacgcca acggtgccta      6180
taacatcgcc aggaaagtcc tgtgggcgat cggccagttc aaaaaggccg aagacgaaaa      6240
attggacaag gtcaaaatcg ctatcagcaa caaagagtgg ctggagtatg ctcagacatc      6300
cgtaaagcat aagcgtcctg ctgccaccaa aaaggccgga caggctaaga aaaagaaggg      6360
agacggctct ggatcggggt cgggttctgg ctcagtcgac cttgatcttg acctcgaact      6420
cagacttgga tttgctctcg atctcgacct tgaacttaga ctcggatttg ctcttgacct      6480
cgatcttgag cttagactcg gattcgctta ggacgtccta agaaaaagaa gtaggatcca      6540
aaaaaaaaaa aaaaaaaaaa aaaaaaaaaa aaaaaaaaaa aaaaaaaaat ccggaaaggg      6600
cgaattcgca actttgtata caaaagttga acgagaaacg taaaatgata taaatatcaa      6660
tatattaaat tagattttgc ataaaaaaca gactacataa tactgtaaaa cacaacatat      6720
ccagtcacta tgccatccag ctgatatccc ctatagtgag tcgtattaca tggtcatagc      6780
tgtttcctgg cagctctggc ccgtgtctca aaatctctga tgttacattg cacaagataa      6840
aaatatatca tcatgcctcc tc                                             6862
```

<210> SEQ ID NO 48
<211> LENGTH: 6948
<212> TYPE: DNA
<213> ORGANISM: Artificial Sequence
<220> FEATURE:
<223> OTHER INFORMATION: Synthetic construct

<400> SEQUENCE: 48

```
cgcttgcatg gatgttttcc cagtcacgac gttgtaaaac gacggccagt cttaagctcg       60
ggccccaaat aatgatttta ttttgactga tagtgacctg ttcgttgcaa caaattgatg      120
agcaatgctt ttttataatg ccaactttgt acaaaaaagc aggctccgaa ttcgcccttc      180
accatggctc ctaagaagaa gcggaaggtt ggtattcacg gggtgcctgc ggcttcgatc      240
tatcaagaat tcgttaataa gtattcgctt tctaaacac tgagattcga actcatacct      300
caaggaaaga cactcgagaa cataaaggct aggggcctca tattggatga tgaaaagaga      360
gccaaggact ataaaaaagc caaacagata atcgacaagt accaccaatt cttcatagaa      420
gaaatccttt ccagcgtctg cattagcgag gatttgttgc aaaattacag cgatgtctac      480
ttcaagctta agaagagcga tgacgacaat ctccagaaag acttcaaatc agcgaaggac      540
acaattaaga agcagatcag cgagtatatc aaagatagtg aaaaattcaa gaacctttc      600 aatcagaacc tgatagacgc aaaaaaagga caagaaagcg acctcattct ttggttgaag      660
cagtctaagg acaacgggat tgagcttttt aaggcgaata gcgatataac cgacatcgac      720
```

-continued

```
gaggcgcttg agatcataaa gtcgtttaag ggatggacaa catacttcaa aggcttccat      780
gagaatcgca aaaacgtcta ctccagcaac gacattccaa cgtcgattat atacagaatt      840
gttgatgata acctccctaa attcctcgaa aataaggcaa aatatgaaag ccttaaagat      900
aaagcgcctg aagcaatcaa ttatgaacaa atcaaaaagg atcttgctga agaattgacg      960
tttgatatag actacaagac gtcagaagtt aaccagaggg tgttttcact cgacgaggtg     1020
tttgagattg ctaatttcaa caactacctc aatcagagtg ggatcacgaa gttcaacact     1080
attataggtg gtaagttcgt gaatggtgag aacactaaaa gaaaagggat taacgaatat     1140
ataaaccttt atagtcaaca gatcaacgac aagactttga agaaatataa gatgagcgtc     1200
ctcttcaagc agatactcag tgacacggaa tccaagagct ttgtgatcga caagctcgaa     1260
gatgactcgg atgtggtcac taccatgcaa tccttctacg agcaaattgc cgctttcaaa     1320
actgtggagg agaagagtat aaaggagaca ctgtctctgc tttttgacga tcttaaggcc     1380
cagaaattgg atctttccaa aatatatttc aagaatgata agtcacttac ggacctttcc     1440
caacaagttt ttgacgatta ttcagttatt ggtacggcgg ttcttgagta cattacgcag     1500
cagatagccc ccaagaatct ggacaacccc tctaagaaag aacaggagtt gatagcgaag     1560
aagacagaga aggcgaaata cctctcgctg gagaccataa aattggcact ggaagaattt     1620
aacaagcatc gcgacataga taaacagtgc cgcttcgagg aaattttggc aaattttgca     1680
gccattccaa tgattttcga cgagatacg caaaacaagg ataatttggc acaaatttca     1740
ataaaatatc aaaaccaggg caagaaggac ctcttgcagg cttcggcaga ggatgatgtt     1800
aaggctatta aagacttgtt ggaccaaacg aacaatctgt tgcacaagtt gaaaattttc     1860
cacattagtc aaagcgagga taaagcaaac atattggaca aagacgagca cttttatctg     1920
gtgtttgagg agtgctactt cgagcttgct aatattgtcc cactttataa taaaataaga     1980
aactacatta cgcaaaagcc atattcagat gaaaagttta agctcaattt cgaaaatagt     2040
actcttgcca acggctggga caagaataag gagccagata ataccgccat acttttttatc     2100 aaagatgata aatattatct tggggtgatg aataagaaga ataataagat cttcgatgat     2160
aaagcgataa aggaaaataa gggtgaaggc tataaaaaaa ttgtttacaa actgttgccg     2220
ggagcaaata aaatgctccc caaggttttt ttttcggcaa agagcattaa atttttacaat     2280 ccttcagaag acattctgcg cataagaaat cattcgacac acactaaaaa tggttcgcca     2340
caaaagggct acgagaaatt tgaattcaac attgaggact gtcggaagtt cattgatttc     2400
tacaagcagt ccatctccaa gcacccggag tggaaagatt ttgggtttcg gttttccgac     2460
acgcagagat acaacagcat tgatgaattt tatagagagg tcgagaatca aggttataag     2520
cttacctttg aaaacatttc tgaatcatac attgattcag tggtcaatca gggcaaactc     2580
tatctttttc aaatatacaa caaggacttt agtgcttata gtaaagggcg gcccaatttg     2640
catactctct attggaaagc gctgtttgat gagcggaacc ttcaagacgt cgtgtataag     2700
ctcaacgggg aagccgagct cttttaccgc aagcagtcca taccgaaaaa aataacacac     2760
cctgccaaag aagccatcgc caacaagaat aaagacaatc ctaaaaaaga gtccgtcttc     2820
gaatatgatc ttattaagga caagaggttt acagaagata aatttttctt ccattgtccc     2880
ataactatca atttcaaaag ctctggcgcg aacaaattta cgacgaaat caatctcttg     2940 ttgaaagaaa aagccaacga tgtgcacatt ctgtcgatcg acagggggaga gcgccacttg     3000 gcatactaca cccttgttga tgggaaagga aatattatta acaggacac atttaatatc     3060 atcggcaacg atcgcatgaa gaccaactat catgacaaac tggcagcaat tgaaaaggac     3120
```

-continued

```
cgcgactcag cgagaaaaga ctggaagaag atcaataata tcaaagaaat gaaagagggt   3180
tatttgtctc aagtggtcca tgagatcgcg aagttggtca ttgaatataa tgccatagtg   3240
gtcttcgaag atctgaattt tggatttaag cgcggcaggt tcaaagtcga aaaacaggtc   3300
taccaaaagt tggaaaagat gctcatcgaa aagctgaatt accttgtctt caaagataac   3360
gaattcgata aaaccggggg ggtcttgagg gcctaccaac tgactgcacc ctttgagact   3420
tttaaaaaga tgggtaaaca gacaggaata atttactatg ttcctgccgg tttcactagc   3480
aagatttgcc ccgttaccgg attcgtgaat caactctatc ccaaatacga atccgtgagc   3540
aagagtcagg aattcttctc caaatttgat aaaaatatgct ataatctcga caaaggttat   3600
ttcgagttct cgttcgacta taagaacttc ggggataagg ctgccaaggg aaagtggact   3660
atagcaagct ttggtagtcg ccttataaat tttaggaaca gcgacaagaa tcacaactgg   3720
gacactcggg aagtctaccc aacaaaagaa ctggagaaac tcttgaagga ttatagtatc   3780
gagtatgggc atgggagtg tatcaaggca gcgatttgtg gagagtccga caaaaagttt   3840
tttgctaaac tcacctcggt gctcaacact atcctccaga tgagaaattc aaaaacaggg   3900
acagagctcg attacctcat tagccccgtt gccgacgtca atggaaactt tttcgactca   3960
agacaggctc caaaaaacat gccgcaagat gcggacgcga atggggccta tcacataggc   4020
ctgaaagggc ttatgctcct tgggagaatt aaaaataacc aagaaggcaa aaaactcaac   4080
ctcgtcatta agaacgaaga atacttcgaa tttgttcaga acaggaataa caagcgtcct   4140
gctgccacca aaaaggccgg acaggctaag aaaaagaagt gagacgacta gtggcggccg   4200
ccgacgtcct aagaaaaga agtaggatcc aaaaaaaaaa aaaaaaaaaa aaaaaaaaaa   4260
aaaaaaaaaa aaaaaaaaaa tccggaaagg gcgaattcgc aactttgtat acaaagttg   4320 aacgagaaac gtaaaatgat ataaatatca atatattaaa ttagattttg cataaaaaac   4380
agactacata atactgtaaa acacaacata tccagtcact atgccatcca gctgatatcc   4440
cctatagtga gtcgtattac atggtcatag ctgtttcctg gcagctctgg cccgtgtctc   4500
aaaatctctg atgttacatt gcacaagata aaaatatatc atcatgcctc tctggacca   4560 gccaggacag aaatgcctcg acttcgctgc tacccaaggt tgccgggtga cgcacaccgt   4620
ggaaacggat gaaggcacga acccagtgga cataagcctg ttcggttcgt aagctgtaat   4680
gcaagtagcg tatgcgctca cgcaactggt ccagaacctt gaccgaacgc agcggtggta   4740
acggcgcagt ggcggttttc atggcttgtt atgactgttt ttttggggta cagtctatgc   4800
ctcgggcatc caagcagcaa gcgcgttacg ccgtgggtcg atgtttgatg ttatggagca   4860
gcaacgatgt tacgcagcag ggcagtcgcc ctaaaacaaa gttaaacatc atgagggaag   4920
cggtgatcgc cgaagtatcg actcaactat cagaggtagt tggcgtcatc gagcgccatc   4980
tcgaaccgac gttgctggcc gtacatttgt acggctccgc agtggatggc ggcctgaagc   5040
cacacagtga tattgatttg ctggttacgg tgaccgtaag gcttgatgaa acaacgcggc   5100
gagctttgat caacgacctt ttggaaactt cggcttcccc tggagagagc gagattctcc   5160
gcgctgtaga agtcaccatt gttgtgcacg acgacatcat tccgtggcgt tatccagcta   5220
agcgcgaact gcaatttgga gaatggcagc gcaatgacat tcttgcaggt atcttcgagc   5280
cagccacgat cgacattgat ctggctatct tgctgacaaa agcaagagaa catagcgttg   5340
ccttggtagg tccagcggcg gaggaactct ttgatccggt tcctgaacag gatctatttg   5400
aggcgctaaa tgaaacctta acgctatgga actcgccgcc cgactgggct ggcgatgagc   5460
```

-continued

```
gaaatgtagt gcttacgttg tcccgcattt ggtacagcgc agtaaccggc aaaatcgcgc    5520
cgaaggatgt cgctgccgac tgggcaatgg agcgcctgcc ggcccagtat cagcccgtca    5580
tacttgaagc tagacaggct tatcttggac aagaagaaga tcgcttggcc tcgcgcgcag    5640
atcagttgga agaatttgtc cactacgtga aaggcgagat caccaaggta gtcggcaaat    5700
aaccctcgag ccacccatga ccaaaatccc ttaacgtgag ttacgcgtcg ttccactgag    5760
cgtcagaccc cgtagaaaag atcaaaggat cttcttgaga tcctttttt ctgcgcgtaa    5820 tctgctgctt gcaaacaaaa aaaccaccgc taccagcggt ggtttgtttg ccggatcaag    5880
agctaccaac tctttttccg aaggtaactg gcttcagcag agcgcagata ccaaatactg    5940
tccttctagt gtagccgtag ttaggccacc acttcaagaa ctctgtagca ccgcctacat    6000
acctcgctct gctaatcctg ttaccagtgg ctgctgccag tggcgataag tcgtgtctta    6060
ccgggttgga ctcaagacga tagttaccgg ataaggcgca gcggtcgggc tgaacggggg    6120
gttcgtgcac acagcccagc ttggagcgaa cgacctacac cgaactgaga tacctacagc    6180
gtgagctatg agaaagcgcc acgcttcccg aagggagaaa ggcggacagg tatccggtaa    6240
gcggcagggt cggaacagga gagcgcacga gggagcttcc aggggggaaac gcctggtatc    6300 tttatagtcc tgtcgggttt cgccacctct gacttgagcg tcgatttttg tgatgctcgt    6360
caggggggcg gagcctatgg aaaaacgcca gcaacgcggc cttttttacgg ttcctggcct    6420 tttgctggcc ttttgctcac atgttctttc ctgcgttatc ccctgattct gtggataacc    6480
gtattaccgc ctttgagtga gctgataccg ctcgccgcag ccgaacgacc gagcgcagcg    6540
agtcagtgag cgaggaagcg gaagagcgcc caatacgcaa accgcctctc cccgcgcgtt    6600
ggccgattca ttaatgcagc tggcacgaca ggtttcccga ctggaaagcg ggcagtgagc    6660
gcaacgcaat taatacgcgt accgcgagcc aggaagagtt tgtagaaacg caaaaaggcc    6720
atccgtcagg atggccttct gcttagtttg atgcctggca gtttatggcg ggcgtcctgc    6780
ccgccaccct ccgggccgtt gcttcacaac gttcaaatcc gctcccggcg gatttgtcct    6840
actcaggaga gcgttcaccg acaaacaaca gataaaacga aaggcccagt cttccgactg    6900
agcctttcgt tttatttgat gcctggcagt tccctactct cgcgttaa             6948
```

<210> SEQ ID NO 49
<211> LENGTH: 12807
<212> TYPE: DNA
<213> ORGANISM: Artificial Sequence
<220> FEATURE:
<223> OTHER INFORMATION: Synthetic construct

<400> SEQUENCE: 49

```
ccatccggcc cggtacaaat cggcgcggcg ctgggtgatg acctggtgga gaagttgaag     60
gccgcgcagg ccgcccagcg gcaacgcatc gaggcagaag cacgccccgg tgaatcgtgg    120
caagcggccg ctgatcgaat ccgcaaagaa tcccggcaac cgccggcagc cggtgcgccg    180
tcgattagga agccgcccaa gggcgacgag caaccagatt ttttcgttcc gatgctctat    240
gacgtgggca cccgcgatag tcgcagcatc atggacgtgg ccgtttttccg tctgtcgaag    300 cgtgaccgac gagctggcga ggtgatccgc tacgagcttc cagacgggca cgtagaggtt    360
tccgcagggc cggccggcat ggccagtgtg tgggattacg acctggtact gatggcggtt    420
tcccatctaa ccgaatccat gaaccgatac cgggaaggga agggagacaa gcccggccgc    480
gtgttccgtc cacacgttgc ggacgtactc aagttctgcc ggcgagccga tggcggaaag    540
cagaaagacg acctggtaga aacctgcatt cggttaaaca ccacgcacgt tgccatgcag    600
```

-continued

```
cgtacgaaga aggccaagaa cggccgcctg gtgacggtat ccgagggtga agccttgatt    660
agccgctaca agatcgtaaa gagcgaaacc gggcggccgg agtacatcga gatcgagcta    720
gctgattgga tgtaccgcga gatcacagaa ggcaagaacc cggacgtgct gacggttcac    780
cccgattact ttttgatcga tcccggcatc ggccgttttc tctaccgcct ggcacgccgc    840
gccgcaggca aggcagaagc cagatggttg ttcaagacga tctacgaacg cagtggcagc    900
gccggagagt tcaagaagtt ctgtttcacc gtgcgcaagc tgatcgggtc aaatgacctg    960
ccggagtacg atttgaagga ggaggcgggg caggctggcc cgatcctagt catgcgctac   1020
cgcaacctga tcgagggcga agcatccgcc ggttcctaat gtacggagca gatgctaggg   1080
caaattgccc tagcagggga aaaaggtcga aaaggtctct ttcctgtgga tagcacgtac   1140
attgggaacc caaagccgta cattgggaac cggaacccgt acattgggaa cccaaagccg   1200
tacattggga accggtcaca catgtaagtg actgatataa aagagaaaaa aggcgatttt   1260
tccgcctaaa actctttaaa acttattaaa actcttaaaa cccgcctggc ctgtgcataa   1320
ctgtctggcc agcgcacagc cgaagagctg caaaaagcgc ctaccttcg gtcgctgcgc    1380 tccctacgcc ccgccgcttc gcgtcggcct atcgcggccg ctggccgctc aaaaatggct   1440
ggcctacggc caggcaatct accagggcgc ggacaagccg cgccgtcgcc actcgaccgc   1500
cggcgcccac atcaaggcac cctgcctcgc gcgtttcggt gatgacggtg aaaacctctg   1560
acacatgcag ctcccggaga cggtcacagc ttgtctgtaa gcggatgccg ggagcagaca   1620
agcccgtcag ggcgcgtcag cgggtgttgg cgggtgtcgg ggcgcagcca tgacccagtc   1680
acgtagcgat agcggagtgt atactggctt aactatgcgg catcagagca gattgtactg   1740
agagtgcacc atatgcggtg tgaaataccg cacagatgcg taaggagaaa ataccgcatc   1800
aggcgctctt ccgcttcctc gctcactgac tcgctgcgct cggtcgttcg ctgcggcga    1860 gcggtatcag ctcactcaaa ggcggtaata cggttatcca cagaatcagg ggataacgca   1920
ggaaagaaca tgtgagcaaa aggccagcaa aaggccagga accgtaaaaa ggccgcgttg   1980
ctggcgtttt tccataggct ccgcccccct gacgagcatc acaaaaatcg acgctcaagt   2040
cagaggtggc gaaacccgac aggactataa agataccagg cgtttccccc tggaagctcc   2100
ctcgtgcgct ctcctgttcc gaccctgccg cttaccggat acctgtccgc ctttctccct   2160
tcgggaagcg tggcgctttc tcatagctca cgctgtaggt atctcagttc ggtgtaggtc   2220
gttcgctcca agctgggctg tgtgcacgaa ccccccgttc agcccgaccg ctgcgcctta   2280
tccggtaact atcgtcttga gtccaacccg gtaagacacg acttatcgcc actggcagca   2340
gccactggta acaggattag cagagcgagg tatgtaggcg gtgctacaga gttcttgaag   2400
tggtggccta actacggcta cactagaagg acagtatttg gtatctgcgc tctgctgaag   2460
ccagttacct tcggaaaaag agttggtagc tcttgatccg gcaaacaaac caccgctggt   2520
agcggtggtt tttttgtttg caagcagcag attacgcgca gaaaaaaagg atctcaagaa   2580
gatcctttga tcttttctac ggggtctgac gctcagtgga acgaaaactc acgttaaggg   2640
attttggtca tgcattctag gtactaaaac aattcatcca gtaaaatata atattttatt   2700
ttctcccaat caggcttgat ccccagtaag tcaaaaaata gctcgacata ctgttcttcc   2760
ccgatatcct ccctgatcga ccggacgcag aaggcaatgt cataccactt gtccgccctg   2820
ccgcttctcc caagatcaat aaagccactt actttgccat cttttcacaaa gatgttgctg   2880 tctcccaggt cgccgtggga aaagacaagt tcctcttcgg cttttccgt ctttaaaaaa    2940
```

-continued

```
tcatacagct cgcgcggatc tttaaatgga gtgtcttctt cccagttttc gcaatccaca   3000
tcggccagat cgttattcag taagtaatcc aattcggcta agcggctgtc taagctattc   3060
gtatagggac aatccgatat gtcgatggag tgaaagagcc tgatgcactc cgcatacagc   3120
tcgataatct tttcagggct ttgttcatct tcatactctt ccgagcaaag gacgccatcg   3180
gcctcactca tgagcagatt gctccagcca tcatgccgtt caaagtgcag gacctttgga   3240
acaggcagct ttccttccag ccatagcatc atgtcctttt cccgttccac atcataggtg   3300 gtcccttat accggctgtc cgtcattttt aaatataggt tttcattttc tcccaccagc     3360
ttatatacct tagcaggaga cattccttcc gtatctttta cgcagcggta tttttcgatc   3420
agttttttca attccggtga tattctcatt ttagccattt attatttcct tcctcttttc   3480
tacagtattt aaagataccc caagaagcta aggaaggtgc gaataagcgg ggaaattctt   3540
ctcggctgac tcagtcattt catttcttca tgtttgagcc gattttttct cccgtaaatg   3600
ccttgaatca gcctatttag accgtttctt cgccatttaa ggcgttatcc ccagttttta   3660
gtgagatctc tcccactgac gtatcatttg gtccgcccga aacaggttgg ccagcgtgaa   3720
taacatcgcc agttggttat cgttttcag caacccttg tatctggctt tcacgaagcc     3780
gaactgtcgc ttgatgatgc gaaatgggtg ctccaccctg gcccggatgc tggctttcat   3840
gtattcgatg ttgatggccg ttttgttctt gcgtggatgc tgtttcaagg ttcttacctt   3900
gccggggcgc tcggcgatca gccagtccac atccacctcg gccagctcct cgcgctgtgg   3960
cgccccttgg tagccggcat cggctgagac aaattgctcc tctccatgca gcagattacc   4020
cagctgattg aggtcatgct cgttggccgc ggtggtgacc aggctgtggg tcaggccact   4080
cttggcatcg acaccaatgt gggccttcat gccaaagtgc cactgattgc ctttcttggt   4140
ctgatgcatc tccggatcgc gttgctgctc tttgttcttg gtcgagctgg gtgcctcaat   4200
gatggtggca tcgaccaagg tgccttgagt catcatgacg cctgcttcgg ccagccagcg   4260
attgatggtc ttgaacaatt ggcgggccag ttgatgctgc tccagcaggt ggcggaaatt   4320
catgatggtg gtgcggtccg gcaaggcgct atccagggat aaccgggcaa acagacgcat   4380
ggaggcgatt tcgtacagag catcttccat cgcgccatcg ctcaggttgt accaatgctg   4440
catgcagtga atgcgtagca tggtttccag cggataaggt cgccggccat taccagcctt   4500
ggggtaaaac ggctcgatga cttccaccat gttttgccat ggcagaatct gctccatgcg   4560
ggacaagaaa atctcttttc tggtctgacg gcgcttactg ctgaattcac tgtcggcgaa   4620
ggtaagttga tgactcatga tgaaccctgt tctatggctc cagatgacaa acatgatctc   4680
atatcaggga cttgttcgca ccttccctaa ttataacaag acgaactcca attcactgtt   4740
ccttgcattc taaaacctta aataccagaa aacagctttt tcaaagttgt tttcaaagtt   4800
ggcgtataac atagtatcga cggagccgat tttgaaaccg cggtgatcac aggcagcaac   4860
gctctgtcat cgttacaatc aacatgctac cctccgcgag atcatccgtg tttcaaaccc   4920
ggcagcttag ttgccgttct tccgaatagc atcggtaaca tgagcaaagt ctgccgcctt   4980
acaacggctc tcccgctgac gccgtcccgg actgatgggc tgcctgtatc gagtggtgat   5040
tttgtgccga gctgccggtc ggggagctgt tggctggctg gtggcaggat atattgtggt   5100
gtaaacaaat tgacgcttag acaacttaat aacacattgc ggacgttttt aatgtactga   5160
attaacgccg aattaattcg ggggatctgg attttagtac tggattttgg ttttaggaat   5220
tagaaatttt attgatagaa gtattttaca aatacaaata catactaagg gtttcttata   5280
tgctcaacac atgagcgaaa ccctatagga accctaattc ccttatctgg gaactactca   5340
```

-continued

```
cacattatta tggagaaact cgagcttgtc gatcgacaga tcccggtcgg catctactct    5400
atttctttgc cctcggacga gtgctggggc gtcggtttcc actatcggcg agtacttcta    5460
cacagccatc ggtccagacg gccgcgcttc tgcgggcgat ttgtgtacgc ccgacagtcc    5520
cggctccgga tcggacgatt gcgtcgcatc gaccctgcgc ccaagctgca tcatcgaaat    5580
tgccgtcaac caagctctga tagagttggt caagaccaat gcggagcata tacgcccgga    5640
gtcgtggcga tcctgcaagc tccggatgcc tccgctcgaa gtagcgcgtc tgctgctcca    5700
tacaagccaa ccacggcctc cagaagaaga tgttggcgac ctcgtattgg gaatccccga    5760
acatcgcctc gctccagtca atgaccgctg ttatgcggcc attgtccgtc aggacattgt    5820
tggagccgaa atccgcgtgc acgaggtgcc ggacttcggg gcagtcctcg gcccaaagca    5880
tcagctcatc gagagcctgc gcgacggacg cactgacggt gtcgtccatc acagtttgcc    5940
agtgatacac atggggatca gcaatcgcgc atatgaaatc acgccatgta gtgtattgac    6000
cgattccttg cggtccgaat gggccgaacc cgctcgtctg gctaagatcg gccgcagcga    6060
tcgcatccat agcctccgcg accggttgta gaacagcggg cagttcggtt tcaggcaggt    6120
cttgcaacgt gacaccctgt gaacggcggg agatgcaata ggtcaggctc tcgctaaact    6180
ccccaatgtc aagcacttcc ggaatcggga gcgcggccga tgcaaagtgc cgataaacat    6240
aacgatcttt gtagaaacca tcggcgcagc tatttacccg caggacatat ccacgccctc    6300
ctacatcgaa gctgaaagca cgagattctt cgccctccga gagctgcatc aggtcggaga    6360
cgctgtcgaa cttttcgatc agaaacttct cgacagacgt cgcggtgagt tcaggctttt    6420
tcatatctca ttgccccccg gatctgcgaa agctcgagag agatagattt gtagagagag    6480
actggtgatt tcagcgtgtc ctctccaaat gaaatgaact tccttatata gaggaagggt    6540
cttgcgaagg atagtgggat tgtgcgtcat cccttacgtc agtggagata tcacatcaat    6600
ccacttgctt tgaagacgtg gttggaacgt cttcttttc cacgatgctc ctcgtgggtg    6660
ggggtccatc tttgggacca ctgtcggcag aggcatcttg aacgatagcc tttcctttat    6720
cgcaatgatg gcatttgtag gtgccacctt ccttttctac tgtccttttg atgaagtgac    6780
agatagctgg gcaatggaat ccgaggaggt ttcccgatat taccctttgt tgaaaagtct    6840
caatagccct ttggtcttct gagactgtat ctttgatatt cttggagtag acgagagtgt    6900
cgtgctccac catgttcaca tcaatccact tgctttgaag acgtggttgg aacgtcttct    6960
ttttccacga tgctcctcgt gggtgggggt ccatctttgg gaccactgtc ggcagaggca    7020
tcttgaacga tagcctttcc tttatcgcaa tgatggcatt gtaggtgcc accttccttt    7080 tctactgtcc ttttgatgaa gtgacagata gctgggcaat ggaatccgag gaggtttccc    7140
gatattaccc tttgttgaaa agtctcaata gccctttggt cttctgagac tgtatctttg    7200
atattcttgg agtagacgag agtgtcgtgc tccaccatgt tggcaagctg ctctagccaa    7260
tacgcaaacc gcctctcccc gcgcgttggc cgattcatta atgcagctgg cacgacaggt    7320
ttcccgactg gaaagcgggc agtgagcgca acgcaattaa tgtgagttag ctcactcatt    7380
aggcacccca ggctttacac tttatgcttc cggctcgtat gttgtgtgga attgtgagcg    7440
gataacaatt tcacacagga aacagctatg acatgattac gaattcccga tctagtaaca    7500
tagatgacac cgcgcgcgat aatttatcct agtttgcgcg ctatattttg ttttctatcg    7560
cgtattaaat gtataattgc gggactctaa tcataaaaac ccatctcata ataacgtca     7620 tgcattacat gttaattatt acatgcttaa cgtaattcaa cagaaattat atgataatca    7680
```

-continued

```
tcgcaagacc ggcaacagga ttcaatctta agaaacttta ttgccaaatg tttgaacgat   7740
cggggaaatt cgagctccac cgcggtggcg gccgctctag aactagttaa ttaagaatta   7800
tcgaaccact ttgtacaaga aagctgaacg agaaacgtaa aatgatataa atatcaatat   7860 attaaaattag attttgcata aaaaacagac tacataatac tgtaaaacac aacatatcca   7920
gtcactatgg tcgacctgca gactggctgt gtataaggga gcctgacatt tatattcccc   7980
agaacatcag gttaatggcg ttttgatgt cattttcgcg gtggctgaga tcagccactt   8040
cttccccgat aacggagacc ggcacactgg ccatatcggt ggtcatcatg cgccagcttt   8100
catccccgat atgcaccacc gggtaaagtt cacgggggac tttatctgac agcagacgtg   8160
cactggccag ggggatcacc atccgtcgcc cgggcgtgtc aataatatca ctctgtacat   8220
ccacaaacag acgataacgg ctctctcttt tataggtgta aaccttaaac tgcatttcac   8280
cagcccctgt tctcgtcagc aaaagagccg ttcatttcaa taaaccgggc gacctcagcc   8340
atcccttcct gattttccgc tttccagcgt tcggcacgca gacgacgggc ttcattctgc   8400
atggttgtgc ttaccagacc ggagatattg acatcatata tgccttgagc aactgatagc   8460
tgtcgctgtc aactgtcact gtaatacgct gcttcatagc atacctcttt ttgacatact   8520
tcgggtatac atatcagtat atattcttat accgcaaaaa tcagcgcgca aatacgcata   8580
ctgttatctg gcttttagta agccggatcc tctagattac gccccgcctg ccactcatcg   8640
cagtactgtt gtaattcatt aagcattctg ccgacatgga agccatcaca aacggcatga   8700
tgaacctgaa tcgccagcgg catcagcacc ttgtcgcctt gcgtataata tttgcccatg   8760
gtgaaaacgg gggcgaagaa gttgtccata ttggccacgt ttaaatcaaa actggtgaaa   8820
ctcacccagg gattggctga gacgaaaaac atattctcaa taaaccctt agggaaatag   8880 gccaggtttt caccgtaaca cgccacatct tgcgaatata tgtgtagaaa ctgccggaaa   8940
tcgtcgtggt attcactcca gagcgatgaa aacgtttcag tttgctcatg gaaaacggtg   9000
taacaagggt gaacactatc ccatatcacc agctcaccgt ctttcattgc catacggaat   9060
tccggatgag cattcatcag gcgggcaaga atgtgaataa aggccggata aaacttgtgc   9120
ttatttttct ttacggtctt taaaaaggcc gtaatatcca gctgaacggt ctggttatag   9180
gtacattgag caactgactg aaatgcctca aaatgttctt tacgatgcca ttgggatata   9240
tcaacggtgg tatatccagt gatttttttc tccattttag cttccttagc tcctgaaaat   9300
ctcgacggat cctaactcaa aatccacaca ttatacgagc cggaagcata aagtgtaaag   9360
cctggggtgc ctaatgcggc cgccatagtg actggatatg ttgtgtttta cagtattatg   9420
tagtctgttt tttatgcaaa atctaattta atatattgat atttatatca ttttacgttt   9480
ctcgttcagc tttttgtac aaacttgttt gatagcttgg cgcgcctcga gggggggccc   9540
ggtaccctgt taatcagaaa aactcagatt aatctacaaa ttcgatcgca caaactagaa   9600
actaacacca gatctagata gaaatcacaa atcgaagagt aattattcga caaaactcaa   9660
attatttgaa caaatcggat gatatctatg aaaccctaat cgagaattaa gatgatatct   9720
aacgatcaaa cccagaaaat cgtcttcgat ctaagattaa cagaatctaa accaaagaac   9780
atatacgaaa ttgggatcga acgaaaacaa aatcgaagat tttgagagaa taaggaacac   9840
agaaatttac cttgatcacg gtagagagaa ttgagagaaa gttttaaga ttttgagaaa   9900 ttgaaatctg aattgtgaag aagaagagct ctttgggtat tgtttatag aagaagaaga   9960 agaaaagacg aggacgacta ggtcacgaga aagctaaggc ggtgaagcaa tagctaataa   10020
taaaatgaca cgtgtattga gcgttgttta cacgcaaagt tgtttttggc taattgcctt   10080
```

```
attttttaggt tgaggaaaag tatttgtgct ttgagttgat aaacacgact cgtgtgtgcc   10140
ggctgcaacc actttgacgc cgtttattac tgactcgtcg aaagcttggc actggccgtc   10200
gttttacaac gtcgtgactg ggaaaaccct ggcgttaccc aacttaatcg ccttgcagca   10260
catccccctt tcgccagctg gcgtaatagc gaagaggccc gcaccgatcg cccttcccaa   10320
cagttgcgca gcctgaatgg cgaatgctag agcagcttga gcttggatca gattgtcgtt   10380
tcccgccttc agtttaaact atcagtgttt gacaggatat attggcgggt aaacctaaga   10440
gaaaagagcg tttattagaa taatcggata tttaaaaggg cgtgaaaagg tttatccgtt   10500
cgtccatttg tatgtgcatg ccaaccacag ggttcccctc gggatcaaag tactttgatc   10560
caacccctcc gctgctatag tgcagtcggc ttctgacgtt cagtgcagcc gtcttctgaa   10620
aacgacatgt cgcacaagtc ctaagttacg cgacaggctg ccgccctgcc cttttcctgg   10680
cgttttcttg tcgcgtgttt tagtcgcata aagtagaata cttgcgacta gaaccggaga   10740
cattacgcca tgaacaagag cgccgccgct ggcctgctgg gctatgcccg cgtcagcacc   10800
gacgaccagg acttgaccaa ccaacgggcc gaactgcacg cggccggctg caccaagctg   10860
ttttccgaga agatcaccgg caccaggcgc gaccgcccgg agctggccag gatgcttgac   10920
cacctacgcc ctggcgacgt tgtgacagtg accaggctag accgcctggc ccgcagcacc   10980
cgcgacctac tggacattgc cgagcgcatc caggaggccg gcgcgggcct gcgtagcctg   11040
gcagagccgt gggccgacac caccacgccg gccggccgca tggtgttgac cgtgttcgcc   11100
ggcattgccg agttcgagcg ttccctaatc atcgaccgca cccggagcgg gcgcgaggcc   11160
gccaaggccc gaggcgtgaa gtttggcccc cgccctaccc tcaccccggc acagatcgcg   11220
cacgcccgcg agctgatcga ccaggaaggc cgcaccgtga agaggcggc tgcactgctt   11280 ggcgtgcatc gctcgaccct gtaccgcgca cttgagcgca gcgaggaagt gacgcccacc   11340
gaggccaggc ggcgcggtgc cttccgtgag gacgcattga ccgaggccga cgccctggcg   11400
gccgccgaga atgaacgcca agaggaacaa gcatgaaacc gcaccaggac ggccaggacg   11460
aaccgttttt cattaccgaa gagatcgagg cggagatgat cgcggccggg tacgtgttcg   11520 agccgccgc gcacgtctca accgtgcggc tgcatgaaat cctggccggt ttgtctgatg   11580
ccaagctggc ggcctggccg gccagcttgg ccgctgaaga aaccgagcgc cgccgtctaa   11640
aaaggtgatg tgtatttgag taaaacagct tgcgtcatgc ggtcgctgcg tatatgatgc   11700
gatgagtaaa taaacaaata cgcaaggggga acgcatgaag gttatcgctg tacttaacca   11760
gaaaggcggg tcaggcaaga cgaccatcgc aacccatcta gcccgcgccc tgcaactcgc   11820
cggggccgat gttctgttag tcgattccga tccccagggc agtgcccgcg attgggcggc   11880
cgtgcgggaa gatcaaccgc taaccgttgt cggcatcgac cgcccgacga ttgaccgcga   11940
cgtgaaggcc atcggccggc gcgacttcgt agtgatcgac ggagcgcccc aggcggcgga   12000
cttggctgtg tccgcgatca aggcagccga cttcgtgctg attccggtgc agccaagccc   12060
ttacgacata tgggccaccg ccgacctggt ggagctggtt aagcagcgca ttgaggtcac   12120
ggatggaagg ctacaagcgg cctttgtcgt gtcgcgggcg atcaaaggca cgcgcatcgg   12180
cggtgaggtt gccgaggcgc tggccgggta cgagctgccc attcttgagt cccgtatcac   12240
gcagcgcgtg agctacccag gcactgccgc cgccggcaca accgttcttg aatcagaacc   12300
cgagggcgac gctgcccgcg aggtccaggc gctggccgct gaaattaaat caaaactcat   12360
ttgagttaat gaggtaaaga gaaaatgagc aaaagcacaa acacgctaag tgccggccgt   12420
```

```
ccgagcgcac gcagcagcaa ggctgcaacg ttggccagcc tggcagacac gccagccatg    12480
aagcgggtca actttcagtt gccggcggag gatcacacca agctgaagat gtacgcggta    12540
cgccaaggca agaccattac cgagctgcta tctgaataca tcgcgcagct accagagtaa    12600
atgagcaaat gaataaatga gtagatgaat tttagcggct aaaggaggcg gcatggaaaa    12660
tcaagaacaa ccaggcaccg acgccgtgga atgccccatg tgtggaggaa cgggcggttg    12720
gccaggcgta agcggctggg ttgcctgccg gccctgcaat ggcactggaa cccccaagcc    12780
cgaggaatcg gcgtgagcgg tcgcaaa                                         12807

<210> SEQ ID NO 50
<211> LENGTH: 14174
<212> TYPE: DNA
<213> ORGANISM: Artificial Sequence
<220> FEATURE:
<223> OTHER INFORMATION: Synthetic construct

<400> SEQUENCE: 50
cgtaatcatg tcatagctgt ttcctgtgtg aaattgttat ccgctcacaa ttccacacaa      60
catacgagcc ggaagcataa agtgtaaagc ctggggtgcc taatgagtga gctaactcac     120
attaattgcg ttgcgctcac tgcccgcttt ccagtcggga aacctgtcgt gccagctgca     180
ttaatgaatc ggccaacgcg cggggagagg cggtttgcgt attggctaga gcagcttgcc     240
aacatggtgg agcacgacac tctcgtctac tccaagaata tcaaagatac agtctcagaa     300
gaccaaaggg ctattgagac ttttcaacaa agggtaatat cgggaaacct cctcggattc     360
cattgcccag ctatctgtca cttcatcaaa aggacagtag aaaaggaagg tggcacctac     420
aaatgccatc attgcgataa aggaaaggct atcgttcaag atgcctctgc cgacagtggt     480
cccaaagatg gacccccacc cacgaggagc atcgtggaaa aagaagacgt tccaaccacg     540
tcttcaaagc aagtggattg atgtgaacat ggtggagcac gacactctcg tctactccaa     600
gaatatcaaa gatacagtct cagaagacca aagggctatt gagactttc aacaaagggt     660 aatatcggga aacctcctcg gattccattg cccagctatc tgtcacttca tcaaaaggac     720
agtagaaaag gaaggtggca cctacaaatg ccatcattgc gataaaggaa aggctatcgt     780
tcaagatgcc tctgccgaca gtggtcccaa agatggaccc ccacccacga ggagcatcgt     840
ggaaaaagaa gacgttccaa ccacgtcttc aaagcaagtg gattgatgtg atatctccac     900
tgacgtaagg gatgacgcac aatcccacta tccttcgcaa gacccttcct ctatataagg     960
aagttcattt catttggaga ggacacgctg aaatcaccag tctctctcta caaatctatc    1020
tctctcgagc tttcgcagat ccgggggca atgagatatg aaaaagcctg aactcaccgc    1080
gacgtctgtc gagaagtttc tgatcgaaaa gttcgacagc gtctccgacc tgatgcagct    1140
ctcggagggc gaagaatctc gtgctttcag cttcgatgta ggagggcgtg gatatgtcct    1200
gcgggtaaat agctgcgccg atggtttcta caaagatcgt tatgtttatc ggcactttgc    1260
atcggccgcg ctcccgattc cggaagtgct tgacattggg gagtttagcg agagcctgac    1320
ctattgcatc tcccgccgtt cacagggtgt cacgttgcaa gacctgcctg aaaccgaact    1380
gcccgctgtt ctacaaccgg tcgcggaggc tatggatgcg atcgctgcgg ccgatcttag    1440
ccagacgagc gggttcggcc cattcggacc gcaaggaatc ggtcaataca ctacatggcg    1500
tgatttcata tgcgcgattg ctgatcccca tgtgtatcac tggcaaactg tgatggacga    1560
caccgtcagt gcgtccgtcg cgcaggctct cgatgagctg atgctttggg ccgaggactg    1620
ccccgaagtc cggcacctcg tgcacgcgga tttcggctcc aacaatgtcc tgacggacaa    1680
```

-continued

```
tggccgcata acagcggtca ttgactggag cgaggcgatg ttcgggggatt cccaatacga   1740 ggtcgccaac atcttcttct ggaggccgtg gttggcttgt atggagcagc agacgcgcta   1800
cttcgagcgg aggcatccgg agcttgcagg atcgccacga ctccgggcgt atatgctccg   1860
cattggtctt gaccaactct atcagagctt ggttgacggc aatttcgatg atgcagcttg   1920
ggcgcagggt cgatgcgacg caatcgtccg atccggagcc gggactgtcg ggcgtacaca   1980
aatcgcccgc agaagcgcgg ccgtctggac cgatggctgt gtagaagtac tcgccgatag   2040
tggaaaccga cgccccagca ctcgtccgag ggcaaagaaa tagagtagat gccgaccggg   2100
atctgtcgat cgacaagctc gagtttctcc ataataatgt gtgagtagtt cccagataag   2160
ggaattaggg ttcctatagg gtttcgctca tgtgttgagc atataagaaa cccttagtat   2220
gtatttgtat ttgtaaaata cttctatcaa taaaatttct aattcctaaa accaaaatcc   2280
agtactaaaa tccagatccc ccgaattaat tcggcgttaa ttcagtacat taaaaacgtc   2340
cgcaatgtgt tattaagttg tctaagcgtc aatttgttta caccacaata tatcctgcca   2400
ccagccagcc aacagctccc cgaccggcag ctcggcacaa aatcaccact cgatacaggc   2460
agcccatcag tccgggacgg cgtcagcggg agagccgttg taaggcggca gactttgctc   2520
atgttaccga tgctattcgg aagaacggca actaagctgc cgggtttgaa acacggatga   2580
tctcgcggag ggtagcatgt tgattgtaac gatgacagag cgttgctgcc tgtgatcacc   2640
gcggtttcaa aatcggctcc gtcgatacta tgttatacgc caactttgaa aacaactttg   2700
aaaaagctgt tttctggtat ttaaggtttt agaatgcaag gaacagtgaa ttggagttcg   2760
tcttgttata attagggaag gtgcgaacaa gtccctgata tgagatcatg tttgtcatct   2820
ggagccatag aacagggttc atcatgagtc atcaacttac cttcgccgac agtgaattca   2880
gcagtaagcg ccgtcagacc agaaaagaga ttttcttgtc ccgcatggag cagattctgc   2940
catggcaaaa catggtggaa gtcatcgagc cgttttaccc caaggctggt aatggccggc   3000
gaccttatcc gctggaaacc atgctacgca ttcactgcat gcagcattgg tacaacctga   3060
gcgatggcgc gatggaagat gctctgtacg aaatcgcctc catgcgtctg tttgcccggt   3120
tatccctgga tagcgccttg ccggaccgca ccaccatcat gaatttccgc cacctgctgg   3180
agcagcatca actggcccgc caattgttca agaccatcaa tcgctggctg ccgaagcag   3240 gcgtcatgat gactcaaggc accttggtcg atgccaccat cattgaggca cccagctcga   3300
ccaagaacaa agagcagcaa cgcgatccgg agatgcatca gaccaagaaa ggcaatcagt   3360
ggcactttgg catgaaggcc cacattggtg tcgatgccaa gagtggcctg acccacagcc   3420
tggtcaccac cgcggccaac gagcatgacc tcaatcagct gggtaatctg ctgcatggag   3480
aggagcaatt tgtctcagcc gatgccggct accaaggggc gccacagcgc gaggagctgg   3540
ccgaggtgga tgtggactgg ctgatcgccg agcgcccgg caaggtaaga accttgaaac   3600
agcatccacg caagaacaaa acggccatca acatcgaata catgaaagcc agcatccggg   3660
ccagggtgga gcacccattt cgcatcatca agcgacagtt cggcttcgtg aaagccagat   3720
acaaggggtt gctgaaaaac gataaccaac tggcgatgtt attcacgctg gccaacctgt   3780
ttcgggcgga ccaaatgata cgtcagtggg agagatctca ctaaaaactg gggataacgc   3840
cttaaatggc gaagaaacgg tctaaatagg ctgattcaag gcatttacgg gagaaaaaat   3900
cggctcaaac atgaagaaat gaaatgactg agtcagccga gaagaatttc cccgcttatt   3960 cgcacccttcc ttagcttctt ggggtatctt taaatactgt agaaaagagg aaggaaataa   4020
```

-continued

```
taaatggcta aaatgagaat atcaccggaa ttgaaaaaac tgatcgaaaa ataccgctgc    4080
gtaaaagata cggaaggaat gtctcctgct aaggtatata agctggtggg agaaaatgaa    4140
aacctatatt taaaaatgac ggacagccgg tataaaggga ccacctatga tgtggaacgg    4200
gaaaaggaca tgatgctatg gctggaagga aagctgcctg ttccaaaggt cctgcacttt    4260
gaacggcatg atggctggag caatctgctc atgagtgagg ccgatggcgt cctttgctcg    4320
gaagagtatg aagatgaaca aagccctgaa aagattatcg agctgtatgc ggagtgcatc    4380
aggctctttc actccatcga catatcggat tgtccctata cgaatagctt agacagccgc    4440
ttagccgaat tggattactt actgaataac gatctggccg atgtggattg cgaaaactgg    4500
gaagaagaca ctccatttaa agatccgcgc gagctgtatg attttttaaa gacggaaaag    4560
cccgaagagg aacttgtctt ttcccacggc gacctgggag acagcaacat ctttgtgaaa    4620
gatggcaaag taagtggctt tattgatctt gggagaagcg gcagggcgga caagtggtat    4680
gacattgcct tctgcgtccg gtcgatcagg gaggatatcg gggaagaaca gtatgtcgag    4740 ctatttttg acttactggg gatcaagcct gattgggaga aaataaaata ttatattta     4800 ctggatgaat tgttttagta cctagaatgc atgaccaaaa tcccttaacg tgagtttttcg   4860 ttccactgag cgtcagaccc cgtagaaaag atcaaaggat cttcttgaga tccttttttt   4920
ctgcgcgtaa tctgctgctt gcaaacaaaa aaaccaccgc taccagcggt ggtttgtttg    4980
ccggatcaag agctaccaac tcttttttccg aaggtaactg gcttcagcag agcgcagata   5040
ccaaatactg tccttctagt gtagccgtag ttaggccacc acttcaagaa ctctgtagca    5100
ccgcctacat acctcgctct gctaatcctg ttaccagtgg ctgctgccag tggcgataag    5160
tcgtgtctta ccgggttgga ctcaagacga tagttaccgg ataaggcgca gcggtcgggc    5220
tgaacggggg gttcgtgcac acagcccagc ttggagcgaa cgacctacac cgaactgaga    5280
tacctacagc gtgagctatg agaaagcgcc acgcttcccg aagggagaaa ggcggacagg    5340
tatccggtaa gcggcagggt cggaacagga gagcgcacga gggagcttcc aggggggaaac   5400 gcctggtatc tttatagtcc tgtcgggttt cgccacctct gacttgagcg tcgattttg     5460 tgatgctcgt caggggggcg gagcctatgg aaaaacgcca gcaacgcggc cttttttacgg   5520 ttcctggcct tttgctggcc ttttgctcac atgttctttc ctgcgttatc ccctgattct    5580
gtggataacc gtattaccgc ctttgagtga gctgataccg ctcgccgcag ccgaacgacc    5640
gagcgcagcg agtcagtgag cgaggaagcg gaagagcgcc tgatgcggta ttttctcctt    5700
acgcatctgt gcggtatttc acaccgcata tggtgcactc tcagtacaat ctgctctgat    5760
gccgcatagt taagccagta tacactccgc tatcgctacg tgactgggtc atggctgcgc    5820
cccgacaccc gccaacaccc gctgacgcgc cctgacgggc ttgtctgctc ccggcatccg    5880
cttacagaca agctgtgacc gtctccggga ctgcatgtg tcagaggttt tcaccgtcat     5940
caccgaaacg cgcgaggcag ggtgccttga tgtgggcgcc ggcggtcgag tggcgacggc    6000
gcggcttgtc cgcgccctgg tagattgcct ggccgtaggc cagccatttt tgagcggcca    6060
gcggccgcga taggccgacg cgaagcggcg gggcgtaggg agcgcagcga ccgaagggta    6120
ggcgcttttt gcagctcttc ggctgtgcgc tggccagaca gttatgcaca ggccaggcgg    6180
gttttaagag ttttaataag ttttaaagag ttttaggcgg aaaaatcgcc ttttttctct    6240
tttatatcag tcacttacat gtgtgaccgg ttcccaatgt acggctttgg gttcccaatg    6300
tacgggttcc ggttcccaat gtacggcttt gggttcccaa tgtacgtgct atccacagga    6360
aagagacctt ttcgaccttt ttcccctgct agggcaattt gccctagcat ctgctccgta    6420
```

-continued

```
cattaggaac cggcggatgc ttcgccctcg atcaggttgc ggtagcgcat gactaggatc    6480
gggccagcct gccccgcctc ctccttcaaa tcgtactccg gcaggtcatt tgacccgatc    6540
agcttgcgca cggtgaaaca gaacttcttg aactctccgg cgctgccact gcgttcgtag    6600
atcgtcttga acaaccatct ggcttctgcc ttgcctgcgg cgcggcgtgc caggcggtag    6660
agaaaacggc cgatgccggg atcgatcaaa aagtaatcgg ggtgaaccgt cagcacgtcc    6720
gggttcttgc cttctgtgat ctcgcggtac atccaatcag ctagctcgat ctcgatgtac    6780
tccggccgcc cggtttcgct ctttacgatc ttgtagcggc taatcaaggc ttcaccctcg    6840
gataccgtca ccaggcggcc gttcttggcc ttcttcgtac gctgcatggc aacgtgcgtg    6900
gtgtttaacc gaatgcaggt ttctaccagg tcgtctttct gctttccgcc atcggctcgc    6960
cggcagaact tgagtacgtc cgcaacgtgt ggacggaaca cgcggccggg cttgtctccc    7020
ttcccttccc ggtatcggtt catggattcg gttagatggg aaaccgccat cagtaccagg    7080
tcgtaatccc acacactggc catgccggcc ggccctgcgg aaacctctac gtgcccgtct    7140
ggaagctcgt agcggatcac ctcgccagct cgtcggtcac gcttcgacag acggaaaacg    7200
gccacgtcca tgatgctgcg actatcgcgg gtgcccacgt catagagcat cggaacgaaa    7260
aaatctggtt gctcgtcgcc cttgggcggc ttcctaatcg acggcgcacc ggctgccggc    7320
ggttgccggg attctttgcg gattcgatca gcggccgctt gccacgattc accggggcgt    7380
gcttctgcct cgatgcgttg ccgctgggcg gcctgcgcgg ccttcaactt ctccaccagg    7440
tcatcaccca gcgccgcgcc gatttgtacc gggccggatg gtttgcgacc gctcacgccg    7500
attcctcggg cttgggggtt ccagtgccat tgcagggccg gcaggcaacc cagccgctta    7560
cgcctggcca accgcccgtt cctccacaca tggggcattc cacggcgtcg gtgcctggtt    7620
gttcttgatt ttccatgccg cctcctttag ccgctaaaat tcatctactc atttattcat    7680
ttgctcattt actctggtag ctgcgcgatg tattcagata gcagctcggt aatggtcttg    7740
ccttggcgta ccgcgtacat cttcagcttg gtgtgatcct ccgccggcaa ctgaaagttg    7800
acccgcttca tggctggcgt gtctgccagg ctggccaacg ttgcagcctt gctgctgcgt    7860
gcgctcggac ggccggcact tagcgtgttt gtgcttttgc tcattttctc tttacctcat    7920
taactcaaat gagttttgat ttaatttcag cggccagcgc ctggacctcg cgggcagcgt    7980
cgccctcggg ttctgattca agaacggttg tgccggcggc ggcagtgcct gggtagctca    8040
cgcgctgcgt gatacgggac tcaagaatgg gcagctcgta cccggccagc gcctcggcaa    8100
cctcaccgcc gatgcgcgtg cctttgatcg cccgcgacac gacaaaggcc gcttgtagcc    8160
ttccatccgt gacctcaatg cgctgcttaa ccagctccac caggtcggcg gtggcccata    8220
tgtcgtaagg gcttggctgc accggaatca gcacgaagtc ggctgccttg atcgcggaca    8280
cagccaagtc cgccgcctgg ggcgctccgt cgatcactac gaagtcgcgc cggccgatgg    8340
ccttcacgtc gcggtcaatc gtcgggcggt cgatgccgac aacggttagc ggttgatctt    8400
cccgcacggc cgcccaatcg cgggcactgc cctggggatc ggaatcgact aacagaacat    8460
cggccccggc gagttgcagg cgcgcgggcta gatgggttgc gatggtcgtc ttgcctgacc    8520
cgcctttctg gttaagtaca gcgataacct tcatgcgttc cccttgcgta tttgtttatt    8580
tactcatcgc atcatatacg cagcgaccgc atgacgcaag ctgtttttact caaatacaca    8640 tcaccttttt agacgcggc gctcggtttc ttcagcggcc aagctggccg gccaggccgc    8700
cagcttggca tcagacaaac cggccaggat ttcatgcagc cgcacggttg agacgtgcgc    8760
```

-continued

```
gggcggctcg aacacgtacc cggccgcgat catctccgcc tcgatctctt cggtaatgaa    8820
aaacggttcg tcctggccgt cctggtgcgg tttcatgctt gttcctcttg gcgttcattc    8880
tcggcggccg ccagggcgtc ggcctcggtc aatgcgtcct aggcaccgcg ccgcctggcc    8940
tcggtgggcg tcacttcctc gctgcgctca agtgcgcggt acagggtcga gcgatgcacg    9000
ccaagcagtg cagccgcctc tttcacggtg cggccttcct ggtcgatcag ctcgcgggcg    9060
tgcgcgatct gtgccggggt gagggtaggg cgggggccaa acttcacgcc tcgggccttg    9120
gcggcctcgc gcccgctccg ggtgcggtcg atgattaggg aacgctcgaa ctcggcaatg    9180
ccggcgaaca cggtcaacac catgcggccg gccggcgtgg tggtgtcggc ccacggctct    9240
gccaggctac gcaggcccgc gccggcctcc tggatgcgct cggcaatgtc cagtaggtcg    9300
cgggtgctgc gggccaggcg gtctagcctg gtcactgtca caacgtcgcc agggcgtagg    9360
tggtcaagca tcctggccag ctccgggcgg tcgcgcctgg tgccggtgat cttctcggaa    9420
aacagcttgg tgcagccggc cgcgtgcagt tcggcccgtt ggttggtcaa gtcctggtcg    9480
tcggtgctga cgcgggcata gcccagcagg ccagcggcgg cgctcttgtt catggcgtaa    9540
tgtctccggt tctagtcgca agtattctac tttatgcgac taaaacacgc gacaagaaaa    9600
cgccaggaaa agggcagggc ggcagcctgt cgcgtaactt aggacttgtg cgacatgtcg    9660
ttttcagaag acggctgcac tgaacgtcag aagccgactg cactatagca gcggaggggt    9720
tggatcaaag tactttgatc ccgaggggaa ccctgtggtt ggcatgcaca tacaaatgga    9780
cgaacggata aaccttttca cgcccttta aatatccgat tattctaata aacgctcttt     9840
tctcttaggt ttacccgcca atatatcctg tcaaacactg atagtttaaa ctgaaggcgg    9900
gaaacgacaa tctgatccaa gctcaagctg ctctagcatt cgccattcag gctgcgcaac    9960
tgttgggaag ggcgatcggt gcgggcctct tcgctattac gccagctggc gaaaggggga   10020
tgtgctgcaa ggcgattaag ttgggtaacg ccagggtttt cccagtcacg acgttgtaaa   10080
acgacggcca gtgccaagct tgcatgcctg cagtgcagcg tgacccggtc gtgcccctct   10140
ctagagataa tgagcattgc atgtctaagt tataaaaaat taccacatat ttttttgtc    10200 acacttgttt gaagtgcagt ttatctatct ttatacatat atttaaactt tactctacga   10260
ataatataat ctatagtact acaataatat cagtgtttta gagaatcata taaatgaaca   10320
gttagacatg gtctaaagga caattgagta ttttgacaac aggactctac agttttatct   10380
ttttagtgtg catgtgttct cctttttttt tgcaaatagc ttcacctata taatacttca   10440
tccattttat tagtacatcc atttagggtt tagggttaat ggtttttata gactaatttt   10500
tttagtacat ctattttatt ctattttagc ctctaaatta agaaaactaa aactctattt   10560 tagtttttt atttaataat ttagatataa aatagaataa aataaagtga ctaaaaatta    10620
aacaaatacc ctttaagaaa ttaaaaaaac taaggaaaca tttttcttgt ttcgagtaga   10680
taatgccagc ctgttaaacg ccgtcgacga gtctaacgga caccaaccag cgaaccagca   10740
gcgtcgcgtc gggccaagcg aagcagacgg cacggcatct ctgtcgctgc ctctggaccc   10800
ctctcgagag ttccgctcca ccgttggact tgctccgctg tcggcatcca gaaattgcgt   10860
ggcggagcgg cagacgtgag ccggcacggc aggcggcctc ctcctcctct cacggcaccg   10920
gcagctacgg gggattcctt tcccaccgct ccttcgcttt cccttcctcg cccgccgtaa   10980
taaatagaca ccccctccac accctctttc cccaacctcg tgttgttcgg agcgcacaca   11040
cacacaacca gatctccccc aaatccaccc gtcggcacct ccgcttcaag gtacgccgct   11100
cgtcctcccc ccccccccc tctctacctt ctctagatcg gcgttccggt ccatggttag   11160
```

-continued

```
ggcccggtag ttctacttct gttcatgttt gtgttagatc cgtgtttgtg ttagatccgt    11220
gctgctagcg ttcgtacacg gatgcgacct gtacgtcaga cacgttctga ttgctaactt    11280
gccagtgttt ctctttgggg aatcctggga tggctctagc cgttccgcag acgggatcga    11340
tttcatgatt ttttttgttt cgttgcatag ggtttggttt gcccttttcc tttatttcaa    11400
tatatgccgt gcacttgttt gtcgggtcat cttttcatgc ttttttttgt cttggttgtg    11460
atgatgtggt ctggttgggc ggtcgttcta gatcggagta gaattaattc tgtttcaaac    11520
tacctggtgg atttattaat tttggatctg tatgtgtgtg ccatacatat tcatagttac    11580
gaattgaaga tgatggatgg aaatatcgat ctaggatagg tatacatgtt gatgcgggtt    11640
ttactgatgc atatacagag atgctttttg ttcgcttggt tgtgatgatg tggtgtggtt    11700
gggcggtcgt tcattcgttc tagatcggag tagaatactg tttcaaacta cctggtgtat    11760
ttattaattt tggaactgta tgtgtgtgtc atacatcttc atagttacga gtttaagatg    11820
gatggaaata tcgatctagg ataggtatac atgttgatgt gggtttttact gatgcatata    11880 catgatggca tatgcagcat ctattcatat gctctaacct tgagtaccta tctattataa    11940
taaacaagta tgttttataa ttattttgat cttgatatac ttggatgatg gcatatgcag    12000
cagctatatg tggatttttt tagccctgcc ttcatacgct atttatttgc ttggtactgt    12060 ttctttgtc gatgctcacc ctgttgtttg gtgttacttc tgcaggtcga ctctagagga    12120
tcccctcgag gcgcgccaag ctatcaaaca agtttgtaca aaaaagctga acgagaaacg    12180
taaaatgata taaatatcaa tatattaaat tagattttgc ataaaaaaca gactacataa    12240
tactgtaaaa cacaacatat ccagtcacta tggcggccgc attaggcacc ccaggcttta    12300
cactttatgc ttccggctcg tataatgtgt ggattttgag ttaggatccg tcgagatttt    12360
caggagctaa ggaagctaaa atggagaaaa aaatcactgg atataccacc gttgatatat    12420
cccaatggca tcgtaaagaa catttTgagg catttcagtc agttgctcaa tgtacctata    12480
accagaccgt tcagctggat attacggcct ttttaaagac cgtaaagaaa aataagcaca    12540
agttttatcc ggcctttatt cacattcttg cccgcctgat gaatgctcat ccggaattcc    12600
gtatggcaat gaaagacggt gagctggtga tatgggatag tgttcaccct tgttacaccg    12660
ttttccatga gcaaactgaa acgttttcat cgctctggag tgaataccac gacgatttcc    12720
ggcagtttct acacatatat tcgcaagatg tggcgtgtta cggtgaaaac ctggcctatt    12780
tccctaaagg gtttattgag aatatgtttt tcgtctcagc caatccctgg gtgagtttca    12840
ccagttttga tttaaacgtg gccaatatgg acaacttctt cgcccccgtt ttcaccatgg    12900
gcaaatatta tacgcaaggc gacaaggtgc tgatgccgct ggcgattcag gttcatcatg    12960
ccgtttgtga tggcttccat gtcggcagaa tgcttaatga attacaacag tactgcgatg    13020
agtggcaggc ggggcgtaat ctagaggatc cggcttacta aaagccagat aacagtatgc    13080
gtatttgcgc gctgattttt gcggtataag aatatatact gatatgtata cccgaagtat    13140
gtcaaaaaga ggtatgctat gaagcagcgt attacagtga cagttgacag cgacagctat    13200
cagttgctca aggcatatat gatgtcaata tctccggtct ggtaagcaca accatgcaga    13260
atgaagcccg tcgtctgcgt gccgaacgct ggaaagcgga aaatcaggaa gggatggctg    13320
aggtcgcccg gtttattgaa atgaacggct cttttgctga cgagaacagg ggctggtgaa    13380
atgcagttta aggtttacac ctataaaaga gagagccgtt atcgtctgtt tgtggatgta    13440
cagagtgata ttattgacac gcccgggcga cggatggtga tccccctggc cagtgcacgt    13500
```

-continued

```
ctgctgtcag ataaagtccc ccgtgaactt tacccggtgg tgcatatcgg ggatgaaagc   13560
tggcgcatga tgaccaccga tatggccagt gtgccggtct ccgttatcgg ggaagaagtg   13620
gctgatctca gccaccgcga aaatgacatc aaaaacgcca ttaacctgat gttctgggga   13680
atataaatgt caggctccct tatacacagc cagtctgcag gtcgaccata gtgactggat   13740
atgttgtgtt ttacagtatt atgtagtctg tttttttatgc aaaatctaat ttaatatatt   13800
gatatttata tcattttacg tttctcgttc agctttcttg tacaaagtgg ttcgataatt   13860
cttaattaac tagttctaga gcggccgcca ccgcggtgga gctcgaattt ccccgatcgt   13920
tcaaacattt ggcaataaag tttcttaaga ttgaatcctg ttgccggtct tgcgatgatt   13980
atcatataat ttctgttgaa ttacgttaag catgtaataa ttaacatgta atgcatgacg   14040
ttatttatga gatgggtttt tatgattaga gtcccgcaat tatacattta atacgcgata   14100
gaaaacaaaa tatagcgcgc aaactaggat aaattatcgc gcgcggtgtc atctatgtta   14160
ctagatcggg aatt                                                      14174
```

<210> SEQ ID NO 51
<211> LENGTH: 37
<212> TYPE: DNA
<213> ORGANISM: Artificial Sequence
<220> FEATURE:
<223> OTHER INFORMATION: Synthetic construct

<400> SEQUENCE: 51

```
cttttccaga aagagaagga ggcacagatc ttgccgt                                37
```

<210> SEQ ID NO 52
<211> LENGTH: 39
<212> TYPE: DNA
<213> ORGANISM: Artificial Sequence
<220> FEATURE:
<223> OTHER INFORMATION: Synthetic construct

<400> SEQUENCE: 52

```
tccatttgtt tgaagaaggg ttatggccaa tgcttgccc                              39
```

<210> SEQ ID NO 53
<211> LENGTH: 37
<212> TYPE: DNA
<213> ORGANISM: Artificial Sequence
<220> FEATURE:
<223> OTHER INFORMATION: Synthetic construct

<400> SEQUENCE: 53

```
gttcctcaag gtgagcgccc cgcggcggcg gcggctg                                37
```

<210> SEQ ID NO 54
<211> LENGTH: 39
<212> TYPE: DNA
<213> ORGANISM: Artificial Sequence
<220> FEATURE:
<223> OTHER INFORMATION: Synthetic construct

<400> SEQUENCE: 54

```
gagttgctgg gctcggcgtc ctcgacgtcg tcctcgccg                              39
```

<210> SEQ ID NO 55
<211> LENGTH: 23
<212> TYPE: DNA
<213> ORGANISM: Artificial Sequence
<220> FEATURE:
<223> OTHER INFORMATION: Synthetic construct -continued

```
<400> SEQUENCE: 55
aagaagggtt atggccaatg gat                                                     23

<210> SEQ ID NO 56
<211> LENGTH: 23
<212> TYPE: DNA
<213> ORGANISM: Artificial Sequence
<220> FEATURE:
<223> OTHER INFORMATION: Synthetic construct

<400> SEQUENCE: 56
aagaagggtt atggcctctg ctt                                                     23

<210> SEQ ID NO 57
<211> LENGTH: 23
<212> TYPE: DNA
<213> ORGANISM: Artificial Sequence
<220> FEATURE:
<223> OTHER INFORMATION: Synthetic construct

<400> SEQUENCE: 57
aagaagggtt attaccaatg ctt                                                     23

<210> SEQ ID NO 58
<211> LENGTH: 23
<212> TYPE: DNA
<213> ORGANISM: Artificial Sequence
<220> FEATURE:
<223> OTHER INFORMATION: Synthetic construct

<400> SEQUENCE: 58
aagaagggaa atggccaatg ctt                                                     23

<210> SEQ ID NO 59
<211> LENGTH: 23
<212> TYPE: DNA
<213> ORGANISM: Artificial Sequence
<220> FEATURE:
<223> OTHER INFORMATION: Synthetic construct

<400> SEQUENCE: 59
aagatcggtt atggccaatg ctt                                                     23

<210> SEQ ID NO 60
<211> LENGTH: 23
<212> TYPE: DNA
<213> ORGANISM: Artificial Sequence
<220> FEATURE:
<223> OTHER INFORMATION: Synthetic construct

<400> SEQUENCE: 60
ttgaagggtt atggccaatg ctt                                                     23

<210> SEQ ID NO 61
<211> LENGTH: 23
<212> TYPE: DNA
<213> ORGANISM: Artificial Sequence
<220> FEATURE:
<223> OTHER INFORMATION: Synthetic construct

<400> SEQUENCE: 61
aagaagggtt atggccaatg ctt                                                     23

<210> SEQ ID NO 62
```

<211> LENGTH: 23
<212> TYPE: DNA
<213> ORGANISM: Artificial Sequence
<220> FEATURE:
<223> OTHER INFORMATION: Synthetic construct

<400> SEQUENCE: 62
aagaagggtt atggccaatg ctt                                                      23

<210> SEQ ID NO 63
<211> LENGTH: 21
<212> TYPE: DNA
<213> ORGANISM: Artificial Sequence
<220> FEATURE:
<223> OTHER INFORMATION: Synthetic construct

<400> SEQUENCE: 63
aagaagggtt atggccaatg c                                                        21

<210> SEQ ID NO 64
<211> LENGTH: 19
<212> TYPE: DNA
<213> ORGANISM: Artificial Sequence
<220> FEATURE:
<223> OTHER INFORMATION: Synthetic construct

<400> SEQUENCE: 64
aagaagggtt atggccaat                                                           19

<210> SEQ ID NO 65
<211> LENGTH: 17
<212> TYPE: DNA
<213> ORGANISM: Artificial Sequence
<220> FEATURE:
<223> OTHER INFORMATION: Synthetic construct

<400> SEQUENCE: 65
aagaagggtt atggcca                                                             17

<210> SEQ ID NO 66
<211> LENGTH: 15
<212> TYPE: DNA
<213> ORGANISM: Artificial Sequence
<220> FEATURE:
<223> OTHER INFORMATION: Synthetic construct

<400> SEQUENCE: 66
aagaagggtt atggc                                                               15

<210> SEQ ID NO 67
<211> LENGTH: 73
<212> TYPE: DNA
<213> ORGANISM: Artificial Sequence
<220> FEATURE:
<223> OTHER INFORMATION: Synthetic construct

<400> SEQUENCE: 67
gtagtcagca tgtgagcttt ggagtgaaat ctcttgtctt aaggaataaa ggaaaaagat             60
tccgtcggag gct                                                                 73

<210> SEQ ID NO 68
<211> LENGTH: 62
<212> TYPE: DNA
<213> ORGANISM: Artificial Sequence
<220> FEATURE:
<223> OTHER INFORMATION: Synthetic construct -continued

<400> SEQUENCE: 68
gtagtcagca tgtgagcttt ggagtgaaat ctctataaag gaaaaagatt ccgtcggagg        60
ct                                                                       62

<210> SEQ ID NO 69
<211> LENGTH: 66
<212> TYPE: DNA
<213> ORGANISM: Artificial Sequence
<220> FEATURE:
<223> OTHER INFORMATION: Synthetic construct

<400> SEQUENCE: 69
gtagtcagca tgtgagcttt ggagtgaaat ctcttggaat aaaggaaaaa gattccgtcg        60
gaggct                                                                   66

<210> SEQ ID NO 70
<211> LENGTH: 65
<212> TYPE: DNA
<213> ORGANISM: Artificial Sequence
<220> FEATURE:
<223> OTHER INFORMATION: Synthetic construct

<400> SEQUENCE: 70
gtagtcagca tgtgagcttt ggagtgaaat ctcttgaata aaggaaaaag attccgtcgg        60
aggct                                                                    65

<210> SEQ ID NO 71
<211> LENGTH: 63
<212> TYPE: DNA
<213> ORGANISM: Artificial Sequence
<220> FEATURE:
<223> OTHER INFORMATION: Synthetic construct

<400> SEQUENCE: 71
gtagtcagca tgtgagcttt ggagtgaaat ctcttataaa ggaaaaagat ccgtcggag        60 gct                                                                      63

<210> SEQ ID NO 72
<211> LENGTH: 73
<212> TYPE: DNA
<213> ORGANISM: Artificial Sequence
<220> FEATURE:
<223> OTHER INFORMATION: Synthetic construct

<400> SEQUENCE: 72
gtagtcagca tgtgagcttt ggagtgaaat ctcttgtctt aaggaataaa ggaaaaagat        60
tccgtcggag gct                                                           73

<210> SEQ ID NO 73
<211> LENGTH: 73
<212> TYPE: DNA
<213> ORGANISM: Artificial Sequence
<220> FEATURE:
<223> OTHER INFORMATION: Synthetic construct

<400> SEQUENCE: 73
gtagtcagca tgtgagcttt ggagtgaaat ctcttgtctt aaggaataaa ggaaaaagat        60
tccgtcggag gct                                                           73

<210> SEQ ID NO 74

-continued

```
<211> LENGTH: 47
<212> TYPE: DNA
<213> ORGANISM: Artificial Sequence
<220> FEATURE:
<223> OTHER INFORMATION: Synthetic construct

<400> SEQUENCE: 74
gtagtcagca tgtgagcttt ggagtgaaaa agattccgtc ggaggct                   47

<210> SEQ ID NO 75
<211> LENGTH: 64
<212> TYPE: DNA
<213> ORGANISM: Artificial Sequence
<220> FEATURE:
<223> OTHER INFORMATION: Synthetic construct

<400> SEQUENCE: 75
gtagtcagca tgtgagcttt ggagtgaaat ctcttaataa aggaaaaaga ttccgtcgga    60
ggct                                                                  64

<210> SEQ ID NO 76
<211> LENGTH: 73
<212> TYPE: DNA
<213> ORGANISM: Artificial Sequence
<220> FEATURE:
<223> OTHER INFORMATION: Synthetic construct

<400> SEQUENCE: 76
tgcatttcat gtctttgcta ctgttgcaag tgctcaccca agtgcaaaag accaaggtgc    60
ctcaattgtt ctt                                                        73

<210> SEQ ID NO 77
<211> LENGTH: 57
<212> TYPE: DNA
<213> ORGANISM: Artificial Sequence
<220> FEATURE:
<223> OTHER INFORMATION: Synthetic construct

<400> SEQUENCE: 77
tgcatttcat gtctttgcta ctgttgcaag aaagaccaag gtgcctcaat tgttctt       57

<210> SEQ ID NO 78
<211> LENGTH: 47
<212> TYPE: DNA
<213> ORGANISM: Artificial Sequence
<220> FEATURE:
<223> OTHER INFORMATION: Synthetic construct

<400> SEQUENCE: 78
tgcatttcat gtctttgcta ctgttgcaag gtgcctcaat tgttctt                   47

<210> SEQ ID NO 79
<211> LENGTH: 64
<212> TYPE: DNA
<213> ORGANISM: Artificial Sequence
<220> FEATURE:
<223> OTHER INFORMATION: Synthetic construct

<400> SEQUENCE: 79
tgcatttcat gtctttgcta ctgttgcaac aagtgcaaaa gaccaaggtg cctcaattgt    60
tctt                                                                  64

<210> SEQ ID NO 80
<211> LENGTH: 46
```

-continued

```
<212> TYPE: DNA
<213> ORGANISM: Artificial Sequence
<220> FEATURE:
<223> OTHER INFORMATION: Synthetic construct

<400> SEQUENCE: 80
tgcatttcat gtctttgcta ctgttgcaag tgcctcaatt gttctt                    46

<210> SEQ ID NO 81
<211> LENGTH: 73
<212> TYPE: DNA
<213> ORGANISM: Artificial Sequence
<220> FEATURE:
<223> OTHER INFORMATION: Synthetic construct

<400> SEQUENCE: 81
tgcatttcat gtctttgcta ctgttgcaag tgctcaccca agtgcaaaag accaaggtgc    60
ctcaattgtt ctt                                                        73

<210> SEQ ID NO 82
<211> LENGTH: 73
<212> TYPE: DNA
<213> ORGANISM: Artificial Sequence
<220> FEATURE:
<223> OTHER INFORMATION: Synthetic construct

<400> SEQUENCE: 82
tgcatttcat gtctttgcta ctgttgcaag tgctcaccca agtgcaaaag accaaggtgc    60
ctcaattgtt ctt                                                        73

<210> SEQ ID NO 83
<211> LENGTH: 73
<212> TYPE: DNA
<213> ORGANISM: Artificial Sequence
<220> FEATURE:
<223> OTHER INFORMATION: Synthetic construct

<400> SEQUENCE: 83
tgcatttcat gtctttgcta ctgttgcaag tgctcaccca agtgcaaaag accaaggtgc    60
ctcaattgtt ctt                                                        73

<210> SEQ ID NO 84
<211> LENGTH: 73
<212> TYPE: DNA
<213> ORGANISM: Artificial Sequence
<220> FEATURE:
<223> OTHER INFORMATION: Synthetic construct

<400> SEQUENCE: 84
tgcatttcat gtctttgcta ctgttgcaag tgctcaccca agtgcaaaag accaaggtgc    60
ctcaattgtt ctt                                                        73

<210> SEQ ID NO 85
<211> LENGTH: 73
<212> TYPE: DNA
<213> ORGANISM: Artificial Sequence
<220> FEATURE:
<223> OTHER INFORMATION: Synthetic construct

<400> SEQUENCE: 85
ccagcagcaa cgcgccattt ctgcttcctg caatgccggt agacacctcc tcaagcactg    60
ttgccttagc aat                                                        73
```

-continued

```
<210> SEQ ID NO 86
<211> LENGTH: 58
<212> TYPE: DNA
<213> ORGANISM: Artificial Sequence
<220> FEATURE:
<223> OTHER INFORMATION: Synthetic construct

<400> SEQUENCE: 86
ccagcagcaa cgcgccattt ctgcttccta cctcctcaag cactgttgcc ttagcaat          58

<210> SEQ ID NO 87
<211> LENGTH: 63
<212> TYPE: DNA
<213> ORGANISM: Artificial Sequence
<220> FEATURE:
<223> OTHER INFORMATION: Synthetic construct

<400> SEQUENCE: 87
ccagcagcaa cgcgccattt ctgcttcctg caatgcctcc tcaagcactg ttgccttagc          60
aat                                                                        63

<210> SEQ ID NO 88
<211> LENGTH: 66
<212> TYPE: DNA
<213> ORGANISM: Artificial Sequence
<220> FEATURE:
<223> OTHER INFORMATION: Synthetic construct

<400> SEQUENCE: 88
ccagcagcaa cgcgccattt ctgcttcctg caatgccacc tcctcaagca ctgttgcctt          60
agcaat                                                                     66

<210> SEQ ID NO 89
<211> LENGTH: 65
<212> TYPE: DNA
<213> ORGANISM: Artificial Sequence
<220> FEATURE:
<223> OTHER INFORMATION: Synthetic construct

<400> SEQUENCE: 89
ccagcagcaa cgcgccattt ctgcttcctg caatgcccct cctcaagcac tgttgcctta          60
gcaat                                                                      65

<210> SEQ ID NO 90
<211> LENGTH: 20
<212> TYPE: DNA
<213> ORGANISM: Artificial Sequence
<220> FEATURE:
<223> OTHER INFORMATION: Synthetic construct

<400> SEQUENCE: 90
agcactgttg ccttagcaat                                                      20

<210> SEQ ID NO 91
<211> LENGTH: 65
<212> TYPE: DNA
<213> ORGANISM: Artificial Sequence
<220> FEATURE:
<223> OTHER INFORMATION: Synthetic construct

<400> SEQUENCE: 91
ccagcagcaa cgcgccattt ctgcttcctg caatgcacct cctcaagcac tgttgcctta          60
gcaat                                                                      65
```

-continued

```
<210> SEQ ID NO 92
<211> LENGTH: 39
<212> TYPE: DNA
<213> ORGANISM: Artificial Sequence
<220> FEATURE:
<223> OTHER INFORMATION: Synthetic construct

<400> SEQUENCE: 92
ccagcagcaa cgcgccattt ctgctgttgc cttagcaat                              39

<210> SEQ ID NO 93
<211> LENGTH: 64
<212> TYPE: DNA
<213> ORGANISM: Artificial Sequence
<220> FEATURE:
<223> OTHER INFORMATION: Synthetic construct

<400> SEQUENCE: 93
ccagcagcaa cgcgccattt ctgcttcctg caatgccctc ctcaagcact gttgccttag      60
caat                                                                   64

<210> SEQ ID NO 94
<211> LENGTH: 73
<212> TYPE: DNA
<213> ORGANISM: Artificial Sequence
<220> FEATURE:
<223> OTHER INFORMATION: Synthetic construct

<400> SEQUENCE: 94
tgaagctgga cttcactttt gcctctctct cctgtgcttg cctcttccat tcctgctgct      60
aggctgttct gtg                                                         73

<210> SEQ ID NO 95
<211> LENGTH: 58
<212> TYPE: DNA
<213> ORGANISM: Artificial Sequence
<220> FEATURE:
<223> OTHER INFORMATION: Synthetic construct

<400> SEQUENCE: 95
tgaagctgga cttcactttt gcctctctct cctgttcctg ctgctaggct gttctgtg       58

<210> SEQ ID NO 96
<211> LENGTH: 67
<212> TYPE: DNA
<213> ORGANISM: Artificial Sequence
<220> FEATURE:
<223> OTHER INFORMATION: Synthetic construct

<400> SEQUENCE: 96
tgaagctgga cttcactttt gcctctctct cctgcttctt ccattcctgc tgctaggctg      60
ttctgtg                                                                67

<210> SEQ ID NO 97
<211> LENGTH: 56
<212> TYPE: DNA
<213> ORGANISM: Artificial Sequence
<220> FEATURE:
<223> OTHER INFORMATION: Synthetic construct

<400> SEQUENCE: 97
tgaagctgga cttcactttt gcctctctct ccttcctgct gctaggctgt tctgtg         56
```

-continued

```
<210> SEQ ID NO 98
<211> LENGTH: 56
<212> TYPE: DNA
<213> ORGANISM: Artificial Sequence
<220> FEATURE:
<223> OTHER INFORMATION: Synthetic construct

<400> SEQUENCE: 98
tgaagctgga cttcactttt gcctctctct ccttcctgct gctaggctgt tctgtg          56

<210> SEQ ID NO 99
<211> LENGTH: 65
<212> TYPE: DNA
<213> ORGANISM: Artificial Sequence
<220> FEATURE:
<223> OTHER INFORMATION: Synthetic construct

<400> SEQUENCE: 99
tgaagctgga cttcactttt gcctctctct cctgtcttcc attcctgctg ctaggctgtt          60
ctgtg                                                                    65

<210> SEQ ID NO 100
<211> LENGTH: 69
<212> TYPE: DNA
<213> ORGANISM: Artificial Sequence
<220> FEATURE:
<223> OTHER INFORMATION: Synthetic construct

<400> SEQUENCE: 100
tgaagctgga cttcactttt gcctctctct cctgtgcttc ttccattcct gctgctaggc          60
tgttctgtg                                                                69

<210> SEQ ID NO 101
<211> LENGTH: 65
<212> TYPE: DNA
<213> ORGANISM: Artificial Sequence
<220> FEATURE:
<223> OTHER INFORMATION: Synthetic construct

<400> SEQUENCE: 101
tgaagctgga cttcactttt gcctctctct cctgtcttcc attcctgctg ctaggctgtt          60
ctgtg                                                                    65

<210> SEQ ID NO 102
<211> LENGTH: 62
<212> TYPE: DNA
<213> ORGANISM: Artificial Sequence
<220> FEATURE:
<223> OTHER INFORMATION: Synthetic construct

<400> SEQUENCE: 102
tgaagctgga cttcactttt gcctctctct cctgtccatt cctgctgcta ggctgttctg          60
tg                                                                       62

<210> SEQ ID NO 103
<211> LENGTH: 43
<212> TYPE: DNA
<213> ORGANISM: Artificial Sequence
<220> FEATURE:
<223> OTHER INFORMATION: Synthetic construct

<400> SEQUENCE: 103
catgtctttg ctactgttgc aagtgctcac ccaagtgcaa aag                          43
```

-continued

```
<210> SEQ ID NO 104
<211> LENGTH: 37
<212> TYPE: DNA
<213> ORGANISM: Artificial Sequence
<220> FEATURE:
<223> OTHER INFORMATION: Synthetic construct

<400> SEQUENCE: 104
catgtctttg ctactgttgc aagtgcaagt gcaaaag                               37

<210> SEQ ID NO 105
<211> LENGTH: 43
<212> TYPE: DNA
<213> ORGANISM: Artificial Sequence
<220> FEATURE:
<223> OTHER INFORMATION: Synthetic construct

<400> SEQUENCE: 105
catgtctttg ctactgttgc aagtgctcac ccaagtgcaa aag                        43

<210> SEQ ID NO 106
<211> LENGTH: 31
<212> TYPE: DNA
<213> ORGANISM: Artificial Sequence
<220> FEATURE:
<223> OTHER INFORMATION: Synthetic construct

<400> SEQUENCE: 106
catgtctttg ctactgttgc aagtgcaaaa g                                     31

<210> SEQ ID NO 107
<211> LENGTH: 43
<212> TYPE: DNA
<213> ORGANISM: Artificial Sequence
<220> FEATURE:
<223> OTHER INFORMATION: Synthetic construct

<400> SEQUENCE: 107
catgtctttg ctactgttgc aagtgctcac ccaagtgcaa aag                        43

<210> SEQ ID NO 108
<211> LENGTH: 32
<212> TYPE: DNA
<213> ORGANISM: Artificial Sequence
<220> FEATURE:
<223> OTHER INFORMATION: Synthetic construct

<400> SEQUENCE: 108
catgtctttg ctactgttgc aaagtgcaaa ag                                    32

<210> SEQ ID NO 109
<211> LENGTH: 43
<212> TYPE: DNA
<213> ORGANISM: Artificial Sequence
<220> FEATURE:
<223> OTHER INFORMATION: Synthetic construct

<400> SEQUENCE: 109
catgtctttg ctactgttgc aagtgctcac ccaagtgcaa aag                        43

<210> SEQ ID NO 110
<211> LENGTH: 24
<212> TYPE: DNA
<213> ORGANISM: Artificial Sequence
<220> FEATURE:
```

-continued

```
<223> OTHER INFORMATION: Synthetic construct

<400> SEQUENCE: 110
catgtctttg ctacagtgca aaag                                       24

<210> SEQ ID NO 111
<211> LENGTH: 25
<212> TYPE: DNA
<213> ORGANISM: Artificial Sequence
<220> FEATURE:
<223> OTHER INFORMATION: Synthetic construct

<400> SEQUENCE: 111
catgtctttg ctactgtagc aaaag                                      25

<210> SEQ ID NO 112
<211> LENGTH: 30
<212> TYPE: DNA
<213> ORGANISM: Artificial Sequence
<220> FEATURE:
<223> OTHER INFORMATION: Synthetic construct

<400> SEQUENCE: 112
catgtctttg ctactgttgc aatgcaaaag                                 30

<210> SEQ ID NO 113
<211> LENGTH: 43
<212> TYPE: DNA
<213> ORGANISM: Artificial Sequence
<220> FEATURE:
<223> OTHER INFORMATION: Synthetic construct

<400> SEQUENCE: 113
catgtctttg ctactgttgc aagtgctcac ccaagtgcaa aag                  43

<210> SEQ ID NO 114
<211> LENGTH: 25
<212> TYPE: DNA
<213> ORGANISM: Artificial Sequence
<220> FEATURE:
<223> OTHER INFORMATION: Synthetic construct

<400> SEQUENCE: 114
catgtctttg ctactgttgc aaaag                                      25

<210> SEQ ID NO 115
<211> LENGTH: 43
<212> TYPE: DNA
<213> ORGANISM: Artificial Sequence
<220> FEATURE:
<223> OTHER INFORMATION: Synthetic construct

<400> SEQUENCE: 115
catgtctttg ctactgttgc aagtgctcac ccaagtgcaa aag                  43

<210> SEQ ID NO 116
<211> LENGTH: 34
<212> TYPE: DNA
<213> ORGANISM: Artificial Sequence
<220> FEATURE:
<223> OTHER INFORMATION: Synthetic construct

<400> SEQUENCE: 116
catgtctttg ctactgttgc aagtagtgca aaag                            34
```

-continued

```
<210> SEQ ID NO 117
<211> LENGTH: 41
<212> TYPE: DNA
<213> ORGANISM: Artificial Sequence
<220> FEATURE:
<223> OTHER INFORMATION: Synthetic construct

<400> SEQUENCE: 117
catgtctttg ctactgttgc aagtgcaccc aagtgcaaaa g                            41

<210> SEQ ID NO 118
<211> LENGTH: 10
<212> TYPE: DNA
<213> ORGANISM: Artificial Sequence
<220> FEATURE:
<223> OTHER INFORMATION: Synthetic construct

<400> SEQUENCE: 118
agtgcaaaag                                                               10

<210> SEQ ID NO 119
<211> LENGTH: 13
<212> TYPE: DNA
<213> ORGANISM: Artificial Sequence
<220> FEATURE:
<223> OTHER INFORMATION: Synthetic construct

<400> SEQUENCE: 119
ccaagtgcaa aag                                                           13

<210> SEQ ID NO 120
<211> LENGTH: 11
<212> TYPE: DNA
<213> ORGANISM: Artificial Sequence
<220> FEATURE:
<223> OTHER INFORMATION: Synthetic construct

<400> SEQUENCE: 120
aagtgcaaaa g                                                             11

<210> SEQ ID NO 121
<211> LENGTH: 12
<212> TYPE: DNA
<213> ORGANISM: Artificial Sequence
<220> FEATURE:
<223> OTHER INFORMATION: Synthetic construct

<400> SEQUENCE: 121
caagtgcaaa ag                                                            12

<210> SEQ ID NO 122
<211> LENGTH: 12
<212> TYPE: DNA
<213> ORGANISM: Artificial Sequence
<220> FEATURE:
<223> OTHER INFORMATION: Synthetic construct

<400> SEQUENCE: 122
caagtgcaaa ag                                                            12

<210> SEQ ID NO 123
<211> LENGTH: 33
<212> TYPE: DNA
<213> ORGANISM: Artificial Sequence
<220> FEATURE:
<223> OTHER INFORMATION: Synthetic construct
```

-continued

<400> SEQUENCE: 123
catgtctttg ctactgttgc aaaagtgcaa aag                                   33

<210> SEQ ID NO 124
<211> LENGTH: 31
<212> TYPE: DNA
<213> ORGANISM: Artificial Sequence
<220> FEATURE:
<223> OTHER INFORMATION: Synthetic construct

<400> SEQUENCE: 124
catgtctttg ctactgttgc aagtgcaaaa g                                     31

<210> SEQ ID NO 125
<211> LENGTH: 39
<212> TYPE: DNA
<213> ORGANISM: Artificial Sequence
<220> FEATURE:
<223> OTHER INFORMATION: Synthetic construct

<400> SEQUENCE: 125
catgtctttg ctactgttgc aagtacccaa gtgcaaaag                             39

<210> SEQ ID NO 126
<211> LENGTH: 43
<212> TYPE: DNA
<213> ORGANISM: Artificial Sequence
<220> FEATURE:
<223> OTHER INFORMATION: Synthetic construct

<400> SEQUENCE: 126
tttccttttc cagaaagaga aggaggcaca gatcttgccg tct                        43

<210> SEQ ID NO 127
<211> LENGTH: 32
<212> TYPE: DNA
<213> ORGANISM: Artificial Sequence
<220> FEATURE:
<223> OTHER INFORMATION: Synthetic construct

<400> SEQUENCE: 127
tttccttttc cagaaagaga aggatgccgt ct                                    32

<210> SEQ ID NO 128
<211> LENGTH: 35
<212> TYPE: DNA
<213> ORGANISM: Artificial Sequence
<220> FEATURE:
<223> OTHER INFORMATION: Synthetic construct

<400> SEQUENCE: 128
tttccttttc cagaaagaga aggagcttgc cgtct                                 35

<210> SEQ ID NO 129
<211> LENGTH: 19
<212> TYPE: DNA
<213> ORGANISM: Artificial Sequence
<220> FEATURE:
<223> OTHER INFORMATION: Synthetic construct

<400> SEQUENCE: 129
tttccttttc cagaaagag                                                   19

<210> SEQ ID NO 130
<211> LENGTH: 43

-continued

```
<212> TYPE: DNA
<213> ORGANISM: Artificial Sequence
<220> FEATURE:
<223> OTHER INFORMATION: Synthetic construct

<400> SEQUENCE: 130 tttcctttc cagaaagaga aggaggcaca gatcttgccg tct                         43

<210> SEQ ID NO 131
<211> LENGTH: 37
<212> TYPE: DNA
<213> ORGANISM: Artificial Sequence
<220> FEATURE:
<223> OTHER INFORMATION: Synthetic construct

<400> SEQUENCE: 131 tttcctttc cagaaagaga aggaggcctt gccgtct                                37

<210> SEQ ID NO 132
<211> LENGTH: 43
<212> TYPE: DNA
<213> ORGANISM: Artificial Sequence
<220> FEATURE:
<223> OTHER INFORMATION: Synthetic construct

<400> SEQUENCE: 132 tttcctttc cagaaagaga aggaggcaca gatcttgccg tct                         43

<210> SEQ ID NO 133
<211> LENGTH: 35
<212> TYPE: DNA
<213> ORGANISM: Artificial Sequence
<220> FEATURE:
<223> OTHER INFORMATION: Synthetic construct

<400> SEQUENCE: 133 tttcctttc cagaaagaga aggagcttgc cgtct                                  35

<210> SEQ ID NO 134
<211> LENGTH: 43
<212> TYPE: DNA
<213> ORGANISM: Artificial Sequence
<220> FEATURE:
<223> OTHER INFORMATION: Synthetic construct

<400> SEQUENCE: 134 tttcctttc cagaaagaga aggaggcaca gatcttgccg tct                         43

<210> SEQ ID NO 135
<211> LENGTH: 33
<212> TYPE: DNA
<213> ORGANISM: Artificial Sequence
<220> FEATURE:
<223> OTHER INFORMATION: Synthetic construct

<400> SEQUENCE: 135 tttcctttc cagaaagaga aggattgccg tct                                    33

<210> SEQ ID NO 136
<211> LENGTH: 34
<212> TYPE: DNA
<213> ORGANISM: Artificial Sequence
<220> FEATURE:
<223> OTHER INFORMATION: Synthetic construct

<400> SEQUENCE: 136
```

-continued

--- tttcctttc cagaaagaga aggagttgcc gtct                                    34

<210> SEQ ID NO 137
<211> LENGTH: 35
<212> TYPE: DNA
<213> ORGANISM: Artificial Sequence
<220> FEATURE:
<223> OTHER INFORMATION: Synthetic construct

<400> SEQUENCE: 137 tttcctttc cagaaagaga aggagcttgc cgtct                                   35

<210> SEQ ID NO 138
<211> LENGTH: 40
<212> TYPE: DNA
<213> ORGANISM: Artificial Sequence
<220> FEATURE:
<223> OTHER INFORMATION: Synthetic construct

<400> SEQUENCE: 138 tttcctttc cagaaagaga agattttgac attgccgtct                              40

<210> SEQ ID NO 139
<211> LENGTH: 33
<212> TYPE: DNA
<213> ORGANISM: Artificial Sequence
<220> FEATURE:
<223> OTHER INFORMATION: Synthetic construct

<400> SEQUENCE: 139 tttcctttc cagaaagaga aggagtgccg tct                                     33

<210> SEQ ID NO 140
<211> LENGTH: 38
<212> TYPE: DNA
<213> ORGANISM: Artificial Sequence
<220> FEATURE:
<223> OTHER INFORMATION: Synthetic construct

<400> SEQUENCE: 140 tttcctttc cagaaagaga aggaggatct tgccgtct                                38

<210> SEQ ID NO 141
<211> LENGTH: 25
<212> TYPE: DNA
<213> ORGANISM: Artificial Sequence
<220> FEATURE:
<223> OTHER INFORMATION: Synthetic construct

<400> SEQUENCE: 141 tttcctttc cagaaagaga aggag                                              25

<210> SEQ ID NO 142
<211> LENGTH: 36
<212> TYPE: DNA
<213> ORGANISM: Artificial Sequence
<220> FEATURE:
<223> OTHER INFORMATION: Synthetic construct

<400> SEQUENCE: 142 tttcctttc cagaaagaga aggagtcttg ccgtct                                  36

<210> SEQ ID NO 143
<211> LENGTH: 17
<212> TYPE: DNA
<213> ORGANISM: Artificial Sequence -continued

```
<220> FEATURE:
<223> OTHER INFORMATION: Synthetic construct

<400> SEQUENCE: 143
tttccttttc cagaaag                                                        17

<210> SEQ ID NO 144
<211> LENGTH: 25
<212> TYPE: DNA
<213> ORGANISM: Artificial Sequence
<220> FEATURE:
<223> OTHER INFORMATION: Synthetic construct

<400> SEQUENCE: 144
tttccttttc cagaaagaga aggag                                               25

<210> SEQ ID NO 145
<211> LENGTH: 22
<212> TYPE: DNA
<213> ORGANISM: Artificial Sequence
<220> FEATURE:
<223> OTHER INFORMATION: Synthetic construct

<400> SEQUENCE: 145
tttccttttc cagaaagaga ag                                                  22

<210> SEQ ID NO 146
<211> LENGTH: 26
<212> TYPE: DNA
<213> ORGANISM: Artificial Sequence
<220> FEATURE:
<223> OTHER INFORMATION: Synthetic construct

<400> SEQUENCE: 146
tttccttttc cagaaagaga aggagg                                              26

<210> SEQ ID NO 147
<211> LENGTH: 23
<212> TYPE: DNA
<213> ORGANISM: Artificial Sequence
<220> FEATURE:
<223> OTHER INFORMATION: Synthetic construct

<400> SEQUENCE: 147
tttccttttc cagaaagaga agg                                                 23

<210> SEQ ID NO 148
<211> LENGTH: 25
<212> TYPE: DNA
<213> ORGANISM: Artificial Sequence
<220> FEATURE:
<223> OTHER INFORMATION: Synthetic construct

<400> SEQUENCE: 148
tttccttttc cagaaagaga aggag                                               25

<210> SEQ ID NO 149
<211> LENGTH: 41
<212> TYPE: DNA
<213> ORGANISM: Artificial Sequence
<220> FEATURE:
<223> OTHER INFORMATION: Synthetic construct

<400> SEQUENCE: 149
tttccttttc cagaaagaga aggaggcaca tcttgccgtc t                             41
```

-continued

```
<210> SEQ ID NO 150
<211> LENGTH: 43
<212> TYPE: DNA
<213> ORGANISM: Artificial Sequence
<220> FEATURE:
<223> OTHER INFORMATION: Synthetic construct

<400> SEQUENCE: 150 tttcctttc cagaaagaga aggaggcaca gatcttgccg tct                          43

<210> SEQ ID NO 151
<211> LENGTH: 35
<212> TYPE: DNA
<213> ORGANISM: Artificial Sequence
<220> FEATURE:
<223> OTHER INFORMATION: Synthetic construct

<400> SEQUENCE: 151 tttcctttc cagaaagaga aggaggctgc cgtct                                   35

<210> SEQ ID NO 152
<211> LENGTH: 32
<212> TYPE: DNA
<213> ORGANISM: Artificial Sequence
<220> FEATURE:
<223> OTHER INFORMATION: Synthetic construct

<400> SEQUENCE: 152 tttcctttc cagaaagaga aggaggccgt ct                                      32

<210> SEQ ID NO 153
<211> LENGTH: 38
<212> TYPE: DNA
<213> ORGANISM: Artificial Sequence
<220> FEATURE:
<223> OTHER INFORMATION: Synthetic construct

<400> SEQUENCE: 153 tttcctttc cagaaagaga aggaggatct tgccgtct                                38

<210> SEQ ID NO 154
<211> LENGTH: 32
<212> TYPE: DNA
<213> ORGANISM: Artificial Sequence
<220> FEATURE:
<223> OTHER INFORMATION: Synthetic construct

<400> SEQUENCE: 154 tttcctttc cagaaagaga aggatgccgt ct                                      32

<210> SEQ ID NO 155
<211> LENGTH: 41
<212> TYPE: DNA
<213> ORGANISM: Artificial Sequence
<220> FEATURE:
<223> OTHER INFORMATION: Synthetic construct

<400> SEQUENCE: 155 tttcctttc cagaaagaga aggaggcaca gcttgccgtc t                            41

<210> SEQ ID NO 156
<211> LENGTH: 43
<212> TYPE: DNA
<213> ORGANISM: Artificial Sequence
<220> FEATURE:
<223> OTHER INFORMATION: Synthetic construct
```

<400> SEQUENCE: 156
gcgccatttc tgcttcctgc aatgccggta gacacctcct caa                          43

<210> SEQ ID NO 157
<211> LENGTH: 38
<212> TYPE: DNA
<213> ORGANISM: Artificial Sequence
<220> FEATURE:
<223> OTHER INFORMATION: Synthetic construct

<400> SEQUENCE: 157
gcgccatttc tgcttcctgc aatgcgacac ctcctcaa                                38

<210> SEQ ID NO 158
<211> LENGTH: 43
<212> TYPE: DNA
<213> ORGANISM: Artificial Sequence
<220> FEATURE:
<223> OTHER INFORMATION: Synthetic construct

<400> SEQUENCE: 158
gcgccatttc tgcttcctgc aatgccggta gacacctcct caa                          43

<210> SEQ ID NO 159
<211> LENGTH: 30
<212> TYPE: DNA
<213> ORGANISM: Artificial Sequence
<220> FEATURE:
<223> OTHER INFORMATION: Synthetic construct

<400> SEQUENCE: 159
gcgccatttc tgcttcctgc acctcctcaa                                         30

<210> SEQ ID NO 160
<211> LENGTH: 43
<212> TYPE: DNA
<213> ORGANISM: Artificial Sequence
<220> FEATURE:
<223> OTHER INFORMATION: Synthetic construct

<400> SEQUENCE: 160
gcgccatttc tgcttcctgc aatgccggta gacacctcct caa                          43

<210> SEQ ID NO 161
<211> LENGTH: 32
<212> TYPE: DNA
<213> ORGANISM: Artificial Sequence
<220> FEATURE:
<223> OTHER INFORMATION: Synthetic construct

<400> SEQUENCE: 161
gcgccatttc tgcttcctgc aatgctcctc aa                                      32

<210> SEQ ID NO 162
<211> LENGTH: 35
<212> TYPE: DNA
<213> ORGANISM: Artificial Sequence
<220> FEATURE:
<223> OTHER INFORMATION: Synthetic construct

<400> SEQUENCE: 162
gcgccatttc tgcttcctgc aatacacctc ctcaa                                   35

<210> SEQ ID NO 163

-continued

```
<211> LENGTH: 31
<212> TYPE: DNA
<213> ORGANISM: Artificial Sequence
<220> FEATURE:
<223> OTHER INFORMATION: Synthetic construct

<400> SEQUENCE: 163
gcgccatttc tgcttcctgc aatgtcctca a                                       31

<210> SEQ ID NO 164
<211> LENGTH: 36
<212> TYPE: DNA
<213> ORGANISM: Artificial Sequence
<220> FEATURE:
<223> OTHER INFORMATION: Synthetic construct

<400> SEQUENCE: 164
gcgccatttc tgcttcctgc aatgccgcct cctcaa                                  36

<210> SEQ ID NO 165
<211> LENGTH: 34
<212> TYPE: DNA
<213> ORGANISM: Artificial Sequence
<220> FEATURE:
<223> OTHER INFORMATION: Synthetic construct

<400> SEQUENCE: 165
gcgccatttc tgcttcctgc aatcacctcc tcaa                                    34

<210> SEQ ID NO 166
<211> LENGTH: 36
<212> TYPE: DNA
<213> ORGANISM: Artificial Sequence
<220> FEATURE:
<223> OTHER INFORMATION: Synthetic construct

<400> SEQUENCE: 166
gcgccatttc tgcttcctgc aatgacacct cctcaa                                  36

<210> SEQ ID NO 167
<211> LENGTH: 36
<212> TYPE: DNA
<213> ORGANISM: Artificial Sequence
<220> FEATURE:
<223> OTHER INFORMATION: Synthetic construct

<400> SEQUENCE: 167
gcgccatttc tgcttcctgc aatgacacct cctcaa                                  36

<210> SEQ ID NO 168
<211> LENGTH: 43
<212> TYPE: DNA
<213> ORGANISM: Artificial Sequence
<220> FEATURE:
<223> OTHER INFORMATION: Synthetic construct

<400> SEQUENCE: 168
gcgccatttc tgcttcctgc aatgccggta gacacctcct caa                          43

<210> SEQ ID NO 169
<211> LENGTH: 30
<212> TYPE: DNA
<213> ORGANISM: Artificial Sequence
<220> FEATURE:
<223> OTHER INFORMATION: Synthetic construct

<400> SEQUENCE: 169
```

-continued

```
gcgccatttc tgcttcctgc aactcctcaa                                    30

<210> SEQ ID NO 170
<211> LENGTH: 34
<212> TYPE: DNA
<213> ORGANISM: Artificial Sequence
<220> FEATURE:
<223> OTHER INFORMATION: Synthetic construct

<400> SEQUENCE: 170
gcgccatttc tgcttcctgc aatgacctcc tcaa                               34

<210> SEQ ID NO 171
<211> LENGTH: 32
<212> TYPE: DNA
<213> ORGANISM: Artificial Sequence
<220> FEATURE:
<223> OTHER INFORMATION: Synthetic construct

<400> SEQUENCE: 171
gcgccatttc tgcttcctgc aatcctcctc aa                                 32

<210> SEQ ID NO 172
<211> LENGTH: 43
<212> TYPE: DNA
<213> ORGANISM: Artificial Sequence
<220> FEATURE:
<223> OTHER INFORMATION: Synthetic construct

<400> SEQUENCE: 172
gcgccatttc tgcttcctgc aatgccggta gacacctcct caa                     43

<210> SEQ ID NO 173
<211> LENGTH: 36
<212> TYPE: DNA
<213> ORGANISM: Artificial Sequence
<220> FEATURE:
<223> OTHER INFORMATION: Synthetic construct

<400> SEQUENCE: 173
gcgccatttc tgcttcctgc aatgacacct cctcaa                             36

<210> SEQ ID NO 174
<211> LENGTH: 43
<212> TYPE: DNA
<213> ORGANISM: Artificial Sequence
<220> FEATURE:
<223> OTHER INFORMATION: Synthetic construct

<400> SEQUENCE: 174
gcgccatttc tgcttcctgc aatgccggta gacacctcct caa                     43

<210> SEQ ID NO 175
<211> LENGTH: 33
<212> TYPE: DNA
<213> ORGANISM: Artificial Sequence
<220> FEATURE:
<223> OTHER INFORMATION: Synthetic construct

<400> SEQUENCE: 175
gcgccatttc tgcttcctgc aatacctcct caa                                33

<210> SEQ ID NO 176
<211> LENGTH: 43
<212> TYPE: DNA
```

-continued

<213> ORGANISM: Artificial Sequence
<220> FEATURE:
<223> OTHER INFORMATION: Synthetic construct

<400> SEQUENCE: 176
gcgccatttc tgcttcctgc aatgccggta gacacctcct caa                          43

<210> SEQ ID NO 177
<211> LENGTH: 30
<212> TYPE: DNA
<213> ORGANISM: Artificial Sequence
<220> FEATURE:
<223> OTHER INFORMATION: Synthetic construct

<400> SEQUENCE: 177
gcgccatttc tgcttcctgc acctcctcaa                                         30

<210> SEQ ID NO 178
<211> LENGTH: 43
<212> TYPE: DNA
<213> ORGANISM: Artificial Sequence
<220> FEATURE:
<223> OTHER INFORMATION: Synthetic construct

<400> SEQUENCE: 178
gcgccatttc tgcttcctgc aatgccggta gacacctcct caa                          43

<210> SEQ ID NO 179
<211> LENGTH: 16
<212> TYPE: DNA
<213> ORGANISM: Artificial Sequence
<220> FEATURE:
<223> OTHER INFORMATION: Synthetic construct

<400> SEQUENCE: 179
gcgcacacct cctcaa                                                        16

<210> SEQ ID NO 180
<211> LENGTH: 36
<212> TYPE: DNA
<213> ORGANISM: Artificial Sequence
<220> FEATURE:
<223> OTHER INFORMATION: Synthetic construct

<400> SEQUENCE: 180
gcgccatttc tgcttcctgc aatgacacct cctcaa                                  36

<210> SEQ ID NO 181
<211> LENGTH: 43
<212> TYPE: DNA
<213> ORGANISM: Artificial Sequence
<220> FEATURE:
<223> OTHER INFORMATION: Synthetic construct

<400> SEQUENCE: 181
tccggttttg taagcagctg gctgagggtg catgggcagt agt                          43

<210> SEQ ID NO 182
<211> LENGTH: 25
<212> TYPE: DNA
<213> ORGANISM: Artificial Sequence
<220> FEATURE:
<223> OTHER INFORMATION: Synthetic construct

<400> SEQUENCE: 182
tccggttttg taagcagcta gtagt                                              25

-continued

```
<210> SEQ ID NO 183
<211> LENGTH: 25
<212> TYPE: DNA
<213> ORGANISM: Artificial Sequence
<220> FEATURE:
<223> OTHER INFORMATION: Synthetic construct

<400> SEQUENCE: 183
tccggttttg taagcagcta gtagt                                       25

<210> SEQ ID NO 184
<211> LENGTH: 32
<212> TYPE: DNA
<213> ORGANISM: Artificial Sequence
<220> FEATURE:
<223> OTHER INFORMATION: Synthetic construct

<400> SEQUENCE: 184
tccggttttg taagcagctg gctggcagta gt                               32

<210> SEQ ID NO 185
<211> LENGTH: 36
<212> TYPE: DNA
<213> ORGANISM: Artificial Sequence
<220> FEATURE:
<223> OTHER INFORMATION: Synthetic construct

<400> SEQUENCE: 185
tccggttttg taagcagctg gctgatgggc agtagt                           36

<210> SEQ ID NO 186
<211> LENGTH: 33
<212> TYPE: DNA
<213> ORGANISM: Artificial Sequence
<220> FEATURE:
<223> OTHER INFORMATION: Synthetic construct

<400> SEQUENCE: 186
tccggttttg taagcagctg gctgggcagt agt                              33

<210> SEQ ID NO 187
<211> LENGTH: 35
<212> TYPE: DNA
<213> ORGANISM: Artificial Sequence
<220> FEATURE:
<223> OTHER INFORMATION: Synthetic construct

<400> SEQUENCE: 187
tccggttttg taagcagctg gctgagggca gtagt                            35

<210> SEQ ID NO 188
<211> LENGTH: 37
<212> TYPE: DNA
<213> ORGANISM: Artificial Sequence
<220> FEATURE:
<223> OTHER INFORMATION: Synthetic construct

<400> SEQUENCE: 188
tccggttttg taagcagctg gctgaatggg cagtagt                          37

<210> SEQ ID NO 189
<211> LENGTH: 39
<212> TYPE: DNA
<213> ORGANISM: Artificial Sequence
<220> FEATURE:
```

<223> OTHER INFORMATION: Synthetic construct

<400> SEQUENCE: 189
tccggttttg taagcagctg gctgtgcatg ggcagtagt                                39

<210> SEQ ID NO 190
<211> LENGTH: 32
<212> TYPE: DNA
<213> ORGANISM: Artificial Sequence
<220> FEATURE:
<223> OTHER INFORMATION: Synthetic construct

<400> SEQUENCE: 190
tccggttttg taagcagctg gctggcagta gt                                       32

<210> SEQ ID NO 191
<211> LENGTH: 33
<212> TYPE: DNA
<213> ORGANISM: Artificial Sequence
<220> FEATURE:
<223> OTHER INFORMATION: Synthetic construct

<400> SEQUENCE: 191
tccggttttg taagcagctg gctgggcagt agt                                      33

<210> SEQ ID NO 192
<211> LENGTH: 33
<212> TYPE: DNA
<213> ORGANISM: Artificial Sequence
<220> FEATURE:
<223> OTHER INFORMATION: Synthetic construct

<400> SEQUENCE: 192
tccggttttg taagcagctg gctgggcagt agt                                      33

<210> SEQ ID NO 193
<211> LENGTH: 35
<212> TYPE: DNA
<213> ORGANISM: Artificial Sequence
<220> FEATURE:
<223> OTHER INFORMATION: Synthetic construct

<400> SEQUENCE: 193
tccggttttg taagcagctg gctgtgggca gtagt                                    35

<210> SEQ ID NO 194
<211> LENGTH: 34
<212> TYPE: DNA
<213> ORGANISM: Artificial Sequence
<220> FEATURE:
<223> OTHER INFORMATION: Synthetic construct

<400> SEQUENCE: 194
tccggttttg taagcagctg gcttgggcag tagt                                     34

<210> SEQ ID NO 195
<211> LENGTH: 41
<212> TYPE: DNA
<213> ORGANISM: Artificial Sequence
<220> FEATURE:
<223> OTHER INFORMATION: Synthetic construct

<400> SEQUENCE: 195
tccggttttg taagcagctg gctgggtgca tgggcagtag t                             41

-continued

```
<210> SEQ ID NO 196
<211> LENGTH: 33
<212> TYPE: DNA
<213> ORGANISM: Artificial Sequence
<220> FEATURE:
<223> OTHER INFORMATION: Synthetic construct

<400> SEQUENCE: 196
tccggttttg taagcagctg gctgggcagt agt                              33

<210> SEQ ID NO 197
<211> LENGTH: 43
<212> TYPE: DNA
<213> ORGANISM: Artificial Sequence
<220> FEATURE:
<223> OTHER INFORMATION: Synthetic construct

<400> SEQUENCE: 197
tccggttttg taagcagctg gctgagggtg catgggcagt agt                   43

<210> SEQ ID NO 198
<211> LENGTH: 32
<212> TYPE: DNA
<213> ORGANISM: Artificial Sequence
<220> FEATURE:
<223> OTHER INFORMATION: Synthetic construct

<400> SEQUENCE: 198
tccggttttg taagcagctg gctggcagta gt                               32

<210> SEQ ID NO 199
<211> LENGTH: 32
<212> TYPE: DNA
<213> ORGANISM: Artificial Sequence
<220> FEATURE:
<223> OTHER INFORMATION: Synthetic construct

<400> SEQUENCE: 199
tccggttttg taagcagctg gctggcagta gt                               32

<210> SEQ ID NO 200
<211> LENGTH: 33
<212> TYPE: DNA
<213> ORGANISM: Artificial Sequence
<220> FEATURE:
<223> OTHER INFORMATION: Synthetic construct

<400> SEQUENCE: 200
tccggttttg taagcagctg gctgggcagt agt                              33

<210> SEQ ID NO 201
<211> LENGTH: 37
<212> TYPE: DNA
<213> ORGANISM: Artificial Sequence
<220> FEATURE:
<223> OTHER INFORMATION: Synthetic construct

<400> SEQUENCE: 201
tccggttttg taagcagctg gctgaatggg cagtagt                          37

<210> SEQ ID NO 202
<211> LENGTH: 34
<212> TYPE: DNA
<213> ORGANISM: Artificial Sequence
<220> FEATURE:
<223> OTHER INFORMATION: Synthetic construct
```

-continued

```
<400> SEQUENCE: 202
tccggttttg taagcagctg gctgaggcag tagt                                      34

<210> SEQ ID NO 203
<211> LENGTH: 37
<212> TYPE: DNA
<213> ORGANISM: Artificial Sequence
<220> FEATURE:
<223> OTHER INFORMATION: Synthetic construct

<400> SEQUENCE: 203
tccggttttg taagcagctg gctgcatggg cagtagt                                   37

<210> SEQ ID NO 204
<211> LENGTH: 26
<212> TYPE: DNA
<213> ORGANISM: Artificial Sequence
<220> FEATURE:
<223> OTHER INFORMATION: Synthetic construct

<400> SEQUENCE: 204
tccggttttg taagcagctg gctagt                                               26

<210> SEQ ID NO 205
<211> LENGTH: 33
<212> TYPE: DNA
<213> ORGANISM: Artificial Sequence
<220> FEATURE:
<223> OTHER INFORMATION: Synthetic construct

<400> SEQUENCE: 205
tccggttttg taagcagctg gctgggcagt agt                                       33

<210> SEQ ID NO 206
<211> LENGTH: 14
<212> TYPE: DNA
<213> ORGANISM: Artificial Sequence
<220> FEATURE:
<223> OTHER INFORMATION: Synthetic construct

<400> SEQUENCE: 206
tccggttttg taag                                                            14

<210> SEQ ID NO 207
<211> LENGTH: 34
<212> TYPE: DNA
<213> ORGANISM: Artificial Sequence
<220> FEATURE:
<223> OTHER INFORMATION: Synthetic construct

<400> SEQUENCE: 207
tccggttttg taagcagctg gcatgggcag tagt                                      34

<210> SEQ ID NO 208
<211> LENGTH: 35
<212> TYPE: DNA
<213> ORGANISM: Artificial Sequence
<220> FEATURE:
<223> OTHER INFORMATION: Synthetic construct

<400> SEQUENCE: 208
tccggttttg taagcagctg gctgagggca gtagt                                     35

<210> SEQ ID NO 209
<211> LENGTH: 43
```

```
<212> TYPE: DNA
<213> ORGANISM: Artificial Sequence
<220> FEATURE:
<223> OTHER INFORMATION: Synthetic construct

<400> SEQUENCE: 209
tccggttttg taagcagctg gctgagggtg catgggcagt agt                43

<210> SEQ ID NO 210
<211> LENGTH: 34
<212> TYPE: DNA
<213> ORGANISM: Artificial Sequence
<220> FEATURE:
<223> OTHER INFORMATION: Synthetic construct

<400> SEQUENCE: 210
tccggttttg taagcagctg gctgaggcag tagt                         34

<210> SEQ ID NO 211
<211> LENGTH: 43
<212> TYPE: DNA
<213> ORGANISM: Artificial Sequence
<220> FEATURE:
<223> OTHER INFORMATION: Synthetic construct

<400> SEQUENCE: 211
tccggttttg taagcagctg gctgagggtg catgggcagt agt                43

<210> SEQ ID NO 212
<211> LENGTH: 36
<212> TYPE: DNA
<213> ORGANISM: Artificial Sequence
<220> FEATURE:
<223> OTHER INFORMATION: Synthetic construct

<400> SEQUENCE: 212
tccggttttg taagcagctg gctgatgggc agtagt                       36

<210> SEQ ID NO 213
<211> LENGTH: 36
<212> TYPE: DNA
<213> ORGANISM: Artificial Sequence
<220> FEATURE:
<223> OTHER INFORMATION: Synthetic construct

<400> SEQUENCE: 213
tccggttttg taagcagctg gctgatgggc agtagt                       36

<210> SEQ ID NO 214
<211> LENGTH: 35
<212> TYPE: DNA
<213> ORGANISM: Artificial Sequence
<220> FEATURE:
<223> OTHER INFORMATION: Synthetic construct

<400> SEQUENCE: 214
tccggttttg taagcagctg gctgtgggca gtagt                        35

<210> SEQ ID NO 215
<211> LENGTH: 37
<212> TYPE: DNA
<213> ORGANISM: Artificial Sequence
<220> FEATURE:
<223> OTHER INFORMATION: Synthetic construct

<400> SEQUENCE: 215
```

-continued tccggttttg taagcagctg gctgaatggg cagtagt                                37

<210> SEQ ID NO 216
<211> LENGTH: 33
<212> TYPE: DNA
<213> ORGANISM: Artificial Sequence
<220> FEATURE:
<223> OTHER INFORMATION: Synthetic construct

<400> SEQUENCE: 216
tccggttttg taagcagctg gctgggcagt agt                                    33

<210> SEQ ID NO 217
<211> LENGTH: 40
<212> TYPE: DNA
<213> ORGANISM: Artificial Sequence
<220> FEATURE:
<223> OTHER INFORMATION: Synthetic construct

<400> SEQUENCE: 217
tccggttttg taagcagctg gctgagggat gggcagtagt                             40

<210> SEQ ID NO 218
<211> LENGTH: 45
<212> TYPE: DNA
<213> ORGANISM: Artificial Sequence
<220> FEATURE:
<223> OTHER INFORMATION: Synthetic construct

<400> SEQUENCE: 218
agctttggag tgaaatctct tgtcttaagg aataaaggaa aaaga                       45

<210> SEQ ID NO 219
<211> LENGTH: 19
<212> TYPE: DNA
<213> ORGANISM: Artificial Sequence
<220> FEATURE:
<223> OTHER INFORMATION: Synthetic construct

<400> SEQUENCE: 219
agctttggag tgaaaaaga                                                    19

<210> SEQ ID NO 220
<211> LENGTH: 37
<212> TYPE: DNA
<213> ORGANISM: Artificial Sequence
<220> FEATURE:
<223> OTHER INFORMATION: Synthetic construct

<400> SEQUENCE: 220
agctttggag tgaaatctct tgaataaagg aaaaaga                                37

<210> SEQ ID NO 221
<211> LENGTH: 36
<212> TYPE: DNA
<213> ORGANISM: Artificial Sequence
<220> FEATURE:
<223> OTHER INFORMATION: Synthetic construct

<400> SEQUENCE: 221
agctttggag tgaaatctct taataaagga aaaaga                                 36

<210> SEQ ID NO 222
<211> LENGTH: 36
<212> TYPE: DNA
<213> ORGANISM: Artificial Sequence -continued

```
<220> FEATURE:
<223> OTHER INFORMATION: Synthetic construct

<400> SEQUENCE: 222
agctttggag tgaaatctct taataaagga aaaaga                                  36

<210> SEQ ID NO 223
<211> LENGTH: 45
<212> TYPE: DNA
<213> ORGANISM: Artificial Sequence
<220> FEATURE:
<223> OTHER INFORMATION: Synthetic construct

<400> SEQUENCE: 223
gtctttgcta ctgttgcaag tgctcaccca agtgcaaaag accaa                        45

<210> SEQ ID NO 224
<211> LENGTH: 45
<212> TYPE: DNA
<213> ORGANISM: Artificial Sequence
<220> FEATURE:
<223> OTHER INFORMATION: Synthetic construct

<400> SEQUENCE: 224
gtctttgcta ctgttgcaag tgctcaccca agtgcaaaag accaa                        45

<210> SEQ ID NO 225
<211> LENGTH: 33
<212> TYPE: DNA
<213> ORGANISM: Artificial Sequence
<220> FEATURE:
<223> OTHER INFORMATION: Synthetic construct

<400> SEQUENCE: 225
gtctttgcta ctgttgcaag tgcaaaagac caa                                     33

<210> SEQ ID NO 226
<211> LENGTH: 35
<212> TYPE: DNA
<213> ORGANISM: Artificial Sequence
<220> FEATURE:
<223> OTHER INFORMATION: Synthetic construct

<400> SEQUENCE: 226
gtctttgcta ctgttgcaaa agtgcaaaag accaa                                   35

<210> SEQ ID NO 227
<211> LENGTH: 27
<212> TYPE: DNA
<213> ORGANISM: Artificial Sequence
<220> FEATURE:
<223> OTHER INFORMATION: Synthetic construct

<400> SEQUENCE: 227
gtctttgcta ctgttgcaag agaccaa                                            27

<210> SEQ ID NO 228
<211> LENGTH: 45
<212> TYPE: DNA
<213> ORGANISM: Artificial Sequence
<220> FEATURE:
<223> OTHER INFORMATION: Synthetic construct

<400> SEQUENCE: 228
ccatttctgc ttcctgcaat gccggtagac acctcctcaa gcact                        45
```

```
<210> SEQ ID NO 229
<211> LENGTH: 38
<212> TYPE: DNA
<213> ORGANISM: Artificial Sequence
<220> FEATURE:
<223> OTHER INFORMATION: Synthetic construct

<400> SEQUENCE: 229
ccatttctgc ttcctgcaat gacacctcct caagcact                        38

<210> SEQ ID NO 230
<211> LENGTH: 37
<212> TYPE: DNA
<213> ORGANISM: Artificial Sequence
<220> FEATURE:
<223> OTHER INFORMATION: Synthetic construct

<400> SEQUENCE: 230
ccatttctgc ttcctgcaat gcacctcctc aagcact                         37

<210> SEQ ID NO 231
<211> LENGTH: 34
<212> TYPE: DNA
<213> ORGANISM: Artificial Sequence
<220> FEATURE:
<223> OTHER INFORMATION: Synthetic construct

<400> SEQUENCE: 231
ccatttctgc ttcctgcaaa cctcctcaag cact                            34

<210> SEQ ID NO 232
<211> LENGTH: 33
<212> TYPE: DNA
<213> ORGANISM: Artificial Sequence
<220> FEATURE:
<223> OTHER INFORMATION: Synthetic construct

<400> SEQUENCE: 232
ccatttctgc ttcctgcaat ctcctcaagc act                             33

<210> SEQ ID NO 233
<211> LENGTH: 45
<212> TYPE: DNA
<213> ORGANISM: Artificial Sequence
<220> FEATURE:
<223> OTHER INFORMATION: Synthetic construct

<400> SEQUENCE: 233
acttttgcct ctctctcctg tgcttgcctc ttccattcct gctgc                45

<210> SEQ ID NO 234
<211> LENGTH: 45
<212> TYPE: DNA
<213> ORGANISM: Artificial Sequence
<220> FEATURE:
<223> OTHER INFORMATION: Synthetic construct

<400> SEQUENCE: 234
acttttgcct ctctctcctg tgcttgcctc ttccattcct gctgc                45

<210> SEQ ID NO 235
<211> LENGTH: 45
<212> TYPE: DNA
<213> ORGANISM: Artificial Sequence
<220> FEATURE:
<223> OTHER INFORMATION: Synthetic construct
```

<400> SEQUENCE: 235 actttttgcct ctctctcctg tgcttgcctc ttccattcct gctgc                45

<210> SEQ ID NO 236
<211> LENGTH: 45
<212> TYPE: DNA
<213> ORGANISM: Artificial Sequence
<220> FEATURE:
<223> OTHER INFORMATION: Synthetic construct

<400> SEQUENCE: 236 actttttgcct ctctctcctg tgcttgcctc ttccattcct gctgc                45

<210> SEQ ID NO 237
<211> LENGTH: 45
<212> TYPE: DNA
<213> ORGANISM: Artificial Sequence
<220> FEATURE:
<223> OTHER INFORMATION: Synthetic construct

<400> SEQUENCE: 237 actttttgcct ctctctcctg tgcttgcctc ttccattcct gctgc                45

<210> SEQ ID NO 238
<211> LENGTH: 45
<212> TYPE: DNA
<213> ORGANISM: Artificial Sequence
<220> FEATURE:
<223> OTHER INFORMATION: Synthetic construct

<400> SEQUENCE: 238
ttgtttgaag aagggttatg gccaatgctt gccccacatc tacca                45

<210> SEQ ID NO 239
<211> LENGTH: 41
<212> TYPE: DNA
<213> ORGANISM: Artificial Sequence
<220> FEATURE:
<223> OTHER INFORMATION: Synthetic construct

<400> SEQUENCE: 239
ttgtttgaag aagggttatg gcgcttgccc cacatctacc a                41

<210> SEQ ID NO 240
<211> LENGTH: 39
<212> TYPE: DNA
<213> ORGANISM: Artificial Sequence
<220> FEATURE:
<223> OTHER INFORMATION: Synthetic construct

<400> SEQUENCE: 240
ttgtttgaag aagggttatg gcttgcccca catctacca                39

<210> SEQ ID NO 241
<211> LENGTH: 38
<212> TYPE: DNA
<213> ORGANISM: Artificial Sequence
<220> FEATURE:
<223> OTHER INFORMATION: Synthetic construct

<400> SEQUENCE: 241
ttgtttgaag aagggttatg gctgccccac atctacca                38

<210> SEQ ID NO 242

-continued

```
<211> LENGTH: 38
<212> TYPE: DNA
<213> ORGANISM: Artificial Sequence
<220> FEATURE:
<223> OTHER INFORMATION: Synthetic construct

<400> SEQUENCE: 242
ttgtttgaag aagggttatg gttgccccac atctacca                          38

<210> SEQ ID NO 243
<211> LENGTH: 45
<212> TYPE: DNA
<213> ORGANISM: Artificial Sequence
<220> FEATURE:
<223> OTHER INFORMATION: Synthetic construct

<400> SEQUENCE: 243
ggatttgggg catggagaca ggagacatag atggcccggc catgt                  45

<210> SEQ ID NO 244
<211> LENGTH: 36
<212> TYPE: DNA
<213> ORGANISM: Artificial Sequence
<220> FEATURE:
<223> OTHER INFORMATION: Synthetic construct

<400> SEQUENCE: 244
ggatttgggg catggagaca gatggcccgg ccatgt                            36

<210> SEQ ID NO 245
<211> LENGTH: 33
<212> TYPE: DNA
<213> ORGANISM: Artificial Sequence
<220> FEATURE:
<223> OTHER INFORMATION: Synthetic construct

<400> SEQUENCE: 245
ggatttgggg catggagaca ggcccggcca tgt                               33

<210> SEQ ID NO 246
<211> LENGTH: 37
<212> TYPE: DNA
<213> ORGANISM: Artificial Sequence
<220> FEATURE:
<223> OTHER INFORMATION: Synthetic construct

<400> SEQUENCE: 246
ggatttgggg catggagaca ggatggcccg gccatgt                           37

<210> SEQ ID NO 247
<211> LENGTH: 25
<212> TYPE: DNA
<213> ORGANISM: Artificial Sequence
<220> FEATURE:
<223> OTHER INFORMATION: Synthetic construct

<400> SEQUENCE: 247
ggatttgggg catggagaca gatgt                                        25

<210> SEQ ID NO 248
<211> LENGTH: 45
<212> TYPE: DNA
<213> ORGANISM: Artificial Sequence
<220> FEATURE:
<223> OTHER INFORMATION: Synthetic construct

<400> SEQUENCE: 248
```

-continued

```
acctttggca ccatatgctt gctgatcaaa tactttattt aagtc                      45

<210> SEQ ID NO 249
<211> LENGTH: 34
<212> TYPE: DNA
<213> ORGANISM: Artificial Sequence
<220> FEATURE:
<223> OTHER INFORMATION: Synthetic construct

<400> SEQUENCE: 249
acctttggca ccatatgctt actttattta agtc                                  34

<210> SEQ ID NO 250
<211> LENGTH: 31
<212> TYPE: DNA
<213> ORGANISM: Artificial Sequence
<220> FEATURE:
<223> OTHER INFORMATION: Synthetic construct

<400> SEQUENCE: 250
acctttggca ccatatgctt ttatttaagt c                                     31

<210> SEQ ID NO 251
<211> LENGTH: 38
<212> TYPE: DNA
<213> ORGANISM: Artificial Sequence
<220> FEATURE:
<223> OTHER INFORMATION: Synthetic construct

<400> SEQUENCE: 251
acctttggca ccatatgctt gcttacttta tttaagtc                              38

<210> SEQ ID NO 252
<211> LENGTH: 34
<212> TYPE: DNA
<213> ORGANISM: Artificial Sequence
<220> FEATURE:
<223> OTHER INFORMATION: Synthetic construct

<400> SEQUENCE: 252
acctttggca ccatatgctt gctttattta agtc                                  34

<210> SEQ ID NO 253
<211> LENGTH: 45
<212> TYPE: DNA
<213> ORGANISM: Artificial Sequence
<220> FEATURE:
<223> OTHER INFORMATION: Synthetic construct

<400> SEQUENCE: 253
acctttaacc ctgtgtgaat ggtcagtaag cccacctaca ttgat                      45

<210> SEQ ID NO 254
<211> LENGTH: 19
<212> TYPE: DNA
<213> ORGANISM: Artificial Sequence
<220> FEATURE:
<223> OTHER INFORMATION: Synthetic construct

<400> SEQUENCE: 254
acctttaacc ctgtgtgat                                                   19

<210> SEQ ID NO 255
<211> LENGTH: 34
<212> TYPE: DNA
```

-continued

```
<213> ORGANISM: Artificial Sequence
<220> FEATURE:
<223> OTHER INFORMATION: Synthetic construct

<400> SEQUENCE: 255
acctttaacc ctgtgtgaat ccacctacat tgat                                     34

<210> SEQ ID NO 256
<211> LENGTH: 36
<212> TYPE: DNA
<213> ORGANISM: Artificial Sequence
<220> FEATURE:
<223> OTHER INFORMATION: Synthetic construct

<400> SEQUENCE: 256
acctttaacc ctgtgtgaat gcccacctac attgat                                   36

<210> SEQ ID NO 257
<211> LENGTH: 45
<212> TYPE: DNA
<213> ORGANISM: Artificial Sequence
<220> FEATURE:
<223> OTHER INFORMATION: Synthetic construct

<400> SEQUENCE: 257
acctttaacc ctgtgtgaat ggtcagtaag cccacctaca ttgat                         45

<210> SEQ ID NO 258
<211> LENGTH: 45
<212> TYPE: DNA
<213> ORGANISM: Artificial Sequence
<220> FEATURE:
<223> OTHER INFORMATION: Synthetic construct

<400> SEQUENCE: 258
cactttctgt atctccgaca cccggatcac gtcgtggtag gagga                         45

<210> SEQ ID NO 259
<211> LENGTH: 17
<212> TYPE: DNA
<213> ORGANISM: Artificial Sequence
<220> FEATURE:
<223> OTHER INFORMATION: Synthetic construct

<400> SEQUENCE: 259
cactttctgt aggagga                                                        17

<210> SEQ ID NO 260
<211> LENGTH: 39
<212> TYPE: DNA
<213> ORGANISM: Artificial Sequence
<220> FEATURE:
<223> OTHER INFORMATION: Synthetic construct

<400> SEQUENCE: 260
cactttctgt atctccgaca tcacgtcgtg gtaggagga                                39

<210> SEQ ID NO 261
<211> LENGTH: 12
<212> TYPE: DNA
<213> ORGANISM: Artificial Sequence
<220> FEATURE:
<223> OTHER INFORMATION: Synthetic construct

<400> SEQUENCE: 261
cactttctgt at                                                             12
```

```
<210> SEQ ID NO 262
<211> LENGTH: 29
<212> TYPE: DNA
<213> ORGANISM: Artificial Sequence
<220> FEATURE:
<223> OTHER INFORMATION: Synthetic construct

<400> SEQUENCE: 262
cactttctgt atctccgaca ctaggagga                                29

<210> SEQ ID NO 263
<211> LENGTH: 45
<212> TYPE: DNA
<213> ORGANISM: Artificial Sequence
<220> FEATURE:
<223> OTHER INFORMATION: Synthetic construct

<400> SEQUENCE: 263
gactttggat gatgcatcag gtactagaac gccctcgggc acacc              45

<210> SEQ ID NO 264
<211> LENGTH: 32
<212> TYPE: DNA
<213> ORGANISM: Artificial Sequence
<220> FEATURE:
<223> OTHER INFORMATION: Synthetic construct

<400> SEQUENCE: 264
gactttggat gatgcatcac ctcgggcaca cc                            32

<210> SEQ ID NO 265
<211> LENGTH: 39
<212> TYPE: DNA
<213> ORGANISM: Artificial Sequence
<220> FEATURE:
<223> OTHER INFORMATION: Synthetic construct

<400> SEQUENCE: 265
gactttggat gatgcatcag gaacgccctc gggcacacc                     39

<210> SEQ ID NO 266
<211> LENGTH: 34
<212> TYPE: DNA
<213> ORGANISM: Artificial Sequence
<220> FEATURE:
<223> OTHER INFORMATION: Synthetic construct

<400> SEQUENCE: 266
gactttggat gatgcatccg ccctcgggca cacc                          34

<210> SEQ ID NO 267
<211> LENGTH: 35
<212> TYPE: DNA
<213> ORGANISM: Artificial Sequence
<220> FEATURE:
<223> OTHER INFORMATION: Synthetic construct

<400> SEQUENCE: 267
gactttggat gatgcatcag gtactcgggc acacc                         35

<210> SEQ ID NO 268
<211> LENGTH: 45
<212> TYPE: DNA
<213> ORGANISM: Artificial Sequence
<220> FEATURE:
```

-continued

```
<223> OTHER INFORMATION: Synthetic construct

<400> SEQUENCE: 268
gcatttaccg gtgaaaagga ccttgtccca tctgtgctcc atgag                          45

<210> SEQ ID NO 269
<211> LENGTH: 15
<212> TYPE: DNA
<213> ORGANISM: Artificial Sequence
<220> FEATURE:
<223> OTHER INFORMATION: Synthetic construct

<400> SEQUENCE: 269
gcatttaccg gtgag                                                           15

<210> SEQ ID NO 270
<211> LENGTH: 36
<212> TYPE: DNA
<213> ORGANISM: Artificial Sequence
<220> FEATURE:
<223> OTHER INFORMATION: Synthetic construct

<400> SEQUENCE: 270
gcatttaccg gtgaaaagga ctctgtgctc catgag                                    36

<210> SEQ ID NO 271
<211> LENGTH: 37
<212> TYPE: DNA
<213> ORGANISM: Artificial Sequence
<220> FEATURE:
<223> OTHER INFORMATION: Synthetic construct

<400> SEQUENCE: 271
gcatttaccg gtgaaaagga catctgtgct ccatgag                                   37

<210> SEQ ID NO 272
<211> LENGTH: 35
<212> TYPE: DNA
<213> ORGANISM: Artificial Sequence
<220> FEATURE:
<223> OTHER INFORMATION: Synthetic construct

<400> SEQUENCE: 272
gcatttaccg gtgaaaagga cccgtgctcc atgag                                     35

<210> SEQ ID NO 273
<211> LENGTH: 45
<212> TYPE: DNA
<213> ORGANISM: Artificial Sequence
<220> FEATURE:
<223> OTHER INFORMATION: Synthetic construct

<400> SEQUENCE: 273
ccatttctgg ggccttgcaa ggtcacctcc atagattaca aggag                          45

<210> SEQ ID NO 274
<211> LENGTH: 34
<212> TYPE: DNA
<213> ORGANISM: Artificial Sequence
<220> FEATURE:
<223> OTHER INFORMATION: Synthetic construct

<400> SEQUENCE: 274
ccatttctgg ggccttgcaa tagattacaa ggag                                      34
```

-continued

```
<210> SEQ ID NO 275
<211> LENGTH: 30
<212> TYPE: DNA
<213> ORGANISM: Artificial Sequence
<220> FEATURE:
<223> OTHER INFORMATION: Synthetic construct

<400> SEQUENCE: 275
ccatttctgg ggccttgcga ttacaaggag                                         30

<210> SEQ ID NO 276
<211> LENGTH: 37
<212> TYPE: DNA
<213> ORGANISM: Artificial Sequence
<220> FEATURE:
<223> OTHER INFORMATION: Synthetic construct

<400> SEQUENCE: 276
ccatttctgg ggccttgcaa gcatagatta caaggag                                 37

<210> SEQ ID NO 277
<211> LENGTH: 42
<212> TYPE: DNA
<213> ORGANISM: Artificial Sequence
<220> FEATURE:
<223> OTHER INFORMATION: Synthetic construct

<400> SEQUENCE: 277
ccatttctgg ggccttgcaa ggcctccata gattacaagg ag                           42

<210> SEQ ID NO 278
<211> LENGTH: 45
<212> TYPE: DNA
<213> ORGANISM: Artificial Sequence
<220> FEATURE:
<223> OTHER INFORMATION: Synthetic construct

<400> SEQUENCE: 278
aaatttgccg gcagctaata gggatctaaa cacactagtc atatc                        45

<210> SEQ ID NO 279
<211> LENGTH: 38
<212> TYPE: DNA
<213> ORGANISM: Artificial Sequence
<220> FEATURE:
<223> OTHER INFORMATION: Synthetic construct

<400> SEQUENCE: 279
aaatttgccg gcagctaata ggacacacta gtcatatc                                38

<210> SEQ ID NO 280
<211> LENGTH: 37
<212> TYPE: DNA
<213> ORGANISM: Artificial Sequence
<220> FEATURE:
<223> OTHER INFORMATION: Synthetic construct

<400> SEQUENCE: 280
aaatttgccg gcagctaata aacacactag tcatatc                                 37

<210> SEQ ID NO 281
<211> LENGTH: 36
<212> TYPE: DNA
<213> ORGANISM: Artificial Sequence
<220> FEATURE:
<223> OTHER INFORMATION: Synthetic construct
```

<400> SEQUENCE: 281
aaatttgccg gcagctaata ggacactagt catatc                                      36

<210> SEQ ID NO 282
<211> LENGTH: 35
<212> TYPE: DNA
<213> ORGANISM: Artificial Sequence
<220> FEATURE:
<223> OTHER INFORMATION: Synthetic construct

<400> SEQUENCE: 282
aaatttgccg gcagctaata cacactagtc atatc                                       35

<210> SEQ ID NO 283
<211> LENGTH: 45
<212> TYPE: DNA
<213> ORGANISM: Artificial Sequence
<220> FEATURE:
<223> OTHER INFORMATION: Synthetic construct

<400> SEQUENCE: 283
tgctttatac gtggaaacaa tgacagttca cacaggagga ggttg                            45

<210> SEQ ID NO 284
<211> LENGTH: 34
<212> TYPE: DNA
<213> ORGANISM: Artificial Sequence
<220> FEATURE:
<223> OTHER INFORMATION: Synthetic construct

<400> SEQUENCE: 284
tgctttatac gtggaaacaa tcaggaggag gttg                                        34

<210> SEQ ID NO 285
<211> LENGTH: 23
<212> TYPE: DNA
<213> ORGANISM: Artificial Sequence
<220> FEATURE:
<223> OTHER INFORMATION: Synthetic construct

<400> SEQUENCE: 285
tgctttatac gtggaaacaa ttg                                                    23

<210> SEQ ID NO 286
<211> LENGTH: 28
<212> TYPE: DNA
<213> ORGANISM: Artificial Sequence
<220> FEATURE:
<223> OTHER INFORMATION: Synthetic construct

<400> SEQUENCE: 286
tgctttatac gtggaaacaa ggaggttg                                               28

<210> SEQ ID NO 287
<211> LENGTH: 34
<212> TYPE: DNA
<213> ORGANISM: Artificial Sequence
<220> FEATURE:
<223> OTHER INFORMATION: Synthetic construct

<400> SEQUENCE: 287
tgctttatac gtggaaacaa tcaggaggag gttg                                        34

<210> SEQ ID NO 288
<211> LENGTH: 45

```
<212> TYPE: DNA
<213> ORGANISM: Artificial Sequence
<220> FEATURE:
<223> OTHER INFORMATION: Synthetic construct

<400> SEQUENCE: 288
ctctttctcc tgaggagcaa gagccatcac aggtaagaaa gaact                45

<210> SEQ ID NO 289
<211> LENGTH: 29
<212> TYPE: DNA
<213> ORGANISM: Artificial Sequence
<220> FEATURE:
<223> OTHER INFORMATION: Synthetic construct

<400> SEQUENCE: 289
ctctttctcc tgaggagcaa gaaagaact                                  29

<210> SEQ ID NO 290
<211> LENGTH: 39
<212> TYPE: DNA
<213> ORGANISM: Artificial Sequence
<220> FEATURE:
<223> OTHER INFORMATION: Synthetic construct

<400> SEQUENCE: 290
ctctttctcc tgaggagcaa ggtcaggtaa gaaagaact                       39

<210> SEQ ID NO 291
<211> LENGTH: 33
<212> TYPE: DNA
<213> ORGANISM: Artificial Sequence
<220> FEATURE:
<223> OTHER INFORMATION: Synthetic construct

<400> SEQUENCE: 291
ctctttctcc tgaggagcaa gtaagaaaga act                             33

<210> SEQ ID NO 292
<211> LENGTH: 25
<212> TYPE: DNA
<213> ORGANISM: Artificial Sequence
<220> FEATURE:
<223> OTHER INFORMATION: Synthetic construct

<400> SEQUENCE: 292
ctctttctcc tgaggagcaa gaact                                      25

<210> SEQ ID NO 293
<211> LENGTH: 45
<212> TYPE: DNA
<213> ORGANISM: Artificial Sequence
<220> FEATURE:
<223> OTHER INFORMATION: Synthetic construct

<400> SEQUENCE: 293
atgtttgagc atatggttgt aacttcagaa aaactgaatc cccaa               45

<210> SEQ ID NO 294
<211> LENGTH: 35
<212> TYPE: DNA
<213> ORGANISM: Artificial Sequence
<220> FEATURE:
<223> OTHER INFORMATION: Synthetic construct

<400> SEQUENCE: 294
```

-continued

```
atgtttgagc atatggttgt aaactgaatc cccaa                                    35
```

<210> SEQ ID NO 295
<211> LENGTH: 35
<212> TYPE: DNA
<213> ORGANISM: Artificial Sequence
<220> FEATURE:
<223> OTHER INFORMATION: Synthetic construct

<400> SEQUENCE: 295

```
atgtttgagc atatggttgt aaactgaatc cccaa                                    35
```

<210> SEQ ID NO 296
<211> LENGTH: 12
<212> TYPE: DNA
<213> ORGANISM: Artificial Sequence
<220> FEATURE:
<223> OTHER INFORMATION: Synthetic construct

<400> SEQUENCE: 296

```
atgtttgagc aa                                                             12
```

<210> SEQ ID NO 297
<211> LENGTH: 15
<212> TYPE: DNA
<213> ORGANISM: Artificial Sequence
<220> FEATURE:
<223> OTHER INFORMATION: Synthetic construct

<400> SEQUENCE: 297

```
atgtttgagc atatg                                                          15
```

<210> SEQ ID NO 298
<211> LENGTH: 1251
<212> TYPE: PRT
<213> ORGANISM: Artificial Sequence
<220> FEATURE:
<223> OTHER INFORMATION: Synthetic construct

<400> SEQUENCE: 298

```
Met Leu Phe Gln Asp Phe Thr His Leu Tyr Pro Leu Ser Lys Thr Val
1               5                   10                  15

Arg Phe Glu Leu Lys Pro Ile Gly Arg Thr Leu Glu His Ile His Ala
            20                  25                  30

Lys Asn Phe Leu Ser Gln Asp Glu Thr Met Ala Asp Met Tyr Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
                85                  90                  95

Lys Asp Leu Gln Ala Val Leu Arg Lys Glu Ser Val Lys Pro Ile Gly
            100                 105                 110

Ser Gly Gly Lys Tyr Lys Thr Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
```

-continued

```
                  165               170               175

Met Tyr Ser Asp Glu Asp Lys His Thr Ala Ile Ala Tyr Arg Leu Ile
            180               185               190

His Glu Asn Leu Pro Arg Phe Ile Asp Asn Leu Gln Ile Leu Thr Thr
            195               200               205

Ile Lys Gln Lys His Ser Ala Leu Tyr Asp Gln Ile Ile Asn Glu Leu
        210               215               220

Thr Ala Ser Gly Leu Asp Val Ser Leu Ala Ser His Leu Asp Gly Tyr
    225               230               235               240

His Lys Leu Leu Thr Gln Glu Gly Ile Thr Ala Tyr Asn Arg Ile Ile
                245               250               255

Gly Glu Val Asn Gly Tyr Thr Asn Lys His Asn Gln Ile Cys His Lys
            260               265               270

Ser Glu Arg Ile Ala Lys Leu Arg Pro Leu His Lys Gln Ile Leu Ser
            275               280               285

Asp Gly Met Gly Val Ser Phe Leu Pro Ser Lys Phe Ala Asp Asp Ser
        290               295               300

Glu Met Cys Gln Ala Val Asn Glu Phe Tyr Arg His Tyr Thr Asp Val
    305               310               315               320

Phe Ala Lys Val Gln Ser Leu Phe Asp Gly Phe Asp Asp His Gln Lys
                325               330               335

Asp Gly Ile Tyr Val Glu His Lys Asn Leu Asn Glu Leu Ser Lys Gln
            340               345               350

Ala Phe Gly Asp Phe Ala Leu Leu Gly Arg Val Leu Asp Gly Tyr Tyr
            355               360               365

Val Asp Val Val Asn Pro Glu Phe Asn Glu Arg Phe Ala Lys Ala Lys
        370               375               380

Thr Asp Asn Ala Lys Ala Lys Leu Thr Lys Glu Lys Asp Lys Phe Ile
    385               390               395               400

Lys Gly Val His Ser Leu Ala Ser Leu Glu Gln Ala Ile Glu His His
                405               410               415

Thr Ala Arg His Asp Asp Glu Ser Val Gln Ala Gly Lys Leu Gly Gln
            420               425               430

Tyr Phe Lys His Gly Leu Ala Gly Val Asp Asn Pro Ile Gln Lys Ile
            435               440               445

His Asn Asn His Ser Thr Ile Lys Gly Phe Leu Glu Arg Glu Arg Pro
        450               455               460

Ala Gly Glu Arg Ala Leu Pro Lys Ile Lys Ser Gly Lys Asn Pro Glu
    465               470               475               480

Met Thr Gln Leu Arg Gln Leu Lys Glu Leu Leu Asp Asn Ala Leu Asn
                485               490               495

Val Ala His Phe Ala Lys Leu Leu Thr Thr Lys Thr Thr Leu Asp Asn
            500               505               510

Gln Asp Gly Asn Phe Tyr Gly Glu Phe Gly Val Leu Tyr Asp Glu Leu
            515               520               525

Ala Lys Ile Pro Thr Leu Tyr Asn Lys Val Arg Asp Tyr Leu Ser Gln
        530               535               540

Lys Pro Phe Ser Thr Glu Lys Tyr Lys Leu Asn Phe Gly Asn Pro Thr
    545               550               555               560

Leu Leu Asn Gly Trp Asp Leu Asn Lys Glu Lys Asp Asn Phe Gly Val
                565               570               575

Ile Leu Gln Lys Asp Gly Cys Tyr Tyr Leu Ala Leu Leu Asp Lys Ala
            580               585               590
```

-continued

```
His Lys Lys Val Phe Asp Asn Ala Pro Asn Thr Gly Lys Asn Val Tyr
        595             600             605

Gln Lys Met Val Tyr Lys Leu Leu Pro Gly Pro Asn Lys Met Leu Pro
        610             615             620

Lys Val Phe Phe Ala Lys Ser Asn Leu Asp Tyr Tyr Asn Pro Ser Ala
625             630             635             640

Glu Leu Leu Asp Lys Tyr Ala Lys Gly Thr His Lys Lys Gly Asp Asn
            645             650             655

Phe Asn Leu Lys Asp Cys His Ala Leu Ile Asp Phe Phe Lys Ala Gly
            660             665             670

Ile Asn Lys His Pro Glu Trp Gln His Phe Gly Phe Lys Phe Ser Pro
        675             680             685

Thr Ser Ser Tyr Arg Asp Leu Ser Asp Phe Tyr Arg Glu Val Glu Pro
        690             695             700

Gln Gly Tyr Gln Val Lys Phe Val Asp Ile Asn Ala Asp Tyr Ile Asp
705             710             715             720

Glu Leu Val Glu Gln Gly Lys Leu Tyr Leu Phe Gln Ile Tyr Asn Lys
            725             730             735

Asp Phe Ser Pro Lys Ala His Gly Lys Pro Asn Leu His Thr Leu Tyr
            740             745             750

Phe Lys Ala Leu Phe Ser Glu Asp Asn Leu Ala Asp Pro Ile Tyr Lys
        755             760             765

Leu Asn Gly Glu Ala Gln Ile Phe Tyr Arg Lys Ala Ser Leu Asp Met
        770             775             780

Asn Glu Thr Thr Ile His Arg Ala Gly Glu Val Leu Glu Asn Lys Asn
785             790             795             800

Pro Asp Asn Pro Lys Lys Arg Gln Phe Val Tyr Asp Ile Ile Lys Asp
            805             810             815

Lys Arg Tyr Thr Gln Asp Lys Phe Met Leu His Val Pro Ile Thr Met
            820             825             830

Asn Phe Gly Val Gln Gly Met Thr Ile Lys Glu Phe Asn Lys Lys Val
            835             840             845

Asn Gln Ser Ile Gln Gln Tyr Asp Glu Val Asn Val Ile Gly Ile Asp
        850             855             860

Arg Gly Glu Arg His Leu Leu Tyr Leu Thr Val Ile Asn Ser Lys Gly
865             870             875             880

Glu Ile Leu Glu Gln Arg Ser Leu Asn Asp Ile Thr Thr Ala Ser Ala
            885             890             895

Asn Gly Thr Gln Val Thr Thr Pro Tyr His Lys Ile Leu Asp Lys Arg
        900             905             910

Glu Ile Glu Arg Leu Asn Ala Arg Val Gly Trp Gly Glu Ile Glu Thr
        915             920             925

Ile Lys Glu Leu Lys Ser Gly Tyr Leu Ser His Val Val His Gln Ile
        930             935             940

Asn Gln Leu Met Leu Lys Tyr Asn Ala Ile Val Val Leu Glu Asp Leu
945             950             955             960

Asn Phe Gly Phe Lys Arg Gly Arg Phe Lys Val Glu Lys Gln Ile Tyr
            965             970             975

Gln Asn Phe Glu Asn Ala Leu Ile Lys Lys Leu Asn His Leu Val Leu
            980             985             990

Lys Asp Lys Ala Asp Asp Glu Ile  Gly Ser Tyr Lys Asn  Ala Leu Gln
        995             1000            1005
```

```
Leu Thr  Asn Asn Phe Thr Asp  Leu Lys Ser Ile Gly  Lys Gln Thr
    1010             1015             1020

Gly Phe  Leu Phe Tyr Val Pro  Ala Trp Asn Thr Ser  Lys Ile Asp
    1025             1030             1035

Pro Glu  Thr Gly Phe Val Asp  Leu Leu Lys Pro Arg  Tyr Glu Asn
    1040             1045             1050

Ile Ala  Gln Ser Gln Ala Phe  Phe Gly Lys Phe Asp  Lys Ile Cys
    1055             1060             1065

Tyr Asn  Thr Asp Lys Gly Tyr  Phe Glu Phe His Ile  Asp Tyr Ala
    1070             1075             1080

Lys Phe  Thr Asp Lys Ala Lys  Asn Ser Arg Gln Lys  Trp Ala Ile
    1085             1090             1095

Cys Ser  His Gly Asp Lys Arg  Tyr Val Tyr Asp Lys  Thr Ala Asn
    1100             1105             1110

Gln Asn  Lys Gly Ala Ala Lys  Gly Ile Asn Val Asn  Asp Glu Leu
    1115             1120             1125

Lys Ser  Leu Phe Ala Arg Tyr  His Ile Asn Asp Lys  Gln Pro Asn
    1130             1135             1140

Leu Val  Met Asp Ile Cys Gln  Asn Asn Asp Lys Glu  Phe His Lys
    1145             1150             1155

Ser Leu  Met Cys Leu Leu Lys  Thr Leu Leu Ala Leu  Arg Tyr Ser
    1160             1165             1170

Asn Ala  Ser Ser Asp Glu Asp  Phe Ile Leu Ser Pro  Val Ala Asn
    1175             1180             1185

Asp Glu  Gly Val Phe Phe Asn  Ser Ala Leu Ala Asp  Asp Thr Gln
    1190             1195             1200

Pro Gln  Asn Ala Asp Ala Asn  Gly Ala Tyr His Ile  Ala Leu Lys
    1205             1210             1215

Gly Leu  Trp Leu Leu Asn Glu  Leu Lys Asn Ser Asp  Asp Leu Asn
    1220             1225             1230

Lys Val  Lys Leu Ala Ile Asp  Asn Gln Thr Trp Leu  Asn Phe Ala
    1235             1240             1245

Gln Asn  Arg
    1250

<210> SEQ ID NO 299
<211> LENGTH: 1251
<212> TYPE: PRT
<213> ORGANISM: Artificial Sequence
<220> FEATURE:
<223> OTHER INFORMATION: Synthetic construct

<400> SEQUENCE: 299

Met Leu Phe Gln Asp Phe Thr His Leu Tyr Pro Leu Ser Lys Thr Val
1               5                   10                  15

Arg Phe Glu Leu Lys Pro Ile Gly Arg Thr Leu Glu His Ile His Ala
            20                  25                  30

Lys Asn Phe Leu Ser Gln Asp Glu Thr Met Ala Asp Met Tyr Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
                85                  90                  95
```

-continued

```
Lys Asp Leu Gln Ala Val Leu Arg Lys Glu Ser Val Lys Pro Ile Gly
            100                 105                 110

Ser Gly Gly Lys Tyr Lys Thr Gly Tyr Asp Arg Leu Phe Gly Ala Lys
            115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
            195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Arg Ile Ile
                245                 250                 255

Gly Glu Val Asn Gly Tyr Thr Asn Lys His Asn Gln Ile Cys His Lys
            260                 265                 270

Ser Glu Arg Ile Ala Lys Leu Arg Pro Leu His Lys Gln Ile Leu Ser
            275                 280                 285

Asp Gly Met Gly Val Ser Phe Leu Pro Ser Lys Phe Ala Asp Asp Ser
    290                 295                 300

Glu Met Cys Gln Ala Val Asn Glu Phe Tyr Arg His Tyr Thr Asp Val
305                 310                 315                 320

Phe Ala Lys Val Gln Ser Leu Phe Asp Gly Phe Asp Asp His Gln Lys
                325                 330                 335

Asp Gly Ile Tyr Val Glu His Lys Asn Leu Asn Glu Leu Ser Lys Gln
            340                 345                 350

Ala Phe Gly Asp Phe Ala Leu Leu Gly Arg Val Leu Asp Gly Tyr Tyr
            355                 360                 365

Val Asp Val Val Asn Pro Glu Phe Asn Glu Arg Phe Ala Lys Ala Lys
    370                 375                 380

Thr Asp Asn Ala Lys Ala Lys Leu Thr Lys Glu Lys Asp Lys Phe Ile
385                 390                 395                 400

Lys Gly Val His Ser Leu Ala Ser Leu Glu Gln Ala Ile Glu His His
                405                 410                 415

Thr Ala Arg His Asp Asp Glu Ser Val Gln Ala Gly Lys Leu Gly Gln
            420                 425                 430

Tyr Phe Lys His Gly Leu Ala Gly Val Asp Asn Pro Ile Gln Lys Ile
            435                 440                 445

His Asn Asn His Ser Thr Ile Lys Gly Phe Leu Glu Arg Glu Arg Pro
    450                 455                 460

Ala Gly Glu Arg Ala Leu Pro Lys Ile Lys Ser Gly Lys Asn Pro Glu
465                 470                 475                 480

Met Thr Gln Leu Arg Gln Leu Lys Glu Leu Leu Asp Asn Ala Leu Asn
                485                 490                 495

Val Ala His Phe Ala Lys Leu Leu Thr Thr Lys Thr Thr Leu Asp Asn
            500                 505                 510

Gln Asp Gly Asn Phe Tyr Gly Glu Phe Gly Val Leu Tyr Asp Glu Leu
```

-continued

```
            515                520                525

Ala Lys Ile Pro Thr Leu Tyr Asn Lys Val Arg Asp Tyr Leu Ser Gln
    530                535                540

Lys Pro Phe Ser Thr Glu Lys Tyr Lys Leu Asn Phe Gly Asn Pro Thr
545                550                555                560

Leu Leu Arg Gly Trp Asp Leu Asn Val Glu Lys Asp Arg Phe Gly Val
                565                570                575

Ile Leu Gln Lys Asp Gly Cys Tyr Tyr Leu Ala Leu Leu Asp Lys Ala
                580                585                590

His Lys Lys Val Phe Asp Asn Ala Pro Asn Thr Gly Lys Asn Val Tyr
                595                600                605

Gln Lys Met Val Tyr Lys Leu Leu Pro Gly Pro Asn Lys Met Leu Pro
    610                615                620

Lys Val Phe Phe Ala Lys Ser Asn Leu Asp Tyr Tyr Asn Pro Ser Ala
625                630                635                640

Glu Leu Leu Asp Lys Tyr Ala Lys Gly Thr His Lys Lys Gly Asp Asn
                645                650                655

Phe Asn Leu Lys Asp Cys His Ala Leu Ile Asp Phe Phe Lys Ala Gly
                660                665                670

Ile Asn Lys His Pro Glu Trp Gln His Phe Gly Phe Lys Phe Ser Pro
                675                680                685

Thr Ser Ser Tyr Arg Asp Leu Ser Asp Phe Tyr Arg Glu Val Glu Pro
    690                695                700

Gln Gly Tyr Gln Val Lys Phe Val Asp Ile Asn Ala Asp Tyr Ile Asp
705                710                715                720

Glu Leu Val Glu Gln Gly Lys Leu Tyr Leu Phe Gln Ile Tyr Asn Lys
                725                730                735

Asp Phe Ser Pro Lys Ala His Gly Lys Pro Asn Leu His Thr Leu Tyr
                740                745                750

Phe Lys Ala Leu Phe Ser Glu Asp Asn Leu Ala Asp Pro Ile Tyr Lys
                755                760                765

Leu Asn Gly Glu Ala Gln Ile Phe Tyr Arg Lys Ala Ser Leu Asp Met
    770                775                780

Asn Glu Thr Thr Ile His Arg Ala Gly Glu Val Leu Glu Asn Lys Asn
785                790                795                800

Pro Asp Asn Pro Lys Lys Arg Gln Phe Val Tyr Asp Ile Ile Lys Asp
                805                810                815

Lys Arg Tyr Thr Gln Asp Lys Phe Met Leu His Val Pro Ile Thr Met
                820                825                830

Asn Phe Gly Val Gln Gly Met Thr Ile Lys Glu Phe Asn Lys Lys Val
                835                840                845

Asn Gln Ser Ile Gln Gln Tyr Asp Glu Val Asn Val Ile Gly Ile Asp
    850                855                860

Arg Gly Glu Arg His Leu Leu Tyr Leu Thr Val Ile Asn Ser Lys Gly
865                870                875                880

Glu Ile Leu Glu Gln Arg Ser Leu Asn Asp Ile Thr Thr Ala Ser Ala
                885                890                895

Asn Gly Thr Gln Val Thr Thr Pro Tyr His Lys Ile Leu Asp Lys Arg
                900                905                910

Glu Ile Glu Arg Leu Asn Ala Arg Val Gly Trp Gly Glu Ile Glu Thr
                915                920                925

Ile Lys Glu Leu Lys Ser Gly Tyr Leu Ser His Val Val His Gln Ile
    930                935                940
```

-continued

```
Asn Gln Leu Met Leu Lys Tyr Asn Ala Ile Val Val Leu Glu Asp Leu
945                 950             955             960

Asn Phe Gly Phe Lys Arg Gly Arg Phe Lys Val Glu Lys Gln Ile Tyr
            965             970             975

Gln Asn Phe Glu Asn Ala Leu Ile Lys Lys Leu Asn His Leu Val Leu
            980             985             990

Lys Asp Lys Ala Asp Asp Glu Ile  Gly Ser Tyr Lys Asn  Ala Leu Gln
        995             1000            1005

Leu Thr  Asn Asn Phe Thr Asp  Leu Lys Ser Ile Gly  Lys Gln Thr
    1010            1015            1020

Gly Phe  Leu Phe Tyr Val Pro  Ala Trp Asn Thr Ser  Lys Ile Asp
    1025            1030            1035

Pro Glu  Thr Gly Phe Val Asp  Leu Leu Lys Pro Arg  Tyr Glu Asn
    1040            1045            1050

Ile Ala  Gln Ser Gln Ala Phe  Phe Gly Lys Phe Asp  Lys Ile Cys
    1055            1060            1065

Tyr Asn  Thr Asp Lys Gly Tyr  Phe Glu Phe His Ile  Asp Tyr Ala
    1070            1075            1080

Lys Phe  Thr Asp Lys Ala Lys  Asn Ser Arg Gln Lys  Trp Ala Ile
    1085            1090            1095

Cys Ser  His Gly Asp Lys Arg  Tyr Val Tyr Asp Lys  Thr Ala Asn
    1100            1105            1110

Gln Asn  Lys Gly Ala Ala Lys  Gly Ile Asn Val Asn  Asp Glu Leu
    1115            1120            1125

Lys Ser  Leu Phe Ala Arg Tyr  His Ile Asn Asp Lys  Gln Pro Asn
    1130            1135            1140

Leu Val  Met Asp Ile Cys Gln  Asn Asn Asp Lys Glu  Phe His Lys
    1145            1150            1155

Ser Leu  Met Cys Leu Leu Lys  Thr Leu Leu Ala Leu  Arg Tyr Ser
    1160            1165            1170

Asn Ala  Ser Ser Asp Glu Asp  Phe Ile Leu Ser Pro  Val Ala Asn
    1175            1180            1185

Asp Glu  Gly Val Phe Phe Asn  Ser Ala Leu Ala Asp  Asp Thr Gln
    1190            1195            1200

Pro Gln  Asn Ala Asp Ala Asn  Gly Ala Tyr His Ile  Ala Leu Lys
    1205            1210            1215

Gly Leu  Trp Leu Leu Asn Glu  Leu Lys Asn Ser Asp  Asp Leu Asn
    1220            1225            1230

Lys Val  Lys Leu Ala Ile Asp  Asn Gln Thr Trp Leu  Asn Phe Ala
    1235            1240            1245

Gln Asn  Arg
    1250
```